(12) United States Patent
Castro Pineiro et al.

(10) Patent No.: US 8,217,028 B2
(45) Date of Patent: Jul. 10, 2012

US008217028B2

(54) 1,2,4-OXADIAZOLE INDOLE COMPOUNDS

(75) Inventors: Jose Luis Castro Pineiro, Harlow (GB); Xichen Lin, Shanghai (CN); Qian Liu, Shanghai (CN); Kevin Meng, Shanghai (CN); Feng Ren, Shanghai (CN); David R Vesey, Harlow (GB); Baowei Zhao, Shanghai (CN)

(73) Assignee: Glaxo Group Limited, Middlesex (GB)

( * ) Notice: Subject to any disclaimer, the term of this patent is extended or adjusted under 35 U.S.C. 154(b) by 0 days.

(21) Appl. No.: 12/999,091

(22) PCT Filed: Jun. 18, 2009

(86) PCT No.: PCT/EP2009/057597
§ 371 (c)(1),
(2), (4) Date: Dec. 15, 2010

(87) PCT Pub. No.: WO2009/153307
PCT Pub. Date: Dec. 23, 2009

(65) Prior Publication Data
US 2011/0086839 A1    Apr. 14, 2011

(30) Foreign Application Priority Data

Jun. 20, 2008 (GB) .................................. 0811449.8
Jun. 5, 2009 (GB) .................................. 0909744.5

(51) Int. Cl.
*A61K 31/4245* (2006.01)
*A61K 31/454* (2006.01)
*A61K 31/4545* (2006.01)
*A61K 31/4439* (2006.01)
*A61P 25/00* (2006.01)
*C07D 413/14* (2006.01)
*C07D 413/10* (2006.01)

(52) U.S. Cl. .................. 514/210.18; 514/364; 514/323; 514/318; 514/339; 546/201; 546/194; 546/269.4; 548/131

(58) Field of Classification Search .................. None
See application file for complete search history.

(56) References Cited

U.S. PATENT DOCUMENTS

| | | |
|---|---|---|
| 5,137,898 A | 8/1992 | Klausener et al. |
| 5,182,286 A | 1/1993 | Seitz et al. |
| 5,262,416 A | 11/1993 | Seitz et al. |
| 5,462,943 A | 10/1995 | Seitz et al. |
| 5,514,692 A | 5/1996 | Aldous et al. |
| 5,523,312 A | 6/1996 | Aldous et al. |
| 6,004,565 A | 12/1999 | Chiba et al. |
| 6,667,025 B2 | 12/2003 | Chiba et al. |
| 7,199,142 B2 | 4/2007 | Chen et al. |
| 2002/0102279 A1 | 8/2002 | Chiba et al. |
| 2004/0092603 A1 | 5/2004 | Chiba et al. |
| 2005/0090558 A1 | 4/2005 | Chiba et al. |
| 2005/0245575 A1 | 11/2005 | Chen et al. |
| 2008/0113961 A1 | 5/2008 | Nishi et al. |
| 2008/0188532 A1 | 8/2008 | Takeuchi et al. |
| 2008/0249093 A1 | 10/2008 | Colandrea et al. |
| 2008/0280876 A1 | 11/2008 | Hobson et al. |
| 2008/0306124 A1 | 12/2008 | Albert et al. |
| 2008/0318955 A1 | 12/2008 | Bolli et al. |
| 2009/0042954 A1 | 2/2009 | Hale et al. |
| 2009/0076070 A1 | 3/2009 | Harada et al. |
| 2009/0221547 A1 | 9/2009 | Gao et al. |
| 2010/0010053 A1 | 1/2010 | Pineiro et al. |
| 2010/0029729 A1 | 2/2010 | Pineiro et al. |

FOREIGN PATENT DOCUMENTS

| | | |
|---|---|---|
| EP | 2003132 | 12/2008 |
| WO | WO 2005123676 A1 * | 12/2005 |
| WO | WO 2007/116866 | 10/2007 |
| WO | WO2008/074821 A1 | 6/2008 |

OTHER PUBLICATIONS

Allende, et al 2003 102:3665, Blood.
Brinkman, et al 2002 JBC 277:21453.
Brinkman, et al 2004 American J Transplantation, 4:1019.
Chiba, et al 1998, J Immunology 160:5037.
Chiba 2005 Pharmacology and Therapeutics 108:308.
Chun et al 2002 Pharmacological Reviews 54:265.
Forrest, et al 2004 J Pharmacol Exp Ther 309:758.
Fujino, et al 2003 J Pharmacol Exp Ther 305:70.
Graler and Goetzl 2004 FASEB J 18:551.
Hale, et al 2004 Bioorganic & Medicinal Chemistry Letters 14:3501.
Jo, et al 2005 Chem Biol 12:703.
Kluk and Hla 2002 Biochem et Biophysica Acta 1582:72.
Kahan, et al 2003, Transplanation 76:1079.
Kappos, et al 2006 New Eng J Medicine 355:1124.
Koyrakh, et al 2005 American J Transplantation 5:529.
Mandala, et al 2002 Science 296:346.
Matloubian, et al 2004 Nature 427:355.
Morris, et al 2005 EurJ Immunol 35:3570.
Okamoto, et al 1998 J Biol Chem 273(42):27104.
Pyne and Pyne 2000, Biochem J. 349:385.
Rausch, et al 2004 J Magn Reson Imaging 20:16.
Rosen and Goetzl 2005 Nat Rev Immunol, 5:560.
Sanchez and Hla 2004, J Cell Biochem 92:913.
Sanna, et al 2004 JBC 279:13839.
Singelton, et al 2005 FASEB J 19:1646.
Webb, et al 2004 J Neuroimmunol 153:108.
Wei, et al 2005, Nat. Immunology 6:1228.

* cited by examiner

*Primary Examiner* — Yong Chu
(74) *Attorney, Agent, or Firm* — Linda E. Hall; John L. Lemanowicz

(57) ABSTRACT

The present invention relates to novel oxadiazole derivatives having pharmacological activity, processes for their preparation, pharmaceutical compositions containing them and their use in the treatment of various disorders.

4 Claims, No Drawings

1,2,4-OXADIAZOLE INDOLE COMPOUNDS

This application is a 371 of International Application No. PCT/EP2009/057597, filed June 18, 2009, which claims the priority of GB Application No. GB 0909744.5 filed 05 June 2009 and GB Application No. 0811449.8 filed 20 June 2008, which are incorporated herein in their entirety.

The present invention relates to novel oxadiazole derivatives having pharmacological activity, processes for their preparation, pharmaceutical compositions containing them and their use in the treatment of various disorders.

Sphingosine 1-phosphate (S1P) is a bioactive lipid mediator formed by the phosphorylation of sphingosine by sphingosine kinases and is found in high levels in the blood. It is produced and secreted by a number of cell types, including those of hematopoietic origin such as platelets and mast cells (Okamoto et al 1998 J Biol Chem 273(42):27104; Sanchez and Hla 2004, J Cell Biochem 92:913). It has a wide range of biological actions, including regulation of cell proliferation, differentiation, motility, vascularisation, and activation of inflammatory cells and platelets (Pyne and Pyne 2000, Biochem J. 349: 385). Five subtypes of S1P responsive receptor have been described, S1P1 (Edg-1), S1P2 (Edg-5), S1P3 (Edg-3), S1P4 (Edg-6), and S1P5 (Edg-8), forming part of the G-protein coupled endothelial differentiation gene family of receptors (Chun et al 2002 Pharmacological Reviews 54:265, Sanchez and Hla 2004 J Cellular Biochemistry, 92:913). These 5 receptors show differential mRNA expression, with S1P1-3 being widely expressed, S1P4 expressed on lymphoid and hematopoietic tissues and S1P5 primarily in brain and to a lower degree in spleen. They signal via different subsets of G proteins to promote a variety of biological responses (Kluk and Hla 2002 Biochem et Biophysica Acta 1582:72, Sanchez and Hla 2004, J Cellular Biochem 92:913).

Proposed roles for the S1P1 receptor include lymphocyte trafficking, cytokine induction/suppression and effects on endothelial cells (Rosen and Goetzl 2005 Nat Rev Immunol. 5:560). Agonists of the S1P1 receptor have been used in a number of autoimmune and transplantation animal models, including Experimental Autoimmune Encephalomelitis (EAE) models of MS, to reduce the severity of the induced disease (Brinkman et al 2003 JBC 277:21453; Fujino et al 2003 J Pharmacol Exp Ther 305:70; Webb et al 2004 J Neuroimmunol 153:108; Rausch et al 2004 J Magn Reson Imaging 20:16). This activity is reported to be mediated by the effect of S1P1 agonists on lymphocyte circulation through the lymph system. Treatment with S1P1 agonists results in the sequestration of lymphocytes within secondary lymphoid organs such as the lymph nodes, inducing a reversible peripheral lymphopoenia in animal models (Chiba et al 1998, J Immunology 160:5037, Forrest et al 2004 J Pharmacol Exp Ther 309:758; Sanna et al 2004 JBC 279:13839). Published data on agonists suggests that compound treatment induces loss of the S1P1 receptor from the cell surface via internalisation (Graler and Goetzl 2004 FASEB J 18:551; Matloubian et al 2004 Nature 427:355; Jo et al 2005 Chem Biol 12:703) and it is this reduction of S1P1 receptor on immune cells which contributes to the reduction of movement of T cells from the lymph nodes back into the blood stream.

S1P1 gene deletion causes embryonic lethality. Experiments to examine the role of the S1P1 receptor in lymphocyte migration and trafficking have included the adoptive transfer of labelled S1P1 deficient T cells into irradiated wild type mice. These cells showed a reduced egress from secondary lymphoid organs (Matloubian et al 2004 Nature 427:355).

S1P1 has also been ascribed a role in endothelial cell junction modulation (Allende et al 2003 102:3665, Blood Singelton et al 2005 FASEB J 19:1646). With respect to this endothelial action, S1P1 agonists have been reported to have an effect on isolated lymph nodes which may be contributing to a role in modulating immune disorders. S1P1 agonists caused a closing of the endothelial stromal 'gates' of lymphatic sinuses which drain the lymph nodes and prevent lymphocyte egress (Wei wt al 2005, Nat. Immunology 6:1228).

The immunosuppressive compound FTY720 (JP11080026-A) has been shown to reduce circulating lymphocytes in animals and man, have disease modulating activity in animal models of immune disorders and reduce remission rates in relapsing remitting Multiple Sclerosis (Brinkman et al 2002 JBC 277:21453, Mandala et al 2002 Science 296:346, Fujino et al 2003 J Pharmacology and Experimental Therapeutics 305:45658, Brinkman et al 2004 American J Transplantation 4:1019, Webb et al 2004 J Neuroimmunology 153:108, Morris et al 2005 EurJ Immunol 35:3570, Chiba 2005 Pharmacology and Therapeutics 108:308, Kahan et al 2003, Transplantation 76:1079, Kappos et al 2006 New Eng J Medicine 335:1124). This compound is a prodrug that is phosphorylated in vivo by sphingosine kinases to give a molecule that has agonist activity at the S1P1, S1P3, S1P4 and S1P5 receptors. Clinical studies have demonstrated that treatment with FTY720 results in bradycardia in the first 24 hours of treatment (Kappos et al 2006 New Eng J Medicine 335:1124). The bradycardia is thought to be due to agonism at the S1P3 receptor, based on a number of cell based and animal experiments. These include the use of S1P3 knock-out animals which, unlike wild type mice, do not demonstrate bradycardia following FTY720 administration and the use of S1P1 selective compounds. (Hale et al 2004 Bioorganic & Medicinal Chemistry Letters 14:3501, Sanna et al 2004 JBC 279: 13839, Koyrakh et al 2005 American J Transplantation 5:529)

Hence, there is a need for S1P1 receptor agonist compounds with selectivity over S1P3 which might be expected to show a reduced tendency to induce bradycardia.

The following patent applications describe oxadiazole derivatives as S1P1 agonists: WO03/105771, WO05/058848, WO06/047195, WO06/100633, WO06/115188, WO06/131336, WO07/024922 and WO07/116866.

The following patent application describes indole-oxadiazole derivatives as antipicornaviral agents: WO96/009822. The following patent applications describe indole-carboxylic acid derivatives as leukotriene receptor antagonists, pesticides and agrochemical fungicides respectively: WO06/090817, EP 0 439 785 and DE 39 39 238.

International patent applications WO08/074821 and WO08/76356 describe oxadiazole-indole derivatives as S1P1 agonists.

A structurally novel class of compounds has now been found which provides agonists of the S1P1 receptor.

The present invention therefore provides compounds of formula (I) or a salt thereof:

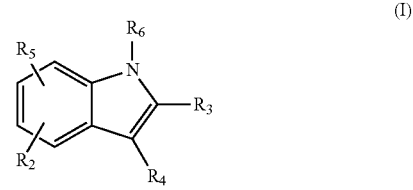

(I)

wherein
$R_5$ is (a) and attached at any one of positions 4, 5, 6 or 7 of the indole group;

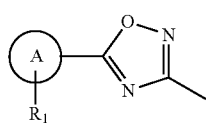
(a)

A is a phenyl or a 5 or 6-membered heteroaryl ring;

$R_1$ is hydrogen or up to three substituents independently selected from halogen, $C_{(1-6)}$alkyl, $C_{(3-6)}$cycloalkyl, $C_{(1-6)}$alkoxy, $C_{(3-6)}$cycloalkyloxy, trifluoromethoxy, difluoromethoxy, trifluoromethyl, cyano, nitro, optionally substituted piperidine, optionally substituted pyrrolidine, optionally substituted phenyl and optionally substituted 5 or 6 membered heteroaryl rings;

when $R_1$ is phenyl, piperidine, pyrrolidine or a 5 or 6 membered heteroaryl ring it may be substituted by up to three substituents selected from halogen, $C_{(1-6)}$alkyl, $C_{(1-6)}$alkoxy, trifluoromethoxy, difluoromethoxy, $C_{3-6}$cycloalkyl, trifluoromethyl and cyano;

$R_2$ is hydrogen or up to three substituents independently selected from halogen, $C_{(1-6)}$alkyl, $C_{(1-4)}$alkoxy, trifluoromethoxy, difluoromethoxy, trifluoromethyl and cyano;

one of $R_3$ and $R_4$ is hydrogen or $C_{(1-6)}$alkyl and the other is Z—COOH or $C_{(1-6)}$alkylOH;

Z is absent, $C_{(1-6)}$alkyl or $C_{(2-6)}$alkenyl;

when Z is $C_{(1-6)}$alkyl it is optionally interrupted by a cyclopropyl, piperidinyl, azetidinyl, pyrrolidinyl, optionally interrupted by N or O and optionally substituted by O, cyclopropyl, halogen or methyl, when Z is $C_{(2-6)}$alkenyl it is optionally substituted by methyl.

$R_6$ is hydrogen or $C_{(1-6)}$alkyl.

The present invention therefore includes compounds of formula (IA) or a salt thereof:

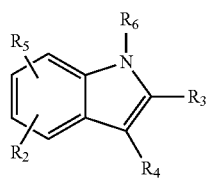
(I)

wherein $R_5$ is (a) and attached at any one of positions 4, 5, 6 or 7 of the indole group;

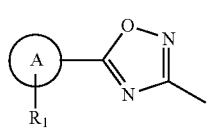
(a)

A is a phenyl or a 5 or 6-membered heteroaryl ring;

$R_1$ is hydrogen or up to three substituents independently selected from halogen, $C_{(1-6)}$alkyl, $C_{(3-6)}$cycloalkyl, $C_{(1-6)}$alkoxy, $C_{(3-6)}$cycloalkyloxy, trifluoromethoxy, difluoromethoxy, trifluoromethyl, cyano, nitro, optionally substituted piperidine, optionally substituted pyrrolidine, optionally substituted phenyl and optionally substituted 5 or 6 membered heteroaryl rings;

when $R_1$ is phenyl, piperidine, pyrrolidine or a 5 or 6 membered heteroaryl ring it may be substituted by up to three substituents selected from halogen, $C_{(1-6)}$alkyl, $C_{(1-6)}$alkoxy, trifluoromethoxy, difluoromethoxy, $C_{3-6}$cycloalkyl, trifluoromethyl and cyano;

$R_2$ is hydrogen or up to three substituents independently selected from halogen, $C_{(1-4)}$alkyl, $C_{(1-4)}$alkoxy, trifluoromethoxy, difluoromethoxy, trifluoromethyl and cyano;

one of $R_3$ and $R_4$ is hydrogen or $C_{(1-6)}$alkyl and the other is Z—COOH or $C_{(1-6)}$alkylOH;

Z is absent, $C_{(1-6)}$alkyl or $C_{(2-6)}$alkenyl;

when Z is $C_{(1-6)}$alkyl it is optionally interrupted by N or O and optionally substituted by halogen or methyl, when Z is $C_{(2-6)}$alkenyl it is optionally substituted by methyl.

$R_6$ is hydrogen or $C_{(1-6)}$alkyl.

In one embodiment of the invention $R_5$ is (a) and attached at any one of positions 5, 6 or 7 of the indole group. In another embodiment $R_5$ is (a) and attached at any one of positions 6 or 7 of the indole group. In another embodiment $R_5$ is (a) and attached at position 7 of the indole group.

In one embodiment of the invention A is phenyl or pyridyl. In another embodiment A is phenyl.

In one embodiment of the invention $R_1$ is up to two substituents independently selected from halogen, $C_{(1-6)}$alkoxy, trifluoromethyl, $C_{(1-6)}$alkyl and cyano. In a further embodiment when A is pyridyl or phenyl $R_1$ is $C_{(1-6)}$alkoxy para to the oxadiazolyl)-point of attachment to A, and the other substituent is adjacent to the $C_{(1-6)}$alkoxy group. In another embodiment of the invention $R_1$ is $C_{(1-6)}$alkoxy and one other substituent independently selected from halogen, $C_{(1-6)}$ alkoxy, trifluoromethyl, $C_{(1-6)}$alkyl and cyano. In a further embodiment $R_1$ is isopropoxy and one substituent independently selected from chloro, fluoro, trifluoromethyl, methoxy, ethoxy, methyl and cyano. In a further embodiment when A is pyridyl or phenyl $R_1$ is isopropoxy para to the oxadiazolyly point of attachment to A, and the other substituent is adjacent to the isopropoxy group.

In one embodiment of the invention $R_1$ is up to two substituents independently selected from halogen, $C_{(1-6)}$alkoxy and cyano. In another embodiment $R_1$ is up to two substituents independently selected from chloro, isopropoxy and cyano. In another embodiment $R_1$ is chloro and isoproxy. In another embodiment $R_1$ is cyano and isopropoxy. In further embodiments, A is phenyl and $R_1$ is 3-chloro and 4-isopropoxy or A is phenyl and $R_1$ is 3-cyano and 4-isopropoxy.

In one embodiment of the invention $R_2$ is halogen or hydrogen. In one embodiment of the invention $R_2$ is fluoro or hydrogen. In another embodiment of the invention $R_2$ is hydrogen.

In one embodiment of the invention one of $R_3$ and $R_4$ is hydrogen and the other is Z—COOH or $CH_2OH$. In another embodiment of the invention one of $R_3$ and $R_4$ is hydrogen and the other is Z—COOH. In another embodiment of the invention $R_3$ is hydrogen and $R_4$ is Z—COOH. In another embodiment of the invention $R_4$ is hydrogen and $R_3$ is $CH_2OH$.

In one embodiment Z is $C_{(1-6)}$alkyl it is optionally interrupted by a cyclopropyl, piperidinyl, azetidinyl or pyrrolidinyl. In another embodiment Z is optionally interrupted by N or O. In another embodiment Z is $C_{(1-6)}$alkyl substituted by O, cyclopropyl, halogen or methyl.

When Z is $C_{(1-6)}$alkyl interrupted by N or O it may also be substituted by methyl or O or methyl and O.

In another embodiment Z is $C_{(2-6)}$alkenyl optionally substituted by methyl.

In one embodiment of the invention Z is absent, $(CH_2)_2$, $(CH_2)_3$ or CH=CH. In another embodiment of the invention Z is $(CH_2)_2$.

In one embodiment of the invention $R_6$ is hydrogen, methyl, ethyl, propyl or butyl In one embodiment of the invention $R_6$ is hydrogen or methyl. In another embodiment of the invention $R_6$ is hydrogen.

In one embodiment of the invention $R_5$ is (a) and attached at positions 6 or 7 of the indole group;

A is phenyl or pyridyl;

$R_1$ is $C_{(1-6)}$alkoxy and one other substituent independently selected from halogen, $C_{(1-6)}$alkoxy, trifluoromethyl, $C_{(1-6)}$alkyl and cyano;

$R_2$ is halogen or hydrogen.

one of $R_3$ and $R_4$ is hydrogen and the other is Z—COOH or $CH_2OH$;

Z is $C_{(1-6)}$alkyl optionally interrupted by cyclopropyl, piperidinyl, azetidinyl, pyrrolidinyl, N or O and optionally substituted by 0, cyclopropyl, halogen or methyl, or Z is $C_{(2-6)}$alkenyl optionally substituted by methyl;

$R_6$ is hydrogen, methyl, ethyl, propyl or butyl.

In one embodiment of the invention $R_5$ is (a) and attached at any one of positions 5, 6 or 7 of the indole group;

A is a phenyl or pyridyl; and $R_1$ is up to two substituents independently selected from halogen, $C_{(1-6)}$alkoxy and cyano; and $R_2$ is hydrogen; and one of $R_3$ and $R_4$ is hydrogen and the other is Z—COOH or $CH_2OH$; and Z is absent, $(CH_2)_2$, $(CH_2)_3$ or CH=CH; and $R_6$ is hydrogen or methyl.

In one embodiment of the invention $R_5$ is (a) and attached at any one of positions 5, 6 or 7 of the indole group;

A is a phenyl; and $R_1$ is up to two substituents independently selected from halogen, $C_{(1-6)}$alkoxy and cyano; and $R_2$ is hydrogen; and one of $R_3$ and $R_4$ is hydrogen and the other is Z—COOH or $CH_2OH$; and Z is absent, $(CH_2)_2$ or CH=CH; and $R_6$ is hydrogen or methyl.

In one embodiment of the invention $R_5$ is (a) and attached at any one of positions 5, 6 or 7 of the indole group;

A is a phenyl; and $R_1$ is up to two substituents independently selected from chloro, isopropoxy and cyano; and $R_2$ is hydrogen; and one of $R_3$ and $R_4$ is hydrogen and the other is Z—COOH or $CH_2OH$; and Z is absent, $(CH_2)_2$ or CH=CH; and $R_6$ is hydrogen or methyl.

In one embodiment of the invention $R_5$ is (a) and attached at position 7 of the indole group;

A is a phenyl; and $R_1$ is up to two substituents independently selected from chloro, isopropoxy and cyano; and $R_2$ is hydrogen; and one of $R_3$ and $R_4$ is hydrogen and the other is Z—COOH; and Z is absent, $(CH_2)_2$ or CH=CH; and $R_6$ is hydrogen.

The term "alkyl" as a group or part of a group e.g. alkoxy or hydroxyalkyl refers to a straight or branched alkyl group in all isomeric forms. The term "$C_{(1-6)}$ alkyl" refers to an alkyl group, as defined above, containing at least 1, and at most 6 carbon atoms Examples of such alkyl groups include methyl, ethyl, propyl, iso-propyl, n-butyl, iso-butyl, sec-butyl, or tert-butyl. Examples of such alkoxy groups include methoxy, ethoxy, propoxy, iso-propoxy, butoxy, iso-butoxy, sec-butoxy and tert-butoxy.

The term "alkenyl" as a group or part of a group refers to a straight or branched alkenyl group in all isomeric forms. The term "$C_{(2-6)}$ alkenyl" refers to an alkenyl group, as defined above, containing at least 2, and at most 6 carbon atoms containing at least one carbon-to-carbon double bond. Examples of such alkenyl groups include ethenyl, propenyl and butenyl, pentenyl and hexenyl.

Suitable $C_{(3-6)}$cycloalkyl groups include cyclopropyl, cyclobutyl, cyclopentyl and cyclohexyl.

Suitable $C_{(3-6)}$cycloalkyloxy groups include cyclopropoxy, cyclobutoxy, cyclopentoxy and cyclohexyloxy.

As used herein, the term "halogen" refers to fluorine (F), chlorine (Cl), bromine (Br), or iodine (I) and the term "halo" refers to the halogen: fluoro (—F), chloro (—Cl), bromo (—Br) and iodo (—I).

The term "heteroaryl" represents an unsaturated ring which comprises one or more heteroatoms selected from O, N or S. Examples of 5 or 6 membered heteroaryl rings include pyrrolyl, triazolyl, thiadiazolyl, tetrazolyl, imidazolyl, pyrazolyl, isothiazolyl, thiazolyl, isoxazolyl, oxazolyl, oxadiazolyl, furazanyl, furanyl, thienyl, pyridyl, pyrimidinyl, pyrazinyl, pyridazinyl and triazinyl.

In certain of the compounds of formula (I), dependent upon the nature of the substituent there are chiral carbon atoms and therefore compounds of formula (I) may exist as stereoisomers. The invention extends to all optical isomers such as stereoisomeric forms of the compounds of formula (I) including enantiomers, diastereoisomers and mixtures thereof, such as racemates. The different stereoisomeric forms may be separated or resolved one from the other by conventional methods or any given isomer may be obtained by conventional stereoselective or asymmetric syntheses.

Certain of the compounds herein can exist in various tautomeric forms and it is to be understood that the invention encompasses all such tautomeric forms.

Suitable compounds of formula (I) are:

3-[7-(5-{3-Chloro-4-[(1-methylethyl)oxy]phenyl}-1,2,4-oxadiazol-3-yl)-1H-indol-3-yl]propanoic acid 3-[7-(5-{3-Chloro-4-[(1-methylethyl)oxy]phenyl}-1,2,4-oxadiazol-3-yl)-1-methyl-1H-indol-3-yl]propanoic acid 3-[7-(5-{3-Cyano-4-[(1-methylethyl)oxy]phenyl}-1,2,4-oxadiazol-3-yl)-1H-indol-3-yl]propanoic acid 3-[7-(5-{3-Cyano-4-[(1-methylethyl)oxy]phenyl}-1,2,4-oxadiazol-3-yl)-1-methyl-1H-indol-3-yl]propanoic acid 3-[6-(5-{3-Chloro-4-[(1-methylethyl)oxy]phenyl}-1,2,4-oxadiazol-3-yl)-1H-indol-3-yl]propanoic acid 3-[6-(5-{3-chloro-4-[(1-methylethyl)oxy]phenyl}-1,2,4-oxadiazol-3-yl)-1-methyl-1H-indol-3-yl]propanoic acid 3-[6-(5-{3-Cyano-4-[(1-methylethyl)oxy]phenyl}-1,2,4-oxadiazol-3-yl)-1H-indol-3-yl]propanoic acid 5-(5-{3-chloro-4-[(1-methylethyl)oxy]phenyl}-1,2,4-oxadiazol-3-yl)-1H-indole-2-carboxylic acid 3-[5-(5-{3-chloro-4-[(1-methylethyl)oxy]phenyl}-1,2,4-oxadiazol-3-yl)-1H-indol-2-yl]propanoic acid (2E)-3-[5-(5-{3-cyano-4-[(1-methylethyl)oxy]phenyl}-1,2,4-oxadiazol-3-yl)-1H-indol-2-yl]-2-propenoic acid

[5-(5-{3-Chloro-4-[(1-methylethyl)oxy]phenyl}-1,2,4-oxadiazol-3-yl)-1H-indol-2-yl]methanol 5-{3[2-(Hydroxymethyl)-1H-indol-5-yl]-1,2,4-oxadiazol-5-yl}-2-[(1-methylethyl)oxy]benzonitrile 3-[7-(5-{5-Chloro-6-[(1-methylethyl)oxy]-3-pyridinyl}-1,2,4-oxadiazol-3-yl)-1H-indol-3-yl]propanoic acid 3-[7-(5-{5-Chloro-6-[(1-methylethyl)oxy]-3-pyridinyl}-1,2,4-oxadiazol-3-yl)-1-methyl-1H-indol-3-yl]propanoic acid 3-(7-{5-[6-[(1-Methylethyl)oxy]-5-(trifluoromethyl)-3-pyridinyl]-1,2,4-oxadiazol-3-yl}-1H-indol-3-yl)propanoic acid
3-[7-(5-{5-Methyl-6-[(1-methylethyl)oxy]-3-pyridinyl}-1,2,4-oxadiazol-3-yl)-1H-indol-3-yl]propanoic acid
3-[1-Methyl-7-(5-{5-methyl-6-[(1-methylethyl)oxy]-3-pyridinyl}-1,2,4-oxadiazol-3-yl)-1H-indol-3-yl]propanoic acid
3-(7-{5-[6-[(1-Methylethyl)oxy]-5-(methyloxy)-3-pyridinyl}-1,2,4-oxadiazol-3-yl]-1H-indol-3-yl)propanoic acid
3-[7-(5-{3-Chloro-4-[(1-methylethyl)oxy]phenyl}-1,2,4-oxadiazol-3-yl)-4-fluoro-1H-indol-3-yl]propanoic acid
3-[7-(5-{3-Chloro-4-[(1-methylethyl)oxy]phenyl}-1,2,4-oxadiazol-3-yl)-4-fluoro-1-methyl-1H-indol-3-yl]propanoic acid
3-[7-(5-{3-Cyano-4-[(1-methylethyl)oxy]phenyl}-1,2,4-oxadiazol-3-yl)-4-fluoro-1H-indol-3-yl]propanoic acid
3-[7-(5-{5-Chloro-6-[(1-methylethyl)oxy]-3-pyridinyl}-1,2,4-oxadiazol-3-yl)-4-fluoro-1H-indol-3-yl]propanoic acid
3-[7-(5-{5-Chloro-6-[(1-methylethyl)oxy]-3-pyridinyl}-1,2,4-oxadiazol-3-yl)-4-fluoro-1-methyl-1H-indol-3-yl]propanoic acid
3-(4-Fluoro-7-{5-[6-[(1-methylethyl)oxy]-5-(trifluoromethyl)-3-pyridinyl]-1,2,4-oxadiazol-3-yl}-1H-indol-3-yl)propanoic acid
3-(4-Fluoro-7-{5-[6-[(1-methylethyl)oxy]-5-(methyloxy)-3-pyridinyl]-1,2,4-oxadiazol-3-yl}-1H-indol-3-yl)propanoic acid
3-[7-(5-{3-chloro-4-[(1-methylethyl)oxy]phenyl}-1,2,4-oxadiazol-3-yl)-1-ethyl-1H-indol-3-yl]propanoic acid
3-[7-(5-{3-chloro-4-[(1-methylethyl)oxy]phenyl}-1,2,4-oxadiazol-3-yl)-1-propyl-1H-indol-3-yl]propanoic acid
3-[7-(5-{3-chloro-4-[(1-methylethyl)oxy]phenyl}-1,2,4-oxadiazol-3-yl)-1-(1-methylethyl)-1H-indol-3-yl]propanoic acid
3-[1-butyl-7-(5-{3-chloro-4-[(1-methylethyl)oxy]phenyl}-1,2,4-oxadiazol-3-yl)-1H-indol-3-yl]propanoic acid
3-[7-(5-{3-chloro-4-[(1-methylethyl)oxy]phenyl}-1,2,4-oxadiazol-3-yl)-1-(2-methylpropyl)-1H-indol-3-yl]propanoic acid
[7-(5-{3-chloro-4-[(1-methylethyl)oxy]phenyl}-1,2,4-oxadiazol-3-yl)-1H-indol-3-yl]acetic acid
4-[7-(5-{3-chloro-4-[(1-methylethyl)oxy]phenyl}-1,2,4-oxadiazol-3-yl)-1H-indol-3-yl]butanoic acid
4-[7-(5-{3-chloro-4-[(1-methylethyl)oxy]phenyl}-1,2,4-oxadiazol-3-yl)-1H-indol-3-yl]-4-oxobutanoic acid
5-[7-(5-{3-chloro-4-[(1-methylethyl)oxy]phenyl}-1,2,4-oxadiazol-3-yl)-1H-indol-3-yl]pentanoic acid
4-[7-(5-{3-chloro-4-[(1-methylethyl)oxy]phenyl}-1,2,4-oxadiazol-3-yl)-1-methyl-1H-indol-3-yl]butanoic acid
(2R)-3-[7-(5-{3-chloro-4-[(1-methylethyl)oxy]phenyl}-1,2,4-oxadiazol-3-yl)-1-methyl-1H-indol-3-yl]-2-methylpropanoic acid
(2E)-3-[7-(5-{3-chloro-4-[(1-methylethyl)oxy]phenyl}-1,2,4-oxadiazol-3-yl)-1-methyl-1H-indol-3-yl]-2-propenoic acid
(2Z)-3-[7-(5-{3-chloro-4-[(1-methylethyl)oxy]phenyl}-1,2,4-oxadiazol-3-yl)-1-methyl-1H-indol-3-yl]-2-propenoic acid
trans-2-[7-(5-{3-chloro-4-[(1-methylethyl)oxy]phenyl}-1,2,4-oxadiazol-3-yl)-1-methyl-1H-indol-3-yl]cyclopropanecarboxylic acid
cis-2-[7-(5-{3-chloro-4-[(1-methylethyl)oxy]phenyl}-1,2,4-oxadiazol-3-yl)-1-methyl-1H-indol-3-yl]cyclopropanecarboxylic acid
3-(7-{5-[3,4-bis(ethyloxy)phenyl]-1,2,4-oxadiazol-3-yl}-1H-indol-3-yl)propanoic acid
3-(7-{5-[3,4-bis(ethyloxy)phenyl]-1,2,4-oxadiazol-3-yl}-1-methyl-1H-indol-3-yl)propanoic acid
3-(7-{5-[3,4-bis(methyloxy)phenyl]-1,2,4-oxadiazol-3-yl}-1H-indol-3-yl)propanoic acid
3-(7-{5-[3,4-bis(methyloxy)phenyl]-1,2,4-oxadiazol-3-yl}-1-methyl-1H-indol-3-yl)propanoic acid
3-(7-{5-[3-chloro-4,5-bis(ethyloxy)phenyl]-1,2,4-oxadiazol-3-yl}-1H-indol-3-yl)propanoic acid
N-{[7-(5-{3-chloro-4-[(1-methylethyl)oxy]phenyl}-1,2,4-oxadiazol-3-yl)-1H-indol-3-yl]methyl}-β-alanine
N-{[7-(5-{3-chloro-4-[(1-methylethyl)oxy]phenyl}-1,2,4-oxadiazol-3-yl)-1H-indol-3-yl]methyl}glycine
1-{[7-(5-{3-chloro-4-[(1-methylethyl)oxy]phenyl}-1,2,4-oxadiazol-3-yl)-1H-indol-3-yl]methyl}-4-piperidinecarboxylic acid
N-{[7-(5-{3-chloro-4-[(1-methylethyl)oxy]phenyl}-1,2,4-oxadiazol-3-yl)-1H-indol-3-yl]methyl}-D-alanine
N-{[7-(5-{3-chloro-4-[(1-methylethyl)oxy]phenyl}-1,2,4-oxadiazol-3-yl)-1H-indol-3-yl]methyl}-L-alanine
3-({[7-(5-{3-chloro-4-[(1-methylethyl)oxy]phenyl}-1,2,4-oxadiazol-3-yl)-1H-indol-3-yl]methyl}amino)butanoic acid
N-{[7-(5-{3-chloro-4-[(1-methylethyl)oxy]phenyl}-1,2,4-oxadiazol-3-yl)-1H-indol-3-yl]methyl}-N-methylglycine
N-{[7-(5-{3-chloro-4-[(1-methylethyl)oxy]phenyl}-1,2,4-oxadiazol-3-yl)-1H-indol-3-yl]methyl}-N-methyl-D-alanine
N-{[7-(5-{3-chloro-4-[(1-methylethyl)oxy]phenyl}-1,2,4-oxadiazol-3-yl)-1H-indol-3-yl]methyl}-N-methyl-L-alanine
N-{[7-(5-{3-cyano-4-[(1-methylethyl)oxy]phenyl}-1,2,4-oxadiazol-3-yl)-1H-indol-3-yl]methyl}-N-methylglycine
N-{[7-(5-{3-chloro-4-[(1-methylethyl)oxy]phenyl}-1,2,4-oxadiazol-3-yl)-1-methyl-1H-indol-3-yl]methyl}glycine
1-{[7-(5-{3-chloro-4-[(1-methylethyl)oxy]phenyl}-1,2,4-oxadiazol-3-yl)-1-methyl-1H-indol-3-yl]methyl}-4-piperidinecarboxylic acid
N-{[7-(5-{3-chloro-4-[(1-methylethyl)oxy]phenyl}-1,2,4-oxadiazol-3-yl)-1-methyl-1H-indol-3-yl]methyl}-β-alanine
N-{[7-(5-{3-chloro-4-[(1-methylethyl)oxy]phenyl}-1,2,4-oxadiazol-3-yl)-1-methyl-1H-indol-3-yl]methyl}-D-alanine
N-{[7-(5-{3-chloro-4-[(1-methylethyl)oxy]phenyl}-1,2,4-oxadiazol-3-yl)-1-methyl-1H-indol-3-yl]methyl}-L-alanine
3-({[7-(5-{3-chloro-4-[(1-methylethyl)oxy]phenyl}-1,2,4-oxadiazol-3-yl)-1-methyl-1H-indol-3-yl]methyl}amino)butanoic acid
N-{2-[7-(5-{3-chloro-4-[(1-methylethyl)oxy]phenyl}-1,2,4-oxadiazol-3-yl)-1H-indol-3-yl]ethyl}-β-alanine
N-{2-[7-(5-{3-chloro-4-[(1-methylethyl)oxy]phenyl}-1,2,4-oxadiazol-3-yl)-1H-indol-3-yl]ethyl}glycine
N-{2-[7-(5-{3-chloro-4-[(1-methylethyl)oxy]phenyl}-1,2,4-oxadiazol-3-yl)-1-methyl-1H-indol-3-yl]ethyl}glycine
N-{2-[7-(5-{3-chloro-4-[(1-methylethyl)oxy]phenyl}-1,2,4-oxadiazol-3-yl)-1-methyl-1H-indol-3-yl]ethyl}-β-alanine
1-{2-[7-(5-{3-chloro-4-[(1-methylethyl)oxy]phenyl}-1,2,4-oxadiazol-3-yl)-1-methyl-1H-indol-3-yl]ethyl}-4-piperidinecarboxylic acid
1-{2-[7-(5-{3-chloro-4-[(1-methylethyl)oxy]phenyl}-1,2,4-oxadiazol-3-yl)-1-methyl-1H-indol-3-yl]ethyl}-3-azetidinecarboxylic acid
1-({2-[7-(5-{3-chloro-4-[(1-methylethyl)oxy]phenyl}-1,2,4-oxadiazol-3-yl)-1-methyl-1H-indol-3-yl]ethyl}amino)cyclopropanecarboxylic acid 1-{2-[7-(5-{3-chloro-4-[(1-methylethyl)oxy]phenyl}-1,2,4-oxadiazol-3-yl)-1-methyl-1H-indol-3-yl]ethyl}-L-proline N-{3-[7-(5-{3-chloro-4-[(1-methylethyl)oxy]phenyl}-1,2,4-oxadiazol-3-yl)-1H-indol-3-yl]propyl}glycine N-{3-[7-(5-{3-chloro-4-[(1-methylethyl)oxy]phenyl}-1,2,4-oxadiazol-3-yl)-1H-indol-3-yl]propyl}-N-methylglycine N-{[7-(5-{3-chloro-4-[(1-methylethyl)oxy]phenyl}-1,2,4-oxadiazol-3-yl)-1H-indol-3-yl]carbonyl}glycine N-{[7-(5-{3-chloro-4-[(1-methylethyl)oxy]phenyl}-1,2,4-oxadiazol-3-yl)-1H-indol-3-yl]carbonyl}-β-alanine 4-({[7-(5-{3-chloro-4-[(1-methylethyl)oxy]phenyl}-1,2,4-oxadiazol-3-yl)-1H-indol-3-yl]carbonyl}amino)butanoic acid N-{[7-(5-{3-chloro-4-[(1-methylethyl)oxy]phenyl}-1,2,4-oxadiazol-3-yl)-1H-indol-3-yl]carbonyl}-N-methyl-β-alanine N-{[7-(5-{3-chloro-4-[(1-methylethyl)oxy]phenyl}-1,2,4-oxadiazol-3-yl)-1-methyl-1H-indol-3-yl]carbonyl}-β-alanine N-{3-[7-(5-{3-chloro-4-[(1-methylethyl)oxy]phenyl}-1,2,4-oxadiazol-3-yl)-1H-indol-3-yl]propanoyl}glycine 1-{[6-(5-{5-chloro-6-[(1-methylethyl)oxy]-3-pyridinyl}-1,2,4-oxadiazol-3-yl)-1H-indol-3-yl]methyl}-4-piperidinecarboxylic acid ({2-[7-(5-{3-chloro-4-[(1-methylethyl)oxy]phenyl}-1,2,4-oxadiazol-3-yl)-1-methyl-1H-indol-3-yl]ethyl}oxy)acetic acid ({3-[7-(5-{3-chloro-4-[(1-methylethyl)oxy]phenyl}-1,2,4-oxadiazol-3-yl)-1-methyl-1H-indol-3-yl]propyl}oxy)acetic acid 3-[6-(5-{5-Chloro-6-[(1-methylethyl)oxy]-3-pyridinyl}-1,2,4-oxadiazol-3-yl)-1H-indol-3-yl]propanoic acid 3-[6-(5-{5-Chloro-6-[(1-methylethyl)oxy]-3-pyridinyl}-1,2,4-oxadiazol-3-yl)-1-methyl-1H-indol-3-yl]propanoic acid 3-(6-{5-[6-[(1-Methylethyl)oxy]-5-(trifluoromethyl)-3-pyridinyl]-1,2,4-oxadiazol-3-yl}-1H-indol-3-yl)propanoic acid 3-[6-(5-{5-Fluoro-6-[(1-methylethyl)oxy]-3-pyridinyl}-1,2,4-oxadiazol-3-yl)-1H-indol-3-yl]propanoic acid 3-[6-(5-{5-Methyl-6-[(1-methylethyl)oxy]-3-pyridinyl}-1,2,4-oxadiazol-3-yl)-1H-indol-3-yl]propanoic acid 3-[1-Methyl-6-(5-{5-methyl-6-[(1-methylethyl)oxy]-3-pyridinyl}-1,2,4-oxadiazol-3-yl)-1H-indol-3-yl]propanoic acid 3-(6-{5-[6-[(1-Methylethyl)oxy]-5-(methyloxy)-3-pyridinyl]-1,2,4-oxadiazol-3-yl}-1H-indol-3-yl)propanoic acid 3-[5-(5-{3-chloro-4-[(1-methylethyl)oxy]phenyl}-1,2,4-oxadiazol-3-yl)-1-methyl-1H-indol-2-yl]propanoic acid 3-[5-(5-{3-cyano-4-[(1-methylethyl)oxy]phenyl}-1,2,4-oxadiazol-3-yl)-1H-indol-2-yl]propanoic acid 3-[5-(5-{5-chloro-6-[(1-methylethyl)oxy]-3-pyridinyl}-1,2,4-oxadiazol-3-yl)-1H-indol-2-yl]propanoic acid 3-[5-(5-{5-chloro-6-[(1-methylethyl)oxy]-3-pyridinyl}-1,2,4-oxadiazol-3-yl)-1-methyl-1H-indol-2-yl]propanoic acid 3-(5-{5-[6-[(1-methylethyl)oxy]-5-(trifluoromethyl)-3-pyridinyl]-1,2,4-oxadiazol-3-yl}-1H-indol-2-yl)propanoic acid 3-(5-{5-[6-[(1-methylethyl)oxy]-5-(methyloxy)-3-pyridinyl]-1,2,4-oxadiazol-3-yl}-1H-indol-2-yl)propanoic acid 7-(5-{3-chloro-4-[(1-methylethyl)oxy]phenyl}-1,2,4-oxadiazol-3-yl)-1H-indole-3-carboxylic acid 7-(5-{3-chloro-4-[(1-methylethyl)oxy]phenyl}-1,2,4-oxadiazol-3-yl)-1-methyl-1H-indole-3-carboxylic acid 3-[7-(5-{3-cyano-4-[(1-methylethyl)oxy]phenyl}-1,2,4-oxadiazol-3-yl)-4-fluoro-1-methyl-1H-indol-3-yl]propanoic acid 3-[7-(5-{3-Chloro-4-[(1-methylethyl)oxy]phenyl}-1,2,4-oxadiazol-3-yl)-5-fluoro-1H-indol-3-yl]propanoic acid 3-[7-(5-{3-Chloro-4-[(1-methylethyl)oxy]phenyl}-1,2,4-oxadiazol-3-yl)-5-fluoro-1-methyl-1H-indol-3-yl]propanoic acid 3-[7-(5-{3-Cyano-4-[(1-methylethyl)oxy]phenyl}-1,2,4-oxadiazol-3-yl)-5-fluoro-1H-indol-3-yl]propanoic acid 3-[7-(5-{3-Cyano-4-[(1-methylethyl)oxy]phenyl}-1,2,4-oxadiazol-3-yl)-5-fluoro-1-methyl-1H-indol-3-yl]propanoic acid 3-[7-(5-{5-Chloro-6-[(1-methylethyl)oxy]-3-pyridinyl}-1,2,4-oxadiazol-3-yl)-5-fluoro-1H-indol-3-yl]propanoic acid 3-[7-(5-{5-Chloro-6-[(1-methylethyl)oxy]-3-pyridinyl}-1,2,4-oxadiazol-3-yl)-5-fluoro-1-methyl-1H-indol-3-yl]propanoic acid 3-[7-(5-{3-Chloro-4-[(1-methylethyl)oxy]phenyl}-1,2,4-oxadiazol-3-yl)-6-fluoro-1H-indol-3-yl]propanoic acid 3-[7-(5-{3-Chloro-4-[(1-methylethyl)oxy]phenyl}-1,2,4-oxadiazol-3-yl)-6-fluoro-1-methyl-1H-indol-3-yl]propanoic acid 3-[7-(5-{3-Cyano-4-[(1-methylethyl)oxy]phenyl}-1,2,4-oxadiazol-3-yl)-6-fluoro-1H-indol-3-yl]propanoic acid 3-[7-(5-{3-Cyano-4-[(1-methylethyl)oxy]phenyl}-1,2,4-oxadiazol-3-yl)-6-fluoro-1-methyl-1H-indol-3-yl]propanoic acid 3-[7-(5-{5-Chloro-6-[(1-methylethyl)oxy]-3-pyridinyl}-1,2,4-oxadiazol-3-yl)-6-fluoro-1H-indol-3-yl]propanoic acid 3-[7-(5-{5-Chloro-6-[(1-methylethyl)oxy]-3-pyridinyl}-1,2,4-oxadiazol-3-yl)-6-fluoro-1-methyl-1H-indol-3-yl]propanoic acid 3-[6-(5-{3-Chloro-4-[(1-methylethyl)oxy]phenyl}-1,2,4-oxadiazol-3-yl)-5-fluoro-1H-indol-3-yl]propanoic acid 3-[6-(5-{3-Cyano-4-[(1-methylethyl)oxy]phenyl}-1,2,4-oxadiazol-3-yl)-5-fluoro-1H-indol-3-yl]propanoic acid 3-[6-(5-{5-Chloro-6-[(1-methylethyl)oxy]-3-pyridinyl}-1,2,4-oxadiazol-3-yl)-5-fluoro-1H-indol-3-yl]propanoic acid 3-[5-(5-{3-Chloro-4-[(1-methylethyl)oxy]phenyl}-1,2,4-oxadiazol-3-yl)-7-fluoro-1H-indol-2-yl]propanoic acid 3-[5-(5-{3-Cyano-4-[(1-methylethyl)oxy]phenyl}-1,2,4-oxadiazol-3-yl)-7-fluoro-1H-indol-2-yl]propanoic acid 3-[5-(5-{5-Chloro-6-[(1-methylethyl)oxy]-3-pyridinyl}-1,2,4-oxadiazol-3-yl)-7-fluoro-1H-indol-2-yl]propanoic acid or salts thereof.

In one embodiment a compound of formula (I) is 3-[7-(5-{3-Chloro-4-[(1-methylethyl)oxy]phenyl}-1,2,4-oxadiazol-3-yl)-1H-indol-3-yl]propanoic acid.

In another embodiment a compound of formula (I) is 3-[7-(5-{3-Chloro-4-[(1-methylethyl)oxy]phenyl}-1,2,4-oxadiazol-3-yl)-4-fluoro-1-methyl-1H-indol-3-yl]propanoic acid.

Pharmaceutically acceptable derivatives of compounds of formula (I) include any pharmaceutically acceptable salt, ester or salt of such ester of a compound of formula (I) which, upon administration to the recipient is capable of providing (directly or indirectly) a compound of formula (I) or an active metabolic or residue thereof.

The compounds of formula (I) can form salts. It will be appreciated that for use in medicine the salts of the compounds of formula (I) should be pharmaceutically acceptable. Suitable pharmaceutically acceptable salts will be apparent to those skilled in the art and include those described in J. Pharm. Sci., 1977, 66, 1-19, such as acid addition salts formed with inorganic acids e.g. hydrochloric, hydrobromic, sulfuric, nitric or phosphoric acid; and organic acids e.g. succinic, maleic, acetic, fumaric, citric, tartaric, benzoic, p-toluenesulfonic, methanesulfonic or naphthalenesulfonic acid. Certain of the compounds of formula (I) may form acid addition salts with one or more equivalents of the acid. The present invention includes within its scope all possible stoichiometric and non-stoichiometric forms. Salts may also be prepared from pharmaceutically acceptable bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Salts derived from pharmaceutically acceptable organic bases include salts of primary, secondary, and tertiary amines; substituted amines including naturally occurring substituted amines; and cyclic amines. Particular pharmaceutically acceptable organic bases include arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, procaine, purines, theobromine, triethylamine, trimethylamine, tripropylamine, tris(hydroxymethyl)aminomethane (TRIS, trometamol) and the like. Salts may also be formed from basic ion exchange resins, for example polyamine resins. When the compound of the present invention is basic, salts may be prepared from pharmaceutically acceptable acids, including inorganic and organic acids. Such acids include acetic, benzenesulfonic, benzoic, camphorsulfonic, citric, ethanesulfonic, ethanedisulfonic, fumaric, gluconic, glutamic, hydrobromic, hydrochloric, isethionic, lactic, maleic, malic, mandelic, methanesulfonic, mucic, pamoic, pantothenic, phosphoric, propionic, succinic, sulfuric, tartaric, p-toluenesulfonic acid, and the like.

The compounds of formula (I) may be prepared in crystalline or non-crystalline form, and, if crystalline, may optionally be hydrated or solvated. This invention includes within its scope stoichiometric hydrates or solvates as well as compounds containing variable amounts of water and/or solvent.

Included within the scope of the invention are all salts, solvates, hydrates, complexes, polymorphs, prodrugs, radio-labelled derivatives, stereoisomers and optical isomers of the compounds of formula (I).

In a further aspect, this invention provided processes for the preparation of a compound of formula (I). In one aspect, certain compounds of formula (I) were prepared by the process in Scheme I where A, Z, $R_1$, $R_2$ and $R_6$, are as defined for formula (I) and $R_7$ is an alkyl group:

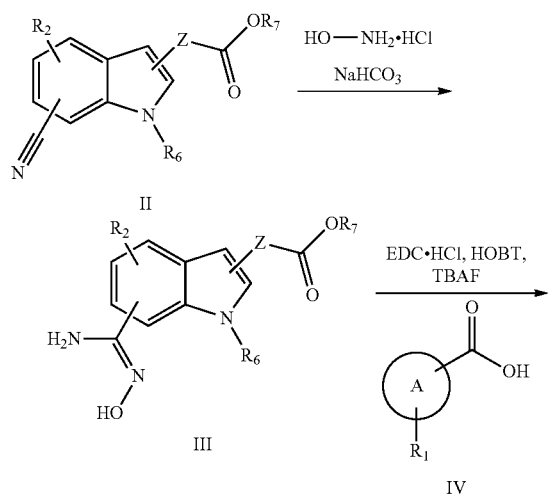

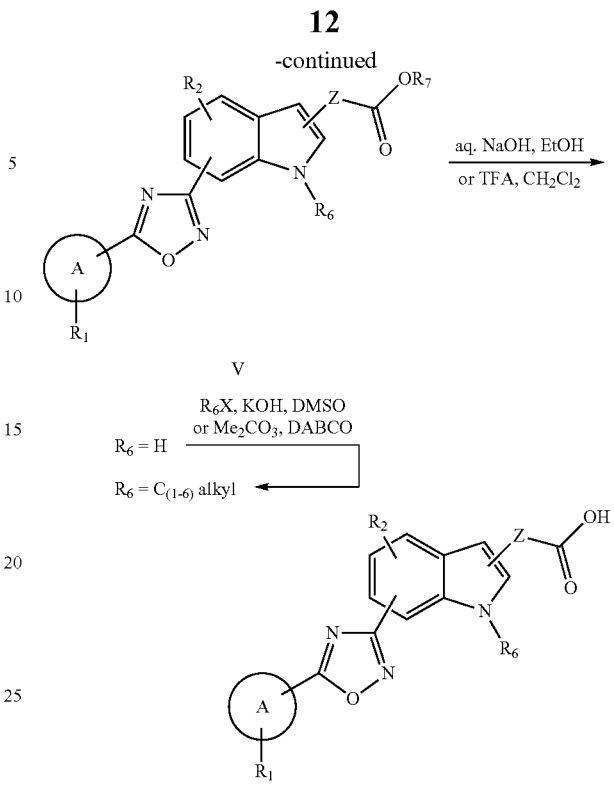

The first step of the process (II to III) was carried out in a suitable solvent, such as methanol or ethanol and was heated to a temperature such at 50-80° C. In the second step of the process (III to V) suitable reagents included EDC.HCl, HOBt and TBAF in a solvent such as THF at a temperature between room temperature and 140° C. under thermal or microwave condition or alternatively in NMP. The third step of the process (V to certain compounds of formula (I)) was carried out by treatment with basic conditions (such as sodium hydroxide in a suitable solvent such as methanol or alternatively ethanol) and at either room temperature or elevated temperature (such as 40 or 50° C.). Alternatively V was converted to certain compounds of formula (I) by treatment with acidic (such as TFA) conditions in a suitable solvent such as dichloromethane at room temperature or elevated temperature. $R_6$ ($C_{(1-6)}$ alkyl) was introduced at the different stages (from II, V or certain compounds of formula (I)) using alkyl bromide or alkyl iodide or alternatively using dimethyl carbonate.

Compounds of formula (IV) were either commercially available, prepared by using methods described in the literature or prepared as described in the experimental section. Compounds of formula (II) were prepared as described in the experimental section.

In another aspect, certain compounds of formula (I) were prepared by the process in Scheme II where A, $R_1$ and $R_6$, are as defined for formula (I):

Scheme II

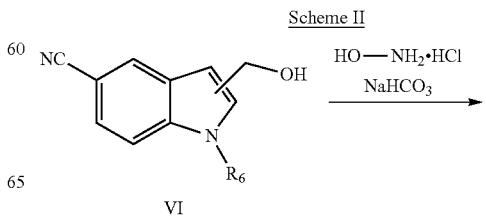

13
-continued
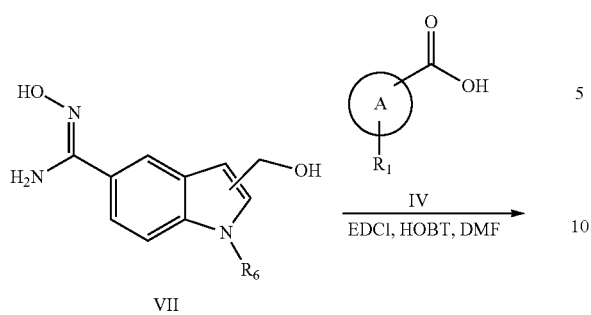
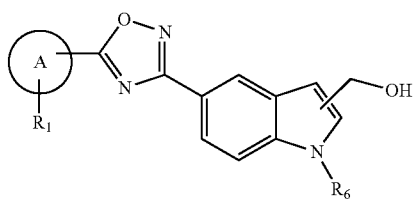
14
-continued
In another aspect, certain compounds of formula (I) were prepared by the process in Scheme III where A, $R_1$, $R_2$ and $R_6$, are as defined for formula (I) and $R_8$ is a hydrogen atom or an alkyl wow:
Scheme III
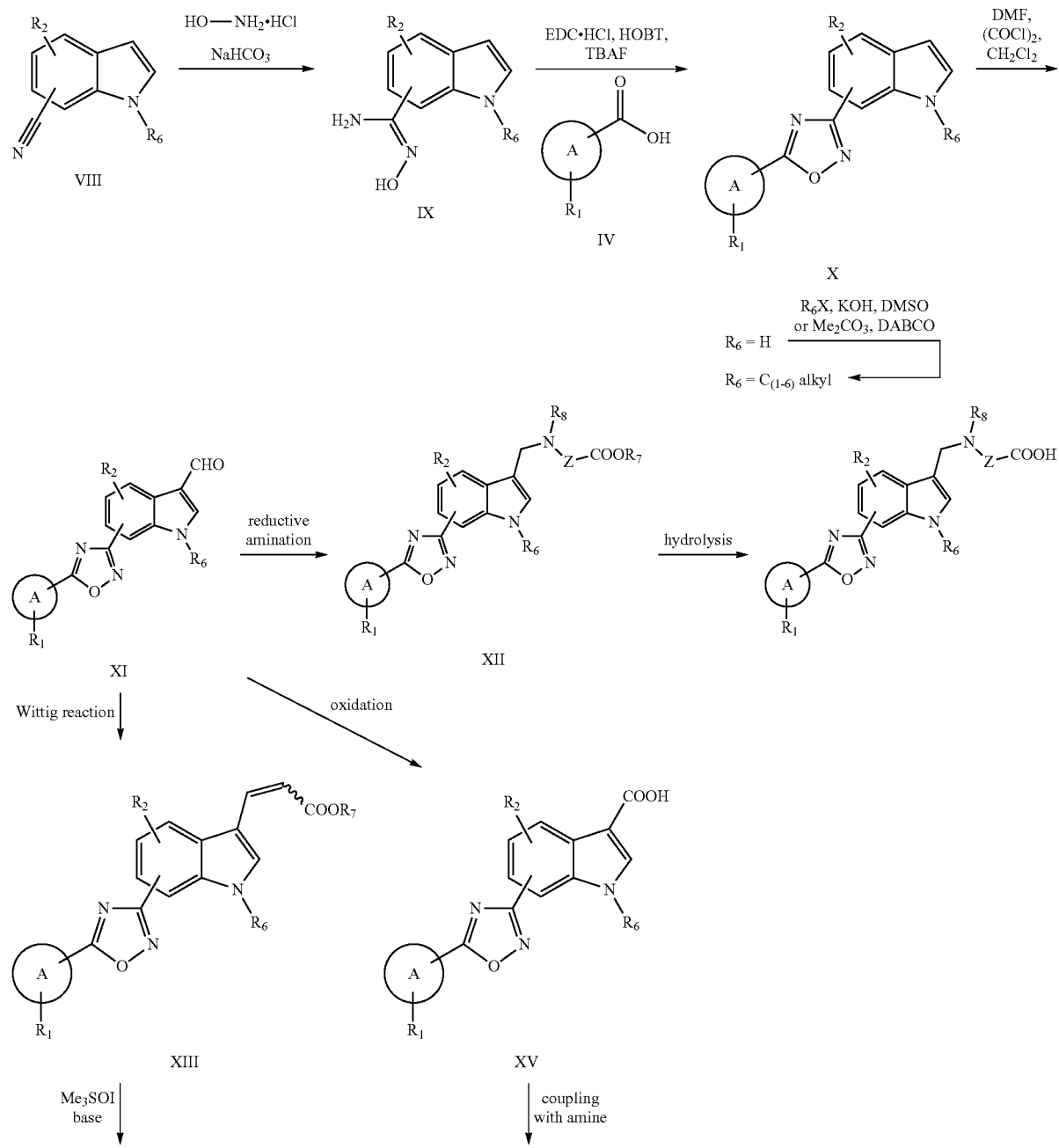

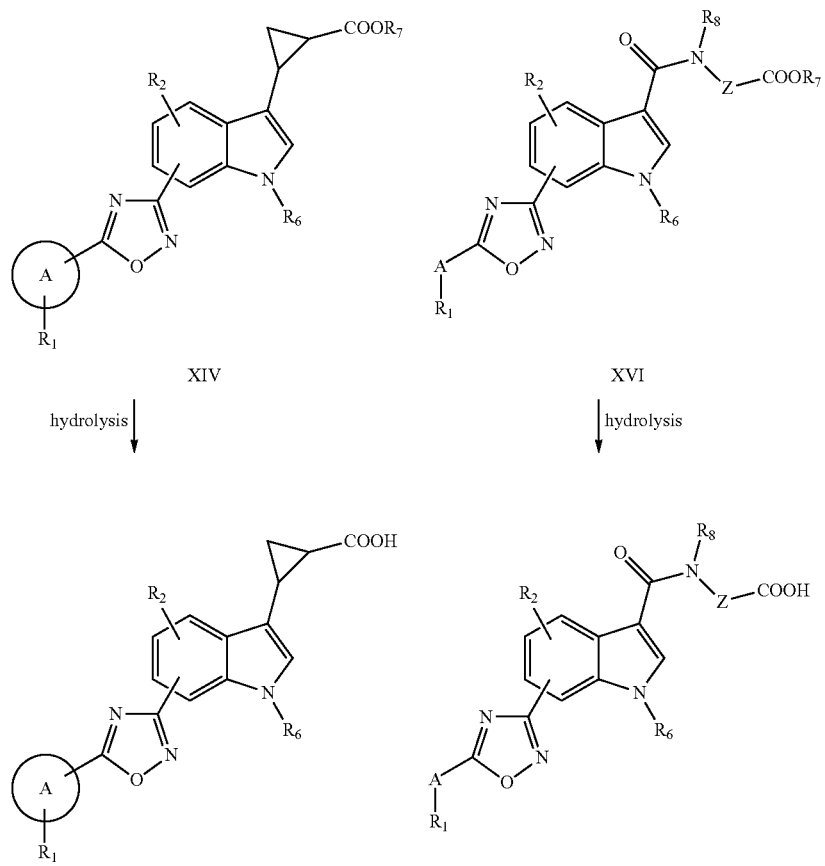

1,2,4-oxadiazole intermediate X was elaborated using procedures similar to those described in Scheme I to convert II to V. Formylation of X was carried out under Vilsmeier-Haack conditions, i.e. by treating X with a mixture of oxalyl chloride and DMF in a suitable solvent (methylene chloride) to give intermediate XI. Intermediate XI was further functionalized to afford different derivatives including reductive amination to form amine analogs; Wittig reaction to form alkenyl intermediate XIII then with trimethylsulfoxonium iodide and a strong base (NaHMDS) in dimethylsulfoxide to form cyclopropylcaboxic acid analogs; oxidation and then coupling with amine to form amide analogues.

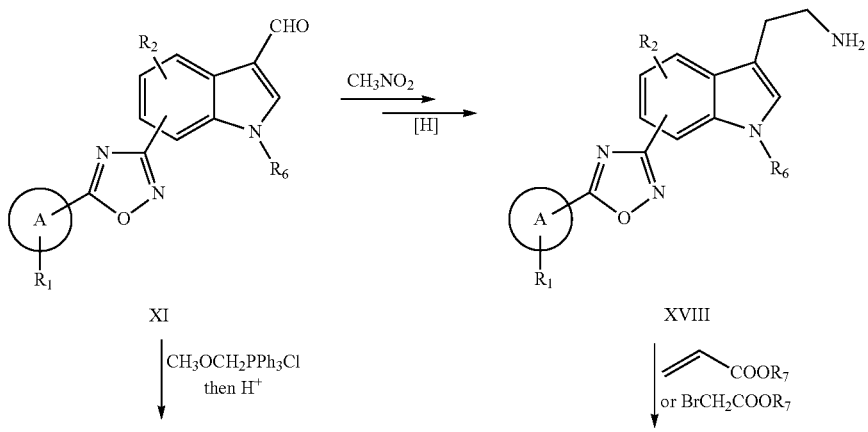

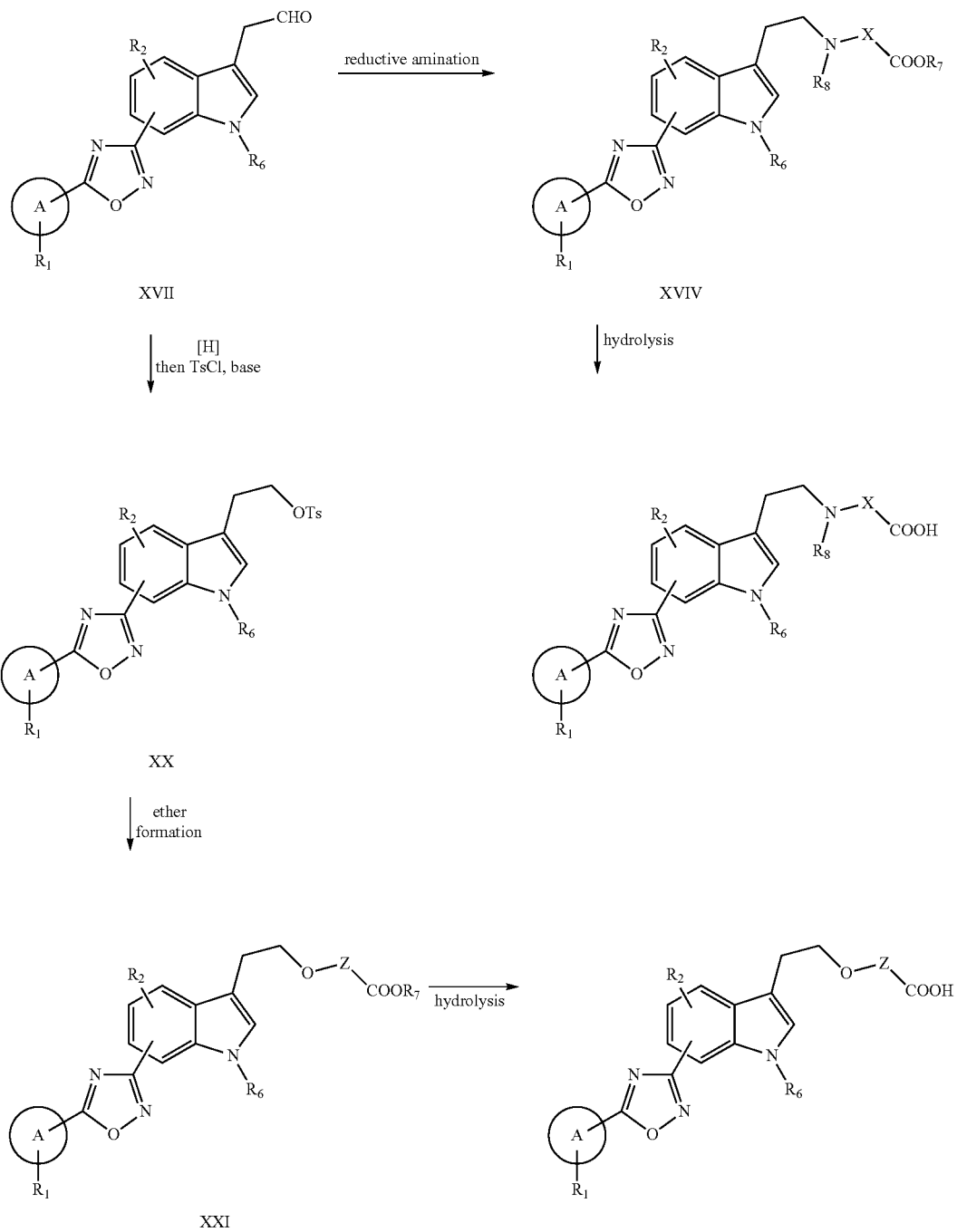

In another aspect, certain compounds of formula (I) were prepared by the process in Scheme IV where A, $R_1$, $R_2$ and $R_6$, are as defined for formula (I) and $R_8$ is a hydrogen atom or an alkyl group:

Conversion XI to the corresponding acetaldehyde XVII was accomplished by treating XI with (methoxymethyl)triphenylphosphonium chloride and a strong base in dimethylsulfoxide and then with acid. Reductive amination with acetaldehyde XVII afforded different amine analogs. Alternatively, some amine analogs were elaborated using the intermediate XVIII that was prepared from XI through two steps. Acetaldehyde XVII was reduced to the corresponding alcohol and then through further manipulation to afford the ether derivatives.

In another aspect, certain compounds of formula (I) were prepared by the process in Scheme V where A, $R_1$, $R_2$ and $R_6$, are as defined for formula (I) and $R_8$ is a hydrogen atom or an alkyl group:

Scheme V

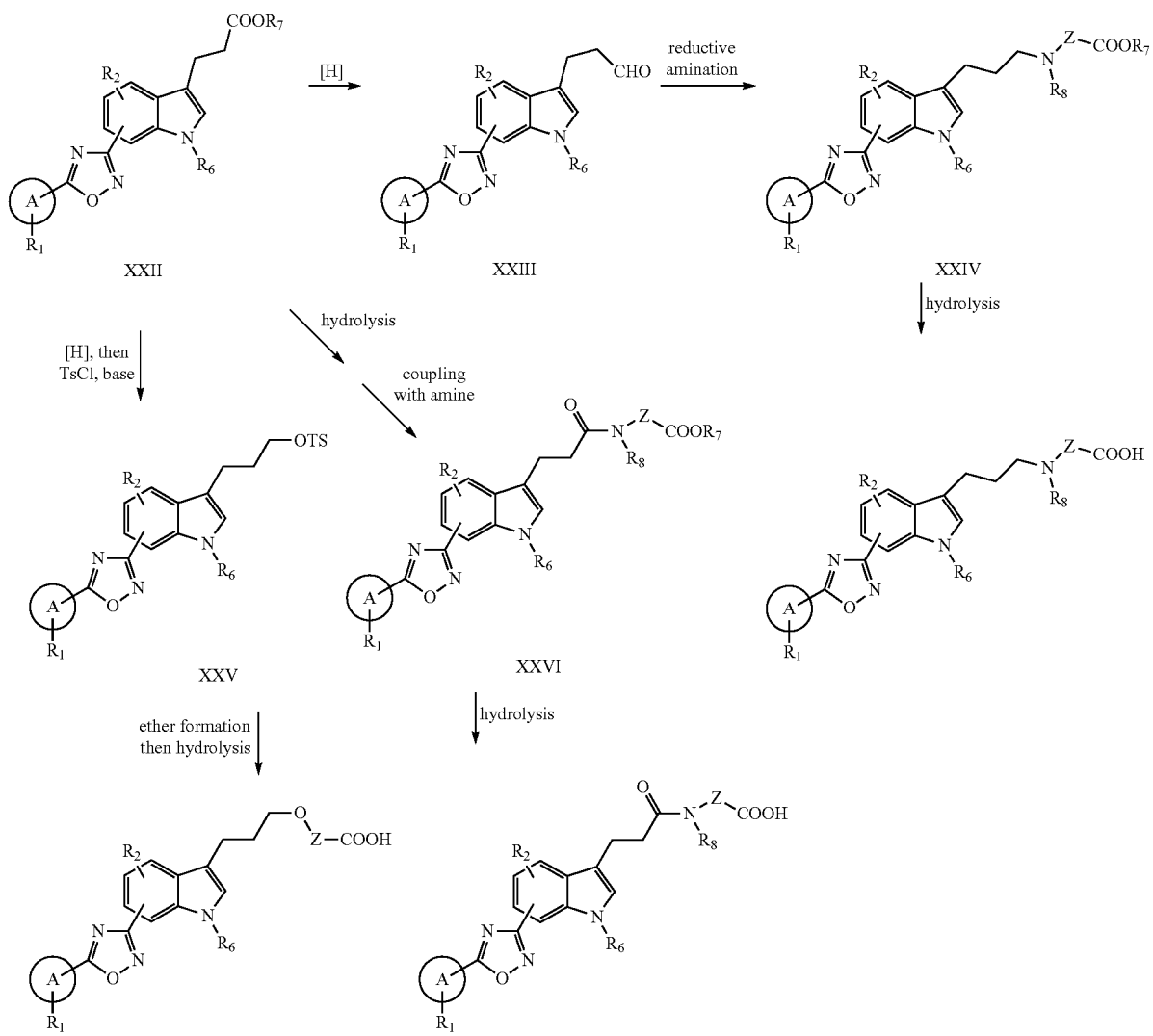

Starting from the propanoate XXII, a series of amine, amide and ether derivatives were elaborated using procedures similar to those described in Scheme III or Scheme IV.

Pharmaceutically acceptable salts may be prepared conventionally by reaction with the appropriate acid or acid derivative.

The potencies and efficacies of the compounds of this invention for the S1P1 receptor can be determined by GTPγS assay or S1P1 Tango assay performed on the human cloned receptor as described herein. Compounds of formula (I) have demonstrated agonist activity at the S1P1 receptor, using functional assays described herein.

Compounds of formula (I) and their pharmaceutically acceptable salts are therefore of use in the treatment of conditions or disorders which are mediated via the S1P1 receptor. In particular the compounds of formula (I) and their pharmaceutically acceptable salts are of use in the treatment of multiple sclerosis, autoimmune diseases, chronic inflammatory disorders, asthma, inflammatory neuropathies, arthritis, transplantation, Crohn's disease, ulcerative colitis, lupus erythematosis, psoriasis, ischemia-reperfusion injury, solid tumours, and tumour metastasis, diseases associated with angiogenesis, vascular diseases, pain conditions, acute viral diseases, inflammatory bowel conditions, insulin and non-insulin dependant diabetes.

Compounds of formula (I) and their pharmaceutically acceptable salts are therefore of use in the treatment of multiple sclerosis.

Compounds of formula (I) and their pharmaceutically acceptable salts may also be of use in the treatment of Parkinson's Disease, Alzheimer's disease, Huntington's chorea, amyotrophic lateral sclerosis, spinal muscular atrophy, polyglutamine expansion disorders, vascular dementia, Down's syndrome, HIV dementia, dementia, ocular diseases including glaucoma, aged related macular degeneration, cataracts, traumatic eye injury, diabetic retinopathy, traumatic brain injury, stroke, tauopathies and hearing loss.

It is to be understood that "treatment" as used herein includes prophylaxis as well as alleviation of established symptoms.

Thus the invention also provides a compound of formula (I) or a pharmaceutically acceptable salt thereof, for use as a therapeutic substance, in particular in the treatment of the conditions or disorders mediated via the S1P1 receptor. In particular the invention provides a compound of formula (I) or a pharmaceutically acceptable salt thereof for use as a therapeutic substance in the treatment of multiple sclerosis, autoimmune diseases, chronic inflammatory disorders, asthma, inflammatory neuropathies, arthritis, transplantation, Crohn's disease, ulcerative colitis, lupus erythematosis, psoriasis, ischemia-reperfusion injury, solid tumours, and tumour metastasis, diseases associated with angiogenesis, vascular diseases, pain conditions, acute viral diseases, inflammatory bowel conditions, insulin and non-insulin dependant diabetes. The invention further provides a method of treatment of conditions or disorders in mammals including humans which can be mediated via the S1P1 receptor, which comprises administering to the sufferer a therapeutically safe and effective amount of a compound of formula (I) or a pharmaceutically acceptable salt thereof.

Compounds of formula (I) and their pharmaceutically acceptable salts are of use as therapeutic substances in the treatment of multiple sclerosis.

In another aspect, the invention provides for the use of a compound of formula (I) or a pharmaceutically acceptable salt thereof in the manufacture of a medicament for use in the treatment of the conditions or disorders mediated via the S1P1 receptor The invention provides a method of treatment of multiple sclerosis, which comprises administering to the sufferer a therapeutically safe and effective amount of a compound of formula (I) or a pharmaceutically acceptable salt thereof.

In order to use the compounds of formula (I) and pharmaceutically acceptable salts thereof in therapy, they will normally be formulated into a pharmaceutical composition in accordance with standard pharmaceutical practice. The present invention also provides a pharmaceutical composition, which comprises a compound of formula (I) or a pharmaceutically acceptable salt thereof, and a pharmaceutically acceptable carrier or excipient.

In a further aspect, the present invention provides a process for preparing a pharmaceutical composition, the process comprising mixing a compound of formula (I) or a pharmaceutically acceptable salt thereof and a pharmaceutically acceptable carrier or excipient.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents (e.g. pregelatinised maize starch, polyvinylpyrrolidone or hydroxypropyl methylcellulose); fillers (e.g. lactose, microcrystalline cellulose or calcium hydrogen phosphate); tabletting lubricants (e.g. magnesium stearate, talc or silica); disintegrants (e.g. potato starch or sodium starch glycollate); and acceptable wetting agents (e.g. sodium lauryl sulphate). The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents (e.g. sorbitol syrup, cellulose derivatives or hydrogenated edible fats), emulsifying agents (e.g. lecithin or acacia), non-aqueous vehicles (which may include edible oils e.g. almond oil, oily esters, ethyl alcohol or fractionated vegetable oils), preservatives (e.g. methyl or propyl-p-hydroxybenzoates or sorbic acid), and, if desired, conventional flavourings or colorants, buffer salts and sweetening agents as appropriate. Preparations for oral administration may be suitably formulated to give controlled release of the active compound.

For parenteral administration, fluid unit dosage forms are prepared utilising a compound of the invention or pharmaceutically acceptable salts thereof and a sterile vehicle. Formulations for injection may be presented in unit dosage form e.g. in ampoules or in multi-dose, utilising a compound of the invention or pharmaceutically acceptable derivatives thereof and a sterile vehicle, optionally with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

The compounds of formula (I) or pharmaceutically acceptable salts thereof may also be formulated in rectal compositions such as suppositories or retention enemas, e.g. containing conventional suppository bases such as cocoa butter or other glycerides.

The compounds of formula (I) or pharmaceutically acceptable salts thereof may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds of formula (I) or pharmaceutically acceptable salts thereof, may be formulated as solutions for administration via a suitable metered or unitary dose device or alternatively as a powder mix with a suitable carrier for administration using a suitable delivery device. Thus compounds of formula (I) or pharmaceutically acceptable salts thereof may be formulated for oral, buccal, parenteral, topical (including ophthalmic and nasal), depot or rectal administration or in a form suitable for administration by inhalation or insufflation (either through the mouth or nose).

The compounds of formula (I) or pharmaceutically acceptable salts thereof may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilised components.

The composition may contain from 0.1% to 99% by weight, preferably from 10 to 60% by weight, of the active material, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 1000 mg, 1.0 to 500 mg or 1.0 to 200 mg and such unit doses may be administered more than once a day, for example two or three times a day.

Compounds of formula (I) or pharmaceutically acceptable salts thereof may be used in combination preparations. For example, the compounds of the invention may be used in combination with cyclosporin A, methotrexate, steriods, rapamycin, proinflammatory cytokine inhibitors, immunomodulators including biologicals or other therapeutically active compounds.

The subject invention also includes isotopically-labeled compounds, which are identical to those recited in formulas I and following, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^3H$, $^{11}C$, $^{14}C$, $^{18}F$, $^{123}I$ and $^{125}I$.

Compounds of the present invention and pharmaceutically acceptable salts of said compounds that contain the aforementioned isotopes and/or other isotopes of other atoms are within the scope of the present invention. Isotopically-labeled compounds of the present invention, for example those into which radioactive isotopes such as $^3H$, $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. $^{11}C$ and $^8F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of formula (I) and following of this invention can generally be prepared by carrying out the procedures disclosed in the Schemes and/or in the Examples below, by substituting a readily available isotopically labelled reagent for a non-isotopically labeled reagent.

All publications, including but not limited to patents and patent applications, cited in this specification are herein incorporated by reference as if each individual publication were specifically and individually indicated to be incorporated by reference herein as though fully set forth.

The following Descriptions and Examples illustrate the preparation of compounds of the invention.

Abbreviations g—grams
mg—milligrams
ml—milliliters
min—minute
ul—microliters
MeCN—acetonitrile
MeOH—methanol
EtOH—ethanol
Et$_2$O—diethyl ether
EtOAc—ethyl acetate
DABCO—1,4-diazabiclo[2,2,2]octane
DCM—dichloromethane
DIAD—diisopropyl azodicarboxylate
DME—1,2-bis(methyloxy)ethane
DMF—N,N-dimethylformamide
DMSO—dimethylsulphoxide
EDAC—N-(3-Dimethylaminopropyl)-N'-ethylcarbodiimide hydrochloride
EDC—N-(3-Dimethylaminopropyl)-N'-ethylcarbodiimide hydrochloride
EDCI—N-(3-Dimethylaminopropyl)-N'-ethylcarbodiimide hydrochloride
HOBT/HOBt—Hydroxybenzotriazole
IPA—isopropylalcohol
NCS—N-chlorosuccinimide
PyBOP—Benzotriazol-1-yl-oxytripyrrolidinophosphonium hexafluorophosphate
THF—tetrahydrofuran
dba—dibenzylidene acetone
RT—room temperature
° C.—degrees Celsius
M—Molar
H—proton
s—singlet
d—doublet
t—triplet
q—quartet
MHz—megahertz
MeOD—deuterated methanol
LCMS—Liquid Chromatography Mass Spectrometry
LC/MS—Liquid Chromatography Mass Spectrometry
MS—mass spectrometry
ES—Electrospray
MH$^+$—mass ion+H$^+$
MDAP—mass directed automated preparative liquid chromatography.
sat.—saturated Chromatography Unless stated otherwise, all chromatography was carried out using silica columns.

General Chemistry Section

The intermediates for the preparation of the examples may not necessarily have been prepared from the specific batch of precursor described.

Description for D1

1H-indole-7-carbaldehyde oxime (D1)

Hydroxylamine hydrochloride (0.574 g) was added portionwise to a solution of 1H-indole-7-carbaldehyde (1 g) in pyridine (5 ml) at RT. The resulting solution was heated to reflux and kept at that temperature for 1 hour. The solvent was evaporated. Ethyl acetate (50 mL) was added and the resulting solution was washed with aqueous hydrochloric acid (0.5 M, 40 mL). The organic fraction was separated and dried over anhydrous magnesium sulfate. The dried solution was concentrated to afford 1H-indole-7-carbaldehyde oxime (D1) as a colorless oil which, upon standing, solidified to give a waxy solid (1.1 g). MS (ES): $C_9H_8N_2O$ requires 160; found 161.1 (M+H$^+$).

Description for D2

1H-indole-7-carbonitrile (D2)

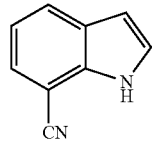

2-chloro-1-methylpyridinium iodide (1.930 g) was added to a solution of 1H-indole-7-carbaldehyde oxime (D1) (1.1 g) in dry THF (80 mL) at RT. After stirring for 10 min, triethylamine (3.35 mL) was added dropwise to the reaction mixture. The reaction mixture was stirred at RT for 2 hours, then was heated to 50° C. and stirred at 50° C. for 2.5 hours. The solvent was evaporated. The residue was dissolved in EtOAc (100 mL) and water (100 mL) was added. The organic fraction was separated, washed with aqueous HCl (0.5 M, 50 mL). The organic fraction was dried over anhydrous magnesium sulfate. The dried solution was concentrated to afford 1H-indole-7-carbonitrile (D2) as a white solid (0.95 g). δH (DMSO-d$_6$, 400 MHz): 6.64 (1H, m), 7.16 (1H, t), 7.56 (1H, m), 7.68 (1H, d), 7.93 (1H, d), 12.02 (1H, br s). MS (ES): $C_9H_6N_2$ requires 142; found 141.0 (M−H$^+$).

Alternative Description for D2

1H-indole-7-carbonitrile (D2)

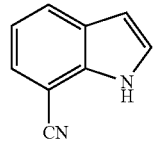

7-Bromoindole (3.5 g), Zn(CN)$_2$ (2.5 g) was added to Pd(PPh$_3$)$_4$ (1.5 g) and degassed DMF (10 mL) in fififteen microwave tubes. The vials were capped and heated in the microwave at 170° C. for 20 mins. The combined reaction mixture was diluted with EtOAc and washed with water and brine. The organic solution was dried over anhydrous sodium sulfate. The dried solution was concentrated, filtered and evaporated in vacuo. The residue was purified by column chromatography, followed by recrystallisation from heptane to give 1H-indole-7-carbonitrile (32.0 g) as a white solid. δH (CDCl$_3$, 400 MHz): 6.66 (1H, dd), 7.18 (1H, t), 7.36 (1H, t), 7.53 (1H, d), 7.88 (1H, d), 8.78 (1H, br s).

Description for D3

3-Formyl-1H-indole-7-carbonitrile (D3)

DMF (0.539 mL) in dry dichloromethane (30 mL) was added dropwise to a solution of oxalyl chloride (0.610 mL) in dry dichloromethane (30 mL) at 0° C. The resulting solution was stirred at 0° C. for 15 min. A solution of 1H-indole-7-carbonitrile (D2) (0.90 g) in dry dichloromethane (5 mL) was added to the reaction mixture. The reaction mixture was warmed to RT and stirred for 30 min. The solvent was evaporated. THF (20 mL) was added, followed by addition of aqueous NaOH (0.5 M, 50 mL). The biphasic mixture was allowed to stand for 10 min. EtOAc (100 mL) and water (70 mL) was added. The organic fraction was separated and was dried over anhydrous magnesium sulfate. The dried solution was concentrated to afford 3-formyl-1H-indole-7-carbonitrile (D3) as a light cream solid (0.75 g, 70%). δH (DMSO-d$_6$, 400 MHz): 7.42 (1H, t), 7.79 (1H, dd), 8.43 (1H, dd), 8.48 (1H, s), 10.00 (1H, s), 13.02 (1H, br s). MS (ES): $C_{10}H_6N_2O$ requires 170; found 171.2 (M+H$^+$).

Description for D4

1,1-dimethylethyl (2E)-3-(7-cyano-1H-indol-3-yl)-2-propenoate (D4)

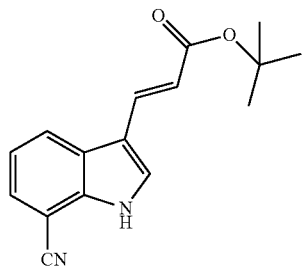

1,1-Dimethylethyl (triphenyl-λ⁵-phosphanylidene)acetate (1.858 g) was added to a suspension of 3-formyl-1H-indole-7-carbonitrile (D3) (0.7 g) in acetonitrile (70 mL). The reaction mixture was heated to reflux and stirred for 2.5 hours. Another portion of 1,1-dimethylethyl (triphenyl-λ⁵-phosphanylidene)acetate (0.3 g) was added and the resulting suspension was refluxed for 2 more hours. The solvent was evaporated. The residue was purified by Biotage (25% EtOAc in hexane) to afford 1,1-dimethylethyl (2E)-3-(7-cyano-1H-indol-3-yl)-2-propenoate (D4) as a white solid (850 mg). $\delta H$ (DMSO-$d_6$, 400 MHz): 1.49 (9H, s), 6.40 (1H, d), 7.30 (1H, t), 7.71 (1H, dd), 7.79 (1H, d), 8.11 (1H, s), 8.25 (1H, dd), 12.59 (1H, br s). MS (ES): $C_{16}H_{16}N_2O_2$ requires 268; found 267.1 (M−H⁺).

Description for D5

1,1-dimethylethyl 3-(7-cyano-1H-indol-3-yl)-2-propanoate (D5)

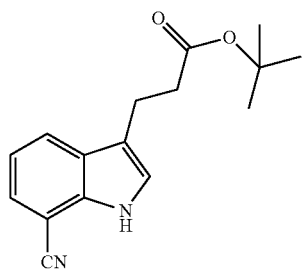

1,1-Dimethylethyl (2E)-3-(7-cyano-1H-indol-3-yl)-2-propenoate (D4) (800 mg) in methanol (100 mL) and EtOAc (50 mL) was hydrogenated using the H-cube (full mode) with a large 10% Pd—C catcart (flow rate: 2.5 mL/min). The solvent was evaporated. The residue was dissolved in EtOAc (50 mL). The organic solution was washed with aqueous HCl (50 mL). The organic fraction was dried over anhydrous magnesium sulfate. The dried solution concentrated to afford 1,1-dimethylethyl 3-(7-cyano-1H-indol-3-yl)-2-propanoate (D5) (640 mg) as a white solid. $\delta H$ (DMSO-$d_6$, 400 MHz): 1.35 (9H, s), 2.58 (2H, t), 2.94 (2H, t), 7.17 (1H, t), 7.28 (1H, d), 7.58 (1H, dd), 7.91 (1H, d), 11.72 (1H, br s). MS (ES): $C_{16}H_{18}N_2O_2$ requires 270; found 269 (M−H⁺).

Description for D6

1,1-Dimethylethyl 3-{7-(hydroxyamino)(imino)methyl]-1H-indol-3-yl}propanoate (D6)

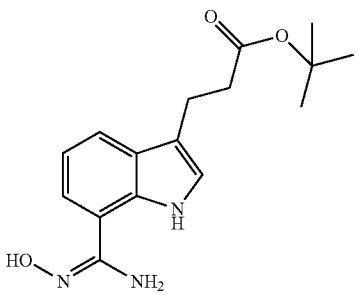

Hydroxylamine hydrochloride (411 mg) and sodium bicarbonate (994 mg) was added to a solution of 1,1-dimethylethyl 3-(7-cyano-1H-indol-3-yl)-2-propanoate (D5) (640 mg) in EtOH (60 mL), in that sequence. The reaction mixture was heated to 50° C., stirred for 3 hours at that temperature and left standing at room temperature over the weekend. Another portion of hydroxylamine hydrochloride (100 mg) was added and the resulting suspension was stirred at 50° C. for 3 more hours. The inorganics was filtered off. The solid was washed with dichloromethane (30 mL). The filtrate was concentrated to afford an oily solid. EtOAc/ether was added to the residue and the solid was filtered off. The filtrate was concentrated to afford 1,1-dimethylethyl 3-{7-(hydroxyamino)(imino)methyl]-1H-indol-3-yl}propanoate (D6) (580 mg) as a white foam. No purification was attempted.

Description for D7

1,1-Dimethylethyl 3-[7-(5-{3-chloro-4-[(1-methylethyl)oxy]phenyl}-1,2,4-oxadiazol-3-yl)-1H-indol-3-yl]propanoate (D7)

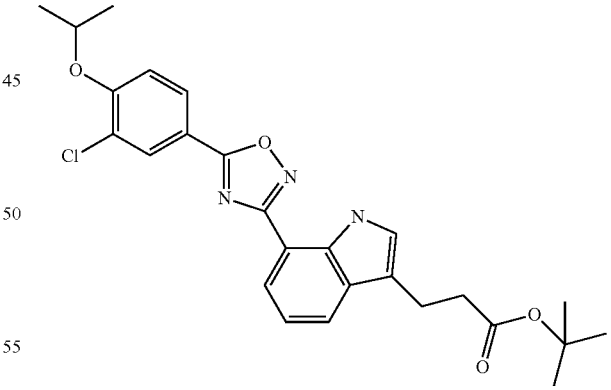

EDCI (152 mg) and HOBT (121 mg) were added to a solution of 3-chloro-4-[(1-methylethyl)oxy]benzoic acid (D32) (142 mg) in DMF (10 mL) at RT. The resulting solution was stirred for 10 min. 1,1-Dimethylethyl 3-{7-(hydroxyamino)(imino)methyl]-1H-indol-3-yl}propanoate (D6) (200 mg) was added and the reaction mixture was stirred at RT for 1 hour. The reaction mixture was heated to 80° C. and stirred at that temperature for overnight. The reaction mixture was heated to 100° C. and stirred at 100° C. for 7 hours. Left standing over the weekend then heated at 100° C.

for 5 hours. Most of the DMF was evaporated. EtOAc (70 mL) was added and the organic solution was washed with saturated aqueous sodium bicarbonate solution (50 mL) and water (70 mL). The organic fraction was dried over anhydrous magnesium sulfate. The dried solution was concentrated. The residue was purified by Biotage (25% EtOAc in hexane 1:3) to afford a yellow solid. Recrystallization from ether/hexane provided 1,1-dimethylethyl 3-[7-(5-{3-chloro-4-[(1-methylethyl)oxy]phenyl}-1,2,4-oxadiazol-3-yl)-1H-indol-3-yl]propanoate (D7) (120 mg) as a pale yellow solid. MS (ES): $C_{26}H_{28}ClN_3O_4$ requires 481; found 482.0 (M+H$^+$).

Description for D8

1,1-Dimethylethyl 3-[7-(5-{3-chloro-4-[(1-methylethyl)oxy]phenyl}-1,2,4-oxadiazol-3-yl)-1-methyl-1H-indol-3-yl]propanoate (D8)

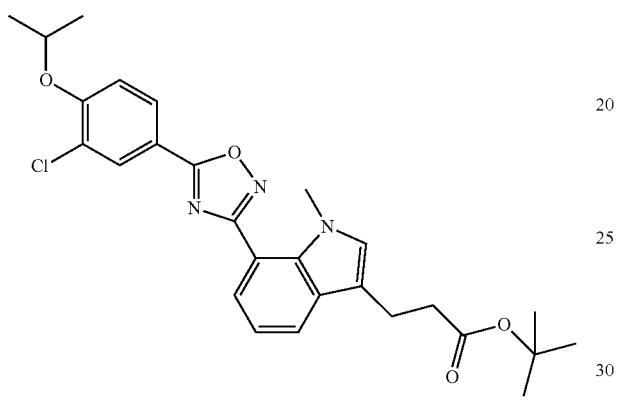

Sodium hydride (60% in mineral oil, 3.98 mg) was added to a solution of 1,1-dimethylethyl 3-[7-(5-{3-chloro-4-[(1-methylethyl)oxy]phenyl}-1,2,4-oxadiazol-3-yl)-1H-indol-3-yl]propanoate (D7) (80 mg) in dry DMF (2 mL) at RT. After stirring for 5 min, iodomethane (0.016 mL) was added. The resulting solution was stirred at RT for 45 min. EtOAc (50 mL) was added and the resulting solution was washed with aqueous HCl (20 mL), followed by water (50 mL). The organic fraction was dried over anhydrous magnesium sulfate. The dried solution was concentrated to afford 1,1-dimethylethyl 3-[7-(5-{3-chloro-4-[(1-methylethyl)oxy]phenyl}-1,2,4-oxadiazol-3-yl)-1-methyl-1H-indol-3-yl]propanoate (D8) (85 mg) as a pale yellow oil. MS (ES): $C_{27}H_{30}ClN_3O_4$ requires 495; found 496.0 (M+H$^+$).

Description for D9

1,1-Dimethylethyl 3-[7-(5-{3-cyano-4-[(1-methylethyl)oxy]phenyl}-1,2,4-oxadiazol-3-yl)-1H-indol-3-yl]propanoate (D9)

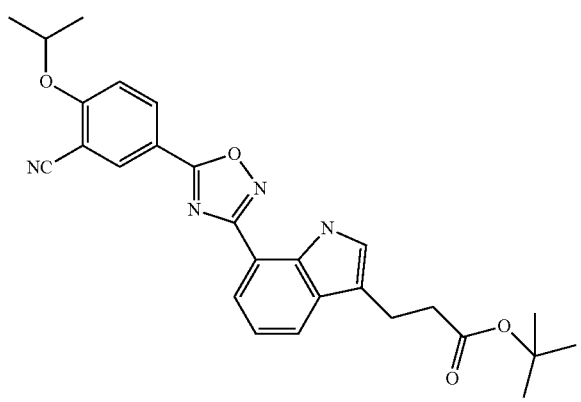

EDCI (76 mg) and HOBT (60.6 mg) were added to a solution of 3-cyano-4-[(1-methylethyl)oxy]benzoic acid (can be prepared as described on WO2005/58848, 67.6 mg) in DMF (5 mL) at RT. The resulting solution was stirred for 10 min. 1,1-Dimethylethyl 3-{7-(hydroxyamino)(imino)methyl]-1H-indol-3-yl}propanoate (D6) (100 mg) was added and the reaction mixture was stirred at RT for 1 hour. The reaction mixture was heated to 90° C. and stirred at that temperature for 1 hour, then standing for overnight. Heated to 90° C. for 8 hours, then left standing for overnight. Heated to 90° C. again and stirred for 4 hours. EtOAc (50 mL) was added and the organic solution was washed with saturated aqueous sodium bicarbonate solution (50 mL) and water (50 mL). The organic fraction was dried over anhydrous magnesium sulfate. The dried solution was concentrated. The residue was purified by Biotage (33% EtOAc in hexane) to afford a yellow oil. Recrystallization from ether/hexane provided 1,1-dimethylethyl 3-[7-(5-{3-cyano-4-[(1-methylethyl)oxy]phenyl}-1,2,4-oxadiazol-3-yl)-1H-indol-3-yl]propanoate (D9) (48 mg) as a white solid. MS (ES): $C_{27}H_{28}N_4O_4$ requires 472; found 473.0 (M+H$^+$).

Description for D10

1,1-Dimethylethyl 3-[7-(5-{3-cyano-4-[(1-methylethyl)oxy]phenyl}-1,2,4-oxadiazol-3-yl)-1-methyl-1H-indol-3-yl]propanoate (D10)

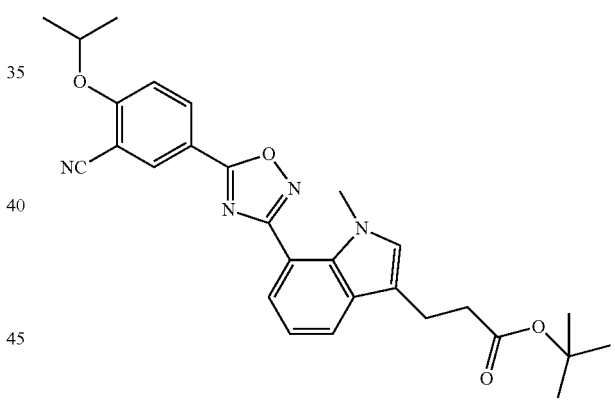

Sodium hydride (60% in mineral oil, 9.14 mg) was added to a solution of 1,1-dimethylethyl 3-[7-(5-{3-cyano-4-[(1-methylethyl)oxy]phenyl}-1,2,4-oxadiazol-3-yl)-1H-indol-3-yl]propanoate (D9) (120 mg) in dry DMF (5 mL) at RT. After stirring for 5 min, iodomethane (0.032 mL) was added. The resulting solution was stirred at RT for 15 min, then 1 hour more. EtOAc (50 mL) was added and the resulting solution was washed with saturated aqueous sodium bicarbonate solution (50 mL), followed by water (50 mL). The organic fraction was dried over anhydrous magnesium sulfate. The dried solution was concentrated. The residue was purified by Biotage (25% EtOAc in hexane) to afford 1,1-dimethylethyl 3-[7-(5-{3-cyano-4-[(1-methylethyl)oxy]phenyl}-1,2,4-oxadiazol-3-yl)-1-methyl-1H-indol-3-yl]propanoate (D10) (60 mg) as a pale yellow oil. MS (ES): $C_{28}H_{30}N_4O_4$ requires 486; found 487.0 (M+H$^+$).

Description for D11

1H-indole-6-carbaldehyde oxime (D11)

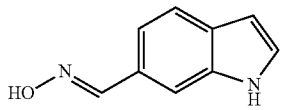

Hydroxylamine hydrochloride (0.574 g) was added portionwise to a solution of 1H-indole-6-carbaldehyde (1 g) in pyridine (5 ml) are RT. The resulting solution was heated to reflux and stirred at that temperature for 1 hour. The solvent was evaporated. The residue was diluted with ethyl acetate (50 mL) and the resulting solution was washed with aqueous hydrochloric acid (0.5 M, 40 mL). The organic fraction was separated and dried over anhydrous magnesium sulfate. The dried solution was concentrated to afford a brown oily solid. The residue was triturated with ether/hexane to afford 1H-indole-6-carbaldehyde oxime (D11) as a pink solid (128 mg). Solid was precipitated out from the filtrate. The solid was collected to give another batch of 1H-indole-6-carbaldehyde oxime (D11) (818 mg). δH (DMSO-$d_6$, 400 MHz): 6.44 (1H, m), 7.24 (1H, dd), 7.32 (1H, m), 7.55 (1H, dd), 7.57 (1H, s), 8.19 (1H, s), 10.88 (1H, s), 11.25 (1H, br s).

Description for D12

1H-Indole-6-carbonitrile (D12)

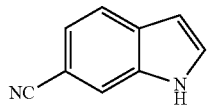

2-Chloro-1-methylpyridium iodide (1.316 g) was added to a solution of 1H-indole-6-carbaldehyde oxime (D11) (750 mg) in dry THF (80 mL) at RT. After stirring for 10 min, triethylamine (2.284 mL) was added to the reaction mixture. The reaction mixture was heated to 50° C. and stirred at 50° C. for 3.5 hours, then left overnight with stirring at RT. The mixture was heated to refluxed for 5 hours. The solvent was evaporated. The residue was dissolved in EtOAc (100 mL) and water (100 mL) was added. The organic fraction was separated. The organic fraction was dried over anhydrous magnesium sulfate. The dried solution was concentrated to afford 1H-indole-6-carbonitrile (D12) as a brown solid (680 mg). δH (DMSO-$d_6$, 400 MHz): 6.60 (1H, m), 7.32 (1H, dd), 7.68 (1H, m), 7.72 (1H, d), 7.88 (1H, m), 11.68 (1H, br s). MS (ES): $C_9H_6N_2$ requires 142; found 141.0 (M–H$^+$).

Description for D13

3-Formyl-1H-indole-6-carbonitrile (D13)

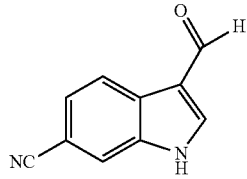

DMF (0.389 mL) was added dropwise to a solution of oxalyl chloride (0.440 mL) in dry dichloromethane (5 mL) at 0° C. The resulting solution was stirred at 0° C. for 10 min. A solution of 1H-indole-6-carbonitrile (D12) (0.650 g) in dry dichloromethane (5 mL) was added to the reaction mixture. The reaction mixture was warmed to RT and stirred at that temperature for 45 min. The solvent was evaporated. THF (50 mL) was added, followed by addition of aqueous NaOH (2 M, 50 mL) and water (200 mL). The biphasic mixture was allowed to stand for 10 min. EtOAc (300 mL) and water (100 mL) was added. The organic fraction was separated and was dried over anhydrous magnesium sulfate. The dried solution was concentrated to afford 3-formyl-1H-indole-6-carbonitrile (D13) as a orange solid (604 mg). δH (DMSO-$d_6$, 400 MHz): 7.59 (1H, dd), 8.05 (1H, d), 8.24 (1H, m), 8.56 (1H, s), 10.00 (1H, s), 12.62 (1H, br s). MS (ES): $C_{10}H_6N_2O$ requires 170; found 169.0 (M–H$^+$).

Description for D14

1,1-Dimethylethyl (2E)-3-(6-cyano-1H-indol-3-yl)-2-propenoate (D14)

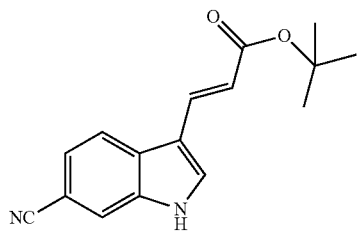

1,1-Dimethylethyl (triphenyl-$\lambda^5$-phosphanylidene)acetate (1.540 g) was added to a suspension of 3-formyl-1H-indole-6-carbonitrile (D13) (604 mg) in acetonitrile (20 mL) at RT. The reaction mixture was heated to refluxing and stirred for 3.5 hours. Another portion of 1,1-dimethylethyl (triphenyl-$\lambda^5$-phosphanylidene)acetate (1 g) was added and the resulting suspension was refluxed for 3 more hours. Another portion of 1,1-dimethylethyl (triphenyl-$\lambda^5$-phosphanylidene)acetate (1 g) was added and the resulting suspension was refluxed for 2.5 more hours. Another portion of 1,1-dimethylethyl (triphenyl-$\lambda^5$-phosphanylidene)acetate (1 g) was added and the resulting suspension was refluxed for 3 more hours. Another portion of 1,1-dimethylethyl (triphenyl-$\lambda^5$-phosphanylidene) acetate (1.5 g) was added and the resulting suspension was refluxed for 3.5 more hours. The solvent was evaporated. The residue was purified by Biotage (33% EtOAc in hexane) to afford 1,1-dimethylethyl (2E)-3-(6-cyano-1H-indol-3-yl)-2-propenoate (D14) as a white solid (556 mg). MS (ES): $C_{16}H_{16}N_2O_2$ requires 268; found 267.0 (M–H$^+$).

Description for D15

1,1-Dimethylethyl 3-(6-cyano-1H-indol-3-yl)-2-propanoate (D15)

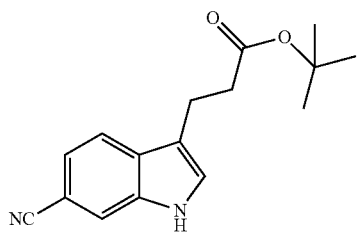

1,1-Dimethylethyl (2E)-3-(6-cyano-1H-indol-3-yl)-2-propanoate (D14) (556 mg) in methanol (75 mL) and EtOAc (20 mL) was hydrogenated twice using the H-cube (full mode) with a large 10% Pd—C catcart (flow rate: 2.5 mL/min). The solvent was evaporated to afford 1,1-dimethylethyl 3-(6-cyano-1H-indol-3-yl)-2-propanoate (D15) (512 mg) as a white solid. δH (DMSO-$d_6$, 400 MHz): 1.35 (9H, s), 2.57 (2H, t), 2.93 (2H, t), 7.31 (1H, dd), 7.45 (1H, d), 7.71 (1H, d), 7.83 (1H, t), 11.42 (1H, br s). MS (ES): $C_{16}H_{18}N_2O_2$ requires 270; found 269.1 (M–H$^+$).

Description for 16

1,1-Dimethylethyl 3-{6-(hydroxyamino)(imino)methyl]-1H-indol-3-yl}propanoate (D16)

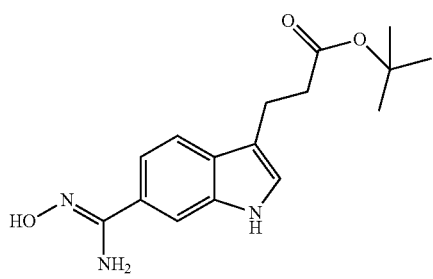

Hydroxylamine hydrochloride (127 mg) and sodium bicarbonate (769 mg) was added to a solution of 1,1-dimethylethyl 3-(6-cyano-1H-indol-3-yl)-2-propanoate (D15) (495 mg) in EtOH (50 mL), in that sequence. The reaction mixture was heated to 50° C. and stirred for 0.5 hour at that temperature. After standing for over weekend, it was heated to 50° C. for 3 hours. Another portion of hydroxylamine hydrochloride (250 mg) was added and the resulting suspension was stirred at 50° C. for 4 hours, then overnight. A third portion of hydroxylamine hydrochloride (250 mg) was added, followed by addition of sodium bicarbonate (500 mg). The resulting suspension was stirred at 50° C. for 30 hours. The inorganics was filtered off. The solid was washed with dichloromethane (30 mL). The filtrate was concentrated to afford 1,1-dimethylethyl 3-{6-[(hydroxyamino)(imino)methyl]-1H-indol-3-yl}propanoate (D16) (591 mg) as a yellow solid. No purification was attempted. δH (DMSO-$d_6$, 400 MHz): 1.37 (9H, s), 2.57 (2H, t), 2.91 (2H, t), 5.71 (2H, s), 7.15 (1H, d), 7.33 (1H, dd), 7.46 (1H, d), 7.62 (1H, m), 9.43 (1H, s), 10.94 (1H, br s). MS (ES): $C_{16}H_{21}N_3O_3$ requires 303; found 304.0 (M+H$^+$).

Description for D17

1,1-dimethylethyl 3-[6-(5-{3-chloro-4-[(1-methylethyl)oxy]phenyl}-1,2,4-oxadiazol-3-yl)-1H-indol-3-yl]propanoate (D17)

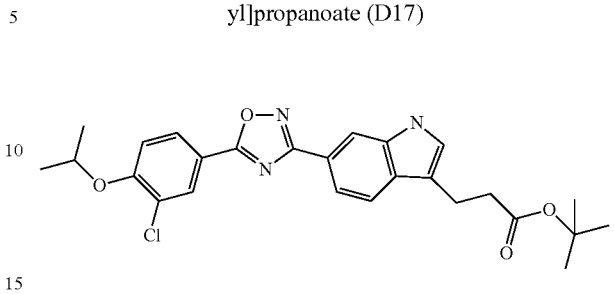

EDCI (297 mg) and HOBT (237 mg) were added to a solution of 3-chloro-4-[(1-methylethyl)oxy]benzoic acid (D32) (277 mg) in DMF (10 mL) at RT. The resulting solution was stirred for 10 min. A solution of 1,1-Dimethylethyl 3-{6-[(hydroxyamino)(imino)methyl]-1H-indol-3-yl}propanoate (D16) (392 mg) in DMF (10 mL) was added and the reaction mixture was stirred at RT for 1 hour. The reaction mixture was heated to 80° C. and stirred at that temperature for 8 hours, then standed at RT for overweekend. The reaction mixture was heated to 80° C. for 2 hours. Most of the DMF was evaporated. EtOAc (100 mL) was added and the organic solution was washed with saturated aqueous sodium bicarbonate solution (100 mL) and water (100 mL). The organic fraction was dried over anhydrous magnesium sulfate. The dried solution was concentrated. The residue was purified by Biotage (25% EtOAc in hexane) to afford 1,1-dimethylethyl 3-[6-(5-{3-chloro-4-[(1-methylethyl)oxy]phenyl}-1,2,4-oxadiazol-3-yl)-1H-indol-3-yl]propanoate (D17) (314 mg) as a white solid. MS (ES): $C_{26}H_{28}ClN_3O_4$ requires 481; found 482.0 (M+H$^+$).

Description for D18

1,1-Dimethylethyl 3-[6-(5-{3-chloro-4-[(1-methylethyl)oxy]phenyl}-1,2,4-oxadiazol-3-yl)-1-methyl-1H-indol-3-yl]propanoate (D18)

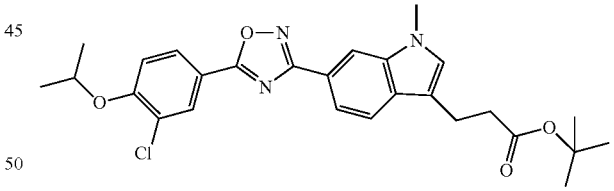

Sodium hydride (60% in mineral oil, 7.47 mg) was added to a solution of 1,1-dimethylethyl 3-[6-(5-{3-chloro-4-[(1-methylethyl)oxy]phenyl}-1,2,4-oxadiazol-3-yl)-1H-indol-3-yl]propanoate (D17) (150 mg) in dry DMF (4 mL) at RT. After stirring for 5 min, iodomethane (0.029 mL) was added. The resulting solution was stirred at RT for 1.2 hours. Another portion of sodium hydride (4 mg) was added. After stirring for 5 min, methyliodide (0.015 mL) was added, and the resulting solution was stirred for 1 hour. DMF was evaporated. EtOAc (50 mL) was added and the resulting solution was washed with aqueous HCl (40 mL), followed by water (100 mL). The organic fraction was dried over anhydrous magnesium sulfate. The dried solution was concentrated. The residue was purified by Biotage (25% EtOAc in hexane) to afford 1,1-dimethylethyl 3-[6-(5-{3-chloro-4-[(1-methylethyl)oxy]

phenyl}-1,2,4-oxadiazol-3-yl)-1-methyl-1H-indol-3-yl]propanoate (D18) (113 mg) as a white solid. δH (DMSO-d$_6$, 400 MHz): 1.38 (15H, m), 2.58 (2H, t), 2.93 (2H, t), 3.85 (3H, s), 4.89 (1H, m), 7.32 (1H, br s), 7.45 (1H, d), 7.75 (2H, m), 8.15 (2H, m), 8.22 (1H, d). MS (ES): C$_{27}$H$_{30}$ClN$_3$O$_4$ requires 495; found 496.0 (M+H$^+$).

Description for D19

1,1-Dimethylethyl 3-[6-(5-{3-cyano-4-[(1-methylethyl)oxy]phenyl}-1,2,4-oxadiazol-3-yl)-1H-indol-3-yl]propanoate (D19)

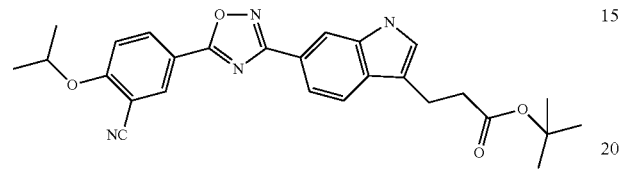

EDCI (151 mg) and HOBT (121 mg) were added to a solution of 3-cyano-4-[(1-methylethyl)oxy]benzoic acid (can be prepared as described in WO2005/58848, 135 mg) in DMF (5 mL) at RT. The resulting solution was stirred for 45 min. 1,1-dimethylethyl 3-{6-[(hydroxyamino)(imino)methyl]-1H-indol-3-yl}propanoate (D16) (199 mg) was added and the reaction mixture was stirred at RT for 3 hours. The reaction mixture was heated to 80° C. and stirred at that temperature for 5 hours. DMF was evaporated. EtOAc (100 mL) was added and the organic solution was washed with saturated aqueous sodium bicarbonate solution (75 mL) and water (75 mL). The organic fraction was dried over anhydrous magnesium sulfate. The dried solution was concentrated. The residue was purified by Biotage (25→33% EtOAc in hexane) to afford 1,1-dimethylethyl 3-[6-(5-{3-cyano-4-[(1-methylethyl)oxy]phenyl}-1,2,4-oxadiazol-3-yl)-1H-indol-3-yl]propanoate (D19) (105 mg) as a white solid. δH (DMSO-d$_6$, 400 MHz): 1.38 (9H, s), 1.39 (6H, d), 2.60 (2H, t), 2.96 (2H, t), 4.98 (1H, m), 7.35 (1H, d), 7.55 (1H, d), 7.72 (2H, m), 8.12 (1H, d), 8.42 (1H, dd), 8.51 (1H, d), 11.21 (1H, s). MS (ES): C$_{27}$H$_{28}$N$_4$O$_4$ requires 472; found 473.0 (M+H$^+$).

Description for D20

5-Cyano-1H-indole-2-carboxylic acid (D20)

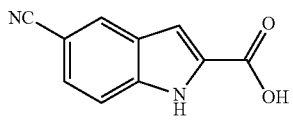

A suspension of 4-amino-3-iodobenzonitrile (2.44 g), 2-oxopropanoic acid (2.64 g), DABCO (3.36 g), and Pd(OAc)$_2$ in DMF (30 mL) was heated to 105° C. and stirred at that temperature for 1 hour. The solvent was evaporated. EtOAc (200 mL) was added and the resulting solution was washed with water (100 mL) and aqueous NaOH solution (20 mL). The combined aqueous solution was extracted with EtOAc (3×150 mL). The organic fractions were combined. The combined solution was dried over anhydrous magnesium sulfate. The dried solution was concentrated. The residue was triturated to afford 5-cyano-1H-indole-2-carboxylic acid (D20) (1.1 g) as a brown solid.

Description for D21

Ethyl 5-cyano-1H-indole-2-carboxylate (D21)

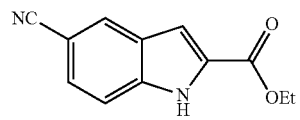

Thionyl chloride (1 mL) was added to a solution of 5-cyano-1H-indole-2-carboxylic acid (D20) (1.1 g) in ethanol (120 mL) at RT. The resulting solution was heated to reflux and stirred when refluxing for 20 hours. Another portion of thionyl chloride (0.5 mL) was added. The reaction mixture was refluxed for 2 hours. The solvent was evaporated to afford ethyl 5-cyano-1H-indole-2-carboxylate (D21) (0.9 g) as a light green solid. MS (ES): C$_{12}$H$_{10}$N$_2$O$_2$ requires 214; found 215.2 (M+H$^+$)

Description for D22

Ethyl 5-[(hydroxyamino)(imino)methyl]-1H-indole-2-carboxylate (D22)

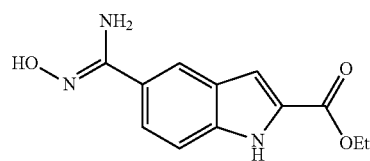

Hydroxylamine hydrochloride (172 mg) and sodium bicarbonate (415 mg) was added to a solution of ethyl 5-cyano-1H-indole-2-carboxylate (D21) (265 mg) in EtOH (15 mL), in that sequence. The reaction mixture was heated to 55° C. and stirred for 16 hours at that temperature. Another portion of hydroxylamine hydrochloride (69.4 mg) was added, followed by addition of sodium bicarbonate (125.5 mg). The resulting suspension was stirred at 55° C. for 12 hours. The inorganics was filtered off. The solid was washed with dichloromethane (30 mL) and methanol (30 mL). The filtrate was concentrated to afford ethyl 5-[(hydroxyamino)(imino)methyl]-1H-indole-2-carboxylate (D22) (280 mg) as a yellow solid. No purification was attempted. MS (ES): C$_{12}$H$_{13}$N$_3$O$_3$ requires 247; found 248.1 (M+H$^+$).

Description for D23

Ethyl 5-(5-{3-chloro-4-[(1-methylethyl)oxy]phenyl}-1,2,4-oxadiazol-3-yl)-1H-indole-2-carboxylate (D23)

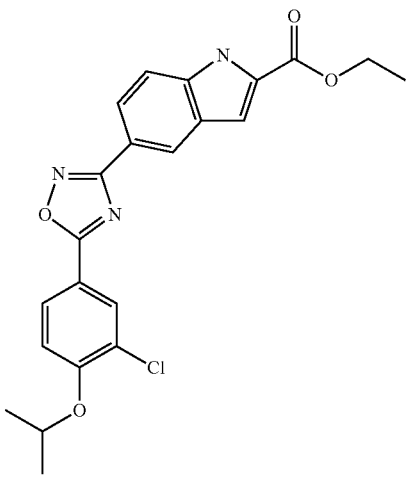

EDCI (144 mg) and HOBT (104 mg) were added to a solution of 3-chloro-4-[(1-methylethyl)oxy]benzoic acid (D32) (150 mg) in DMF (5 mL) at RT. The resulting solution was stirred for 15 min. Ethyl 5-[(hydroxyamino)(imino)methyl]-1H-indole-2-carboxylate (D22) (173 mg) was added and the reaction mixture was stirred at RT for 30 min. The reaction mixture was heated to 80° C. and stirred at that temperature for 5 hours. Most of the DMF was evaporated. EtOAc (50 mL) was added and the organic solution was washed with water (50 mL), saturated aqueous sodium bicarbonate solution (50 mL) and water (50 mL). The organic fraction was dried over anhydrous magnesium sulfate. The dried solution was concentrated. Trituration with ethanol provided ethyl 5-(5-{3-chloro-4-[(1-methylethyl)oxy]phenyl}-1,2,4-oxadiazol-3-yl)-1H-indole-2-carboxylate (D23) (85 mg) as a yellow solid. δH (DMSO-$d_6$, 400 MHz): 1.37 (9H, m), 4.38 (2H, q), 4.89 (1H, m), 7.35 (1H, d), 7.45 (1H, d), 7.62 (1H, d), 7.98 (1H, dd), 8.12 (1H, dd), 8.20 (1H, d), 8.49 (1H, d), 12.27 (1H, s). MS (ES): $C_{22}H_{20}ClN_3O_4$ requires 425; found 426.1 (M+H$^+$).

Description for D24

2-(Hydroxymethyl)-1H-indole-5-carbonitrile (D24)

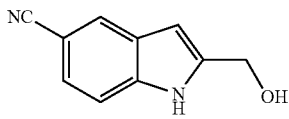

LiAlH$_4$ (1.0 M in THF, 5 mL) was added to a solution of ethyl 5-cyano-1H-indole-2-carboxylate (D21) (1 g) in THF (100 mL). The reaction mixture was stirred for 15 min at RT. MeOH was added to quench the reaction. The solvent was evaporated. EtOAc (500 mL) was added. The organic solution was washed with aqueous HCl (300 mL), then was dried over anhydrous magnesium sulfate. The dried solution was concentrated to afford 2-(hydroxymethyl)-1H-indole-5-carbonitrile (D24) (600 mg) as a pale orange oil. MS (ES): $C_{10}H_8N_2O$ requires 172; found 173.2 (M+H$^+$)

Description for D25

N-Hydroxy-2-(hydroxymethyl)-1H-indole-5-carboximidamide (D25)

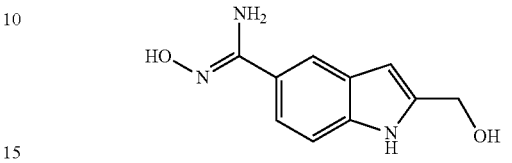

Hydroxylamine hydrochloride (243 mg) and sodium bicarbonate (586 mg) was added to a solution of 2-(hydroxymethyl)-1H-indole-5-carbonitrile (D24) (300 mg) in EtOH (20 mL), in that sequence. The reaction mixture was heated to 50° C. and stirred for 24 hours at that temperature. Another portion of hydroxylamine hydrochloride (100 mg) was added, followed by addition of sodium bicarbonate (220 mg). The resulting suspension was stirred at 50° C. for 7 hours. The inorganics was filtered off. The filtrate was concentrated to afford a pale yellow oil. Trituration of the residue provided N-hydroxy-2-(hydroxymethyl)-1H-indole-5-carboximidamide (D25) (300 mg) as a pale yellow solid. MS (ES): $C_{10}H_{11}N_3O_2$ requires 205; found 206.2 (M+H$^+$).

Description for D26

5-{3-[2-(Hydroxymethyl)-1H-indol-5-yl]-1,2,4-oxadiazol-5-yl}-2-[(1-methylethyl)oxy]benzonitrile (D26)

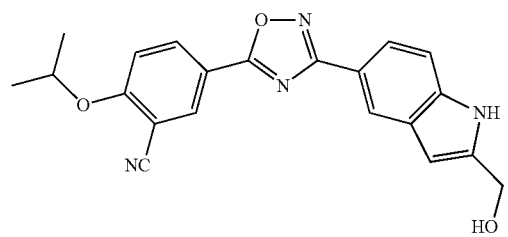

EDCI (144 mg) and HOBT (104 mg) were added to a solution of 3-cyano-4-[(1-methylethyl)oxy]benzoic acid (can be prepared as described in WO2005/58848, 144 mg) in DMF (5 mL) at RT. The resulting solution was stirred for 15 min. N-hydroxy-2-(hydroxymethyl)-1H-indole-5-carboximidamide (D25) (144 mg) was added and the reaction mixture was stirred at RT for 1 hour. The reaction mixture was heated to 80° C. and stirred at that temperature for 4 hours. EtOAc (50 mL) was added and the organic solution was washed with water (50 mL), saturated aqueous sodium bicarbonate solution (50 mL) and water (50 mL). The organic fraction was dried over anhydrous magnesium sulfate. The dried solution was concentrated. The residue was crystallized from EtOAc/ether to afford 5-{3-[2-(hydroxymethyl)-1H-indol-5-yl]-1,2,4-oxadiazol-5-yl}-2-[(1-methylethyl)oxy]benzonitrile (D26) (70 mg) as a pale brown solid. δH (DMSO-$d_6$, 400 MHz): 1.39 (6H, d), 4.65 (2H, d), 4.99 (1H, m), 5.36 (1H, t) 6.46 (1H, s), 7.50 (1H, d), 7.56 (1H, d), 7.79 (1H, dd), 8.28 (1H, s), 8.43 (1H, dd), 8.51 (1H, d), 11.43 (1H, s). MS (ES): $C_{21}H_{18}N_4O_3$ requires 374; found 375.0 (M+H$^+$).

Description for D27

Ethyl (2E)-3-[5-(5-{3-cyano-4-[(1-methylethyl)oxy]phenyl}-1,2,4-oxadiazol-3-yl)-1H-indol-2-yl]-2-propenoate (D27)

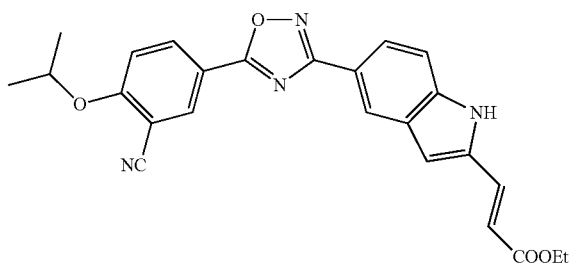

MnO$_2$ (100 mg) was added to a solution of 5-{3-[2-(hydroxymethyl)-1H-indol-5-yl]-1,2,4-oxadiazol-5-yl}-2-[(1-methylethyl)oxy]benzonitrile (D26) (70 mg) in dichloromethane (30 mL) at RT. The reaction mixture was stirred at RT for 12 hours. The solid was filtered off and washed with dichloromethane. The filtrate was concentrated to afford a white solid.

The above solid was dissolved in acetonitrile (3.0 mL). Ethyl (triphenyl-λ$^5$-phosphanylidene)acetate (100 mg) was added to the solution. The reaction was heated to refluxing and was stirred when refluxing for 1 hour. White solid was precipated out upon cooling. The solid was filtered off. The filtrate was concentrated. The residue was recrystallized from acetonitrile to afford ethyl (2E)-3-[5-(5-{3-cyano-4-[(1-methylethyl)oxy]phenyl}-1,2,4-oxadiazol-3-yl)-1H-indol-2-yl]-2-propenoate (D27) (20 mg) as a white solid. MS (ES): C$_{25}$H$_{22}$N$_4$O$_4$ requires 442; found 443.0 (M+H$^+$).

Description for D28

2-Formyl-1H-indole-5-carbonitrile (D28)

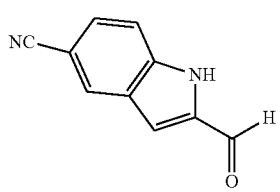

MnO$_2$ (1.76 g) was added to a solution of 2-(hydroxymethyl)-1H-indole-5-carbonitrile (D24) (290 mg) in dichloromethane (100 mL) at RT. The reaction mixture was stirred at RT for 1 hour. The solid was filtered off and washed with dichloromethane. The filtrate was concentrated to afford 2-formyl-1H-indole-5-carbonitrile (D28) (230 mg) as a white solid. MS (ES): C$_{10}$H$_6$N$_2$O requires 170; found 169.1 (M-H$^+$).

Description for D29

Ethyl (2E)-3-(5-cyano-1H-indol-2-yl)-2-propenoate (D29)

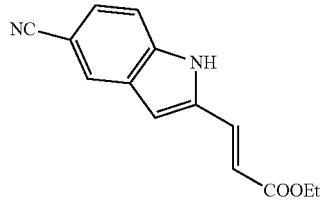

2-Formyl-1H-indole-5-carbonitrile (D28) (230 mg) was dissolved in acetonitrile (50 mL). Ethyl (triphenyl-λ$^5$-phosphanylidene)acetate (522 mg) was added to the solution. The reaction was heated to 60° C. and was stirred at 60° C. for 1 hour. The reaction mixture was concentrated. The residue was purified by Biotage (25%→33% EtOAc in hexane) to afford ethyl (2E)-3-(5-cyano-1H-indol-2-yl)-2-propenoate (D29) (230 mg) as a white solid. MS (ES): C$_{14}$H$_{12}$N$_2$O$_2$ requires 240; found 239.1 (M-H$^+$).

Description for D30

Ethyl 3-(5-cyano-1H-indol-2-yl)propanoate (D30)

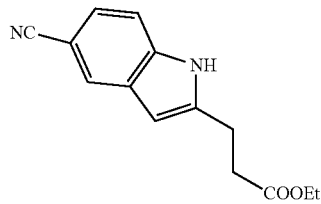

Ethyl (2E)-3-(5-cyano-1H-indol-2-yl)-2-propenoate (D29) (200 mg) in methanol (40 mL) and EtOAc (20 mL) was hydrogenated using the H-cube (full mode) with a large 10% Pd—C catcart (flow rate: 2.5 mL/min). The solvent was evaporated to afford ethyl 3-(5-cyano-1H-indol-2-yl)propanoate (D30) (200 mg) as a white solid. MS (ES): C$_{14}$H$_{14}$N$_2$O$_2$ requires 242; found 243.2 (M+H$^+$).

Description for D31

Ethyl 3-{5-[(hydroxyamino)(imino)methyl]-1H-indol-2-yl}propanoate (D31)

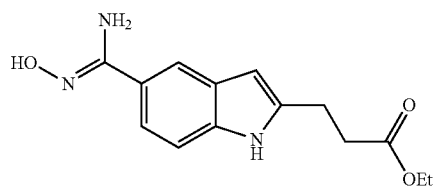

Hydroxylamine hydrochloride (121 mg) and sodium bicarbonate (293 mg) was added to a solution of ethyl 3-(5-cyano-1H-indol-2-yl)propanoate (D30) (200 mg) in EtOH (15 mL), in that sequence. The reaction mixture was heated to 50° C. and stirred for 72 hours at that temperature. Another portion of hydroxylamine hydrochloride (60 mg) was added, followed by addition of sodium bicarbonate (150 mg). The resulting suspension was stirred at 50° C. for 24 hours. The inorganics was filtered off. The solid was washed with dichloromethane. The filtrate was concentrated to afford a pale yellow oil. Trituration of the residue provided ethyl 3-{5-[(hydroxyamino)(imino)methyl]-1H-indol-2-yl}propanoate (D31) (220 mg) as a pale yellow solid.
Description for D32

3-Chloro-4-[(1-methylethyl)oxy]benzoic acid (D32)

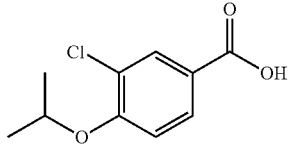

Propan-2-ol (2.45 ml) and $PPh_3$ (1.18 g) were dissolved in THF (30 ml), cooled to 0° C., treated with methyl 3-chloro-4-hydroxybenzoate (6.00 g) followed by the dropwise addition of DIAD (9.44 ml) and stirred at RT overnight. The reaction mixture was then evaporated and purified on silica cartridges (4×100 g), eluting with a 0 to 40% mixture of EtOAc in pentane to give the crude product (7.00 g) as a colourless oil. This was dissolved in MeOH (30 ml) and 2 M aqueous NaOH (30 ml) and stirred at RT for a weekend. The reaction mixture was then evaporated and re-dissolved in $H_2O$. This solution was washed with $Et_2O$, acidified to pH=1 and extracted with $Et_2O$. These latter extracts were dried over $MgSO_4$, filtered and evaporated to give the title compound (4.16 g) as a white solid. δH (MeOD, 400 MHz): 1.37 (6H, d), 4.77 (1H, septet), 7.12 (1H, d), 7.90 (1H, d), 7.98 (1H, s). MS (ES): $C_{10}H_{11}ClO_3$ requires 214; found 215 (MH$^+$).
Alternative Description for D32

3-Chloro-4-[(1-methylethyl)oxy]benzoic acid (D32)

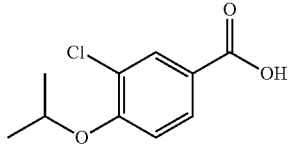

Methyl-4-hydroxy-3-chloro benzoate (13.4 g) was dissolved in DMF (150 ml), treated with $K_2CO_3$ (19.9 g) followed by isopropyl bromide (13.5 ml) and the resultant mixture heated to 70° C. and stirred overnight. The reaction mixture was then cooled to RT, evaporated to dryness, re-dissolved in EtOH, filtered and evaporated once more to give the intermediate ester (22.2 g) as a white solid. This compound was a mixture of ethyl and methyl esters and used crude in the next reaction.

The crude intermediate (22.2 g) was dissolved in MeOH (75 ml), treated with 2M aqueous NaOH (75 ml), heated to 60° C. and stirred for 2 hours. The reaction mixture was then cooled to RT, the MeOH evaporated and the remaining aqueous solution acidified with 5M aqueous HCl (30 ml). The precipitate was filtered off and dried to give the title compound (15.1 g) as a white solid. δH (CDCl$_3$, 400 MHz): 1.42 (6H, d), 4.70 (1H, septet), 6.97 (1H, d), 7.97 (1H, d), 8.12 (1H, s). MS (ES): $C_{10}H_{11}ClO_3$ requires 214; found 213 (M–H$^+$).
Description for D33

Ethyl 3-[5-(5-{3-chloro-4-[(1-methylethyl)oxy]phenyl}-1,2,4-oxadiazol-3-yl)-1H-indol-2-yl]propanoate (D33)

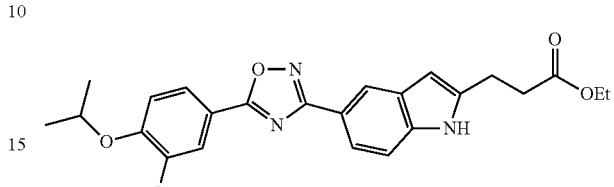

EDCI (144 mg) and HOBT (104 mg) were added to a solution of 3-chloro-4-[(1-methylethyl)oxy]benzoic acid (D32) (150 mg) in DMF (5 mL) at RT. The resulting solution was stirred for 10 min. ethyl 3-{5-[(hydroxyamino)(imino) methyl]-1H-indol-2-yl}propanoate (D31) (193 mg) was added and the reaction mixture was stirred at RT for 1 hour. The reaction mixture was heated to 80° C. and stirred at that temperature for 6 hours. EtOAc (50 mL) was added and the organic solution was washed with water (50 mL), saturated aqueous sodium bicarbonate solution (50 mL), and water (50 mL). The organic fraction was dried over anhydrous magnesium sulfate. The dried solution was concentrated. The residue was recrystallized from ethanol to afford ethyl 3-[5-(5-{3-chloro-4-[(1-methylethyl)oxy]phenyl}-1,2,4-oxadiazol-3-yl)-1H-indol-2-yl]propanoate (D33) (95 mg) as a light pink solid. MS (ES): $C_{24}H_{24}ClN_3O_4$ requires 453; found 454.0 (M+H$^+$).
Description for D34

Ethyl 3-(7-cyano-1H-indol-3-yl)propanoate (D34)

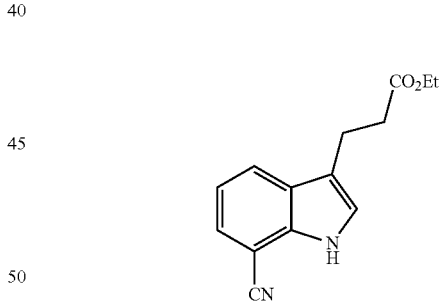

A mixture of 1H-indole-7-carbonitrile (D2) (3.0 g), $FeCl_3$ (3.4 g) and ethyl acrylate (7.5 mL) in DCE (3 mL) was added into 4 tubes respectively. In the fifth tube was added a mixture of 1H-indole-7-carbonitrile (2.0 g), $FeCl_3$ (2.3 g) and ethyl acrylate (5 mL) in DCE (2 mL). The tubes were sealed and heated at 120° C. for 2 hours. After cooling to room temperature, the combined mixture was diluted with DCM and a little amount of THF. The solid was filtered off through celite. The mixture was washed with 0.5 M HCl solution three times and then brine. The organic solution was dried over anhydrous sodium sulfate. After concentration, the residue was purified by flash chromatography to give Ethyl 3-(7-cyano-1H-indol-3-yl)propanoate (13.4 g). δH (CDCl$_3$, 400 MHz): 1.23 (3H, t), 2.70 (2H, t), 3.10 (2H, t), 4.13 (2H, q), 7.16 (2H, m), 7.51 (1H, dd), 7.83 (1H, d), 8.88 (1H, br s).

Description for D35

Ethyl 3-{7-[(Z)-(hydroxyamino)(imino)methyl]-1H-indol-3-yl}propanoate (D35)

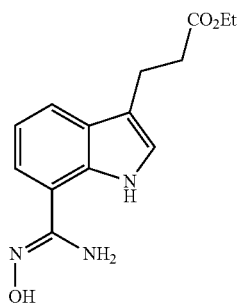

A mixture of ethyl 3-(7-cyano-1H-indol-3-yl)propanoate (D34) (13.4 g), sodium bicarbonate (19.8 g) and hydroxylamine hydrochloride (13.1 g) in ethanol (100 mL) was heated at reflux overnight. The inorganic precipitate was filtered off. The solid was washed thoroughly with ethanol. The filtrate was concentrated. The obtained solid was dried in vacuo to afford ethyl 3-{7-[(Z)-(hydroxyamino)(imino)methyl]-1H-indol-3-yl}propanoate (15.7 g). MS (ES): $C_{14}H_{17}N_3O_3$ requires 275; found 276.1 (M+H$^+$).

Description for D36

Ethyl 3-[7-(5-{5-chloro-6-[(1-methylethyl)oxy]-3-pyridinyl}-1,2,4-oxadiazol-3-yl)-1H-indol-3-yl]propanoate (D36)

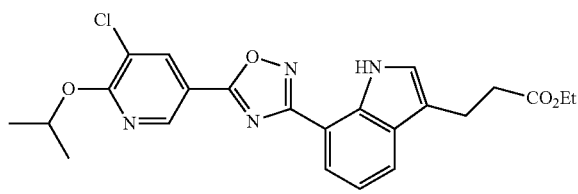

EDCI (189 mg) and HOBT (162 mg) were added to a solution of 5-chloro-6-[(1-methylethyl)oxy]-3-pyridinecarboxylic acid (105 mg) in THF (2.5 mL), The mixture was stirred at room temperature for 0.5 hour, followed by addition of ethyl 3-{7-[(Z)-(hydroxyamino)(imino)methyl]-1H-indol-3-yl}propanoate (D35) (200 mg) in THF (2.5 mL). The resulting mixture was stirred for 1 hour, followed by addition of TBAF (512 mg). The reaction vessel was sealed and stirred at 120° C. in the microwave for 1.5 hour. THF was removed. The residue was dissolved in EtOAc. The organic solution was washed with saturated aqueous sodium bicarbonate solution. The organic solution was dried over anhydrous sodium sulfate. The dried solution was concentrated. The residue was purified by column chromatography to afford ethyl 3-[7-(5-{5-chloro-6-[(1-methylethyl)oxy]-3-pyridinyl}-1,2,4-oxadiazol-3-yl)-1H-indol-3-yl]propanoate (D36) (180 mg) as a white solid. δH (DMSO-d$_6$, 400 MHz): 1.16 (3H, t), 1.40 (6H, d), 2.71 (2H, t), 3.03 (2H, t), 4.06 (2H, q), 5.46 (1H, m), 7.22 (1H, t), 7.28 (1H, d), 7.83 (1H, d), 7.94 (1H, d), 8.76 (1H, d), 9.06 (1H, d), 10.91 (1H, s);

Description for D37

Ethyl 3-(7-{5-[6-[(1-methylethyl)oxy]-5-(trifluoromethyl)-3-pyridinyl]-1,2,4-oxadiazol-3-yl}-1H-indol-3-yl)propanoate (D37)

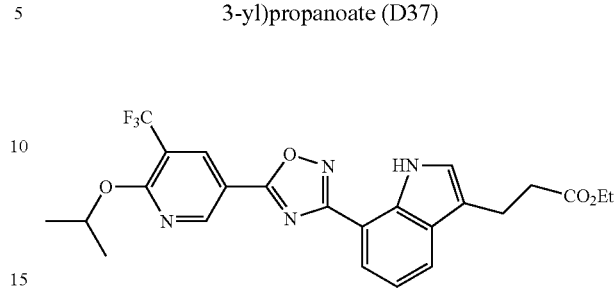

EDCI (153 mg) and HOBT (132 mg) were added to a solution of 6-[(1-methylethyl)oxy]-5-(trifluoromethyl)-3-pyridinecarboxylic acid (100 mg) in THF (2.5 mL). The mixture was stirred at room temperature for 0.5 hour, followed by addition of ethyl 3-{7-[(Z)-(hydroxyamino)(imino)methyl]-1H-indol-3-yl}propanoate (D35) (165 mg) in THF (2.5 mL). The resulting mixture was stirred at room temperature for 1 hour, followed by addition of TBAF (418 mg). The reaction vessel was sealed and the reaction mixture was stirred at 120° C. in the microwave for 1.5 h. THF was removed. The residue was dissolved in EtOAc. The organic solution was washed with saturated aqueous sodium bicarbonate solution. The organic solution was dried over anhydrous sodium sulfate. The dried solution was concentrated. The residue was purified by column chromatography to afford ethyl 3-(7-{5-[6-[(1-methylethyl)oxy]-5-(trifluoromethyl)-3-pyridinyl]-1,2,4-oxadiazol-3-yl}-1H-indol-3-yl)propanoate (D37) (83 mg) as a white solid. δH (CDCl$_3$, 400 MHz): 1.24 (3H, t), 1.45 (6H, d), 2.74 (2H, t), 3.17 (2H, t), 4.15 (2H, q), 5.58 (1H, m), 7.19 (1H, d), 7.29 (1H, d), 7.82 (1H, d), 8.12 (1H, dd), 8.64 (1H, d), 9.17 (1H, d), 9.55 (1H, s); MS (ES): $C_{24}H_{23}F_3N_4O_4$ requires 488; found 489.2 (M+H$^+$).

Description for D38

Ethyl 3-(7-{5-[6-[(1-methylethyl)oxy]-5-(methyloxy)-3-pyridinyl]-1,2,4-oxadiazol-3-yl}-1H-indol-3-yl)propanoate (D38)

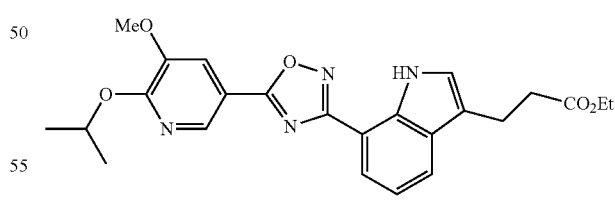

EDCI (289 mg) and HOBT (220 mg) were added to a solution of 6-[(1-methylethyl)oxy]-5-(methyloxy)-3-pyridinecarboxylic acid (152 mg) in THF (3 mL) at RT. The resulting solution was stirred for 30 mins. Ethyl 3-{7-[(Z)-(hydroxyamino)(imino)methyl]-1H-indol-3-yl}propanoate (D35) (250 mg) in THF (3 mL) was added and the reaction mixture was stirred at RT for 2 hours. TBAF (910 mg) was then added. The reaction vessel was sealed and heated in Biotage Initiator using initial normal to 120° C. for 90 mins.

After cooling, the reaction was quenched with water, and extracted with EtOAc for 3 times. The combined organic solution was washed with brine, dried over anhydrous sodium sulfate. The dried solution was concentrated. The residue was purified by column chromatography (20% EtOAc in hexane) to afford ethyl 3-(7-{5-[6-[(1-methylethyl)oxy]-5-(methyloxy)-3-pyridinyl]-1,2,4-oxadiazol-3-yl}-1H-indol-3-yl)propanoate (D38) (286 mg) as a pale yellow solid. MS (ES): $C_{24}H_{26}N_4O_5$ requires 450; found 451.2 (M+H$^+$).

Description for D39

1-Bromo-4-fluoro-2-nitrobenzene (D39)

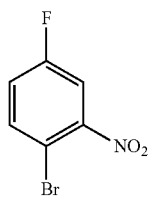

1-Bromo-4-fluorobenzene (50.0 g) was added to concentrated sulfuric acid (200 mL) slowly at 0° C., followed by slow addition of KNO$_3$ (43.3 g). The resulting mixture was stirred at 0° C. for 1 hour. TLC indicated the reaction was complete. The reaction mixture was poured onto ice slowly, and extracted with EtOAc (3×200 mL). The organic solution was dried over anhydrous sodium sulfate. The dried solution was concentrated to afford 1-bromo-4-fluoro-2-nitrobenzene (D39) (52.0 g) as colorless oil.

Description for D40

7-Bromo-4-fluoro-1H-indole (D40)

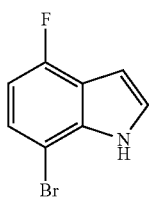

Vinylmagnesium bromide (1 M in THF, 681.5 mL) was added to a solution of 1-bromo-4-fluoro-2-nitrobenzene (D39) (52.0 g) in anhydrous THF (500 mL) dropwise at −78° C. The mixture was allowed to warm to room temperature and stirred for 2 hours. TLC indicated the reaction was complete. The reaction mixture was poured into saturated aqueous NH$_4$Cl solution. The mixture was extracted with EtOAc (3×200 mL). The organic solution was dried over anhydrous sodium sulfate. The dried solution was concentrated. The residue was purified by column chromatography on silica gel to afford 7-bromo-4-fluoro-1H-indole (D40) (20.0 g) as a white solid.

Description for D41

4-Fluoro-1H-indole-7-carbonitrile (D41)

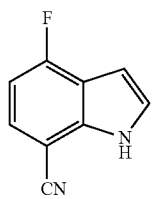

To a solution of 7-bromo-4-fluoro-1H-indole (D40) (20.0 g) in DMF (250 mL) under N$_2$ atmosphere were added Zn(CN)$_2$ (44.0 g) and then Pd(PPh$_3$)$_4$ (20.0 g). The reaction mixture was heated at 120° C. overnight. After cooling, DCM (700 mL) was added to the resulting mixture. The mixture was filtered. Then DCM (1.0 L) and H$_2$O (1.5 L) were added to the filtrate. The organic phase was separated and the aqueous phase was extracted with DCM. The combined organic layers were washed with H$_2$O, dried over anhydrous sodium sulfate and then concentrated. The residue was purified by column chromatography on silical gel to afford 4-fluoro-1H-indole-7-carbonitrile (D41) as a white solid (11.5 g).

Description for D42

4-Fluoro-3-formyl-1H-indole-7-carbonitrile (D42)

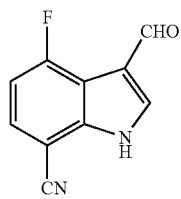

To a solution of (COCl)$_2$ (16.0 g) in DCM (200 mL) at 0° C. was added a solution of DMF (6 mL) in DCM (50 mL) dropwise. Half an hour later, a solution of 4-fluoro-1H-indole-7-carbonitrile (D41) (11.0 g) in DCM (60 mL) was added. The reaction was allowed to warm to RT to form a yellow precipitate. After 6 h the solvent was removed by evaporation. Then THF (100 mL) and 2M aqueous NaOH (100 L) were added to the residue obtained above. After being stirred for about 1 hour, EtOAc (1 L) was added. The organic phase was separated and the aqueous phase was extracted with EtOAc. The combined organic solution was dried over anhydrous sodium sulfate. The dried solution was concentrated to afford 4-fluoro-3-formyl-1H-indole-7-carbonitrile (D42) as a yellow solid (11.0 g).

Description for D43

Ethyl (2E)-3-(7-cyano-4-fluoro-1H-indol-3-yl)-2-propenoate (D43)

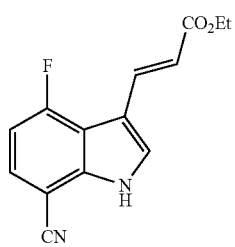

To a mixture of 4-fluoro-3-formyl-1H-indole-7-carbonitrile (D42) (9.0 g) in CH$_3$CN (120 mL) was added ethyl (triphenylphosphoranyliden)acetate (25.0 g). The reaction was heated at reflux overnight. After the mixture was filtered, the filtrate was concentrated and purified by preparative TLC to afford ethyl (2E)-3-(7-cyano-4-fluoro-1H-indol-3-yl)-2-propenoate (D43) (9.2 g) as a yellow solid.

Description for D44

Ethyl 3-(7-cyano-4-fluoro-1H-indol-3-yl)propanoate (D44)

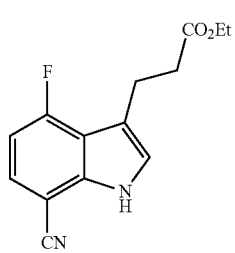

A solution of ethyl (2E)-3-(7-cyano-4-fluoro-1H-indol-3-yl)-2-propenoate (D43) (10.0 g) in THF (100 mL) under H$_2$ (30 psi) atmosphere was hydrogenated by using the catalyst of Pd/C (with 50% water, 3.0 g). The reaction was stirred for about 6 hours. TLC showed the starting material was completely consumed. Then Pd/C was removed by filtration. The filtrate was concentrated. The residue was purified by column chromatography on silical gel to afford ethyl 3-(7-cyano-4-fluoro-1H-indol-3-yl)propanoate (D44) (6.0 g) as a white solid. δH (CDCl$_3$, 400 MHz): 1.25 (3H, t), 2.72 (2H, t), 3.18 (2H, t), 4.14 (2H, q), 6.82 (1H, t), 7.10 (1H, s), 7.45 (1H, q), 8.88 (1H, s). MS (ES): C$_{14}$H$_{13}$FN$_2$O$_2$ requires 260; found 261.1 (M+H$^+$).

Description for D45

Ethyl 3-{4-fluoro-7-[(Z)-(hydroxyamino)(imino)methyl]-1H-indol-3-yl}propanoate (D45)

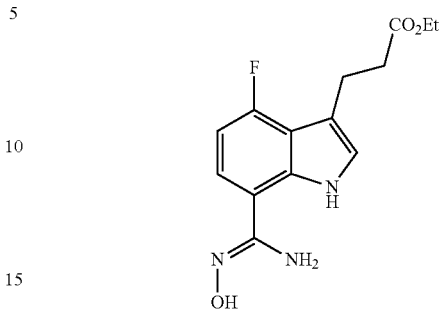

Hydroxylamine hydrochloride (1.1 g) and sodium bicarbonate (2.0 g) were added to a solution of ethyl 3-(7-cyano-4-fluoro-1H-indol-3-yl)propanoate (D44) (2.0 g) in ethanol (60 mL). The reaction mixture was stirred at 90° C. overnight. After cooling, the inorganic precipitate was filtered off. The solid was washed with washed with EtOH. The filtrate was concentrated to afford ethyl 3-{4-fluoro-7-[(Z)-(hydroxyamino)(imino)methyl]-1H-indol-3-yl}propanoate (D45) (2.7 g) as a yellow oil. MS (ES): C$_{14}$H$_{16}$FN$_3$O$_3$ requires 293; found 294.2 (M+H$^+$).

Description for D46

Ethyl 3-[7-(5-{3-chloro-4-[(1-methylethyl)oxy]phenyl}-1,2,4-oxadiazol-3-yl)-4-fluoro-1H-indol-3-yl]propanoate (D46)

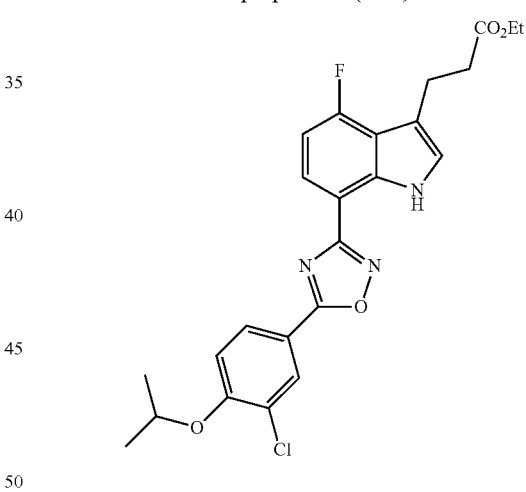

HOBT (166 mg) and EDCI (199 mg) were added to a solution of 3-chloro-4-[(1-methylethyl)oxy]benzoic acid (115 mg) in THF (4 mL). The reaction mixture was stirred at RT for 2 hours. Ethyl 3-{4-fluoro-7-[(Z)-(hydroxyamino)(imino)methyl]-1H-indol-3-yl}propanoate (D45) (205 mg) in THF (4 mL) was added. Then stirring continued overnight. TBAF (760 mg) was then added. The reaction vessel was sealed and heated in Biotage Initiator using initial normal to 120° C. for 3 hours. After cooling, the reaction was quenched with water, and extracted with EtOAc for 3 times. The combined organic solution was washed with brine, and dried over anhydrous sodium sulfate. The dried solution was concentrated. The residue was purified by column chromatography (15% EtOAc in hexane) to afford ethyl 3-[7-(5-{3-chloro-4-[(1-methylethyl)oxy]phenyl}-1,2,4-oxadiazol-3-yl)-4-fluoro-1H-indol-3-yl]propanoate (D46) (216 mg) as a pale yellow solid. δH (CDCl$_3$, 400 MHz): 1.25 (3H, t), 1.47 (6H, d), 2.76 (2H, t), 3.24 (2H, t), 4.14 (2H, q), 4.74 (1H, m), 6.91

(1H, dd), 7.09 (1H, d), 7.14 (1H, d), 8.04 (1H, dd), 8.10 (1H, dd), 8.28 (1H, d), 9.71 (1H, br s). MS (ES): $C_{24}H_{23}ClFN_3O_4$ requires 471; found 472.2 (M+H$^+$).

Description for D47

3-[7-(5-{3-Cyano-4-[(1-methylethyl)oxy]phenyl}-1,2,4-oxadiazol-3-yl)-4-fluoro-1H-indol-3-yl]propanoate (D47)

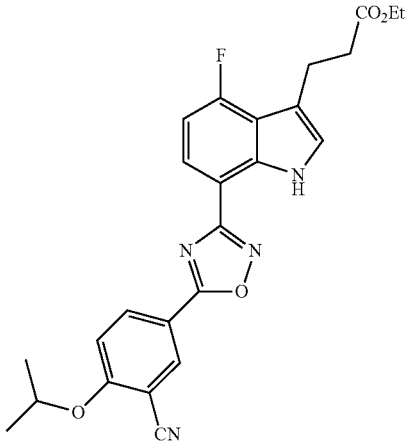

HOBT (149 mg) and EDCI (187 mg) were added to a solution of 3-cyano-4-[(1-methylethyl)oxy]benzoic acid (100 mg) in THF (4 mL). The resulting solution was stirred for 2 h. Ethyl 3-{4-fluoro-7-[(Z)-(hydroxyamino)(imino)methyl]-1H-indol-3-yl}propanoate (D45) (186 mg) in THF (4 mL) was added. The reaction mixture was stirred at RT overnight. TBAF (612 mg) was then added. The reaction vessel was sealed and heated in Biotage Initiator using initial normal to 120° C. for 2.5 hours. After cooling, the reaction was quenched with water, and extracted with EtOAc for 3 times. The combined organic solution was washed with brine, and dried over anhydrous sodium sulfate. The dried solution was concentrated. The residue was purified by column chromatography (25% EtOAc in hexane) to afford ethyl 3-[7-(5-{3-cyano-4-[(1-methylethyl)oxy]phenyl}-1,2,4-oxadiazol-3-yl)-4-fluoro-1H-indol-3-yl]propanoate (D47) (203 mg) as a pale yellow solid. MS (ES): $C_{25}H_{23}FN_4O_4$ requires 462; found 463.2 (M+H$^+$).

Description for D48

Ethyl 3-[7-(5-{5-chloro-6-[(1-methylethyl)oxy]-3-pyridinyl}-1,2,4-oxadiazol-3-yl)-4-fluoro-1H-indol-3-yl]propanoate (D48)

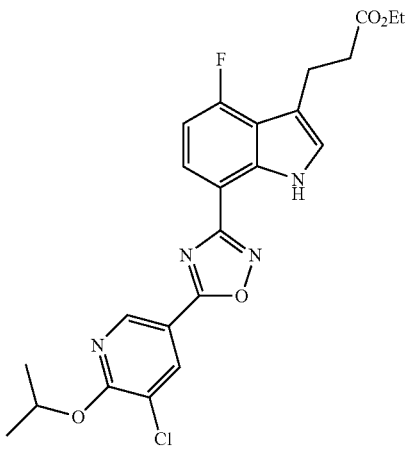

HOBT (163 mg) and EDCI (204 mg) were added to a solution of 5-chloro-6-[(1-methylethyl)oxy]-3-pyridinecarboxylic acid (118 mg) in THF (4 mL). The resulting solution was stirred for 2 hours. Ethyl 3-{4-fluoro-7-[(Z)-(hydroxyamino)(imino)methyl]-1H-indol-3-yl}propanoate (D45) (208 mg) in THF (4 mL) was added, and the reaction mixture was stirred at RT overnight. TBAF (780 mg) was then added. The reaction vessel was sealed and heated in Biotage Initiator using initial normal to 120° C. for 2.5 hours. After cooling, the reaction was quenched with water, and extracted with EtOAc for 3 times. The combined organic solution was washed with brine, and dried over anhydrous sodium sulfate. The dried solution was concentrated. The residue was purified by column chromatography (10% EtOAc in hexane) to afford ethyl 3-[7-(5-{5-chloro-6-[(1-methylethyl)oxy]-3-pyridinyl}-1,2,4-oxadiazol-3-yl)-4-fluoro-1H-indol-3-yl]propanoate (D48) (224 mg) as a pale yellow solid. δH (CDCl$_3$, 400 MHz): 1.25 (3H, t), 1.46 (6H, d), 2.76 (2H, t), 3.24 (2H, t), 4.14 (2H, q), 5.51 (1H, m), 6.91 (1H, dd), 7.15 (1H, d), 8.04 (1H, dd), 8.43 (1H, d), 8.91 (1H, d), 9.67 (1H, br s). MS (ES): $C_{23}H_{22}ClFN_4O_4$ requires 472; found 473.2 (M+H$^+$).

Description for D49

Ethyl 3-(4-fluoro-7-{5-[6-[(1-methylethyl)oxy]-5-(trifluoromethyl)-3-pyridinyl]-1,2,4-oxadiazol-3-yl}-1H-indol-3-yl)propanoate (D49)

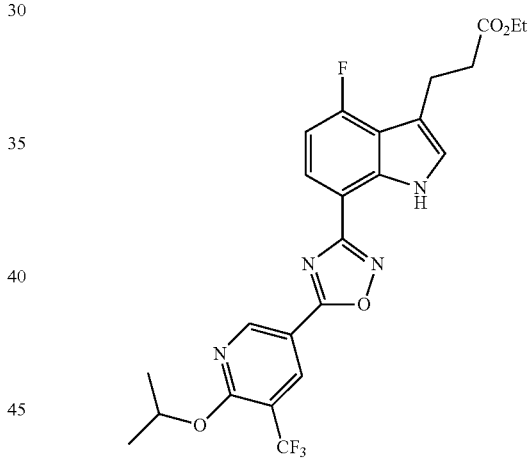

HOBT (161 mg) and EDCI (203 mg) were added to a solution of 6-[(1-methylethyl)oxy]-5-(trifluoromethyl)-3-pyridinecarboxylic acid (132 mg) in THF (4 mL). The resulting solution was stirred for 2 hours. Ethyl 3-{4-fluoro-7-[(Z)-(hydroxyamino)(imino)methyl]-1H-indol-3-yl}propanoate (D45) (210 mg) in THF (4 mL) was added, and the reaction mixture was stirred at RT overnight. TBAF (770 mg) was then added. The reaction vessel was sealed and heated in Biotage Initiator using initial normal to 120° C. for 2.5 hours. After cooling, the reaction was quenched with water, and extracted with EtOAc for 3 times. The combined organic solution was washed with brine, and dried over anhydrous sodium sulfate. The dried solution was concentrated. The residue was purified by column chromatography (10% EtOAc in hexane) to afford ethyl 3-(4-fluoro-7-{5-[6-[(1-methylethyl)oxy]-5-(trifluoromethyl)-3-pyridinyl]-1,2,4-oxadiazol-3-yl}-1H-indol-3-yl)propanoate (D49) (162 mg) as a pale white solid. δH (CDCl$_3$, 400 MHz): 1.25 (3H, t), 1.46 (6H, d), 2.76 (2H, t), 3.24 (2H, t), 4.15 (2H, q), 5.59 (1H, m), 6.92 (1H, dd), 7.15

(1H, d), 8.05 (1H, dd), 8.64 (1H, d), 9.17 (1H, d), 9.65 (1H, br s). MS (ES): $C_{24}H_{22}F_4N_4O_4$ requires 506; found 507.2 (M+H$^+$).

Description for D50

Ethyl 3-(4-fluoro-7-{5-[6-[(1-methylethyl)oxy]-5-(methyloxy)-3-pyridinyl]-1,2,4-oxadiazol-3-yl}-1H-indol-3-yl)propanoate (50)

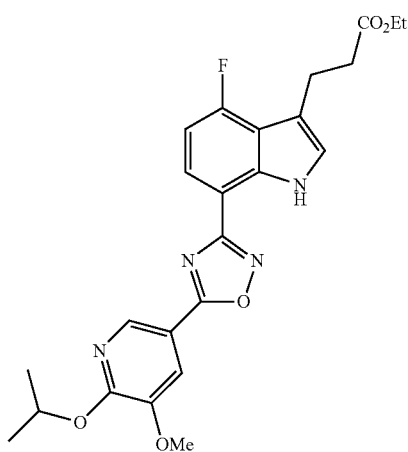

HOBT (161 mg) and EDCI (203 mg) were added to a solution of 6-[(1-methylethyl)oxy]-5-(methyloxy)-3-pyridinecarboxylic acid (110 mg) in THF (4 mL). The resulting solution was stirred for 2 hours. Ethyl 3-{4-fluoro-7-[(Z)-(hydroxyamino)(imino)methyl]-1H-indol-3-yl}propanoate (D45) (199 mg) in THF (4 mL) was added, and the reaction mixture was stirred at RT overnight. TBAF (780 mg) was then added. The reaction vessel was sealed and heated in Biotage Initiator using initial normal to 120° C. for 2.5 hours. After cooling, the reaction was quenched with water, and extracted with EtOAc for 3 times. The combined organic solution was washed with brine, and dried over anhydrous sodium sulfate. The dried solution was concentrated. The residue was purified by column chromatography (10% EtOAc in hexane) to afford ethyl 3-(4-fluoro-7-{5-[6-[(1-methylethyl)oxy]-5-(methyloxy)-3-pyridinyl]-1,2,4-oxadiazol-3-yl}-1H-indol-3-yl)propanoate (D50) (158 mg) as a white solid. δH (CDCl$_3$, 400 MHz): 1.25 (3H, t), 1.47 (6H, d), 2.76 (2H, t), 3.24 (2H, t), 4.01 (3H, s), 4.15 (2H, q), 5.55 (1H, m), 6.91 (1H, dd), 7.14 (1H, d), 7.76 (1H, d), 8.06 (1H, dd), 8.64 (1H, d), 9.69 (1H, br s). MS (ES): $C_{24}H_{25}FN_4O_5$ requires 468; found 469.2 (M+H$^+$).

Description for D51

7-(5-{3-chloro-4-[(1-methylethyl)oxy]phenyl}-1,2,4-oxadiazol-3-yl)-1H-indole (D51)

To a solution of 3-chloro-4-[(1-methylethyl)oxy]benzoic acid (D32) (5.2 g) in tetrahydrofuran (15 mL) stirred at room temp was added EDCI (5.8 g) and HOBT (4.6 g). The reaction mixture was stirred at room temperature for 2 h. Then N-hydroxy-1H-indole-7-carboximidamide (3.5 g) was added. The reaction mixture was stirred at 60° C. for 2 h, and then TBAF (15.7 g) was added. The reaction vessel was sealed and heated in Biotage Initiator using initial normal to 130° C. for 3 h. After cooling the reaction, solvent was removed. Water (200 mL) and ethanol (50 mL) was added. The precipitate was collected, washed with acetonitrile and dried in vacuo to afford 7-(5-{3-chloro-4-[(1-methylethyl)oxy]phenyl}-1,2,4-oxadiazol-3-yl)-1H-indole (D51) (5.1 g) as a yellow solid. δH (CDCl$_3$, 400 MHz): 1.47 (6H, d), 4.70-4.76 (1H, m), 6.68 (1H, dd), 7.08 (1H, d), 7.29 (1H, t), 7.40 (1H, t), 7.85 (1H, d), 8.11 (1H, dd), 8.13 (1H, dd), 8.30 (1H, d), 9.86 (1H, s). MS (ES): $C_{19}H_{16}ClN_3O_2$ requires 353; found 354.1 (M+H$^+$)

Description for D52

Ethyl 4-[7-(5-{3-chloro-4-[(1-methylethyl)oxy]phenyl}-1,2,4-oxadiazol-3-yl)-1H-indol-3-yl]-4-oxobutanoate (D52)

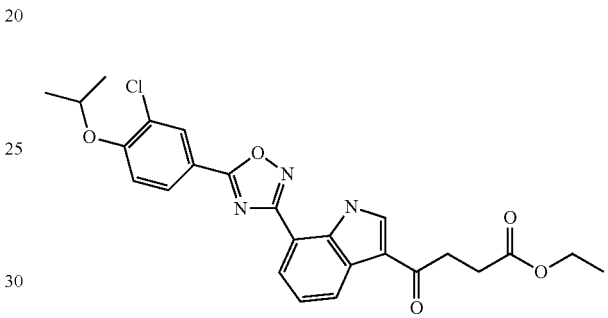

To a stirred suspension of 7-(5-{3-chloro-4-[(1-methylethyl)oxy]phenyl}-1,2,4-oxadiazol-3-yl)-1H-indole (D51) (0.5 g) and ZnCl$_2$ (1.0 g) in DCM (50 mL) was added a solution of ethyl 4-chloro-4-oxobutanoate (2.3 g) in DCM (5 mL) dropwise. After stirring at room temperature overnight, the reaction mixture was washed with water and brine. The organic phase was separated and dried over anhydrous sodium sulphate. Filtration and concentration under vacuum afforded the crude product ethyl 4-[7-(5-{3-chloro-4-[(1-methylethyl)oxy]phenyl}-1,2,4-oxadiazol-3-yl)-1H-indol-3-yl]-4-oxobutanoate (D52) as a brown solid (0.5 g). δH (CDCl$_3$, 400 MHz): 1.27 (3H, t), 1.46 (6H, d), 2.68 (2H, t), 2.83 (2H, t), 3.29 (2H, q), 4.73 (1H, m), 7.07 (1H, d), 7.42 (1H, t), 8.06 (1H, s), 8.08 (1H, dd), 8.16 (1H, dd), 8.26 (1H, dd), 8.56 (1H, d), 10.27 (1H, s). MS (ES): $C_{25}H_{24}ClN_3O_5$ requires 481; found 482.2 (M+H$^+$).

Description for D53

Ethyl 4-[7-(5-{3-chloro-4-[(1-methylethyl)oxy]phenyl}-1,2,4-oxadiazol-3-yl)-1H-indol-3-yl]butanoate (D53)

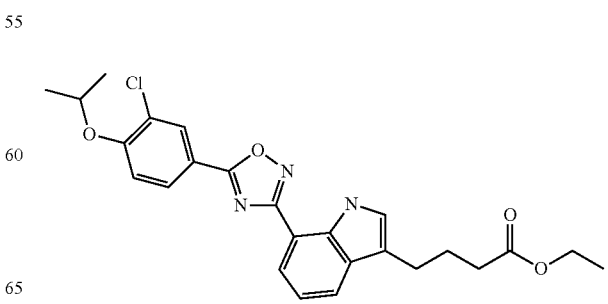

To a solution of ethyl 4-{7-[5-(3-chloro-4-isopropoxyphenyl)-1,2,4-oxadiazol-3-yl]-1H-indol-3-yl}-4-oxobutanoate (D52) (300 mg) and TFA (5 mL) in ethanol (15 mL) and DCM (15 mL) was added sodium cyanoborohydride (235 mg) in portions. The reaction mixture was stirred at 20° C. for 4 days. The mixture was diluted with DCM (30 mL) and washed with water. The organic phase was separated and dried over anhydrous sulphate. After filtration, the solvent was evaporated to give the crude product, which was purified by preparative TLC separation to afford ethyl 4-[7-(5-{3-chloro-4-[(1-methylethyl)oxy]phenyl}-1,2,4-oxadiazol-3-yl)-1H-indol-3-yl]butanoate (D53) as a white solid (150 mg). MS (ES): $C_{25}H_{26}ClN_3O_4$ requires 467; found 468.2 (M+H$^+$).

Description for D54

Ethyl (4E/Z)-5-(7-cyano-1H-indol-3-yl)-4-pentenoate (D54)

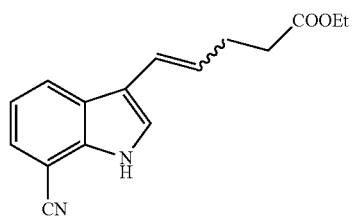

LDA (1.0 mol/L in THF, 20 mL) was added dropwise to a suspension of ethyl 4-[bromo(triphenyl)-λ-phosphanyl]butanoate (4.6 g) at −78° C. After the addition, the reaction mixture was stirred for 1 hour at −78° C. 3-formyl-1H-indole-7-carbonitrile (0.9 g) was added to the above reaction mixture in one portion. The reaction mixture was warmed to room temperature slowly and stirred overnight and then quenched with saturated NH$_4$Cl solution. EtOAc (100 mL) was added and the organic layer was separated and washed with water and brine, dried over MgSO$_4$. After the solvent was evaporated off the residue was purified by column chromatography (10% EtOAc in hexane) to afford ethyl (4E/Z)-5-(7-cyano-1H-indol-3-yl)-4-pentenoate (D54) (349 mg) as a yellow solid. MS (ES): $C_{16}H_{16}N_2O_2$ requires 268; found 269.2 (M+H$^+$).

Description for D55

Ethyl 5-{7-[(E)-(hydroxyamino)(imino)methyl]-1H-indol-3-yl}pentanoate (D55)

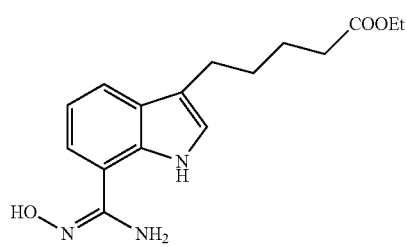

Ethyl (4E/Z)-5-(7-cyano-1H-indol-3-yl)-4-pentenoate (D54) (349 mg) in ethanol (250 mL) was hydrogenated using the H-cube (full mode) with a 10% Pd—C cartridge (flow rate: 2.6 mL/min). After the hydrogenation was finished, the resulted ethanol solution was concentrated to about 100 mL. Then hydroxylamine hydrochloride (278 mg) and sodium bicarbonate (672 mg) was added to the above solution. The reaction mixture was stirred at 70° C. for 24 hours. The inorganic precipitate was filtered off. The solid was washed with CH$_2$Cl$_2$ (20 mL). The filtrate was concentrated to afford ethyl 5-{7-[(E)-(hydroxyamino)(imino)methyl]-1H-indol-3-yl}pentanoate (D55) (390 mg) as a yellow oil. MS (ES): $C_{16}H_{21}N_3O_3$ requires 303; found 304.2 (M+H$^+$).

Description for D56

Ethyl 5-[7-(5-{3-chloro-4-[(1-methylethyl)oxy]phenyl}-1,2,4-oxadiazol-3-yl)-1H-indol-3-yl]pentanoate (D56)

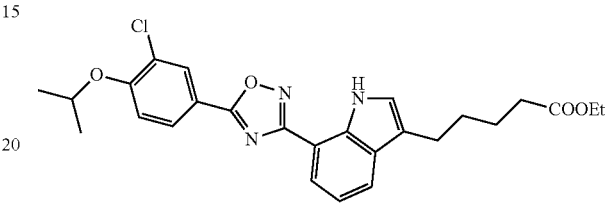

To a solution of 3-chloro-4-[(1-methylethyl)oxy]benzoic acid (279 mg) in tetrahydrofuran (40 mL) stirred at room temp was added EDC (479 mg) and HOBT (363 mg). The reaction mixture was stirred at room temperature for 2 h. Then ethyl 5-{7-[(E)-(hydroxyamino)(imino)methyl]-1H-indol-3-yl}pentanoate (D55) (390 mg) was added. The reaction mixture was stirred at 60° C. for 1 h, and then TBAF (1.0 mol/L in THF, 5 mL) was added. The reaction solution was concentrated and transferred to a microwave vessel. The reaction vessel was sealed and heated in Biotage Initiator using initial normal to 145° C. for 3 h. After cooling the reaction, the solvent was removed and the residue was purified by Mass Directed AutoPrep to afford ethyl 5-[7-(5-{3-chloro-4-[(1-methylethyl)oxy]phenyl}-1,2,4-oxadiazol-3-yl)-1H-indol-3-yl]pentanoate (D56) (120 mg) as a yellow solid. δH (CDCl$_3$, 400 MHz): 1.25 (3H, t), 1.45 (6H, d), 1.75-1.78 (4H, m), 2.37 (2H, t), 2.84 (2H, t), 4.14 (2H, q), 4.68-4.74 (1H, m), 7.05 (1H, d), 7.14-7.15 (1H, m), 7.25 (1H, t), 8.08 (1H, dd), 8.09 (1H, dd), 8.27 (1H, d), 9.58 (1H, s). MS (ES): $C_{26}H_{28}ClN_3O_4$ requires 481; found 482.2 (M+H$^+$).

Description for D57

Ethyl 4-[7-(5-{3-chloro-4-[(1-methylethyl)oxy]phenyl}-1,2,4-oxadiazol-3-yl)-1-methyl-1H-indol-3-yl]butanoate (D57)

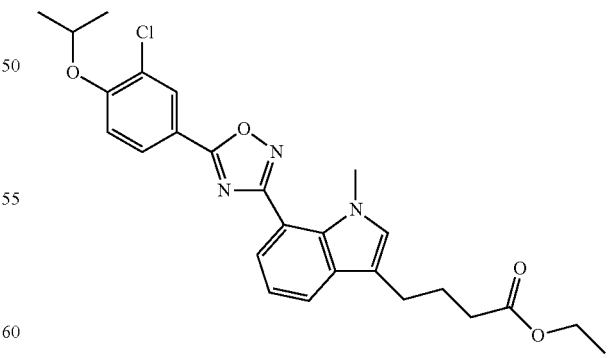

To a solution of ethyl 4-[7-(5-{3-chloro-4-[(1-methylethyl)oxy]phenyl}-1,2,4-oxadiazol-3-yl)-1H-indol-3-yl]butanoate (D53) (150 mg) and dimethyl carbonate (5.0 mL) in N,N-dimethylformamide (DMF) (0.5 mL) was added DABCO (18 mg). The reaction vessel was sealed and heated in Biotage Initiator using initial normal to 150° C. for 1.5 h. After cooling the reaction, the mixture was concentrated to afford the crude product ethyl 4-[7-(5-{3-chloro-4-[(1-methylethyl)oxy]phenyl}-1,2,4-oxadiazol-3-yl)-1-methyl-1H-indol-3-yl]butanoate (D57) (180 mg), which was used for the next hydrolysis step without further purification. MS (ES): $C_{26}H_{28}ClN_3O_4$ requires 481. found 482.2 (M+H$^+$).
Description for D58

7-(5-{3-chloro-4-[(1-methylethyl)oxy]phenyl}-1,2,4-oxadiazol-3-yl)-1-methyl-1H-indole (D58)

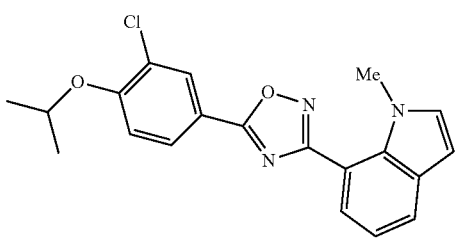

7-(5-{3-chloro-4-[(1-methylethyl)oxy]phenyl}-1,2,4-oxadiazol-3-yl)-1H-indole (D51) (708 mg), DABCO (112 mg), and N,N-Dimethylformamide (4 mL) were added to dimethyl carbonate (10 mL) at room temperature under stirring. The reaction mixture was heated to 130° C. for 36 h. After cooling the reaction, the organic solvent was evaporated off. The residue was purified by column chromatography (25% EtOAc in hexane) to afford 7-(5-{3-chloro-4-[(1-methylethyl)oxy]phenyl}-1,2,4-oxadiazol-3-yl)-1-methyl-1H-indole (D58) (486 mg) as a pale yellow solid. δH (CDCl$_3$, 400 MHz): 1.46 (6H, d), 3.78 (3H, s), 4.71-4.76 (1H, m), 6.60 (1H, d), 7.08 (1H, dd), 7.21 (1H, t), 7.56 (1H, dd), 7.80 (1H, dd), 7.96 (1H, dd), 8.27 (1H, d). MS (ES): $C_{20}H_{15}ClN_3O_2$ requires 367; found 368.1 (M+H$^+$).
Description for D59

3-bromo-7-(5-{3-chloro-4-[(1-methylethyl)oxy]phenyl}-1,2,4-oxadiazol-3-yl)-1-methyl-1H-indole (D59)

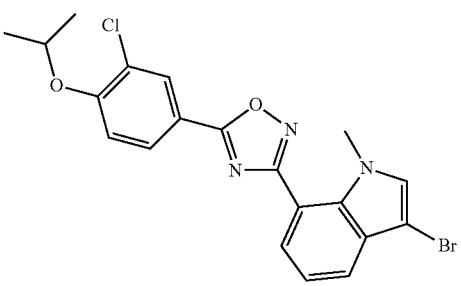

To a solution of 7-(5-{3-chloro-4-[(1-methylethyl)oxy]phenyl}-1,2,4-oxadiazol-3-yl)-1-methyl-1H-indole (D58) (300 mg) in THF (10 mL) was added NBS (160 mg). The reaction mixture was stirred at 20° C. for 16 h. The reaction mixture was concentrated and the residue was purified by column chromatography (15% ethyl acetate in hexane) to afford 3-bromo-7-(5-{3-chloro-4-[(1-methylethyl)oxy]phenyl}-1,2,4-oxadiazol-3-yl)-1-methyl-1H-indole (D59) (330 mg). δH (DMSO-d$_6$, 400 MHz): 1.36 (6H, d), 3.70 (3H, s), 4.88 (1H, m), 7.32 (1H, dd), 7.45 (1H, d), 7.56 (1H, dd), 7.68 (2H, m), 8.12 (1H, dd), 8.20 (1H, d). MS (ES): $C_{20}H_{17}BrClN_3O_2$ requires 445; found 446.0 (M+H$^+$).
Description for D60

Methyl (2R)-3-[7-(5-{3-chloro-4-[(1-methylethyl)oxy]phenyl}-1,2,4-oxadiazol-3-yl)-1-methyl-1H-indol-3-yl]-2-methylpropanoate (D60)

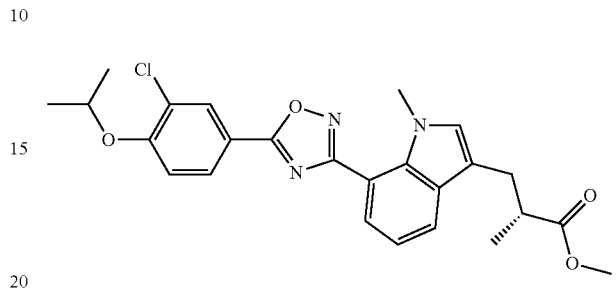

To a suspension of 3-bromo-7-(5-{3-chloro-4-[(1-methylethyl)oxy]phenyl}-1,2,4-oxadiazol-3-yl)-1-methyl-1H-indole (D59) (100 mg), tris(1,1-dimethylethyl)phosphane (13 mg), Pd$_2$(dba)$_3$ (41 mg) and Cs$_2$CO$_3$ (30 mg) in THF (5 mL) stirred under nitrogen at room temperature was added a solution of bromo[(2S)-2-methyl-3-(methyloxy)-3-oxopropyl] zinc (1.0 M in THF, 2 mL) in one portion. The reaction mixture was stirred at 60° C. for 1.5 h. The mixture was cooled to room temperature and filtered. The filtrate was partitioned between ethyl acetate (50 mL) and water (50 mL). The organic phase was washed with water, aqueous HCl (2 M) and brine, dried over sodium sulphate and evaporated to afford methyl (2R)-3-[7-(5-{3-chloro-4-[(1-methylethyl)oxy]phenyl}-1,2,4-oxadiazol-3-yl)-1-methyl-1H-indol-3-yl]-2-methylpropanoate (D60) (120 mg). MS (ES): $C_{25}H_{26}ClN_3O_4$ requires 467; found 468.2 (M+H$^+$).
Description for D61

7-(5-{3-chloro-4-[(1-methylethyl)oxy]phenyl}-1,2,4-oxadiazol-3-yl)-1-methyl-1H-indole-3-carbaldehyde (D61)

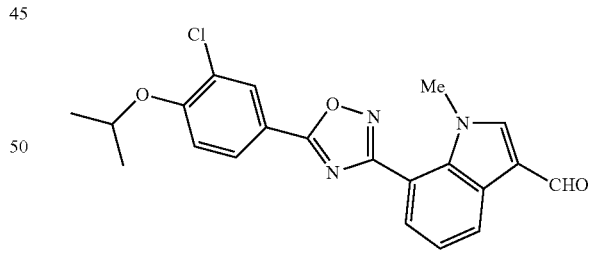

To a solution of oxalyl chloride (2.1 mL) in dichloromethane (125 mL) at 0° C. was added a solution of N,N-dimethylformamide (2.32 mL) in Dichloromethane (DCM) (75 mL) dropwise during 30 mins. The reaction mixture was stirred at 0° C. for another 15 minutes. A solution of 7-(5-{3-chloro-4-[(1-methylethyl)oxy]phenyl}-1,2,4-oxadiazol-3-yl)-1-methyl-1H-indole (D58) (7.4 g) in Dichloromethane (100 mL) was added in one portion. the mixture was stirred and warmed to room temperature slowly. After stirred at room temperature for 5 hours, dichloromethane was evaporated off. Ethyl acetate (300 mL), water (100 mL) and concentrated HCl solution (5 mL) was added to the residue. The mixture was stirred for 30 minutes and KOH was added to adjust pH value to about 8. The organic layer was separated, washed with water and brine, then dried over MgSO$_4$. Filtration and evaporation afforded the product 7-(5-{3-chloro-4-[(1-methylethyl)oxy]phenyl}-1,2,4-oxadiazol-3-yl)-1-methyl-1H-indole-3-carbaldehyde (D61) (5.2 g). δH (CDCl$_3$, 400 MHz): 1.47 (6H, d), 3.87 (3H, s), 4.71-4.77 (1H, m), 7.09 (1H, d), 7.44 (1H, t), 7.68 (1H, dd), 7.72 (1H, s), 7.89 (1H, dd), 8.26 (1H, d), 8.56 (1H, dd), 10.06 (1H, s). MS (ES): C$_{21}$H$_{18}$ClN$_3$O$_3$ requires 395. found 396.1 (M+H$^+$).

Description for D62

Ethyl (2E)-3-[7-(5-{3-chloro-4-[(1-methylethyl)oxy]phenyl}-1,2,4-oxadiazol-3-yl)-1-methyl-1H-indol-3-yl]-2-propenoate (D62)

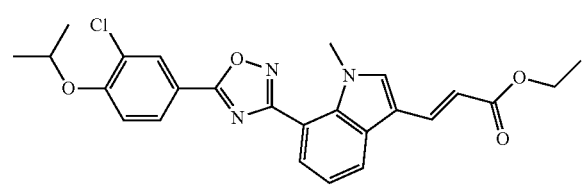

To a solution of 7-(5-{3-chloro-4-[(1-methylethyl)oxy]phenyl}-1,2,4-oxadiazol-3-yl)-1-methyl-1H-indole-3-carbaldehyde (D61) (100 mg) in acetonitrile (15 mL) was added ethyl (triphenyl-λ-phosphanylidene)acetate (176 mg). The reaction mixture was stirred at 90° C. for 24 h. The reaction mixture was cooled to room temperature and concentrated, the residue was purified by column chromatography (10% ethyl acetate in hexane) to afford ethyl (2E)-3-[7-(5-{3-chloro-4-[(1-methylethyl)oxy]phenyl}-1,2,4-oxadiazol-3-yl)-1-methyl-1H-indol-3-yl]-2-propenoate (D62) (110 mg). MS (ES): C$_{25}$H$_{24}$ClN$_3$O$_4$ requires 465; found 466.2 (M+H$^+$).

Description for D63

Methyl (2Z)-3-[7-(5-{3-chloro-4-[(1-methylethyl)oxy]phenyl}-1,2,4-oxadiazol-3-yl)-1-methyl-1H-indol-3-yl]-2-propenoate (D63)

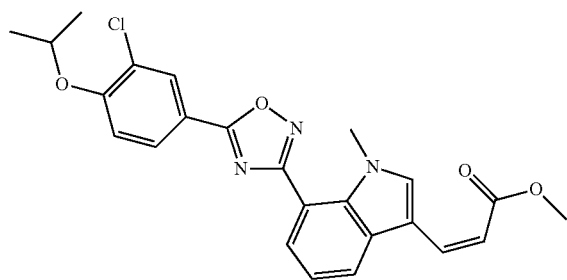

To a solution of methyl {bis[(2,2,2-trifluoroethyl)oxy]phosphoryl}acetate (0.16 mL), 18-crown-6 (1.0 g) in THF (5 mL) stirred under nitrogen at −70° C. was added NaHMDS (1.0 mol/L in THF, 0.8 mL) during 1 min. The reaction mixture was stirred at −70° C. for 10 mins. 7-(5-{3-chloro-4-[(1-methylethyl)oxy]phenyl}-1,2,4-oxadiazol-3-yl)-1-methyl-1H-indole-3-carbaldehyde (200 mg) was added and the mixture was stirred at this temperature for 1.5 h and then left to warm to room temperature overnight. The reaction mixture was quenched with saturated ammonium chloride solution, diluted with water (25 mL) and extracted with ethyl acetate (50 mL). The organic phase was washed with brine, dried over sodium sulphate and evaporated to afford the crude product, which was purified by column chromatography (10% ethyl acetate in hexane) to afford methyl (2Z)-3-[7-(5-{3-chloro-4-[(1-methylethyl)oxy]phenyl}-1,2,4-oxadiazol-3-yl)-1-methyl-1H-indol-3-yl]-2-propenoate (D63) (120 mg). MS (ES): C$_{24}$H$_{22}$ClN$_3$O$_4$ requires 451; found 452.2 (M+H$^+$).

Description for D64

Ethyl-2-[7-(5-{3-chloro-4-[(1-methylethyl)oxy]phenyl}-1,2,4-oxadiazol-3-yl)-1-methyl-1H-indol-3-yl]cyclopropanecarboxylate (D64)

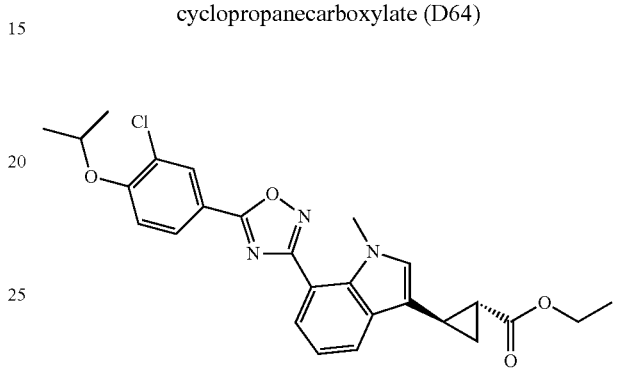

To a suspension of trimethylsulfoxonium iodide (132 mg) in DMSO (3 mL) stirred under nitrogen at 20° C. was added NaHMDS (1.0 mol/L in THF, 0.6 mL) dropwise during 5 mins. The reaction mixture was stirred at this temperature for 15 mins. A solution of ethyl (2E)-3-[7-(5-{3-chloro-4-[(1-methylethyl)oxy]phenyl}-1,2,4-oxadiazol-3-yl)-1-methyl-1H-indol-3-yl]-2-propenoate (D62) (140 mg) in DMSO was added dropwise. After addition was complete, the reaction was stirred at room temperature for 1.5 h, and then warmed to 50° C. for 2 h. The reaction mixture was cooled to room temperature and partitioned between ethyl acetate (25 mL) and water (25 mL). The organic phase was washed with water, aqueous HCl (2 M) and brine, dried over sodium sulphate and evaporated to afford ethyl (1R,2R)-2-[7-(5-{3-chloro-4-[(1-methylethyl)oxy]phenyl}-1,2,4-oxadiazol-3-yl)-1-methyl-1H-indol-3-yl]cyclopropanecarboxylate (D64) (80 mg). MS (ES): C$_{26}$H$_{26}$ClN$_3$O$_4$ requires 479. found 480.2 (M+H$^+$).

Description for D65

Methyl-2-[7-(5-{3-chloro-4-[(1-methylethyl)oxy]phenyl}-1,2,4-oxadiazol-3-yl)-1-methyl-1H-indol-3-yl]cyclopropanecarboxylate (D65)

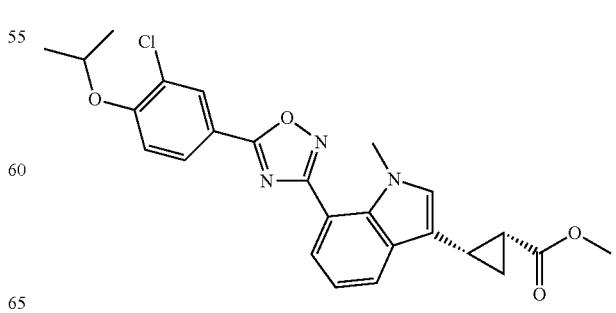

To a suspension of trimethylsulfoxonium iodide (234 mg) in DMSO (3 mL) stirred under nitrogen at 20° C. was added NaHMDS (1.0 mol/L in THF, 1.0 mL) dropwise during 5 mins. The reaction mixture was stirred at this temperature for 15 mins. A solution of methyl (2Z)-3-[7-(5-{3-chloro-4-[(1-methylethyl)oxy]phenyl}-1,2,4-oxadiazol-3-yl)-1-methyl-1H-indol-3-yl]-2-propenoate (D63) (120 mg) in DMSO was added dropwise. After addition was complete, the reaction was stirred at room temperature for 1.5 h, and then warmed to 50° C. for 4 h. The reaction mixture was cooled to room temperature and partitioned between ethyl acetate (25 mL) and water (25 mL). The organic phase was washed with water, aqueous HCl (2 M) and brine, dried over sodium sulphate and evaporated to afford methyl-2-[7-(5-{3-chloro-4-[(1-methylethyl)oxy]phenyl}-1,2,4-oxadiazol-3-yl)-1-methyl-1H-indol-3-yl]cyclopropanecarboxylate (D65) (100 mg). MS (ES): $C_{25}H_{24}ClN_3O_4$ requires 465. found 466.2 (M+H$^+$).

Description for D66

Ethyl 3-(7-{5-[3,4-bis(ethyloxy)phenyl]-1,2,4-oxadiazol-3-yl}-1H-indol-3-yl)propanoate (D66)

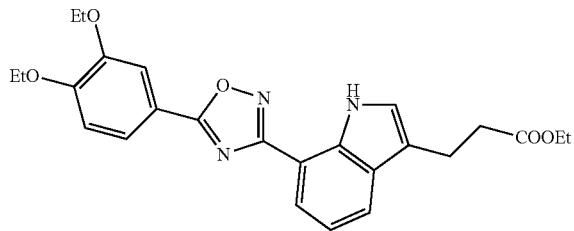

To a solution of 3,4-bis(ethyloxy)benzoic acid (631 mg) in tetrahydrofuran (15 mL) stirred at room temperature was added EDCI (767 mg) and HOBT (613 mg). The reaction mixture was stirred for 2 h. Then ethyl 3-{7-[(Z)-(hydroxyamino)(imino)methyl]-1H-indol-3-yl}propanoate (D35) (551 mg) was added. The reaction mixture was stirred at 60° C. for 2 h, and then TBAF (2092 mg) was added. The reaction vessel was sealed and heated in Biotage Initiator using initial normal to 130° C. for 3 h. After cooling the reaction, the solvent was removed. Water (90 mL) and ethanol (30 mL) was added to the residue, a yellow solid was formed, filtered and dried in vacuo to afford the product ethyl 3-(7-{5-[3,4-bis(ethyloxy)phenyl]-1,2,4-oxadiazol-3-yl}-1H-indol-3-yl)propanoate (D66) (706 mg). δH (CDCl$_3$, 400 MHz): 1.26 (3H, t), 1.52-1.57 (6H, m), 2.76 (2H, t), 3.18 (2H, t), 4.16 (2H, q), 4.19-4.28 (4H, m), 7.02 (1H, d), 7.20 (1H, d), 7.28 (1H, t), 7.74 (1H, d), 7.81 (1H, d), 7.86 (1H, dd), 8.14 (1H, dd), 9.64 (1H, s). MS (ES): $C_{25}H_{27}N_3O_5$ requires 449. found 450.2 (M+H$^+$).

Description for D67

Ethyl 3-(7-{5-[3,4-bis(methyloxy)phenyl]-1,2,4-oxadiazol-3-yl}-1H-indol-3-yl)propanoate (D67)

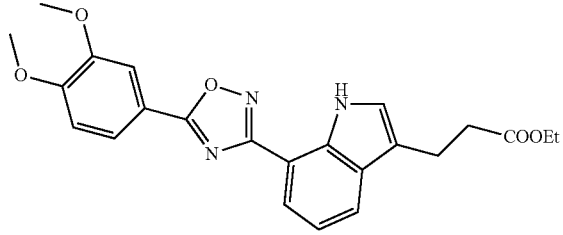

To a solution of 3,4-bis(methyloxy)benzoic acid (547 mg) in tetrahydrofuran (15 mL) stirred at room temp was added EDCI (767 mg) and HOBT (613 mg). The reaction mixture was stirred at room temperature for 2 h. Then ethyl 3-{7-[(Z)-(hydroxyamino)(imino)methyl]-1H-indol-3-yl}propanoate (D35) (551 mg) was added. The reaction mixture was stirred at 60° C. for 2 h, and then TBAF (2092 mg) was added. The reaction vessel was sealed and heated in Biotage Initiator using initial normal to 130° C. for 3 h. After cooling the reaction, the solvent was removed. Water (90 mL) and ethanol (30 mL) was added to the residue, a yellow solid was formed, filtered and dried in vacuo to gave the product ethyl 3-(7-{5-[3,4-bis(methyloxy)phenyl]-1,2,4-oxadiazol-3-yl}-1H-indol-3-yl)propanoate (D67) (658 mg). δH (CDCl$_3$, 400 MHz): 1.27 (3H, t), 2.76 (2H, t), 3.18 (2H, t), 4.01 (3H, s), 4.13 (3H, s), 4.16 (2H, q), 7.04 (1H, d), 7.20 (1H, d), 7.29 (1H, t), 7.74 (1H, d), 7.81 (1H, d), 7.90 (1H, dd), 8.14 (1H, dd), 9.63 (1H, s). MS (ES): $C_{23}H_{23}N_3O_5$ requires 421. found 422.2 (M+H$^+$).

Description for D68

Methyl 3-chloro-4,5-dihydroxybenzoate (D68)

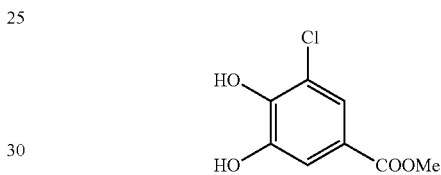

To a suspension of methyl 3,4-dihydroxybenzoate (5.0 g) in diethyl ether (300 mL) stirred at 0° C. was added sulfuryl chloride (3.7 mL) dropwise. The reaction mixture was stirred at 0° C. for 16 h. The solvent was removed in vacuo. The residue was washed with hot chloroform (2×150 mL) to afford methyl 3-chloro-4,5-dihydroxybenzoate (D68) (1.9 g) as a white solid. δH (DMSO-d$_6$, 400 MHz): 3.78 (3H, s), 7.33 (1H, d), 7.37 (1H, d), 10.11 (2H, br s). MS (ES): $C_8H_7ClO_4$ requires 202. found 203.0 (M+H$^+$).

Description for D69

3-chloro-4,5-bis(ethyloxy)benzoic acid (D69)

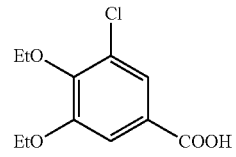

To a solution of methyl 3-chloro-4,5-dihydroxybenzoate (D68) (1.0 g) in acetone (50 mL) stirred at room temp was added K$_2$CO$_3$ (6.9 g) and bromoethane (5.5 g). The reaction mixture was stirred at 60° C. for 18 h. After filteration, the filtrate was concentrated under reduced pressure. The residue was dissolved in tetrahydrofuran (20 mL) and methanol (20 mL), a solution of NaOH (1.0 g) in water (20 mL) was added to the above solution. The resulted mixture was stirred for 4 h and then the organic solvent was removed in vacuo. The aqueous layer was acidified with concentrated HCl to pH around 1. The solid was filtered and dried in vacuo to afford 3-chloro-4,5-bis(ethyloxy)benzoic acid (D69) (769 mg). δH (DMSO-d$_6$, 400 MHz): 1.29 (3H, t), 1.36 (3H, t), 4.08-4.15

(4H, m), 7.46 (1H, d), 7.53 (1H, d), 13.16 (1H, br s). MS (ES): $C_{11}H_{13}ClO_4$ requires 244; found 245.1 (M+H$^+$).

Description for D70

Methyl 3-(7-{5-[3-chloro-4,5-bis(ethyloxy)phenyl]-1,2,4-oxadiazol-3-yl}-1H-indol-3-yl)propanoate (D70)

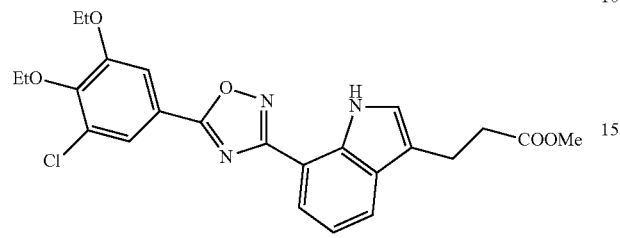

To a solution of 3-chloro-4,5-bis(ethyloxy)benzoic acid (D69) (184 mg) in tetrahydrofuran (10 mL) stirred at room temperature was added EDCI (192 mg) and HOBT (153 mg). The reaction mixture was stirred for 2 h, followed by addition of methyl 3-{7-[(Z)-(hydroxyamino)(imino)methyl]-1H-indol-3-yl}propanoate (D35) (131 mg). The reaction mixture was stirred at 60° C. for another 2 h, and then TBAF (523 mg) was added. The reaction vessel was sealed and heated in Biotage Initiator using initial normal to 130° C. for 3 h. After cooling the reaction, the solvent was removed. Water (10 mL) and ethyl acetate (30 mL) was added, the organic layer was separated and the solvent was evaporated off. The residue was purified by Mass Directed Auto Prep to afford methyl 3-(7-{5-[3-chloro-4,5-bis(ethyloxy)phenyl]-1,2,4-oxadiazol-3-yl}-1H-indol-3-yl)propanoate (D70) (25 mg) as a white solid. δH (CDCl$_3$, 400 MHz): 1.46 (3H, t), 1.55 (3H, m), 2.78 (2H, t), 3.18 (2H, t), 3.70 (3H, s), 4.22-4.28 (4H, m), 7.21 (1H, d), 7.29 (1H, t), 7.67 (1H, d), 7.81 (1H, t), 7.93 (1H, d), 8.13 (1H, d), 9.60 (1H, s).

Description for D71

7-(5-{3-chloro-4-[(1-methylethyl)oxy]phenyl}-1,2,4-oxadiazol-3-yl)-1H-indole-3-carbaldehyde (D71)

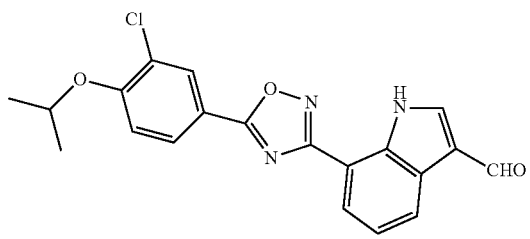

To a solution of oxalyl chloride (1.1 mL) in dichloromethane (60 mL) at 0° C. was added a solution of N,N-dimethylformamide (1.16 mL) in dichloromethane (30 mL) dropwise during 30 mins. The reaction mixture was stirred at this temperature for 15 minutes. A solution of 7-(5-{3-chloro-4-[(1-methylethyl)oxy]phenyl}-1,2,4-oxadiazol-3-yl)-1H-indole (D51) (3.5 g) in dichloromethane (60 mL) was added in one portion. The mixture was warmed to room temperature slowly. After stirred at room temperature for 5 hours, dichloromethane was evaporated off. Ethyl acetate (300 mL), water (100 mL) and concentrated HCl solution (5 mL) was added to the residue. The obtained mixture was stirred for 30 minutes. KOH was added to basify the solution to pH value about 8. The organic layer was separated, washed with water and brine, dried over MgSO$_4$. Filtration and evaporation afforded the product 7-(5-{3-chloro-4-[(1-methylethyl)oxy]phenyl}-1,2,4-oxadiazol-3-yl)-1H-indole-3-carbaldehyde (D71) (4.0 g). δH (DMSO-d$_6$, 400 MHz): 1.37 (6H, d), 4.87-4.93 (1H, m), 7.43-7.47 (2H, m), 8.07 (1H, dd), 8.21 (1H, dd), 8.37 (1H, d), 8.40-8.41 (2H, m), 10.06 (1H, s), 11.98 (1H, br s). MS (ES): $C_{20}H_{16}ClN_3O_3$ requires 381; found 382.1 (M+H$^+$).

Description for D72

Ethyl N-{[7-(5-{3-chloro-4-[(1-methylethyl)oxy]phenyl}-1,2,4-oxadiazol-3-yl)-1H-indol-3-yl]methyl}-β-alaninate (D72)

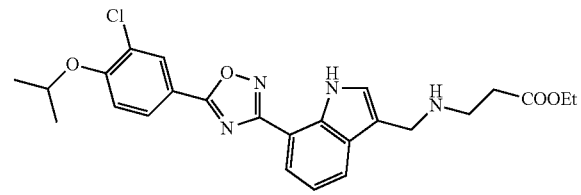

7-(5-{3-chloro-4-[(1-methylethyl)oxy]phenyl}-1,2,4-oxadiazol-3-yl)-1H-indole-3-carbaldehyde (D71) (381 mg) and ethyl β-alaninate hydrochloride (246 mg) were added to a solution of NaOH (27 mg) in ethanol (20 mL), followed by addition of AcOH (3 mL). Under stirring NaBH$_3$CN (50 mg) in ethanol (2 mL) was added dropwise. The reaction mixture was stirred at room temperature overnight and then basified to pH ~9 by K$_2$CO$_3$ solution. The mixture was concentrated and EtOAc (50 mL) was added. The organic layer was separated and washed with water and brine. After the solvent was evaporated off the residue was purified by Mass Directed AutoPrep to afford ethyl N-{[7-(5-{3-chloro-4-[(1-methylethyl)oxy]phenyl}-1,2,4-oxadiazol-3-yl)-1H-indol-3-yl]methyl}-β-alaninate (D72) (176 mg) as a yellow solid. δH (DMSO-d$_6$, 400 MHz): 1.16 (3H, t), 1.38 (6H, d), 2.47 (2H, t), 2.80 (2H, t), 3.90 (2H, s), 4.04 (2H, q), 4.88-4.94 (1H, m), 7.21 (1H, t), 7.37 (1H, t), 7.46 (1H, d), 7.89 (1H, d), 7.94 (1H, dd), 8.22 (1H, dd), 8.39 (1H, d), 10.89 (1H, s).

Description for D73

Ethyl N-{[7-(5-{3-chloro-4-[(1-methylethyl)oxy]phenyl}-1,2,4-oxadiazol-3-yl)-1H-indol-3-yl]methyl}glycinate (D73)

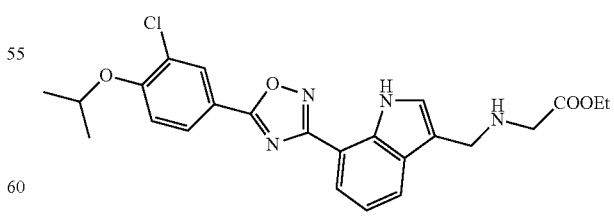

7-(5-{3-chloro-4-[(1-methylethyl)oxy]phenyl}-1,2,4-oxadiazol-3-yl)-1H-indole-3-carbaldehyde (D71) (381 mg) and ethyl glycinate hydrochloride (223 mg) were added to a solution of NaOH (27 mg) in ethanol (20 mL), followed by addition of AcOH (3 mL). Under stirring NaBH$_3$CN (50 mg)

in ethanol (2 mL) was added dropwise. The reaction mixture was stirred at room temperature overnight and then basified to pH 9 by K₂CO₃ solution. The mixture was concentrated and EtOAc (50 mL) was added. The organic layer was separated and washed with water and brine. After the solvent was evaporated off the residue was purified by Mass Directed AutoPrep to afford ethyl N-{[7-(5-{3-chloro-4-[(1-methylethyl)oxy]phenyl}-1,2,4-oxadiazol-3-yl)-1H-indol-3-yl]methyl}glycinate (D73) (130 mg) as a yellow solid. δH (DMSO-d₆, 400 MHz): 1.20 (3H, t), 1.38 (6H, d), 3.48 (2H, s), 4.03 (2H, s), 4.12 (2H, q), 4.88-4.94 (1H, m), 7.25 (1H, t), 7.44 (1H, d), 7.46 (1H, d), 7.96 (1H, t), 8.22 (1H, dd), 8.39 (1H, d), 11.00 (1H, s).

Description for D74

Ethyl 1-{[7-(5-{3-chloro-4-[(1-methylethyl)oxy]phenyl}-1,2,4-oxadiazol-3-yl)-1H-indol-3-yl]methyl}-4-piperidinecarboxylate (D74)

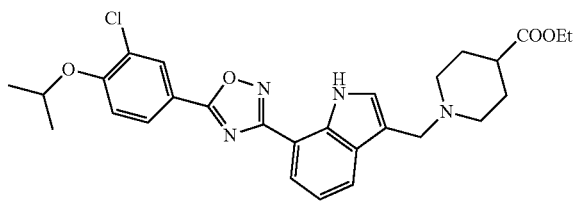

Ethyl 4-piperidinecarboxylate hydrochloride (387 mg) was added to a solution of NaOH (80 mg) in ethanol (20 mL). After stirring for 0.5 hour, ethanol was evaporated off. A solution of AcOH (1.0 mL) in dichloromethane (20 mL) was added to the residue. 7-(5-{3-chloro-4-[(1-methylethyl)oxy]phenyl}-1,2,4-oxadiazol-3-yl)-1H-indole-3-carbaldehyde (D71) (381 mg) and NaBH(OAc)₃ (636 mg) were added to the above mixture. After stirred at room temperature over the weekend, the reaction was heated to 45° C. and stirred for another 2 h. Saturated NaHCO₃ solution was used to quench the reaction. The organic layer was separated and washed with water and brine. After the solvent was evaporated off the residue was purified by Mass Directed AutoPrep to afford ethyl 1-{[7-(5-{3-chloro-4-[(1-methylethyl)oxy]phenyl}-1,2,4-oxadiazol-3-yl)-1H-indol-3-yl]methyl}-4-piperidinecarboxylate (D74) (280 mg) as a yellow solid. δH (CDCl₃, 400 MHz): 1.23 (3H, dt), 1.46 (6H, d), 2.78-4.48 (13H, m), 4.71-4.77 (1H, m), 7.09 (1H, d), 7.37 (1H, m), 7.65 (1H, dd), 7.76 (1H, dd), 8.10 (1H, dd), 8.17 (1H, dd), 8.28 (1H, d), 10.17 (1H, d).

Description for D75

Methyl N-{[7-(5-{3-chloro-4-[(1-methylethyl)oxy]phenyl}-1,2,4-oxadiazol-3-yl)-1H-indol-3-yl]methyl}-D-alaninate (D75)

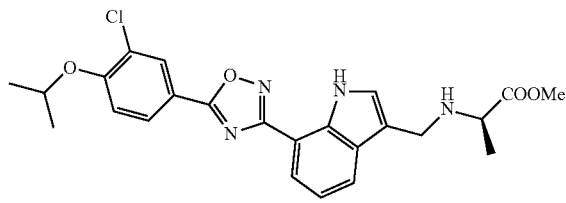

D-alanine methyl ester hydrochloride (420 mg) and 7-(5-{3-chloro-4-[(1-methylethyl)oxy]phenyl}-1,2,4-oxadiazol-3-yl)-1H-indole-3-carbaldehyde (D71) (382 mg) was added to a solution of NaOH (120 mg) in methanol (20 mL). After stirring for 0.5 hour, methanol was evaporated off. A solution of AcOH (0.5 mL) in dichloromethane (40 mL) was added to the residue. NaBH(OAc)₃ (847 mg) was added to the above mixture. The reaction mixture was stirred at room temperature overnight, and quenched by saturated NaHCO₃ solution. The organic layer was separated and washed with water and brine. After the solvent was evaporated off the residue was purified by Mass Directed AutoPrep to afford methyl N-{[7-(5-{3-chloro-4-[(1-methylethyl)oxy]phenyl}-1,2,4-oxadiazol-3-yl)-1H-indol-3-yl]methyl}-D-alaninate (D75) (262 mg) as a white solid. MS (ES): $C_{24}H_{25}ClN_4O_4$ requires 468; found 491.1 (M+Na⁺).

Description for D76

Methyl N-{[7-(5-{3-chloro-4-[(1-methylethyl)oxy]phenyl}-1,2,4-oxadiazol-3-yl)-1H-indol-3-yl]methyl}-L-alaninate (D76)

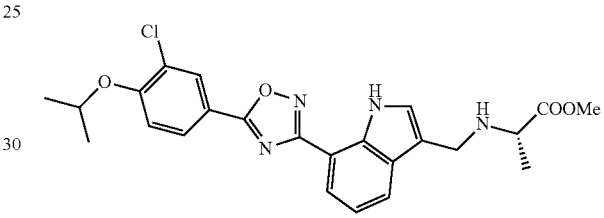

L-alanine methyl ester hydrochloride (420 mg) and 7-(5-{3-chloro-4-[(1-methylethyl)oxy]phenyl}-1,2,4-oxadiazol-3-yl)-1H-indole-3-carbaldehyde (D71) (382 mg) was added to a solution of NaOH (120 mg) in methanol (20 mL). After stirring for 0.5 hour, methanol was evaporated off and then after addition of AcOH (0.5 mL) in dichloromethane (40 mL), NaBH(OAc)₃ (847 mg) was added. The reaction mixture was stirred at room temperature overnight and quenched by saturated NaHCO₃ solution. The organic layer was separated and washed with water and brine. After the solvent was evaporated off the residue was purified by Mass Directed AutoPrep to afford methyl N-{[7-(5-{3-chloro-4-[(1-methylethyl)oxy]phenyl}-1,2,4-oxadiazol-3-yl)-1H-indol-3-yl]methyl}-D-alaninate (D76) (223 mg) as a white solid. MS (ES): $C_{24}H_{25}ClN_4O_4$ requires 468; found 491.1 (M+Na⁺).

Description for D77

Ethyl N-{[7-(5-{3-chloro-4-[(1-methylethyl)oxy]phenyl}-1,2,4-oxadiazol-3-yl)-1-methyl-1H-indol-3-yl]methyl}glycinate (D77)

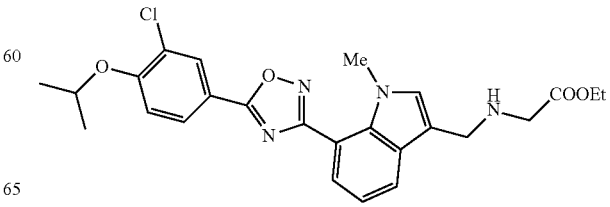

Ethyl glycinate hydrochloride (698 mg) and 7-(5-{3-chloro-4-[(1-methylethyl)oxy]phenyl}-1,2,4-oxadiazol-3-yl)-1-methyl-1H-indole-3-carbaldehyde (D61) (396 mg) were added to a solution of NaOH (200 mg) in ethanol (10 mL). After stirring for 0.5 hour, ethanol was evaporated off and then Dichloromethane (40 mL) containing AcOH (0.5 mL) was added to the residue. NaBH(OAc)$_3$ (1.06 g) was added to the above mixture. The reaction mixture was stirred at room temperature overnight and then terminated by saturated NaHCO$_3$ solution. The organic layer was separated and washed with water and brine. After the solvent was evaporated off the residue was purified by Mass Directed AutoPrep to afford ethyl N-{[7-(5-{3-chloro-4-[(1-methylethyl)oxy]phenyl}-1,2,4-oxadiazol-3-yl)-1-methyl-1H-indol-3-yl]methyl}glycinate (D77) (283 mg) as a yellow solid. δH (CDCl$_3$, 400 MHz): 1.29 (3H, t), 1.46 (6H, d), 1.84 (1H, br s), 3.48 (2H, s), 3.74 (2H, s), 4.03 (3H, s), 4.21 (2H, q), 4.71-4.74 (1H, m), 7.03 (1H, s), 7.07 (1H, d), 7.22 (1H, t), 7.58 (1H, dd), 7.89 (1H, dd), 8.08 (1H, dd), 8.26 (1H, d). MS (ES): C$_{25}$H$_{27}$ClN$_4$O$_4$ requires 482; found 380.2 (M—NHCH$_2$COOEt$^+$).

Description for D78

Ethyl N-{[7-(5-{3-chloro-4-[(1-methylethyl)oxy]phenyl}-1,2,4-oxadiazol-3-yl)-1-methyl-1H-indol-3-yl]methyl}-β-alaninate (D78)

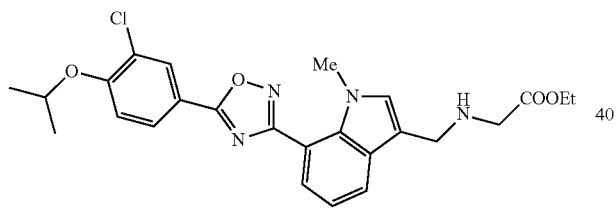

ethyl β-alaninate hydrochloride (768 mg) and 7-(5-{3-chloro-4-[(1-methylethyl)oxy]phenyl}-1,2,4-oxadiazol-3-yl)-1-methyl-1H-indole-3-carbaldehyde (D61) (396 mg) was added to a solution of NaOH (200 mg) in ethanol (10 mL). After stirring for 0.5 hour, ethanol was evaporated off and then dichloromethane (40 mL) containing AcOH (0.5 mL) was added to the residue. NaBH(OAc)$_3$ (1.06 g) was added to the above mixture. The reaction mixture was stirred at room temperature overnight and then terminated by saturated NaHCO$_3$ solution. The organic layer was separated and washed with water and brine. After the solvent was evaporated off the residue was purified by Mass Directed AutoPrep to afford ethyl N-{[7-(5-{3-chloro-4-[(1-methylethyl)oxy]phenyl}-1,2,4-oxadiazol-3-yl)-1-methyl-1H-indol-3-yl]methyl}-6-alaninate (D78) (288 mg) as a yellow solid. δH (CDCl$_3$, 400 MHz): 1.24 (3H, t), 1.46 (6H, d), 1.74 (1H, br s), 2.78 (2H, t), 3.25 (2H, t), 3.74 (3H, s), 4.31 (2H, s), 4.69-4.76 (1H, m), 7.07 (1H, d), 7.70 (1H, t), 7.60 (1H, d), 7.80 (1H, dd), 8.02 (1H, dd), 8.22 (1H, d). MS (ES): C$_{26}$H$_{29}$ClN$_4$O$_4$ requires 496; found 380.2 (M—NHCH$_2$CH$_2$COOEt$^+$).

Description for D79

Ethyl 1-{[7-(5-{3-chloro-4-[(1-methylethyl)oxy]phenyl}-1,2,4-oxadiazol-3-yl)-1-methyl-1H-indol-3-yl]methyl}-4-piperidinecarboxylate (D79)

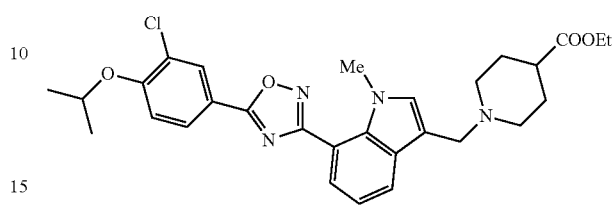

Ethyl 4-piperidinecarboxylate hydrochloride (969 mg) and 7-(5-{3-chloro-4-[(1-methylethyl)oxy]phenyl}-1,2,4-oxadiazol-3-yl)-1-methyl-1H-indole-3-carbaldehyde (D61) (396 mg) was added to a solution of NaOH (200 mg) in ethanol (10 mL). After stirring for 0.5 hour, ethanol was evaporated off and then dichloromethane (40 mL) containing AcOH (0.5 mL) was added to the residue. NaBH(OAc)$_3$ (1.06 g) was added to the above mixture. The reaction mixture was stirred at room temperature overnight and then terminated by saturated NaHCO$_3$ solution. The organic layer was separated and washed with water and brine. After the solvent was evaporated off the residue was purified by Mass Directed AutoPrep to afford ethyl 1-{[7-(5-{3-chloro-4-[(1-methylethyl)oxy]phenyl}-1,2,4-oxadiazol-3-yl)-1-methyl-1H-indol-3-yl]methyl}-4-piperidinecarboxylate (D79) (308 mg) as a yellow solid. MS (ES): C$_{29}$H$_{33}$ClN$_4$O$_4$ requires 536; found 537.3 (M+H$^+$).

Description for D80

Methyl N-{[7-(5-{3-chloro-4-[(1-methylethyl)oxy]phenyl}-1,2,4-oxadiazol-3-yl)-1-methyl-1H-indol-3-yl]methyl}-D-alaninate (D80)

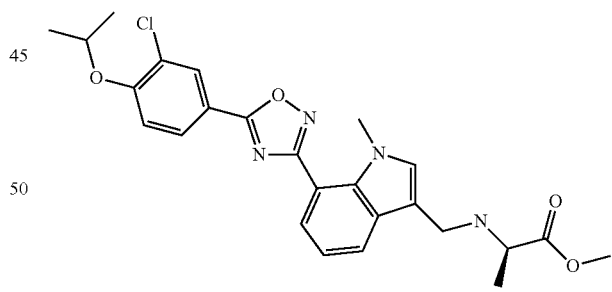

To a stirred solution of 7-(5-{3-chloro-4-[(1-methylethyl)oxy]phenyl}-1,2,4-oxadiazol-3-yl)-1-methyl-1H-indole-3-carbaldehyde (D61) (395 mg), methyl D-alaninate (206 mg) and acetic acid (60 mg) in DCM (10 mL) was added NaBH(OAc)$_3$ (424 mg). The mixture was stirred at 35° C. overnight. After cooled to room temperature, the reaction mixture was diluted with DCM (10 mL), washed with water and saturated aqueous NaHCO$_3$. The organic phase was dried over anhydrous sodium sulphate. The solvent was evaporated to give the crude product, which was purified by Mass Directed Auto Prep to afford methyl-{[7-(5-{3-chloro-4-[(1-methylethyl)oxy]phenyl}-1,2,4-oxadiazol-3-yl)-1-methyl-1H-indol-3- yl]methyl}-D-alaninate (D80) (110 mg) as a white solid. MS (ES): $C_{25}H_{27}ClN_4O_4$ requires 482; found 380.1 $(M—C_4H_8NO_2^+)$.

Description for D81

Methyl N-{[7-(5-{3-chloro-4-[(1-methylethyl)oxy]phenyl}-1,2,4-oxadiazol-3-yl)-1-methyl-1H-indol-3-yl]methyl}-L-alaninate (D81)

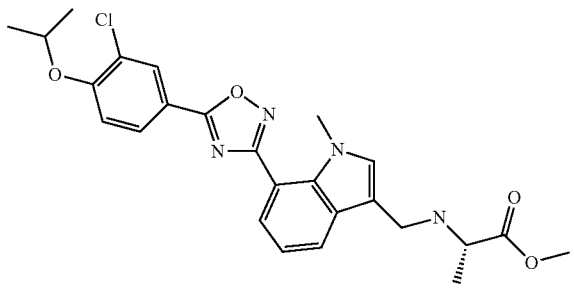

To a stirred solution of 7-(5-{3-chloro-4-[(1-methylethyl)oxy]phenyl}-1,2,4-oxadiazol-3-yl)-1-methyl-1H-indole-3-carbaldehyde (D61) (395 mg), methyl L-alaninate (206 mg) and acetic acid (60 mg) in DCM (10 mL) was added NaBH(OAc)$_3$ (424 mg). The mixture was stirred at 35° C. overnight. After cooled to room temperature, the reaction mixture was diluted with DCM (10 mL), washed with water and saturated sodium bicarbonate solution. The organic phase was separated and dried over anhydrous sodium sulphate. The solvent was evaporated and the residue was purified by Mass Directed Auto Prep to afford methyl N-{[7-(5-{3-chloro-4-[(1-methylethyl)oxy]phenyl}-1,2,4-oxadiazol-3-yl)-1-methyl-1H-indol-3-yl]methyl}-L-alaninate (D81) as a white solid (160 mg). MS (ES): $C_{26}H_{27}ClN_4O_4$ requires 482; found 380.1 $(M—C_4H_8NO_2^+)$.

Description for D82

7-(5-{3-chloro-4-[(1-methylethyl)oxy]phenyl}-1,2,4-oxadiazol-3-yl)-3-[(E)-2-nitroethenyl]-1H-indole (D82)

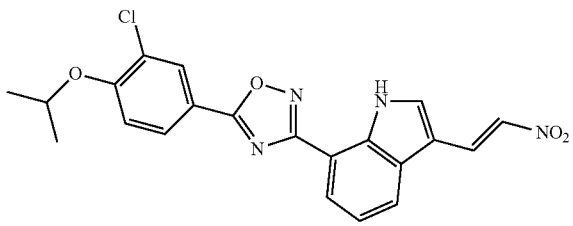

7-(5-{3-chloro-4-[(1-methylethyl)oxy]phenyl}-2,4-oxadiazol-3-yl)-1H-indole-3-carbaldehyde (D71) (2.6 g) and ammonium acetate (0.8 g) were added to nitromethane (13.5 ml) at room temperature. The reaction mixture was heated to 120° C. and stirred for 0.5 h. A yellow solid was formed. The solid was filtered, washed with acetonitrile (20 mL) and collected to give 7-(5-{3-chloro-4-[(1-methylethyl)oxy]phenyl}-1,2,4-oxadiazol-3-yl)-3-[(E)-2-nitroethenyl]-1H-indole (D82) (1.7 g) as a yellow solid. δH (DMSO-d$_6$, 400 MHz): 1.36 (6H, d), 4.86-4.92 (1H, m), 7.42 (1H, t), 7.44 (1H, d), 8.06 (1H, d), 8.15 (1H, d), 8.21 (1H, dd), 8.27 (1H, dd), 8.37 (1H, s), 8.40 (1H, d), 8.51 (1H, d), 11.88 (1H, s). MS (ES): $C_{21}H_{17}ClN_4O_4$ requires 424; found 425.2 (M+H$^+$).

Description for D83

7-(5-{3-chloro-4-[(1-methylethyl)oxy]phenyl}-1,2,4-oxadiazol-3-yl)-3-(2-nitroethyl)-1H-indole (D83)

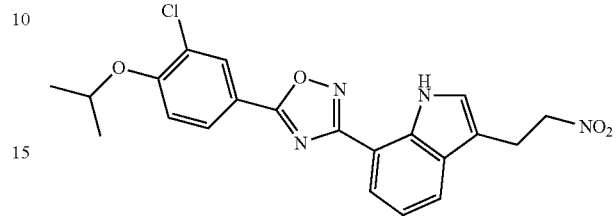

To a suspension of NaBH$_4$ (0.7 g) in 1,4-dioxane (150 mL) and ethanol (50 mL) stirred in air at room temperature was added a solution of 7-(5-{3-chloro-4-[(1-methylethyl)oxy]phenyl}-1,2,4-oxadiazol-3-yl)-3-[(E)-2-nitroethenyl]-1H-indole (D82) (2.6 g) in 1,4-dioxane (150 mL) dropwise. The reaction mixture was stirred at 20° C. for 1 h. The excess NaBH$_4$ was quenched with dilute H$_2$SO$_4$. The reaction solution was concentrated. Ethyl acetate (300 mL) was added to the residue, washed with water and brine, and then dried over MgSO$_4$. Solvent was evaporated off to give the desired product 7-(5-{3-chloro-4-[(1-methylethyl)oxy]phenyl}-1,2,4-oxadiazol-3-yl)-3-(2-nitroethyl)-1H-indole (D83) (2.2 g) as a yellow solid. δH (CDCl$_3$, 400 MHz): 1.46 (6H, d), 3.55 (2H, t), 4.69-4.74 (3H, m), 7.07 (1H, d), 7.23 (1H, d), 7.30 (1H, t), 7.75 (1H, d), 8.08 (1H, dd), 8.12 (1H, d), 8.26 (1H, d), 9.74 (1H, s). MS (ES): $C_{21}H_{19}ClN_4O_4$ requires 426; found 427.2 (M+H$^+$).

Description for D84

2-[7-(5-{3-chloro-4-[(1-methylethyl)oxy]phenyl}-1,2,4-oxadiazol-3-yl)-1H-indol-3-yl]ethanamine (D84)

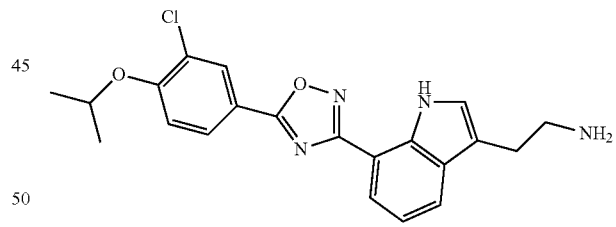

Water (20 mL) and concentrated HCl solution (10 mL) were added to a solution of 7-(5-{3-chloro-4-[(1-methylethyl)oxy]phenyl}-1,2,4-oxadiazol-3-yl)-3-(2-nitroethyl)-1H-indole (D83) (2.1 g) in EtOAc (70 mL) and methanol (150 mL). The mixture was heated to reflux and stirred efficiently. Fe (6.0 g) was added in portions. After the addition was complete, the reaction mixture was refluxed for 8 hours. The solid was filtered off and the filtrate was concentrated and then basified with saturated NaHCO$_3$ solution. The solid was filtered off and the filtrate was extracted with dichloromethane (200 mL). The organic layer was washed with water and brine, and then dried over MgSO$_4$. Removal of the solvent gave the product 2-[7-(5-{3-chloro-4-[(1-methylethyl)oxy]phenyl}-1,2,4-oxadiazol-3-yl)-1H-indol-3-yl]ethanamine (D84) (1.4 g) as a yellow foam solid. No further purification was carried out. MS (ES): C$_{21}$H$_{21}$ClN$_4$O$_2$ requires 396; found 397.2 (M+H$^+$).

Description for D85

Ethyl N-{2-[7-(5-{3-chloro-4-[(1-methylethyl)oxy]phenyl}-1,2,4-oxadiazol-3-yl)-1H-indol-3-yl]ethyl}-β-alaninate (D85)

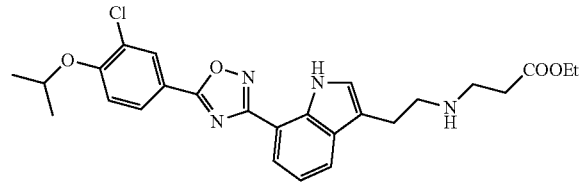

Ethyl acrylate (100 mg) and Sc(OTf)$_3$ (5 mg) were added to the solution of 2-[7-(5-{3-chloro-4-[(1-methylethyl)oxy]phenyl}-1,2,4-oxadiazol-3-yl)-1H-indol-3-yl]ethanamine (D84) (530 mg) in dichloromethane (3 mL). The resulting reaction mixture was stirred at room temperature for 24 hours. The reaction mixture was concentrated and the residue was purified by Mass Directed Auto Prep to afford ethyl N-{2-[7-(5-{3-chloro-4-[(1-methylethyl)oxy]phenyl}-1,2,4-oxadiazol-3-yl)-1H-indol-3-yl]ethyl}-β-alaninate (D85) (186 mg) as a yellow solid. MS (ES): C$_{26}$H$_{29}$ClN$_4$O$_4$ requires 496; found 497.2 (M+H$^+$).

Description for D86

Ethyl N-{2-[7-(5-{3-chloro-4-[(1-methylethyl)oxy]phenyl}-1,2,4-oxadiazol-3-yl)-1H-indol-3-yl]ethyl}glycinate (D86)

Ethyl bromoacetate (167 mg) and Et$_3$N (101 mg) were added to the solution of 2-[7-(5-{3-chloro-4-[(1-methylethyl)oxy]phenyl}-1,2,4-oxadiazol-3-yl)-1H-indol-3-yl]ethanamine (D84) (530 mg) in toluene (3 mL). The resulting reaction mixture was stirred at room temperature for 24 hours. The reaction mixture was concentrated and the residue was purified by Mass Directed Auto Prep to afford ethyl N-{2-[7-(5-{3-chloro-4-[(1-methylethyl)oxy]phenyl}-1,2,4-oxadiazol-3-yl)-1H-indol-3-yl]ethyl}glycinate (D86) (132 mg) as a yellow solid. MS (ES): C$_{25}$H$_{27}$ClN$_4$O$_4$ requires 482; found 483.2 (M+H$^+$).

Description for D87

7-(5-{3-chloro-4-[(1-methylethyl)oxy]phenyl}-1,2,4-oxadiazol-3-yl)-1-methyl-3-[(E)-2-(methyloxy)ethenyl]-1H-indole (D87)

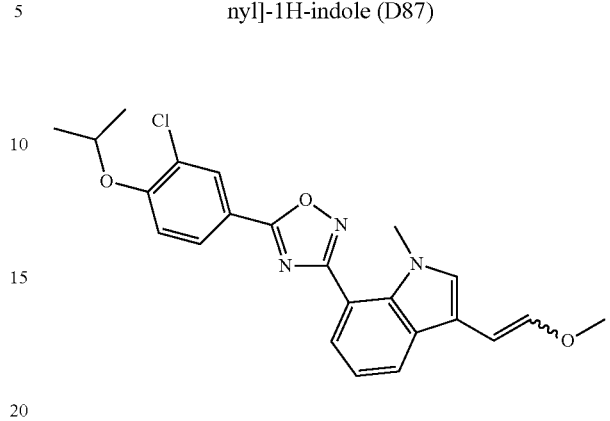

To a solution of (methoxymethyl)triphenylphosphonium chloride (2.9 g) in dimethyl sulfoxide (20 mL) stirred under nitrogen at 20° C. was added a solution of NaHMDS (8.6 mL, 1.0 mol/L in THF) dropwise during 5 mins. The reaction mixture was stirred at this temperature for 20 mins. Then 7-(5-{3-chloro-4-[(1-methylethyl)oxy]phenyl}-1,2,4-oxadiazol-3-yl)-1-methyl-1H-indole-3-carbaldehyde (D87) (1.4 g) was added in one portion. The mixture was stirred at room temperature for 30 mins. The reaction mixture was quenched with water, partitioned between ether (100 mL) and water (50 mL). The organic phase was washed with water and brine, dried over sodium sulphate and evaporated to afford 7-(5-{3-chloro-4-[(1-methylethyl)oxy]phenyl}-1,2,4-oxadiazol-3-yl)-1-methyl-3-[(E)-2-(methyloxy)ethenyl]-1H-indole (D87) as a brown oil (3.8 g), used directly in the next step. MS (ES): C$_{23}$H$_{22}$ClN$_3$O$_3$ requires 423; found 424.2 (M+H$^+$).

Description for D88

[7-(5-{3-chloro-4-[(1-methylethyl)oxy]phenyl}-1,2,4-oxadiazol-3-yl)-1-methyl-1H-indol-3-yl]acetaldehyde (D88)

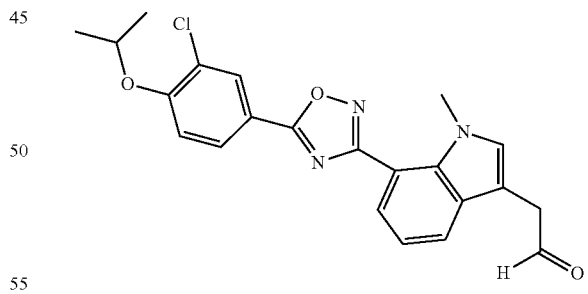

To a solution of 7-(5-{3-chloro-4-[(1-methylethyl)oxy]phenyl}-1,2,4-oxadiazol-3-yl)-1-methyl-3-[(E)-2-(methyloxy)ethenyl]-1H-indole (D61) (1.2 g) in 1,4-dioxane (20 mL) stirred was added a solution of HCl (20 mL) in water. The reaction mixture was stirred at 20° C. for 30 mins. The reaction mixture was quenched with NaHCO$_3$, partitioned between ethyl acetate (100 mL) and water (50 mL). The organic phase was washed with water and brine, dried over sodium sulphate and evaporated to give the crude product as a brown oil, which was purified by Mass Directed Auto Prep (basic) to afford [7-(5-{3-chloro-4-[(1-methylethyl)oxy]phenyl}-1,2,4-oxadiazol-3-yl)-1-methyl-1H-indol-3-yl]acetaldehyde (D88) (220 mg) as a white solid. δH (CDCl₃, 400 MHz): 1.39 (6H, d), 3.70 (3H, s), 3.77 (2H, d), 4.66 (1H, m), 7.00 (2H, m), 7.17 (1H, t), 7.53 (1H, dd), 7.62 (1H, dd), 8.01 (1H, dd), 8.19 (1H, dd), 9.70 (1H, t). MS (ES): $C_{22}H_{20}ClN_3O_3$ requires 409. found 410.2 (M+H⁺).

Description for D89

Ethyl N-{2-[7-(5-{3-chloro-4-[(1-methylethyl)oxy]phenyl}-1,2,4-oxadiazol-3-yl)-1-methyl-1H-indol-3-yl]ethyl}glycinate (D89)

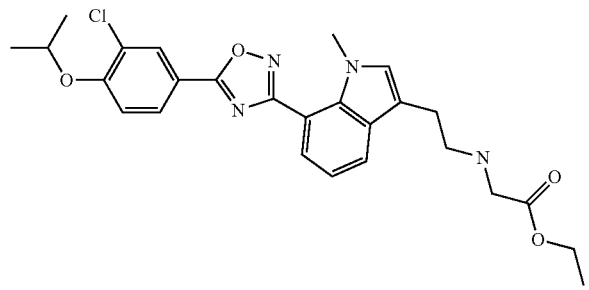

To a stirred solution of [7-(5-{3-chloro-4-[(1-methylethyl)oxy]phenyl}-1,2,4-oxadiazol-3-yl)-1-methyl-1H-indol-3-yl]acetaldehyde (D88) (20 mg), ethyl glycinate (10 mg) and acetic acid (0.1 mL) in DCM (10 mL) was added sodium triacetoxyborohydride (21 mg). The reaction was stirred at 20° C. for 1 h. The reaction mixture was partitioned between DCM (25 mL) and water (25 mL). The organic phase was evaporated to give ethyl N-{2-[7-(5-{3-chloro-4-[(1-methylethyl)oxy]phenyl}-1,2,4-oxadiazol-3-yl)-1-methyl-1H-indol-3-yl]ethyl}glycinate (D89) as a brown oil (20 mg), which was used directly in the next hydrolysis step. MS (ES): $C_{26}H_{29}ClN_4O_4$ requires 496; found 497.2 (M+H⁺).

Description for D90

Ethyl N-{2-[7-(5-{3-chloro-4-[(1-methylethyl)oxy]phenyl}-1,2,4-oxadiazol-3-yl)-1-methyl-1H-indol-3-yl]ethyl}-β-alaninate (D90)

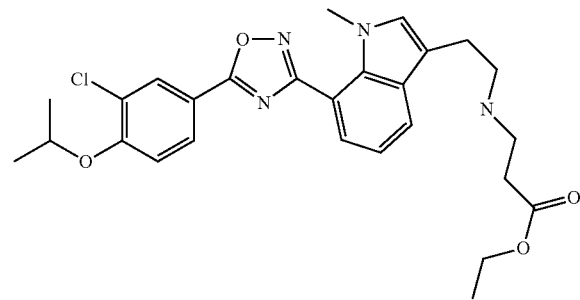

To a stirred solution of [7-(5-{3-chloro-4-[(1-methylethyl)oxy]phenyl}-1,2,4-oxadiazol-3-yl)-1-methyl-1H-indol-3-yl]acetaldehyde (D88) (25 mg), ethyl β-alaninate (14 mg) and acetic acid (0.1 mL) in DCM (5 mL) was added sodium triacetoxyborohydride (26 mg). The reaction was stirred at 20° C. for 2 h. The reaction mixture was partitioned between DCM (25 mL) and water (25 mL). The organic phase was washed with brine (25 mL), and evaporated to afford the crude product ethyl N-{2-[7-(5-{3-chloro-4-[(1-methylethyl)oxy]phenyl}-1,2,4-oxadiazol-3-yl)-1-methyl-1H-indol-3-yl]ethyl}-β-alaninate (D90) (30 mg), which was used directly in the next step. MS (ES): $C_{27}H_{31}ClN_4O_4$ requires 510; found 511.2 (M+H⁺).

Description for D91

Ethyl 1-{2-[7-(5-{3-chloro-4-[(1-methylethyl)oxy]phenyl}-1,2,4-oxadiazol-3-yl)-1-methyl-1H-indol-3-yl]ethyl}-4-piperidinecarboxylate (D91)

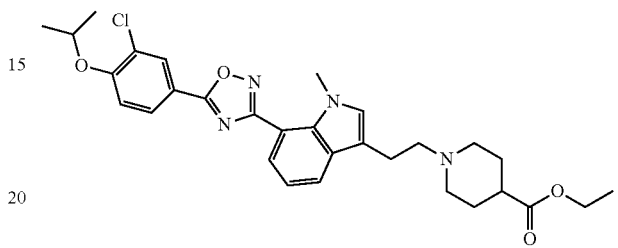

To a stirred solution of [7-(5-{3-chloro-4-[(1-methylethyl)oxy]phenyl}-1,2,4-oxadiazol-3-yl)-1-methyl-1H-indol-3-yl]acetaldehyde (D88) (50 mg), ethyl 4-piperidinecarboxylate (38 mg) and acetic acid (0.1 mL) in DCM (10 mL) was added sodium triacetoxyborohydride (52 mg). The reaction was stirred at 20° C. for 3 h. The mixture was quenched with water, partitioned between DCM (25 mL) and water (25 mL). The organic phase was washed with brine, dried over sodium sulphate and evaporated to afford the crude product ethyl 1-{2-[7-(5-{3-chloro-4-[(1-methylethyl)oxy]phenyl}-1,2,4-oxadiazol-3-yl)-1-methyl-1H-indol-3-yl]ethyl}-4-piperidinecarboxylate (D91) (60 mg). MS (ES): $C_{30}H_{35}ClN_4O_4$ requires 550; found 551.3 (M+H⁺).

Description for D92

3-[7-(5-{3-chloro-4-[(1-methylethyl)oxy]phenyl}-1,2,4-oxadiazol-3-yl)-1H-indol-3-yl]propanal (D92)

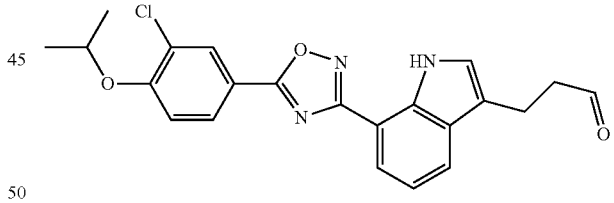

To a solution of methyl 3-[7-(5-{3-chloro-4-[(1-methylethyl)oxy]phenyl}-1,2,4-oxadiazol-3-yl)-1H-indol-3-yl]propanoate (provided by WuxiPharma, China and made in a similar manner to D7) (4.0 g) in DCM (50 mL) at −78° C. under N₂ atmosphere was added DIBAL-H (14 ml) dropwise. The reaction was stirred at −78° C. for 6 h. Then MeOH was added at −78° C. to quench the reaction. The resulting solution was concentrated. And the residue was purified by column chromatography on silical gel (15% EtOAc in hexane) to afford 3-[7-(5-{3-chloro-4-[(1-methylethyl)oxy]phenyl}-1,2,4-oxadiazol-3-yl)-1H-indol-3-yl]propanal (D92) (1.3 g). δH (CDCl₃, 400 MHz): 1.45 (6H, d), 2.90 (2H, t), 3.17 (2H, t), 4.72 (1H, m), 7.07 (1H, d), 7.16 (1H, d), 7.30 (1H, d), 7.78 (1H, d), 8.12 (2H, m), 8.29 (1H, s), 9.63 (1H, br s), 9.89 (1H, s). MS (ES): $C_{22}H_{20}ClN_3O_3$ requires 409; found 410 (M+H⁺).

Description for D93

Ethyl N-{3-[7-(5-{3-chloro-4-[(1-methylethyl)oxy]phenyl}-1,2,4-oxadiazol-3-yl)-1H-indol-3-yl]propyl}glycinate (D93)

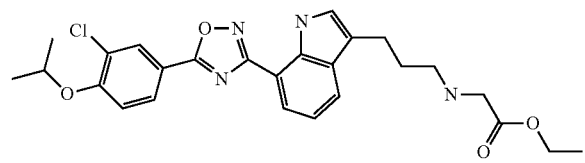

To a stirred solution of 3-[7-(5-{3-chloro-4-[(1-methylethyl)oxy]phenyl}-1,2,4-oxadiazol-3-yl)-1H-indol-3-yl]propanal (D92) (100 mg), ethyl glycinate (50 mg) and acetic acid (5 mg) in DCM (15 mL) was added sodium triacetoxyborohydride (52 mg). The reaction mixture was stirred at 20° C. for 2 h. The reaction mixture was partitioned between DCM (25 mL) and water (25 mL). The organic phase was washed with water, dried over sodium sulphate and evaporated in vacuo to afford the crude product ethyl N-{3-[7-(5-{3-chloro-4-[(1-methylethyl)oxy]phenyl}-1,2,4-oxadiazol-3-yl)-1H-indol-3-yl]propyl}glycinate (D93) (100 mg), which was used directly in the next step. MS (ES): $C_{26}H_{29}ClN_4O_4$ requires 496; found 497.2 (M+H$^+$).

Description for D94/EXAMPLE 94

7-(5-{3-chloro-4-[(1-methylethyl)oxy]phenyl}-1,2,4-oxadiazol-3-yl)-1H-indole-3-carboxylic acid (D94/E94)

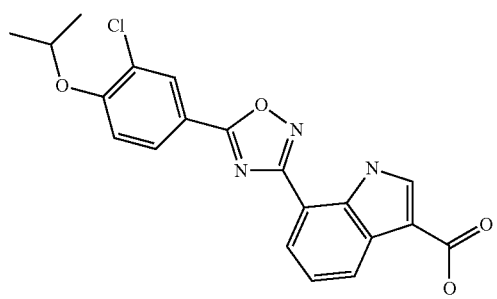

To a solution of 7-(5-{3-chloro-4-[(1-methylethyl)oxy]phenyl}-1,2,4-oxadiazol-3-yl)-1H-indole-3-carbaldehyde (D71) (1.1 g) in THF (20 mL) was added KMnO$_4$ (0.9 g) and aqueous KOH (10 mL). The reaction was stirred at 55° C. overnight. After cooled to room temperature, the mixture was diluted with THF (20 mL) and filtered. The filtrate was concentrated and the aqueous suspension was acidified with aqueous HCl (2 M) to pH 5-6. The resulting solid was collected by filtration, washed with water, dried in vacuo to give the crude compound, which was purified by column chromatography (20% ethyl acetate in hexane) to afford 7-(5-{3-chloro-4-[(1-methylethyl)oxy]phenyl}-1,2,4-oxadiazol-3-yl)-1H-indole-3-carboxylic acid as a white solid (D94) (1.0 g). δH (DMSO-d$_6$, 400 MHz): 1.36 (6H, d), 4.90 (1H, m), 7.38 (1H, t), 7.46 (1H, d), 8.02 (2H, m), 8.22 (1H, dd), 8.30 (1H, dd), 8.41 (1H, d), 11.66 (1H, br s). MS (ES): $C_{20}H_{16}ClN_3O_4$ requires 397; found 398.1 (M+H$^+$).

Description for D95/EXAMPLE 95

7-(5-{3-chloro-4-[(1-methylethyl)oxy]phenyl}-1,2,4-oxadiazol-3-yl)-1-methyl-1H-indole-3-carboxylic acid (D95/E95)

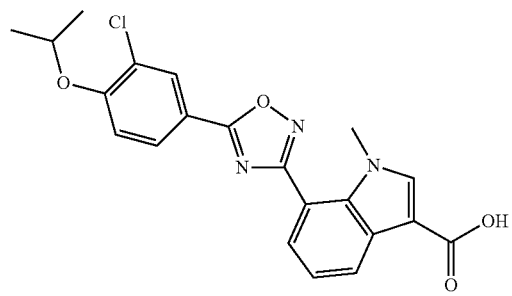

To a solution of 7-(5-{3-chloro-4-[(1-methylethyl)oxy]phenyl}-1,2,4-oxadiazol-3-yl)-1-methyl-1H-indole-3-carbaldehyde (D61) (1.4 g) in THF (20 mL) was added KMnO$_4$ (1.1 g) and aqueous KOH (10 mL). The reaction mixture was stirred at 55° C. overnight. After cooled to room temperature, the mixture was diluted with THF (30 mL), and filtered. The filtrate was concentrated and the aqueous suspension was acidified with aqueous HCl (2 M) to pH 5-6. The resulting white solid was collected, washed with water, dried in vacuo to give the crude compound, which was purified by column chromatography (10% ethyl acetate in hexane) to afford 7-(5-{3-chloro-4-[(1-methylethyl)oxy]phenyl}-1,2,4-oxadiazol-3-yl)-1-methyl-1H-indole-3-carboxylic acid (D95) as a white solid (1.3 g). δH (DMSO-d$_6$, 400 MHz): 1.36 (6H, d), 3.74 (3H, s), 4.88 (1H, m), 7.35 (1H, dd), 7.45 (1H, d), 7.53 (1H, dd), 8.12 (1H, d), 8.14 (1H, d), 8.20 (1H, d), 8.32 (1H, dd), 12.15 (1H, s). MS (ES): $C_{21}H_{18}ClN_3O_4$ requires 411. found 412.1 (M+H$^+$).

Description for D96

Ethyl N-{[7-(5-{3-chloro-4-[(1-methylethyl)oxy]phenyl}-1,2,4-oxadiazol-3-yl)-1H-indol-3-yl]carbonyl}glycinate (D96)

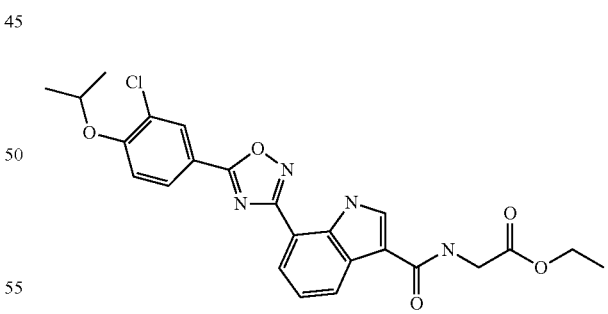

To a stirred solution of 7-(5-{3-chloro-4-[(1-methylethyl)oxy]phenyl}-1,2,4-oxadiazol-3-yl)-1H-indole-3-carboxylic acid (D94) (150 mg) and DMF (0.1 mL) in THF (10 mL) was added a solution of oxalyl chloride (192 mg) in THF (2 mL) dropwise. After stirring for 1 h, the reaction mixture was concentrated and the residue was dissolved in THF (10 mL), followed by addition of ethyl glycinate (78 mg) and Et$_3$N (190 mg). The reaction was stirred at room temperature for 0.5 h. The solvent was evaporated to afford the crude product N-{[7-(5-{3-chloro-4-[(1-methylethyl)oxy]phenyl}-1,2,4- oxadiazol-3-yl)-1H-indol-3-yl]carbonyl}glycinate (D96) (200 mg), which was used directly in the next hydrolysis step. MS (ES): $C_{24}H_{23}ClN_4O_5$ requires 482; found 483.2 (M+H$^+$).
Description for D97

Ethyl N-{[7-(5-{3-chloro-4-[(1-methylethyl)oxy] phenyl}-1,2,4-oxadiazol-3-yl)-1H-indol-3-yl]carbonyl}-β-alaninate (D97)

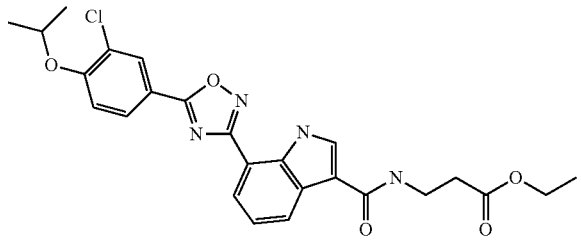

To a stirred solution of 7-(5-{3-chloro-4-[(1-methylethyl) oxy]phenyl}-1,2,4-oxadiazol-3-yl)-1H-indole-3-carboxylic acid (D94) (150 mg) and DMF (0.1 mL) in THF (10 mL) was added a solution of oxalyl chloride (192 mg) in THF (2 mL) dropwise. After stirring for 1 h, the reaction mixture was concentrated and the residue was dissolved in THF (10 mL), followed by addition of ethyl 6-alaninate (87 mg) and Et$_3$N (190 mg). The reaction was stirred at room temperature for 0.5 h. The solvent was evaporated to afford the crude product ethyl N-{[7-(5-{3-chloro-4-[(1-methylethyl)oxy]phenyl}-1, 2,4-oxadiazol-3-yl)-1H-indol-3-yl]carbonyl}-6-alaninate (D97) (200 mg) MS (ES): $C_{25}H_{25}ClN_4O_5$ requires 496; found 497.2 (M+H$^+$).
Description for D98

Ethyl N-{[7-(5-{3-chloro-4-[(1-methylethyl)oxy] phenyl}-1,2,4-oxadiazol-3-yl)-1-methyl-1H-indol-3-yl]carbonyl}-β-alaninate (D98)

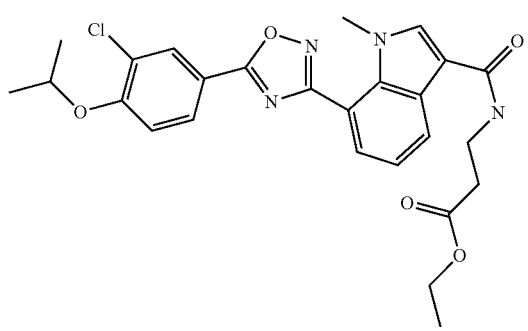

To a solution of 7-(5-{3-chloro-4-[(1-methylethyl)oxy] phenyl}-1,2,4-oxadiazol-3-yl)-1-methyl-1H-indole-3-carboxylic acid (D95) (200 mg), HATU (554 mg) in DCM (20 mL) was added DIPEA (0.254 mL). The reaction mixture was stirred at 40° C. for 4 h. The reaction mixture was cooled to room temperature and partitioned between DCM (50 mL) and water (50 mL). The organic phase was washed with water and brine, dried over sodium sulphate and evaporated in vacuo to afford the crude product ethyl N-{[7-(5-{3-chloro-4-[(1-methylethyl)oxy]phenyl}-1,2,4-oxadiazol-3-yl)-1-methyl-1H-indol-3-yl]carbonyl}-6-alaninate (D98) (200 mg) MS (ES): $C_{26}H_{27}ClN_4O_5$ requires 510. found 511.2 (M+H$^+$).
Description for D99

3-[7-(5-{3-chloro-4-[(1-methylethyl)oxy]phenyl}-1, 2,4-oxadiazol-3-yl)-1H-indol-3-yl]-1-propanol (D99)

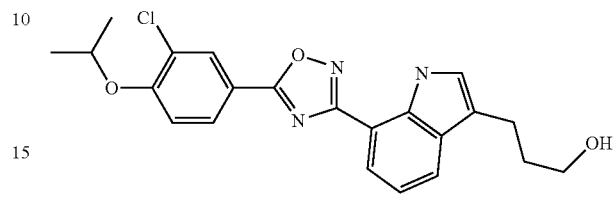

To a solution of 3-[7-(5-{3-chloro-4-[(1-methylethyl)oxy] phenyl}-1,2,4-oxadiazol-3-yl)-1H-indol-3-yl]propanal (D92) (300 mg) was added NaBH$_4$ (138 mg). The reaction mixture was stirred at 20° C. overnight. The reaction mixture was evaporated and the residue was partitioned between DCM (50 mL) and water (25 mL). The organic phase was washed with water and brine, dried over sodium sulphate and evaporated in vacuo to afford the product 3-[7-(5-{3-chloro-4-[(1-methyl ethyl)oxy]phenyl}-1,2,4-oxadiazol-3-yl)-1H-indol-3-yl]-1-propanol as a white solid (D99) (280 mg). MS (ES): $C_{22}H_{22}ClN_3O_3$ requires 411; found 412.2 (M+H$^+$).
Description for D100

N-hydroxy-1H-indole-6-carboximidamide (D100)

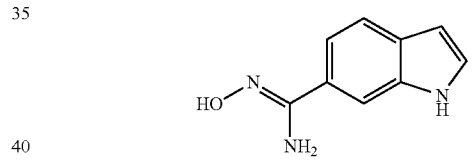

Hydroxylamine hydrochloride (4.7 g) and sodium bicarbonate (8.6 g) were added to a solution of 1H-indole-6-carbonitrile (4.8 g) in EtOH (70 mL) successively. The reaction mixture was heated to reflux and stirred for 36 hours. The inorganic percipitate was filtered off. The solid was washed with EtOH (30 mL). The filtrate was concentrated to afford N-hydroxy-1H-indole-6-carboximidamide (D100) (6.3 g) as a yellow solid. No purification was attempted. MS (ES): $C_9H_9N_3O$ requires 175; found 176.2 (M+H$^+$).
Description for D101

6-(5-{5-chloro-6-[(1-methylethyl)oxy]-3-pyridinyl}-1,2,4-oxadiazol-3-yl)-1H-indole (D101)

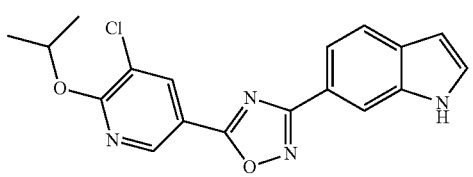

EDCI (1.17 g) and HOBT (1.01 g) were added to a solution of 5-chloro-6-[(1-methylethyl)oxy]-3-pyridinecarboxylic acid (657 mg) in THF (5 mL) at RT. The resulting solution was stirred for 30 min. N-hydroxy-1H-indole-6-carboximidamide (D100) (1.00 g) in THF (5 mL) was added and the reaction mixture was stirred at RT for 2 hours. TBAF (3.2 g) was then added. The reaction vessel was sealed and heated in Biotage Initiator using initial normal to 120° C. for 90 min. After cooling, the reaction was quenched with water, and extracted with EtOAc for 3 times. The combined organic solution was washed with brine, and dried over anhydrous sodium sulfate. The dried solution was concentrated. The residue was purified by column chromatography to afford 6-(5-{5-chloro-6-[(1-methylethyl)oxy]-3-pyridinyl}-1,2,4-oxadiazol-3-yl)-1H-indole (D101) (1.13 g) as a pale yellow solid. δH (CDCl$_3$, 400 MHz): 1.47 (6H, d), 5.51 (1H, m), 6.65 (1H, s), 7.37 (1H, t), 7.76 (1H, d), 7.93 (1H, d), 8.26 (1H, s), 8.42 (2H, d), 8.90 (1H, d). MS (ES): $C_{18}H_{15}ClN_4O_2$ requires 354. found 355.1 (M+H$^+$).

Description for D102

6-(5-{5-chloro-6-[(1-methylethyl)oxy]-3-pyridinyl}-1,2,4-oxadiazol-3-yl)-1H-indole-3-carbaldehyde (D102)

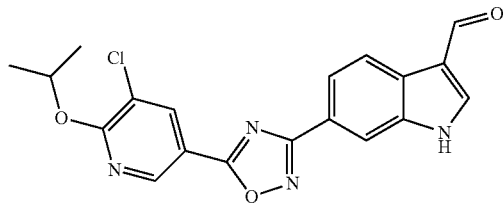

DMF (0.28 mL) was added dropwise to a solution of (COCl)$_2$ (0.31 mL) in DCM (9 mL) at 0° C. The resulting mixture was stirred at 0° C. for 1 hour. Then a solution of 6-(5-{3-chloro-4-[(1-methylethyl)oxy]phenyl}-1,2,4-oxadiazol-3-yl)-1H-indole (D101) (1.06 g) in DCM (30 mL) was added. The reaction mixture was warmed to RT and stirred overnight. Then water and 2 M HCl was added. After stirred for 2 hours, the mixture was neutralized with 2 M aqueous NaOH solution until pH was between 8 and 9. The organic layer was separated and washed with brine, dried over anhydrous sodium sulfate. The dried solution was concentrated. The residue was purified by column chromatography to afford 6-(5-{5-chloro-6-[(1-methylethyl)oxy]-3-pyridinyl}-1,2,4-oxadiazol-3-yl)-1H-indole-3-carbaldehyde (D102) (620 mg) as a yellow solid. δH (DMSO-d$_6$, 400 MHz): 1.46 (6H, d), 5.51 (1H, m), 7.99 (1H, d), 8.14 (1H, d), 8.30 (1H, s), 8.42 (1H, d), 8.46 (1H, d), 8.90 (1H, d), 8.98 (1H, br s), 10.12 (1H, d).

Description for D103

Ethyl 1-{[6-(5-{5-chloro-6-[(1-methylethyl)oxy]-3-pyridinyl}-1,2,4-oxadiazol-3-yl)-1H-indol-3-yl]methyl}-4-piperidinecarboxylate (D103)

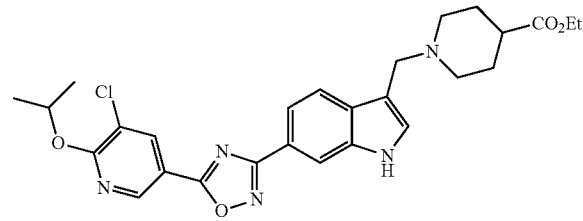

Sodium hydroxide (5.5 mL, 0.5 M in EtOH) was added to a mixture of 6-[5-(5-chloro-6-isopropoxy-pyridin-3-yl)-[1,2,4]oxadiazol-3-yl]-1H-indole-3-carbaldehyde (D102) (200 mg) and piperidine-4-carboxylic acid ethyl ester hydrochloride (507 mg). The reaction mixture was stirred at room temperature for 10 mins, and AcOH (0.5 ml) was added. After the solvent was evaporated, the residue was dissolved in DCM (40 mL). NaBH(OAc)$_3$ (554 mg) was then added in one portion. After stirred overnight, the reaction was quenched with saturated aqueous sodium bicarbonate solution, and extracted with DCM for 3 times. The combined organic solution was washed with brine, and dried over anhydrous sodium sulfate. The dried solution was concentrated. The residue was purified by Mass Directed AutoPrep to afford ethyl 1-{[6-(5-{5-chloro-6-[(1-methylethyl)oxy]-3-pyridinyl}-1,2,4-oxadiazol-3-yl)-1H-indol-3-yl]methyl}-4-piperidinecarboxylate (D103) (140 mg) as a white solid. MS (ES): $C_{27}H_{30}ClN_5O_4$ requires 523; found 524.2.

Description for D104

Ethyl ({2-[7-(5-{3-chloro-4-[(1-methylethyl)oxy]phenyl}-1,2,4-oxadiazol-3-yl)-1-methyl-1H-indol-3-yl]ethyl}oxy)acetate (D104)

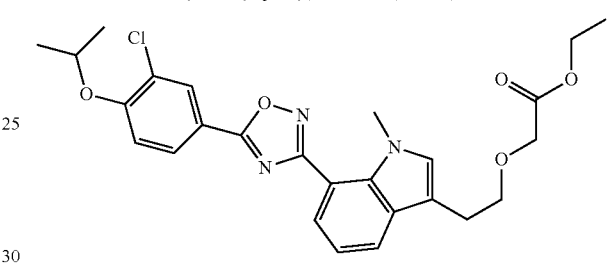

To a stirred solution of ethyl hydroxyacetate (23 mg) in DMF (5 mL) was added NaH (18 mg). The reaction mixture was stirred at 20° C. for 15 mins. Then a solution of 2-[7-(5-{3-chloro-4-[(1-methylethyl)oxy]phenyl}-1,2,4-oxadiazol-3-yl)-1-methyl-1H-indol-3-yl]ethyl 4-methylbenzenesulfonate (D127) (25 mg) in DMF was added dropwise. The mixture was stirred at room temperature for 24 h. The reaction was quenched with water, partitioned between ethyl acetate (25 mL) and water (25 mL). The organic phase was washed with water, 2 M hydrochloric acid and brine, dried over sodium sulphate and evaporated to give the crude product ethyl ({2-[7-(5-{3-chloro-4-[(1-methylethyl)oxy]phenyl}-1,2,4-oxadiazol-3-yl)-1-methyl-1H-indol-3-yl]ethyl}oxy)acetate (D104) (30 mg), used directly in the next step. MS (ES): $C_{26}H_{28}ClN_3O_5$ requires 497; found 498.2 (M+H$^+$).

Description for D105

Ethyl ({3-[7-(5-{3-chloro-4-[(1-methylethyl)oxy]phenyl}-1,2,4-oxadiazol-3-yl)-1-methyl-1H-indol-3-yl]propyl}oxy)acetate (D105)

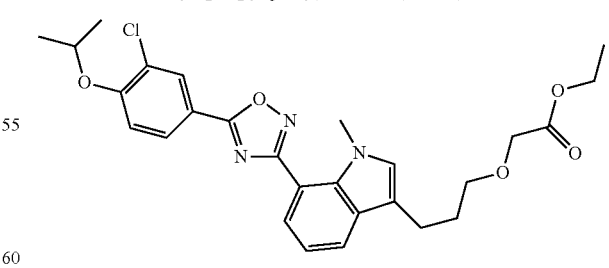

To a stirred solution of ethyl hydroxyacetate (90 mg) in DMF (4 mL) at 20° C. was added NaH (69 mg), the mixture was stirred for 15 mins. Then a solution of 3-[7-(5-{3-chloro-4-[(1-methylethyl)oxy]phenyl}-1,2,4-oxadiazol-3-yl)-1-methyl-1H-indol-3-yl]propyl 4-methylbenzenesulfonate (D129) (100 mg) in DMF (4 mL) was added dropwise during 1 min. The reaction was stirred at 20° C. for 48 h. The reaction mixture was quenched with water, partitioned between ethyl acetate (50 mL) and water (50 mL). The organic phase was washed with water and brine, dried over sodium sulphate and evaporated to give the crude product ethyl ({3-[7-(5-{3-chloro-4-[(1-methylethyl)oxy]phenyl}-1,2,4-oxadiazol-3-yl)-1-methyl-1H-indol-3-yl]propyl}oxy)acetate (D105) (80 mg). MS (ES): $C_{27}H_{30}ClN_3O_5$ requires 511; found 512.2 ($M+H^+$).

Description for D106

Ethyl 3-(6-cyano-1H-indol-3-yl)propanoate

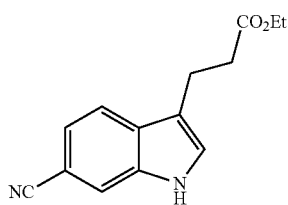

1H-indole-6-carbonitrile (D12) (3.2 g), ferric chloride (3.7 g) and ethyl acrylate (7.3 mL) in DCE (7 mL) was added to a sealed tube. The tube was sealed, and the reaction mixture was stirred at 120° C. for 2 hours. After cooling, the reaction mixture was diluted with DCM. The organic layer was washed with 0.5 M HCl, brine, dried over anhydrous sodium sulfate. The dried solution was concentrated. The residue was purified by column chromatography (20% EtOAc in hexane) to afford ethyl 3-(6-cyano-1H-indol-3-yl)propanoate (D106) (3.1 g) as a yellow solid. δH (CDCl₃, 400 MHz): 1.24 (3H, t), 2.71 (2H, t), 3.11 (2H, t), 4.14 (2H, q), 7.24 (1H, dd), 7.36 (1H, dd), 7.67 (1H, d), 7.70 (1H, dd), 8.36 (1H, br s). MS (ES): $C_{14}H_{14}N_2O_2$ requires 242. found 243.1 ($M+H^+$).

Description for D107

Ethyl 3-{6-[(Z)-(hydroxyamino)(imino)methyl]-1H-indol-3-yl}propanoate (D107)

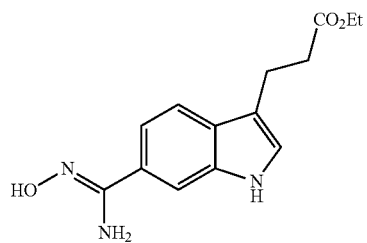

Hydroxylamine hydrochloride (1.8 g) and sodium bicarbonate (3.2 g) was added to a solution of ethyl 3-(6-cyano-1H-indol-3-yl)propanoate (D106) (3.1 g) in EtOH (40 mL) successively. The reaction mixture was heated to reflux and stirred for 10 hours at that temperature. The inorganic precipitate was filtered off. The solid was washed with EtOH (20 mL). The filtrate was concentrated to afford ethyl 3-{6-[(Z)-(hydroxyamino)(imino)methyl]-1H-indol-3-yl}propanoate (D107) (3.8 g) as a pale yellow solid. No purification was attempted. MS (ES): $C_{14}H_{17}N_3O_3$ requires 275; found 276.2 ($M+H^+$).

Description for D108

Ethyl 3-[6-(5-{5-chloro-6-[(1-methylethyl)oxy]-3-pyridinyl}-1,2,4-oxadiazol-3-yl)-1H-indol-3-yl]propanoate (D108)

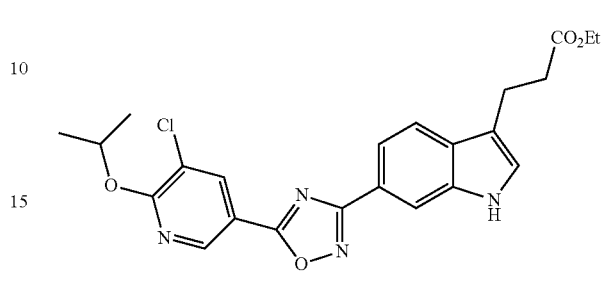

EDCI (356 mg) and HOBT (306 mg) were added to a solution of 5-chloro-6-[(1-methylethyl)oxy]-3-pyridinecarboxylic acid (200 mg) in THF (5 mL) at RT. The resulting solution was stirred for 30 mins. Ethyl 3-{6-[(Z)-(hydroxyamino)(imino)methyl]-1H-indol-3-yl}propanoate (D107) (383 mg) in THF (5 mL) was added and the reaction mixture was stirred at RT for 2 hours. TBAF (970 mg) was then added. The reaction vessel was sealed and heated in Biotage Initiator using initial normal to 120° C. for 90 mins. After cooling, the reaction was quenched with water, and extracted with EtOAc for 3 times. The combined organic solution was washed with brine, dried over anhydrous sodium sulfate. The dried solution was concentrated. The residue was purified by column chromatography (20% EtOAc in hexane) to afford ethyl 3-[6-(5-{5-chloro-6-[(1-methylethyl)oxy]-3-pyridinyl}-1,2,4-oxadiazol-3-yl)-1H-indol-3-yl]propanoate (D108) (310 mg) as a pale yellow solid. δH (CDCl₃, 400 MHz): 1.25 (3H, t), 1.46 (6H, d), 2.74 (2H, t), 3.15 (2H, t), 4.15 (2H, q), 5.51 (1H, m), 7.17 (1H, d), 7.72 (1H, d), 7.93 (1H, dd), 8.20 (2H, d), 8.42 (1H, d), 8.89 (1H, d). MS (ES): $C_{23}H_{23}ClN_4O_4$ requires 454; found 455.2 ($M+H^+$).

Description for D109

Ethyl 3-(6-{5-[6-[(1-methylethyl)oxy]-5-(trifluoromethyl)-3-pyridinyl]-1,2,4-oxadiazol-3-yl}-1H-indol-3-yl)propanoate (D109)

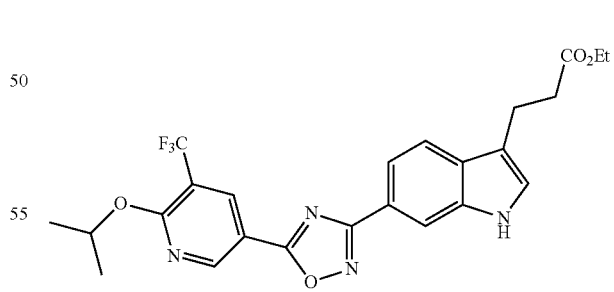

EDCI (385 mg) and HOBT (332 mg) were added to a solution of 6-[(1-methylethyl)oxy]-5-(trifluoromethyl)-3-pyridinecarboxylic acid (250 mg) in THF (5 mL) at RT. The resulting solution was stirred for 30 mins. Ethyl 3-{6-[(Z)-(hydroxyamino)(imino)methyl]-1H-indol-3-yl}propanoate (D107) (413 mg) in THF (5 mL) was added and the reaction mixture was stirred at RT for 2 hours. TBAF (1.1 g) was then added. The reaction vessel was sealed and heated in Biotage Initiator using initial normal to 120° C. for 90 mins. After cooling, the reaction was quenched with water, and extracted with EA for 3 times. The combined organic solution was washed with brine, dried over anhydrous sodium sulfate. The dried solution was concentrated. The residue was purified by column chromatography (20% EtOAc in hexane) to afford ethyl 3-(6-{5-[6-[(1-methylethyl)oxy]-5-(trifluoromethyl)-3-pyridinyl]-1,2,4-oxadiazol-3-yl}-1H-indol-3-yl)propanoate (D109) (310 mg) as a pale yellow solid. δH (CDCl₃, 400 MHz): 1.25 (3H, t), 1.45 (6H, d), 2.74 (2H, t), 3.15 (2H, t), 4.16 (2H, q), 5.60 (1H, m), 7.17 (1H, t), 7.73 (1H, d), 7.94 (1H, dd), 8.21 (2H, dd), 8.64 (1H, t), 9.14 (1H, d). δF (CDCl₃, 376 MHz): −64.3. MS (ES): $C_{24}H_{23}F_3N_4O_4$ requires 488; found 489.2 (M+H⁺).

Description for D110

Ethyl 3-[6-(5-{5-fluoro-6-[(1-methylethyl)oxy]-3-pyridinyl}-1,2,4-oxadiazol-3-yl)-1H-indol-3-yl]propanoate (D110)

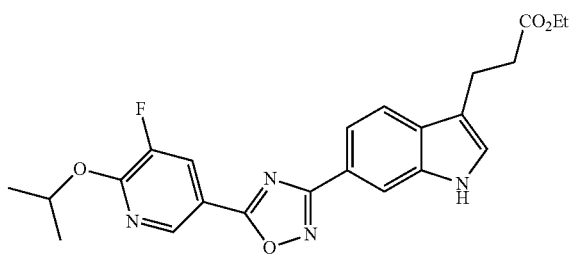

EDCI (385 mg) and HOBT (330 mg) were added to a solution of 5-fluoro-6-[(1-methylethyl)oxy]-3-pyridinecarboxylic acid (200 mg) in THF (5 mL) at RT. The resulting solution was stirred for 30 mins. Ethyl 3-{6-[(Z)-(hydroxyamino)(imino)methyl]-1H-indol-3-yl}propanoate (D107) (413 mg) in THF (5 mL) was added and the reaction mixture was stirred at RT for 2 hours. TBAF (1.1 g) was then added. The reaction vessel was sealed and heated in Biotage Initiator using initial normal to 120° C. for 2 hours. After cooling, the reaction was quenched with water, and extracted with EtOAc for 3 times. The combined organic solution was washed with brine, and dried over anhydrous sodium sulfate. The dried solution was concentrated. The residue was purified by column chromatography (15% EtOAc in hexane) to afford ethyl 3-[6-(5-{5-fluoro-6-[(1-methylethyl)oxy]-3-pyridinyl}-1,2,4-oxadiazol-3-yl)-1H-indol-3-yl]propanoate (D110) (60 mg) as a pale yellow solid. MS (ES): $C_{23}H_{23}FN_4O_4$ requires 438; found 439.2 (M+H⁺).

Description for D111

Ethyl 3-[6-(5-{5-methyl-6-[(1-methylethyl)oxy]-3-pyridinyl}-1,2,4-oxadiazol-3-yl)-1H-indol-3-yl]propanoate (D111)

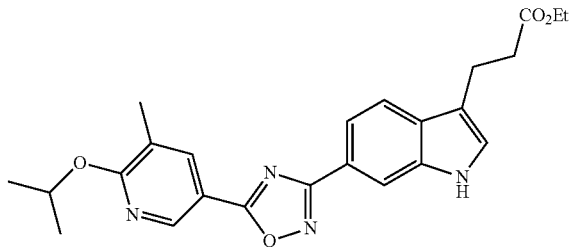

EDCI (590 mg) and HOBT (507 mg) were added to a solution of 5-methyl-6-[(1-methylethyl)oxy]-3-pyridinecarboxylic acid (300 mg) in THF (5 mL) at RT. The resulting solution was stirred for 30 mins. Ethyl 3-{6-[(Z)-(hydroxyamino)(imino)methyl]-1H-indol-3-yl}propanoate (D107) (845 mg) in THF (5 mL) was added and the reaction mixture was stirred at RT for 2 hours. TBAF (1.6 g) was then added. The reaction vessel was sealed and heated in Biotage Initiator using initial normal to 120° C. for 2 hours. After cooling, the reaction was quenched with water, and extracted with EtOAc for 3 times. The combined organic solution was washed with brine, dried over anhydrous sodium sulfate. The dried solution was concentrated. The residue was purified by column chromatography (20% EtOAc in hexane) to afford ethyl 3-[6-(5-{5-methyl-6-[(1-methylethyl)oxy]-3-pyridinyl}-1,2,4-oxadiazol-3-yl)-1H-indol-3-yl]propanoate (D111) (310 mg) as a pale yellow solid. MS (ES): $C_{24}H_{26}N_4O_4$ requires 434; found 435.2 (M+H⁺).

Description for D112

Ethyl 3-(6-{5-[6-[(1-methylethyl)oxy]-5-(methyloxy)-3-pyridinyl]-1,2,4-oxadiazol-3-yl}-1H-indol-3-yl)propanoate (D112)

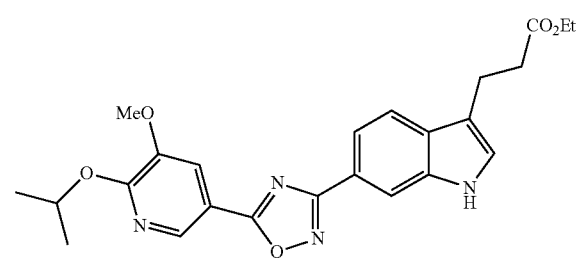

EDCI (281 mg) and HOBT (219 mg) were added to a solution of 6-[(1-methylethyl)oxy]-5-(methyloxy)-3-pyridinecarboxylic acid (152 mg) in THF (3 mL) at RT. The resulting solution was stirred for 30 mins. Ethyl 3-{6-[(Z)-(hydroxyamino)(imino)methyl]-1H-indol-3-yl}propanoate (D107) (261 mg) in THF (5 mL) was added and the reaction mixture was stirred at RT for 2 hours. TBAF (0.91 g) was then added. The reaction vessel was sealed and heated in Biotage Initiator using initial normal to 120° C. for 1.5 hours. After cooling, the reaction was quenched with water, and extracted with EtOAc for 3 times. The combined organic solution was washed with brine, and dried over anhydrous sodium sulfate. The dried solution was concentrated. The residue was purified by column chromatography (30% EtOAc in hexane) to afford ethyl 3-(6-{5-[6-[(1-methylethyl)oxy]-5-(methyloxy)-3-pyridinyl]-1,2,4-oxadiazol-3-yl}-1H-indol-3-yl)propanoate (D112) (258 mg) as a pale yellow solid. MS (ES): $C_{24}H_{26}N_4O_5$ requires 450; found 451.2 (M+H⁺).

Description for D113

Methyl 3-[5-(5-{3-chloro-4-[(1-methylethyl)oxy]phenyl}-1,2,4-oxadiazol-3-yl)-1-methyl-1H-indol-2-yl]propanoate (D113)

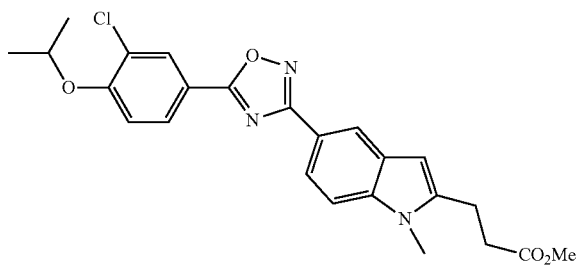

A solution of ethyl 3-[5-(5-{3-chloro-4-[(1-methylethyl)oxy]phenyl}-1,2,4-oxadiazol-3-yl)-1H-indol-2-yl]propanoate (D33) (114 mg), DABCO (56 mg) and dimethyl carbonate (2 mL) in N,N-dimethylformamide (DMF, 2 mL) was stirred at 90° C. for 2 days. After cooled to room temperature, the reaction mixture was diluted with ethyl acetate. The organic solution was washed with water. The organic solution was dried over anhydrous sodium sulfate. The dried solution was concentrated. The residue was purified by column chromatography to afford methyl 3-[5-(5-{3-chloro-4-[(1-methylethyl)oxy]phenyl}-1,2,4-oxadiazol-3-yl)-1-methyl-1H-indol-2-yl]propanoate (D113) (67 mg). MS (ES): $C_{24}H_{24}ClN_3O_4$ requires 453; found 454.2 (M+H$^+$).

Description for D114

Ethyl 3-[5-(5-{3-cyano-4-[(1-methylethyl)oxy]phenyl}-1,2,4-oxadiazol-3-yl)-1H-indol-2-yl]propanoate (D114)

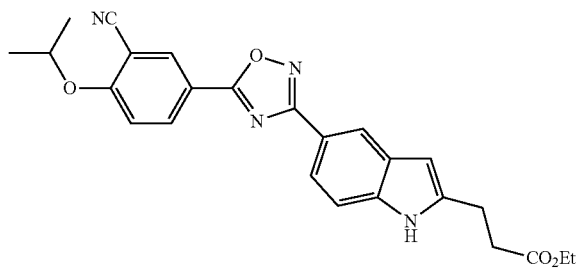

EDCI (187 mg) and HOBT (149 mg) were added to a solution of 3-cyano-4-[(1-methylethyl)oxy]benzoic acid (100 mg) in THF (5 mL). The mixture was stirred at room temperature for 1 hour followed by addition of ethyl 3-{5-[(Z)-(hydroxyamino)(imino)methyl]-1H-indol-2-yl}propanoate (D31) (201 mg). The resulting mixture was stirred at room temperature for 2 hrs followed by addition of TBAF (510 mg). The reaction vessel was sealed and heated in Biotage Initiator to 120° C. for 2 hrs. After cooling the reaction, THF was removed. The residue was dissolved in EtOAc. The organic solution was washed with saturated aqueous sodium bicarbonate solution. The organic solution was dried over anhydrous sodium sulfate. The dried solution was concentrated. The residue was purified by column chromatography to afford ethyl 3-[5-(5-{3-cyano-4-[(1-methylethyl)oxy]phenyl}-1,2,4-oxadiazol-3-yl)-1H-indol-2-yl]propanoate (D114) (68 mg). The product was directly used in the next step without identification.

Description for D115

Ethyl 3-[5-(5-{5-chloro-6-[(1-methylethyl)oxy]-3-pyridinyl}-1,2,4-oxadiazol-3-yl)-1H-indol-2-yl]propanoate (D115)

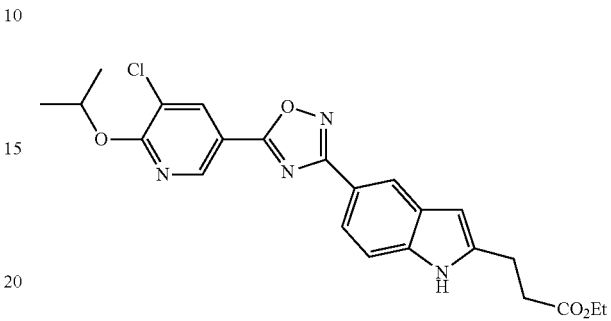

EDCI (92 mg) and HOBT (80 mg) were added to a solution of 5-chloro-6-[(1-methylethyl)oxy]-3-pyridinecarboxylic acid (52 mg) in THF (6 mL). The resulting mixture was stirred for 1 hour followed by addition of ethyl 3-{5-[(Z)-(hydroxyamino)(imino)methyl]-1H-indol-2-yl}propanoate (D31) (100 mg). The resulting mixture was stirred for 3 hours followed by addition of TBAF (251 mg). The reaction vessel was sealed, and heated at 120° C. in the microwave for 3 hours. THF was removed. The residue was dissolved in EtOAc. The organic solution was washed with saturated aqueous sodium bicarbonate solution. The organic solution was dried over anhydrous sodium sulfate. The dried solution was concentrated. The residue was purified by column chromatography to afford ethyl 3-[5-(5-{5-chloro-6-[(1-methylethyl)oxy]-3-pyridinyl}-1,2,4-oxadiazol-3-yl)-1H-indol-2-yl]propanoate (D115) (54 mg). MS (ES): $C_{23}H_{23}ClN_4O_4$ requires 454; found 455.2 (M+H$^+$).

Description for D116

Methyl 3-[5-(5-{5-chloro-6-[(1-methylethyl)oxy]-3-pyridinyl}-1,2,4-oxadiazol-3-yl)-1-methyl-1H-indol-2-yl]propanoate (D116)

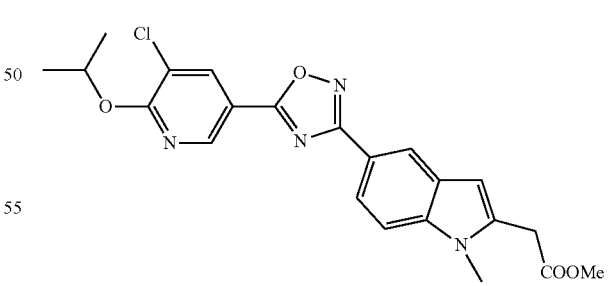

A solution of ethyl 3-[5-(5-{5-chloro-6-[(1-methylethyl)oxy]-3-pyridinyl}-1,2,4-oxadiazol-3-yl)-1H-indol-2-yl]propanoate (D115) (112 mg), dimethyl carbonate (2.0 mL) and DABCO (33 mg) in N,N-dimethylformamide (2 mL) was stirred at 90° C. for 2 days. After cooled to room temperature, the reaction mixture was diluted with ethyl acetate. The organic solution was washed with water. The organic solution was dried over anhydrous sodium sulfate. The dried solution was concentrated. The residue was purified by column chromatography to afford methyl 3-[5-(5-{5-chloro-6-[(1-methylethyl)oxy]-3-pyridinyl}-1,2,4-oxadiazol-3-yl)-1-methyl-1H-indol-2-yl]propanoate (D116) (72 mg). The crude product was used directly in the next step without further identification.

Description for D117

Ethyl 3-(5-{5-[6-[(1-methylethyl)oxy]-5-(trifluoromethyl)-3-pyridinyl]-1,2,4-oxadiazol-3-yl}-1H-indol-2-yl)propanoate (D117)

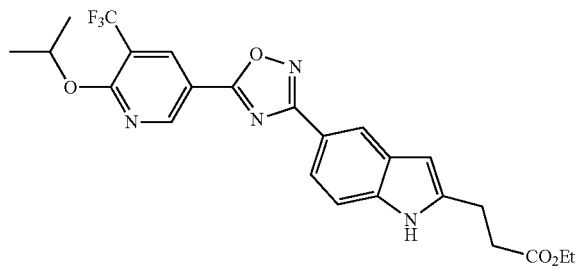

EDCI (92 mg) and HOBT (79 mg) were added to a solution of 6-[(1-methylethyl)oxy]-5-(trifluoromethyl)-3-pyridinecarboxylic acid (60 mg) in THF (6 mL). The resulting solution was stirred for 1 hour followed by addition of ethyl 3-{5-[(Z)-(hydroxyamino)(imino)methyl]-1H-indol-2-yl}propanoate (D31) (100 mg). The resulting mixture was stirred for 3 hours followed by addition of TBAF (251 mg). The reaction vessel was sealed. The reaction mixture was heated at 120° C. in the microwave for 2 hours. THF was removed. The residue was dissolved in EtOAc. The organic solution was washed with saturated aqueous sodium bicarbonate solution. The organic solution was dried over anhydrous sodium sulfate. The dried solution was concentrated. The residue was purified by column chromatography to afford ethyl 3-(5-{5-[6-[(1-methylethyl)oxy]-5-(trifluoromethyl)-3-pyridinyl]-1,2,4-oxadiazol-3-yl}-1H-indol-2-yl)propanoate (D117) (89 mg). MS (ES): $C_{24}H_{23}F_3N_4O_4$ requires 488. found 489.2 (M+H$^+$).

Description for D118

Ethyl 3-(5-{5-[6-[(1-methylethyl)oxy]-5-(methyloxy)-3-pyridinyl]-1,2,4-oxadiazol-3-yl}-1H-indol-2-yl)propanoate (D118)

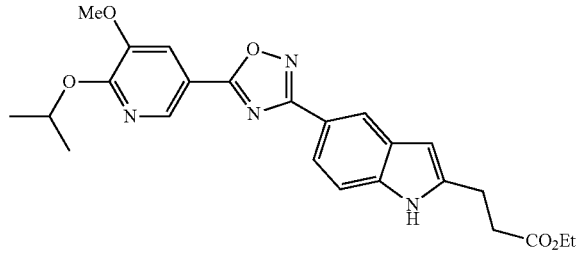

EDCI (182 mg) and HOBT (145 mg) were added to a solution of 6-[(1-methylethyl)oxy]-5-(methyloxy)-3-pyridinecarboxylic acid (100 mg) in THF (5 mL). The resulting mixture was stirred at room temperature for 1 hour followed by addition of ethyl 3-{5-[(Z)-(hydroxyamino)(imino)methyl]-1H-indol-2-yl}propanoate (D31) (196 mg). The resulting mixture was stirred at room temperature for 2 hrs followed by addition of TBAF (495 mg). The reaction vessel was sealed and heated in Biotage Initiator to 120° C. for 2 hrs. After cooling the reaction, THF was removed. The residue was dissolved in EtOAc. The organic solution was washed with saturated aqueous sodium bicarbonate solution. The organic solution was dried over anhydrous sodium sulfate. The dried solution was concentrated. The residue was purified by column chromatography to afford ethyl 3-(5-{5-[6-[(1-methylethyl)oxy]-5-(methyloxy)-3-pyridinyl]-1,2,4-oxadiazol-3-yl}-1H-indol-2-yl)propanoate (D118) (35 mg). MS (ES): $C_{24}H_{26}N_4O_5$ requires 450; found 451.2 (M+H$^+$).

Description For D119

Ethyl 3-[7-(5-{5-methyl-6-[(1-methylethyl)oxy]-3-pyridinyl}-1,2,4-oxadiazol-3-yl)-1H-indol-3-yl]propanoate (D119)

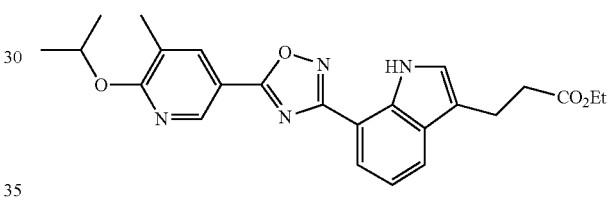

EDCI (432 mg) and HOBT (372 mg) were added to a solution of 5-methyl-6-[(1-methylethyl)oxy]-3-pyridinecarboxylic acid (220 mg) in THF (5 mL) at RT. The resulting solution was stirred for 30 mins. Ethyl 3-{7-[(Z)-(hydroxyamino)(imino)methyl]-1H-indol-3-yl}propanoate (D35) (465 mg) in THF (5 mL) was added and the reaction mixture was stirred at RT for 2 hours. TBAF (1.2 g) was then added. The reaction vessel was sealed and heated in Biotage Initiator using initial normal to 120° C. for 2 hours. More TBAF (1.2 g) was added. The reaction vessel was sealed again and heated in Biotage Initiator using initial normal to 120° C. for 2 hours. Part of ethyl 3-[7-(5-{5-methyl-6-[(1-methylethyl)oxy]-3-pyridinyl}-1,2,4-oxadiazol-3-yl)-1H-indol-3-yl]propanoate was hydrolyzed by TBAF to 3-[7-(5-{5-methyl-6-[(1-methylethyl)oxy]-3-pyridinyl}-1,2,4-oxadiazol-3-yl)-1H-indol-3-yl]propanoic acid (E16). After cooling, the reaction was quenched with water, and extracted with EtOAc for 3 times. The combined organic solution was washed with brine, dried over anhydrous sodium sulfate. The dried solution was concentrated. The residue was purified by column chromatography (50% EtOAc in hexane) to afford ethyl 3-[7-(5-{5-methyl-6-[(1-methylethyl)oxy]-3-pyridinyl}-1,2,4-oxadiazol-3-yl)-1H-indol-3-yl]propanoate (D119) (196 mg), MS (ES): $C_{24}H_{26}N_4O_4$ requires 434; found 435.2 (M+H$^+$) and 3-[7-(5-{5-methyl-6-[(1-methylethyl)oxy]-3-pyridinyl}-1,2,4-oxadiazol-3-yl)-1H-indol-3-yl]propanoic acid (E16) (100 mg) as a white solid.

Description For D120

Ethyl 3-[7-(5-{3-chloro-4-[(1-methylethyl)oxy]phenyl}-1,2,4-oxadiazol-3-yl)-1-ethyl-1H-indol-3-yl]propanoate (D120)

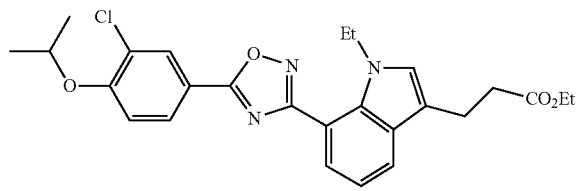

Potassium hydroxide (62 mg) was added to a solution of 3-[7-(5-{3-chloro-4-[(1-methylethyl)oxy]phenyl}-1,2,4-oxadiazol-3-yl)-1H-indol-3-yl]propanoic acid (E1) (100 mg) and bromoethane (0.2 mL) in dimethyl sulfoxide (DMSO) (1 mL). The reaction mixture was stirred at room temperature for 3 hours. The reaction mixture was diluted with ethyl acetate. The organic solution was washed with water. The organic solution was dried over anhydrous sodium sulfate. After concentration, the residue was purified via column chromatography to afford ethyl 3-[7-(5-{3-chloro-4-[(1-methylethyl)oxy]phenyl}-1,2,4-oxadiazol-3-yl)-1-ethyl-1H-indol-3-yl]propanoate (D120) (79 mg). δH (CDCl$_3$, 400 MHz): 1.14 (3H, t), 1.25 (3H, t), 1.45 (6H, d), 2.71 (2H, t), 3.12 (2H, t), 4.15 (2H, q), 4.20 (2H, q), 4.72 (1H, m), 6.97 (1H, s), 7.07 (1H, d), 7.20 (1H, t), 7.55 (1H, dd), 7.76 (1H, dd), 8.08 (1H, dd), 8.26 (1H, d); MS (ES): $C_{26}H_{28}ClN_3O_4$ requires 481; found 482.2 (M+H$^+$).

Description For D121

Propyl 3-[7-(5-{3-chloro-4-[(1-methylethyl)oxy]phenyl}-1,2,4-oxadiazol-3-yl)-1-propyl-1H-indol-3-yl]propanoate (D121)

Potassium hydroxide (130 mg) was added to a solution of 3-[7-(5-{3-chloro-4-[(1-methylethyl)oxy]phenyl}-1,2,4-oxadiazol-3-yl)-1H-indol-3-yl]propanoic acid (E1) (200 mg) and 1-bromopropane (0.3 mL) in dimethyl sulfoxide (DMSO) (1 mL). The reaction mixture was stirred at room temperature for 3 hours. The reaction mixture was diluted with ethyl acetate. The organic solution was washed with water. The organic solution was dried over anhydrous sodium sulfate. After concentration, the residue was purified via column chromatography to afford propyl 3-[7-(5-{3-chloro-4-[(1-methylethyl)oxy]phenyl}-1,2,4-oxadiazol-3-yl)-1-propyl-1H-indol-3-yl]propanoate (D121) (166 mg). δH (CDCl$_3$, 400 MHz): 0.63 (3H, t), 0.92 (3H, t), 1.45 (6H, d), 1.54 (2H, m), 1.65 (2H, m), 2.72 (2H, t), 3.12 (2H, t), 4.04 (2H, t), 4.13 (2H, t), 4.72 (1H, m), 6.95 (1H, s), 7.07 (1H, d), 7.20 (1H, t), 7.54 (1H, dd), 7.76 (1H, dd), 8.09 (1H, dd), 8.26 (1H, d); MS (ES): $C_{28}H_{32}ClN_3O_4$ requires 509; found 510.2 (M+H$^+$).

Description For D122

1-Methylethyl 3-[7-(5-{3-chloro-4-[(1-methylethyl)oxy]phenyl}-1,2,4-oxadiazol-3-yl)-1-(1-methylethyl)-1H-indol-3-yl]propanoate (D122)

Potassium hydroxide (200 mg) was added to a solution of 3-[7-(5-{3-chloro-4-[(1-methylethyl)oxy]phenyl}-1,2,4-oxadiazol-3-yl)-1H-indol-3-yl]propanoic acid (E1) (100 mg) and 2-iodopropane (0.5 mL) in dimethyl sulfoxide (DMSO) (1.0 mL). The reaction mixture was stirred at room temperature for 3 days. The reaction mixture was diluted with ethyl acetate. The organic solution was washed with water. The organic solution was dried over sodium sulfate. After concentration, the residue was purified via column chromatography to afford 1-methylethyl 3-[7-(5-{3-chloro-4-[(1-methylethyl)oxy]phenyl}-1,2,4-oxadiazol-3-yl)-1-(1-methylethyl)-1H-indol-3-yl]propanoate (D122) (60 mg). δH (CDCl$_3$, 400 MHz): 1.22 (6H, d), 1.35 (6H, d), 1.45 (6H, d), 2.69 (2H, t), 3.12 (2H, t), 4.73 (2H, m), 5.03 (1H, m), 7.07 (1H, d), 7.14 (1H, s), 7.18 (1H, t), 7.48 (1H, dd), 7.75 (1H, dd), 8.08 (1H, dd), 8.25 (1H, d); MS (ES): $C_{28}H_{32}ClN_3O_4$ requires 509; found 510.2 (M+H$^+$).

Description For D123

Butyl 3-[1-butyl-7-(5-{3-chloro-4-[(1-methylethyl)oxy]phenyl}-1,2,4-oxadiazol-3-yl)-1H-indol-3-yl]propanoate (D123)

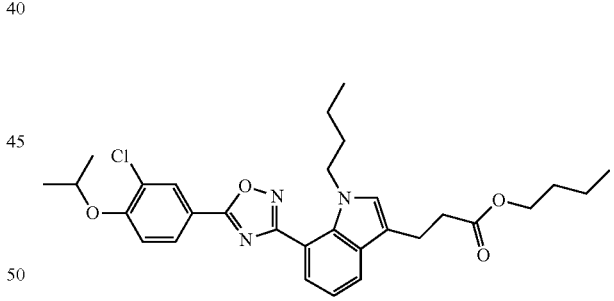

Potassium hydroxide (65 mg) was added to a solution of 3-[7-(5-{3-chloro-4-[(1-methylethyl)oxy]phenyl}-1,2,4-oxadiazol-3-yl)-1H-indol-3-yl]propanoic acid (E1) (100 mg) and 1-iodobutane (0.2 mL) in dimethyl sulfoxide (DMSO) (1 mL). The reaction mixture was stirred at room temperature for 3 hours. The reaction mixture was diluted with ethyl acetate. The organic solution was washed with water. The organic solution was dried over sodium sulfate. After concentration, the residue was purified via column chromatography to afford butyl 3-[1-butyl-7-(5-{3-chloro-4-[(1-methylethyl)oxy]phenyl}-1,2,4-oxadiazol-3-yl)-1H-indol-3-yl]propanoate (D123) (61 mg). δH (CDCl$_3$, 400 MHz): 0.73 (3H, t), 0.92 (3H, t), 1.03 (2H, m), 1.34 (2H, m), 1.45 (8H, m), 1.59 (2H, m), 2.71 (2H, t), 3.12 (2H, t), 4.08 (2H, t), 4.16 (2H, t), 4.72 (1H, m), 6.94 (1H, s), 7.07 (1H, d), 7.19 (1H, t), 7.53 (1H, dd), 7.76 (1H, dd), 8.08 (1H, dd), 8.25 (1H, d); MS (ES): $C_{30}H_{36}ClN_3O_4$ requires 537; found 538.3 (M+H$^+$).

Description For D124

2-Methylpropyl 3-[7-(5-{3-chloro-4-[(1-methylethyl)oxy]phenyl}-1,2,4-oxadiazol-3-yl)-1-(2-methylpropyl)-1H-indol-3-yl]propanoate (D124)

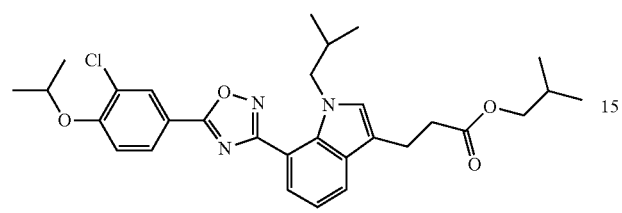

Potassium hydroxide (64 mg) was added to a solution of 3-[7-(5-{3-chloro-4-[(1-methylethyl)oxy]phenyl}-1,2,4-oxadiazol-3-yl)-1H-indol-3-yl]propanoic acid (E1) (100 mg) and 1-iodo-2-methylpropane (0.2 mL) in dimethyl sulfoxide (DMSO) (1 mL). The reaction mixture was stirred at room temperature for 3 hours. The reaction mixture was diluted with ethyl acetate. The organic solution was washed with water. The organic solution was dried over sodium sulfate. After concentration, the residue was purified via column chromatography to afford 2-methylpropyl 3-[7-(5-{3-chloro-4-[(1-methylethyl)oxy]phenyl}-1,2,4-oxadiazol-3-yl)-1-(2-methylpropyl)-1H-indol-3-yl]propanoate (D124) (77 mg). MS (ES): $C_{30}H_{36}ClN_3O_4$ requires 537; found 538.3 (M+H$^+$).

Description For D125

Ethyl N-{3-[7-(5-{3-chloro-4-[(1-methylethyl)oxy]phenyl}-1,2,4-oxadiazol-3-yl)-1H-indol-3-yl]propanoyl}glycinate (D125)

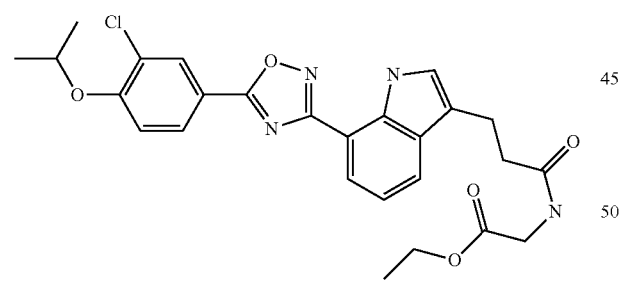

To a solution of 3-[7-(5-{3-chloro-4-[(1-methylethyl)oxy]phenyl}-1,2,4-oxadiazol-3-yl)-1H-indol-3-yl]propanoic acid (E1) (150 mg), ethyl glycinate (73 mg) and HATU (402 mg) in DCM (20 mL) was added DIPEA (0.2 mL). The reaction was stirred at 40° C. for 3 h. The reaction mixture was cooled to room temperature and partitioned between DCM (25 mL) and water (25 mL). The organic phase was washed with water, dried over sodium sulphate and evaporated in vacuo to afford the crude product ethyl N-{3-[7-(5-{3-chloro-4-[(1-methylethyl)oxy]phenyl}-1,2,4-oxadiazol-3-yl)-1H-indol-3-yl]propanoyl}glycinate as an off-white solid (D125) (100 mg), which was used directly in the next step. MS (ES): $C_{26}H_{27}ClN_4O_5$ requires 510; found 511.2 (M+H$^+$).

Description For D126

2-[7-(5-{3-chloro-4-[(1-methylethyl)oxy]phenyl}-1,2,4-oxadiazol-3-yl)-1-methyl-1H-indol-3-yl]ethanol (D126)

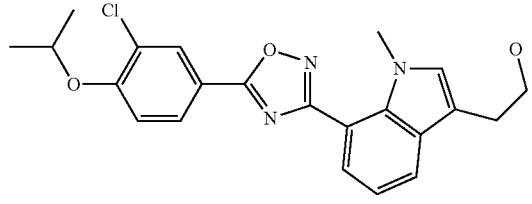

To a solution of [7-(5-{3-chloro-4-[(1-methylethyl)oxy]phenyl}-1,2,4-oxadiazol-3-yl)-1-methyl-1H-indol-3-yl]acetaldehyde (D88) (500 mg) in THF (15 mL) and ethanol (15 mL) was added sodium borohydride (185 mg) in portion during 5 mins. The reaction mixture was stirred at 20° C. for 2 h. The reaction mixture was partitioned between ethyl acetate (50 mL) and water (50 mL). The organic phase was washed with water, 2 M hydrochloric acid and saturated brine, dried over sodium sulphate and evaporated to give the crude product as an off-white gum, which was purified by ISCO (10% ethyl acetate in hexanes) to afford 2-[7-(5-{3-chloro-4-[(1-methylethyl)oxy]phenyl}-1,2,4-oxadiazol-3-yl)-1-methyl-1H-indol-3-yl]ethanol (D126) (450 mg). MS (ES): $C_{22}H_{22}ClN_3O_3$ requires 411; found 412.1 (M+H$^+$).

Description For D127

2-[7-(5-{3-chloro-4-[(1-methylethyl)oxy]phenyl}-1,2,4-oxadiazol-3-yl)-1-methyl-1H-indol-3-yl]ethyl 4-methyl benzenesulfonate (D127)

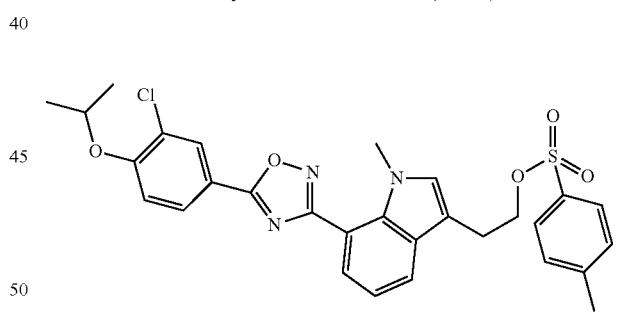

To a stirred solution of 2-[7-(5-{3-chloro-4-[(1-methylethyl)oxy]phenyl}-1,2,4-oxadiazol-3-yl)-1-methyl-1H-indol-3-yl]ethanol (D126) (30 mg), Et$_3$N (0.1 mL) and DMAP (10 mg) in DCM (5 mL) was added 4-methylbenzenesulfonyl chloride (42 mg) in DCM (5 mL). The reaction mixture was stirred at 20° C. for 12 h. The reaction mixture was quenched with water, partitioned between DCM (25 mL) and water (25 mL). The organic phase was washed with water, saturated aqueous sodium carbonate and brine, dried over sodium sulphate and evaporated to give the crude product 2-[7-(5-{3-chloro-4-[(1-methylethyl)oxy]phenyl}-1,2,4-oxadiazol-3-yl)-1-methyl-1H-indol-3-yl]ethyl 4-methylbenzenesulfonate (D127) (100 mg). MS (ES): $C_{29}H_{28}ClN_3O_5S$ requires 565; found 566.2 (M+H$^+$).

Description For D128

3-[7-(5-{3-chloro-4-[(1-methylethyl)oxy]phenyl}-1,2,4-oxadiazol-3-yl)-1-methyl-1H-indol-3-yl]-1-propanol (D128)

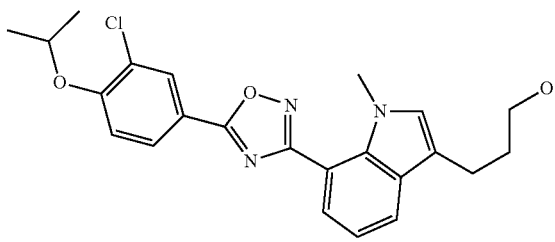

To a suspension of NaBH₄ (0.52 g) in THF (50 mL) was added a solution of 3-[7-(5-{3-chloro-4-[(1-methylethyl)oxy]phenyl}-1,2,4-oxadiazol-3-yl)-1-methyl-1H-indol-3-yl]propanoic acid (E2) (1.5 g) in THF (20 mL) dropwise. The mixture was stirred for 15 mins and a solution of I₂ (1.7 g) in THF (90 mL) was added dropwise. The reaction mixture was stirred at 20° C. for 20 h. The reaction mixture was quenched with water, the solvent was evaporated and the residue was partitioned between ethyl acetate (100 mL) and water (50 mL). The organic phase was washed with aqueous HCl (2 M), water and brine, dried over sodium sulphate and evaporated to give the crude product as yellow foam, which was purified by column chromatography (15% EtOAc in hexanes) to afford 3-[7-(5-{3-chloro-4-[(1-methylethyl)oxy]phenyl}-1,2,4-oxadiazol-3-yl)-1-methyl-1H-indol-3-yl]-1-propanol (D128) (900 mg). δH (DMSO-d₆, 400 MHz): 1.35 (6H, d), 1.80 (2H, m), 2.75 (2H, t), 3.48 (2H, t), 3.60 (3H, s), 4.47 (1H, t), 4.88 (1H, m), 7.16 (2H, m), 7.43 (2H, m), 7.77 (1H, d), 8.12 (1H, dd), 8.19 (1H, d). MS (ES): $C_{23}H_{24}ClN_3O_3$ requires 425; found 426.2 (M+H⁺).

Description For D129

3-[7-(5-{3-chloro-4-[(1-methylethyl)oxy]phenyl}-1,2,4-oxadiazol-3-yl)-1-methyl-1H-indol-3-yl]propyl 4-methylbenzenesulfonate (D129)

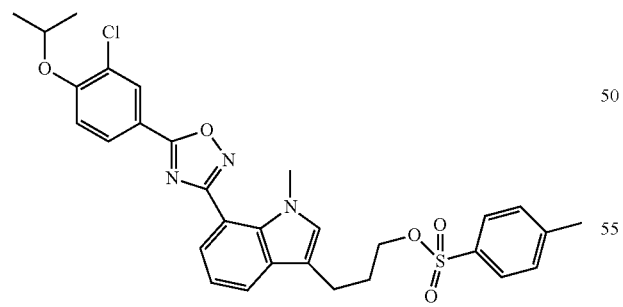

To a mixture of 3-[7-(5-{3-chloro-4-[(1-methylethyl)oxy]phenyl}-1,2,4-oxadiazol-3-yl)-1-methyl-1H-indol-3-yl]-1-propanol (D128) (100 mg), Et₃N (0.2 mL) and DMAP (29 mg) was added DCM (10 mL). The reaction was stirred at 20° C. for 2 h. The reaction mixture was quenched with water, partitioned between DCM (25 mL) and water (25 mL). The organic phase was washed with water, aqueous saturated sodium carbonate and brine, dried over sodium sulphate and evaporated to give the crude product 3-[7-(5-{3-chloro-4-[(1-methylethyl)oxy]phenyl}-1,2,4-oxadiazol-3-yl)-1-methyl-1H-indol-3-yl]propyl 4-methylbenzenesulfonate (D129) (120 mg). MS (ES): $C_{30}H_{30}ClN_3O_6S$ requires 579; found 580.2 (M+H⁺).

Description For D130

Ethyl 3-[7-(5-{3-cyano-4-[(1-methylethyl)oxy]phenyl}-1,2,4-oxadiazol-3-yl)-4-fluoro-1-methyl-1H-indol-3-yl]propanoate (D130)

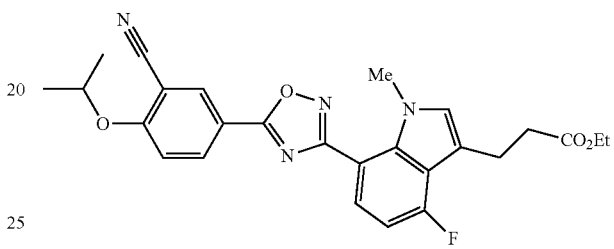

To a solution of ethyl 3-[7-(5-{3-cyano-4-[(1-methylethyl)oxy]phenyl}-1,2,4-oxadiazol-3-yl)-4-fluoro-1H-indol-3-yl]propanoate (D47) (450 mg) and iodomethane (0.91 mL) in dimethyl sulfoxide (DMSO) (15 mL) at room temperature was added potassium hydroxide (218 mg). The reaction mixture was stirred at room temperature for 5 h. The reaction mixture was quenched with saturated ammonium chloride, extracted with EtOAc for 3 times. The organic phase was washed with brine, dried over anhydrous sodium sulphate and evaporated in vacuo to afford the crude product. Purification by column chromatography affords ethyl 3-[7-(5-{3-cyano-4-[(1-methylethyl)oxy]phenyl}-1,2,4-oxadiazol-3-yl)-4-fluoro-1-methyl-1H-indol-3-yl]propanoate (D130) (349 mg). MS (ES): $C_{26}H_{25}FN_4O_4$ requires 476; found 477.3 (M+H⁺)

Description For D131

7-Bromo-5-fluoro-1H-indole (D131)

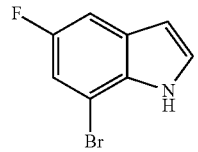

To a solution of 2-bromo-4-fluoro-1-nitrobenzene (24 g) in anhydrous THF (200 mL) was added 1 M vinylmagnesium bromide in THF (328 mL) dropwise at −78° C. slowly, then the mixture was allowed to warm to RT and stirred for 2 hours. TLC indicated the reaction was complete. The reaction mixture was poured into saturated aqueous NH₄Cl solution. The organic phase was separated by extraction with EA (3×200 mL). The crude product was purified by column chromatography to afford 7-bromo-5-fluoro-1H-indole (D131) (15 g) as a brown oil.

Description For D132

5-Fluoro-1H-indole-7-carbonitrile (D132)

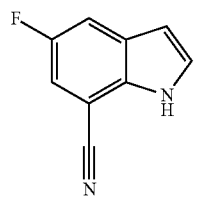

To a solution of 7-bromo-5-fluoro-1H-indole (D131) (15 g) in DMF (150 mL) under $N_2$ atmosphere were added $Zn(CN)_2$ (24.0 g) and then $Pd(PPh_3)_4$ (15.8 g), the reaction mixture was heated to 120° C. and stirred overnight. After cooling, DCM (300 mL) was added to the resulting mixture which was filtered and the filtrate was concentrated. The crude product was purified by column chromatography to afford 7 g (64% yield) of 5-fluoro-1H-indole-7-carbonitrile (D132) as a white solid. δH (CDCl$_3$, 400 MHz): 6.51 (1H, t), 7.20 (1H, dd), 7.30 (1H, t), 7.52 (1H, dd), 8.82 (1H, br s).

Description For D133

5-Fluoro-3-formyl-1H-indole-7-carbonitrile (D133)

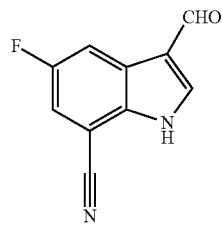

To a solution of $(COCl)_2$ (4 mL) in DCM (100 mL) at 0° C. was added a solution of DMF (4 mL) in DCM (50 mL) dropwise. Half an hour later, a solution of 5-fluoro-1H-indole-7-carbonitrile (D132) (7 g) in DCM (100 mL) was added. The reaction was allowed to warm to RT to form a yellow precipitate. After 5 hours the solvent was removed by evaporation, and then THF (100 mL) and 2 M aqueous NaOH (100 mL) solution were added to the residue obtained above. After being stirred for about 1 h, EtOAc (3×200 mL) was added, the organic phase was separated and the aqueous phase was extracted with EtOAc. The combined organic layers were dried over $Na_2SO_4$ and concentrated to afford 5-fluoro-3-formyl-1H-indole-7-carbonitrile (D133) (8 g) as a yellow solid. δH (DMSO-d$_6$, 400 MHz): 7.20 (1H, dd), 7.82 (1H, dd), 8.08 (1H, s), 9.64 (1H, s).

Description For D134

Ethyl (2E)-3-(7-cyano-5-fluoro-1H-indol-3-yl)-2-propenoate (D134)

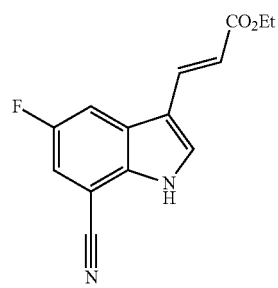

To a mixture of 5-fluoro-3-formyl-1H-indole-7-carbonitrile (D133) (8 g) in CH$_3$CN (80 mL) was added ethyl (triphenylphosphoranylidene)acetate (30 g). The reaction was heated to reflux overnight. After the mixture was filtered, the filtrate was concentrated and purified by column chromatography to afford ethyl (2E)-3-(7-cyano-5-fluoro-1H-indol-3-yl)-2-propenoate (D134) (7 g) as a light yellow solid.

Description For D135

Ethyl 3-(7-cyano-5-fluoro-1H-indol-3-yl)propanoate (D135)

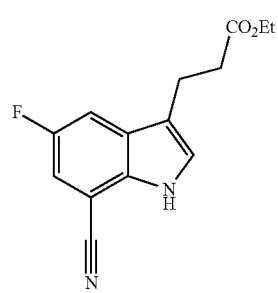

To a solution of ethyl (2E)-3-(7-cyano-5-fluoro-1H-indol-3-yl)-2-propenoate (D134) (4 g) in THF (100 mL) was added Pd/C (0.8 g, with 1% water). The reaction was stirred under $H_2$ (50 psi) atmosphere at 50° C. for about 4 hrs, TLC showed the material was completely consumed. Then Pd/C was removed by filtration, the filtrate was concentrated and washed with PE to afford ethyl 3-(7-cyano-5-fluoro-1H-indol-3-yl)propanoate (D135) (2.57 g) as a white solid. δH (CDCl$_3$, 400 MHz): 1.25 (3H, t), 2.67 (2H, t), 3.05 (2H, t), 4.14 (2H, q), 7.20 (1H, s), 7.25 (1H, dd), 7.52 (1H, dd), 8.64 (1H, br); MS (ES): $C_{14}H_{13}FN_2O_2$ requires 260; found 261.1 (M+H$^+$).

Description For D136

Ethyl 3-{5-fluoro-7-[(Z)-(hydroxyamino)(imino)methyl]-1H-indol-3-yl}propanoate (D136)

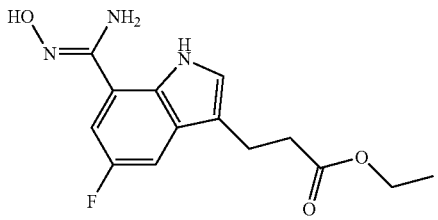

Hydroxylamine hydrochloride (810 mg) and sodium bicarbonate (1.46 g) were added to a solution of ethyl 3-(7-cyano-5-fluoro-1H-indol-3-yl)propanoate (D135) (1.50 g) in ethanol (20 mL). The reaction mixture was stirred at 90° C. for 6 hours. After cooling, the inorganics was filtered off. The solid was washed with EtOH. The filtrate was concentrated to afford ethyl 3-{5-fluoro-7-[(Z)-(hydroxyamino)(imino)methyl]-1H-indol-3-yl}propanoate (D136) (1.78 g) as a yellow oil. MS (ES): $C_{14}H_{16}FN_3O_3$ requires 293. found 294.1 (M+H$^+$).

Description For D137

Ethyl 3-[7-(5-{3-chloro-4-[(1-methylethyl)oxy]phenyl}-1,2,4-oxadiazol-3-yl)-5-fluoro-1H-indol-3-yl]propanoate (D137)

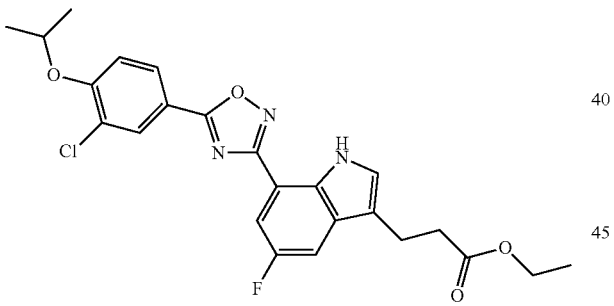

HOBT (216 mg) and EDCI (273 mg) were added to a solution of 3-chloro-4-[(1-methylethyl)oxy]benzoic acid (D32) (151 mg) in THF (4 mL). The reaction mixture was stirred at RT for 1 hour. Ethyl 3-{5-fluoro-7-[(Z)-(hydroxyamino)(imino)methyl]-1H-indol-3-yl}propanoate (D136) (268 mg) in THF (4 mL) was added. Then stirring continued overnight. TBAF (1.18 g) was then added. The reaction vessel was sealed and heated in Biotage Initiator using initial normal to 120° C. for 1.5 hours. After cooling, the reaction was quenched with water, and extracted with EtOAc for 3 times. The combined organic solution was washed with brine, and dried over anhydrous sodium sulfate. The dried solution was concentrated. The residue was purified by column chromatography to afford ethyl 3-[7-(5-{3-chloro-4-[(1-methylethyl)oxy]phenyl}-1,2,4-oxadiazol-3-yl)-5-fluoro-1H-indol-3-yl]propanoate (D137) (287 mg) as a pale yellow solid. MS (ES): $C_{24}H_{23}ClFN_3O_4$ requires 471; found 472.2 (M+H$^+$).

Description For D138

Ethyl 3-[7-(5-{3-cyano-4-[(1-methylethyl)oxy]phenyl}-1,2,4-oxadiazol-3-yl)-5-fluoro-1H-indol-3-yl]propanoate (D138)

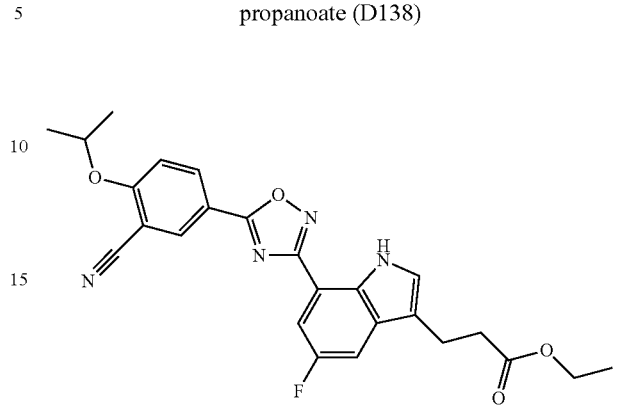

HOBT (672 mg) and EDCI (841 mg) were added to a solution of 3-cyano-4-[(1-methylethyl)oxy]benzoic acid (450 mg) in THF (10 mL). The resulting solution was stirred for 1 hour. Ethyl 3-{5-fluoro-7-[(Z)-(hydroxyamino)(imino)methyl]-1H-indol-3-yl}propanoate (D136) (717 mg) in THF (5 mL) was added, and the reaction mixture was stirred at RT for 2 hours. TBAF (2.34 g) was then added. The reaction vessel was sealed and heated in Biotage Initiator using initial normal to 120° C. for 1.5 hours. After cooling, the reaction was quenched with water, and extracted with EA for 3 times. The combined organic solution was washed with brine, and dried over anhydrous sodium sulfate. The dried solution was concentrated. The residue was purified by column chromatography to afford ethyl 3-[7-(5-{3-cyano-4-[(1-methylethyl)oxy]phenyl}-1,2,4-oxadiazol-3-yl)-5-fluoro-1H-indol-3-yl]propanoate (D138) (1.00 g) as a yellow solid. MS (ES): $C_{25}H_{23}FN_4O_4$ requires 462; found 463.2 (M+H$^+$).

Description For D139

Ethyl 3-[7-(5-{5-chloro-6-[(1-methylethyl)oxy]-3-pyridinyl}-1,2,4-oxadiazol-3-yl)-5-fluoro-1H-indol-3-yl]propanoate (D139)

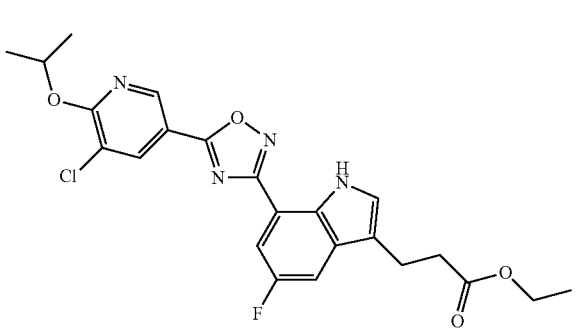

HOBT (211 mg) and EDCI (260 mg) were added to a solution of 5-chloro-6-[(1-methylethyl)oxy]-3-pyridinecarboxylic acid (148 mg) in THF (4 mL). The resulting solution was stirred for 1 hour. Ethyl 3-{5-fluoro-7-[(Z)-(hydroxyamino)(imino)methyl]-1H-indol-3-yl}propanoate (D136) (302 mg) in THF (4 mL) was added, and the reaction mixture was stirred at RT for 1.5 hours. TBAF (780 mg) was then added. The reaction vessel was sealed and heated in Biotage Initiator using initial normal to 120° C. for 1.5 hours. After cooling, the reaction was quenched with water, and extracted with EA for 3 times. The combined organic solution was washed with brine, and dried over anhydrous sodium sulfate. The dried solution was concentrated. The residue was purified by column chromatography to afford ethyl 3-[7-(5-{5-chloro-6-[(1-methylethyl)oxy]-3-pyridinyl}-1,2,4-oxadiazol-3-yl)-5-fluoro-1H-indol-3-yl]propanoate (D139) (341 mg) as a pale yellow solid. δH (CDCl$_3$, 400 MHz): 1.26 (3H, t), 1.47 (6H, d), 2.73 (2H, t), 3.12 (2H, t), 4.15 (2H, q), 5.52 (1H, m), 7.24 (1H, d), 7.47 (1H, dd), 7.86 (1H, dd), 8.43 (1H, d), 8.93 (1H, d), 9.54 (1H, br s). MS (ES): C$_{23}$H$_{22}$ClFN$_4$O$_4$ requires 472; found 473.2 (M+H$^+$).

Description For D140

7-Bromo-6-fluoro-1H-indole (D140)

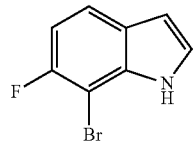

To a solution of 2-bromo-3-fluoro-1-nitrobenzene (13 g) in anhydrous THF (80 mL) was added 1 M vinylmagnesium bromide in THF (178 mL) dropwise at −78° C. slowly. Then the mixture was allowed to warm to RT and stirred for 2 hours. TLC indicated the reaction was complete. The reaction mixture was poured into saturated NH$_4$Cl solution, the organic phase was separated by extraction with EtOAc (3×200 mL). Purification by column chromatography afforded of 7-bromo-6-fluoro-1H-indole (D140) (3 g) as a brown oil.

Description For D141

6-Fluoro-1H-indole-7-carbonitrile (D141)

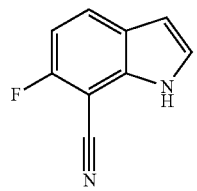

To a solution of 7-bromo-6-fluoro-1H-indole (D140) (1.0 g) in DMF (15 ml) were added Zn(CN)$_2$ (2.2 g) and then Pd(PPh$_3$)$_4$ (1.1 g) in a microwave tube, then N$_2$ atmosphere was bubbled in. The sealed vial was irradiated in the microwave at 150° C. for 2 hours. After cooling, DCM (80 mL) was added to the resulting mixture which was filtered and the filtrate was concentrated. The crude product was purified by column chromatography to afford 6-fluoro-1H-indole-7-carbonitrile (D141) (0.5 g) as a white solid.

Description For D142

6-Fluoro-3-formyl-1H-indole-7-carbonitrile (D142)

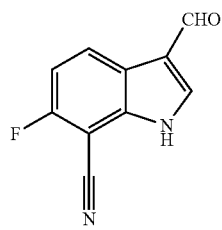

To a solution of (COCl)$_2$ (2.47 g) in DCM (40 mL) at 0° C. was added a solution of DMF (3 mL) in DCM (20 mL) dropwise. Half an hour later, a solution of 6-fluoro-1H-indole-7-carbonitrile (D141) (2.6 g) in DCM (20 mL) was added. The reaction was allowed to warm to RT to form a yellow precipitate. After 5 hours the solvent was removed by evaporation, and then THF (30 mL) and 2 M aqueous NaOH (30 mL) solution were added to the residue obtained above. After stirring for about 1 h, the organic phase was separated and the aqueous phase was extracted with EtOAc (3×50 mL). The combined organic layers were dried over Na$_2$SO$_4$ and concentrated to afford 6-fluoro-3-formyl-1H-indole-7-carbonitrile (D142) (3.0 g) as a yellow solid.

Description For D143

Ethyl (2E)-3-(7-cyano-6-fluoro-1H-indol-3-yl)-2-propenoate (D143)

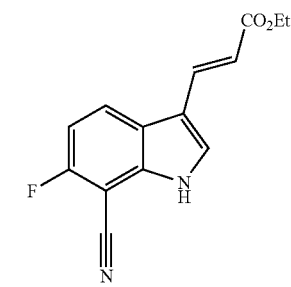

To a mixture of 6-fluoro-3-formyl-1H-indole-7-carbonitrile (D142) (3 g) in CH$_3$CN (30 mL) was added ethyl (triphenylphosphoranylidene)acetate (11.1 g). The reaction was heated to reflux overnight. After the mixture was filtered, the filtrate was concentrated and purified by column chromatography to afford ethyl (2E)-3-(7-cyano-6-fluoro-1H-indol-3-yl)-2-propenoate (D143) (2.4 g) as a light yellow solid.

Description For D144

Ethyl 3-(7-cyano-6-fluoro-1H-indol-3-yl)propanoate (D144)

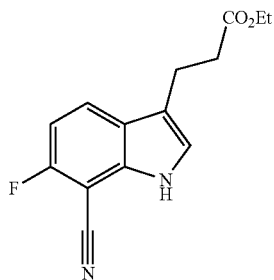

To a solution of ethyl (2E)-3-(7-cyano-6-fluoro-1H-indol-3-yl)-2-propenoate (D143) (1.8 g) in THF (50 mL) was added PdCl$_2$ (0.5 g). The reaction was stirred under H$_2$ (15 psi) atmosphere at RT for about 5 hours. TLC showed the starting material was completely consumed. Then PdCl$_2$ was removed by filtration, the filtrate was concentrated and washed with PE to afford ethyl 3-(7-cyano-6-fluoro-1H-indol-3-yl)propanoate (D144) (1.67 g) as a white solid. δH (DMSO-d$_6$, 400 MHz): 1.15 (3H, t), 2.66 (2H, t), 2.93 (2H, t), 4.03 (2H, q), 7.08 (1H, dd), 7.28 (1H, s), 7.93 (1H, dd), 11.90 (1H, s); MS (ES): C$_{14}$H$_{13}$FN$_2$O$_2$ requires 260; found 261.2 (M+H$^+$).

Description For D145

Ethyl 3-{6-fluoro-7-[(Z)-(hydroxyamino)(imino)methyl]-1H-indol-3-yl}propanoate (D145)

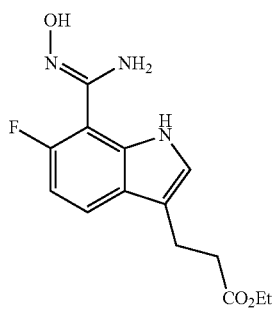

Hydroxylamine hydrochloride (906 mg) and sodium bicarbonate (1.60 g) were added to a solution of ethyl 3-(7-cyano-6-fluoro-1H-indol-3-yl)propanoate (D144) (1.67 g) in ethanol (20 mL). The reaction mixture was stirred at 90° C. for 6 hours. After cooling, the inorganics was filtered off. The solid was washed with EtOH. The filtrate was concentrated to afford ethyl 3-{6-fluoro-7-[(Z)-(hydroxyamino)(imino)methyl]-1H-indol-3-yl}propanoate (D145) (1.67 g) as a brown oil. MS (ES): C$_{14}$H$_{16}$FN$_3$O$_3$ requires 293. found 294.2 (M+H$^+$).

Description For D146

Ethyl 3-[7-(5-{3-chloro-4-[(1-methylethyl)oxy]phenyl}-1,2,4-oxadiazol-3-yl)-6-fluoro-1H-indol-3-yl]propanoate (D146)

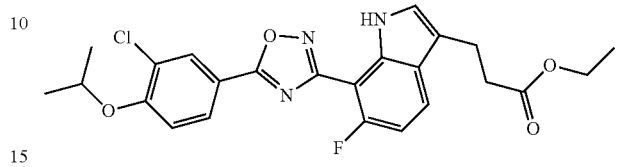

To the solution of 3-chloro-4-[(1-methylethyl)oxy]benzoic acid (D32) (676 mg) in tetrahydrofuran (50 mL) were added EDCI (824 mg) and HOBT (658 mg). The resulting solution was stirred at room temperature for 1 hour. Then ethyl 3-{6-fluoro-7-[(Z)-(hydroxyamino)(imino)methyl]-1H-indol-3-yl}propanoate (D145) (840 mg) was added and the solution was stirred at room temperature for another 2 hours. THF was removed in vacuo and the residue was dissolved in ethyl acetate (50 mL), washed with water (2×10 mL) and dried over sodium sulphate. The organic phase was concentrated. The residue was dissolved in THF (3 mL), TBAF (3 g) was added and the reaction solution was stirred under microwave (120° C., 2.5 hours). The reaction solution was poured into ethyl acetate (100 mL), washed with water (3×20 mL), dried over sodium sulphate. The organic phase was concentrate and the residue was purified by column chromatography to afford ethyl 3-[7-(5-{3-chloro-4-[(1-methylethyl)oxy]phenyl}-1,2,4-oxadiazol-3-yl)-6-fluoro-1H-indol-3-yl]propanoate (D146) (640 mg) as an off white solid. MS (ES): C$_{24}$H$_{23}$ClFN$_3$O$_4$ requires 471; found 472.2 (M+H$^+$).

Description For D147

Ethyl 3-[7-(5-{3-chloro-4-[(1-methylethyl)oxy]phenyl}-1,2,4-oxadiazol-3-yl)-6-fluoro-1-methyl-1H-indol-3-yl]propanoate (D147)

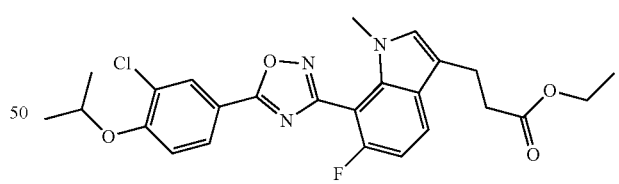

To the solution of ethyl 3-[7-(5-{3-chloro-4-[(1-methylethyl)oxy]phenyl}-1,2,4-oxadiazol-3-yl)-6-fluoro-1H-indol-3-yl]propanoate (D146) (320 mg) in dimethyl sulfoxide (5 mL) was added KOH (152 mg) and MeI (0.64 mL). The reaction solution was stirred at room temperature overnight. Saturated aqueous NH$_4$Cl (10 mL) solution was added, and the resulting solution was extracted with ethyl acetate (3×10 mL). The combined organic phases were washed with brine and dried over sodium sulphate. The organic solution was concentrated to afford ethyl 3-[7-(5-{3-chloro-4-[(1-methylethyl)oxy]phenyl}-1,2,4-oxadiazol-3-yl)-6-fluoro-1-methyl-1H-indol-3-yl]propanoate (D147) (330 mg). MS (ES): C$_{25}$H$_{25}$ClFN$_3$O$_4$ requires 485; found 486.2 (M+H$^+$).

Description For D148

Ethyl 3-[7-(5-{3-cyano-4-[(1-methylethyl)oxy]phenyl}-1,2,4-oxadiazol-3-yl)-6-fluoro-1H-indol-3-yl]propanoate (D148)

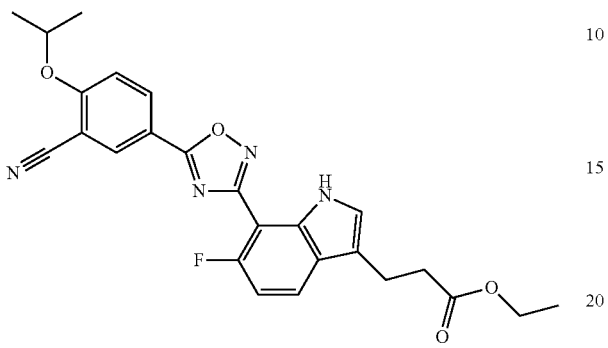

HOBT (672 mg) and EDCI (841 mg) were added to a solution of 3-cyano-4-[(1-methylethyl)oxy]benzoic acid (450 mg) in THF (10 mL). The resulting solution was stirred for 1 hour. Ethyl 3-{6-fluoro-7-[(Z)-(hydroxyamino)(imino)methyl]-1H-indol-3-yl}propanoate (D145) (836 mg) in THF (5 mL) was added, and the reaction mixture was stirred at RT for 2 hours. TBAF (2.02 g) was then added. The reaction vessel was sealed and heated in Biotage Initiator using initial normal to 120° C. for 2 hours. After cooling, the reaction was quenched with water, and extracted with EtOAc for 3 times. The combined organic solution was washed with brine, and dried over anhydrous sodium sulfate. The dried solution was concentrated. The residue was purified by column chromatography to afford ethyl 3-[7-(5-{3-cyano-4-[(1-methylethyl)oxy]phenyl}-1,2,4-oxadiazol-3-yl)-6-fluoro-1H-indol-3-yl]propanoate (D148) (875 mg) as a yellow solid. MS (ES): $C_{25}H_{23}FN_4O_4$ requires 462; found 463.2 (M+H$^+$).

Description For D149

Ethyl 3-[7-(5-{5-chloro-6-[(1-methylethyl)oxy]-3-pyridinyl}-1,2,4-oxadiazol-3-yl)-6-fluoro-1H-indol-3-yl]propanoate (D149)

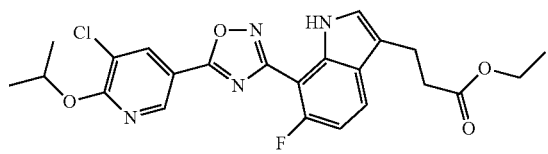

To the solution of 5-chloro-6-[(1-methylethyl)oxy]-3-pyridinecarboxylic acid (1.39 g) in tetrahydrofuran (50 mL) were added EDCI (1.69 g) and HOBT (1.35 g). The resulting solution was stirred at room temperature for 1 hour. Then ethyl 3-{6-fluoro-7-[(Z)-(hydroxyamino)(imino)methyl]-1H-indol-3-yl}propanoate (D145) (1.72 g) was added and the solution was stirred at room temperature for another 2 hours. THF was removed in vacuo and the residue was dissolved in ethyl acetate (50 mL), washed with water (2×10 mL), dried over sodium sulphate and concentrated. The residue was dissolved in THF (3 mL), TBAF (6.13 g) was added and the reaction solution was stirred in the microwave (120° C., 2.5 hours). The reaction solution was poured into ethyl acetate (100 mL), washed with water (3×20 mL) and dried over sodium sulphate. The organic solution was concentrate and the residue was purified by column chromatography to afford ethyl 3-[7-(5-{5-chloro-6-[(1-methylethyl)oxy]-3-pyridinyl}-1,2,4-oxadiazol-3-yl)-6-fluoro-1H-indol-3-yl]propanoate (D149) (520 mg) as a white solid. MS (ES): $C_{23}H_{22}ClFN_4O_4$ requires 472; found 473.2 (M+H$^+$)

Description For D150

Ethyl 3-[7-(5-{5-chloro-6-[(1-methylethyl)oxy]-3-pyridinyl}-1,2,4-oxadiazol-3-yl)-6-fluoro-1-methyl-1H-indol-3-yl]propanoate (D150)

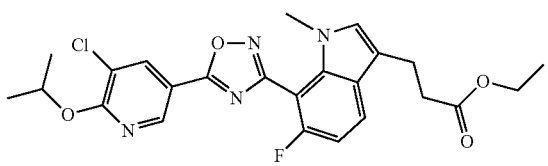

To the solution of ethyl 3-[7-(5-{5-chloro-6-[(1-methylethyl)oxy]-3-pyridinyl}-1,2,4-oxadiazol-3-yl)-6-fluoro-1H-indol-3-yl]propanoate (D149) (260 mg) in dimethyl sulfoxide (10 mL) was added KOH (247 mg) and MeI (1.03 mL). The reaction solution was stirred at room temperature overnight. Saturated aqueous NH$_4$Cl (10 mL) solution was added, and the resulting solution was extracted with ethyl acetate (3×10 mL). The combined organic phases were washed with brine and dried over sodium sulphate. The organic solution was concentrated to afford ethyl 3-[7-(5-{5-chloro-6-[(1-methylethyl)oxy]-3-pyridinyl}-1,2,4-oxadiazol-3-yl)-6-fluoro-1-methyl-1H-indol-3-yl]propanoate (D150) (268 mg) as a brown oil. MS (ES): $C_{24}H_{24}ClFN_4O_4$ requires 486; found 487.2 (M+H$^+$).

Description For D151

5-fluoro-1H-indole-6-carbonitrile (D151)

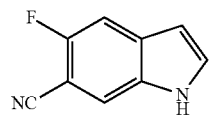

To a microwave reaction vessel was added 5-fluoro-6-iodo-1H-indole (1 g), potassium ferrocyanide (1.41 g), Na$_2$CO$_3$ (0.80 g), PdCl$_2$(dppf)-CH$_2$Cl$_2$ adduct (0.31 g) and N,N-dimethylacetamide (DMA). The reaction vessel was then sealed and heated in Biotage Initiator using initial high to 140° C. for 2 hours. After cooling the reaction, the solvent was evaporated and the residue was partitioned between water (50 mL) and ethyl acetate (50 mL). The insolubles were filtered, the organics were evaporated and the residue was chromatographed on silica gel to give the designed product 5-fluoro-1H-indole-6-carbonitrile (D151) (0.25 g). MS (ES): $C_9H_5FN_2$ requires 160.0; found 161.1 (M+H$^+$).

Description For D152

5-Fluoro-3-formyl-1H-indole-6-carbonitrile (D152)

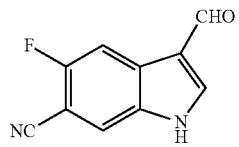

To a solution of oxalyl chloride (0.68 mL) in DCM (10 mL) at 0° C. was dropwise added a solution of DMF (0.60 mL) in DCM (2 mL). The mixture was stirred for 0.5 h at 0° C. and then 5-fluoro-1H-indole-6-carbonitrile (D151) (250 mg) in DCM (3 mL) was added in one portion. The reaction mixture was allowed to warm to rt and stirred overnight. Afterwards, the reaction mixture was added with 2 M aqueous NaOH (30 mL) and extracted with EtOAc (3×50 mL). The combined organic layers were washed with water, dried over anhydrous sodium sulfate, and then concentrated under vacuo to give the designed product 5-fluoro-3-formyl-1H-indole-6-carbonitrile (D152) (280 mg), which was used without purification. MS (ES): $C_{10}H_5FN_2O$ requires 188.0; found 189.1 (M+H$^+$).

Description For D153

Ethyl (2E)-3-(6-cyano-5-fluoro-1H-indol-3-yl)-2-propenoate (D153)

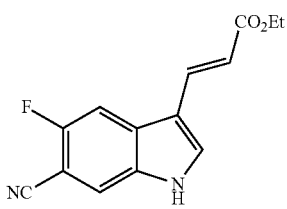

To a solution of 5-fluoro-3-formyl-1H-indole-6-carbonitrile (D152) (250 mg) in acetonitrile (30 mL) was added ethyl (triphenylphosphoranylidene)acetate (926 mg). The reaction mixture was refluxed at 90° C. for 24 hours. The solvent was then evaporated and the residue was chromatographed on silica gel eluting with EA and PA (3:7-7:3) to generate ethyl (2E)-3-(6-cyano-5-fluoro-1H-indol-3-yl)-2-propenoate (D153) (275 mg). MS (ES): $C_{14}H_{11}FN_2O_2$ requires 258.1; found 259.1 (M+H$^+$).

Description For D154

Ethyl 3-(6-cyano-5-fluoro-1H-indol-3-yl)propanoate (D154)

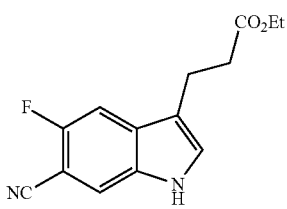

To a solution of ethyl (2E)-3-(6-cyano-5-fluoro-1H-indol-3-yl)-2-propenoate (D153) (200 mg) in methanol (30 mL) was added 10% Pd/C (50 mg). The reaction mixture was then stirred under H$_2$ overnight. The solution was filtered through celite and the filtrate was evaporated to give the designed product ethyl 3-(6-cyano-5-fluoro-1H-indol-3-yl)propanoate (D154) (190 mg). MS (ES): $C_{14}H_{13}FN_2O_2$ requires 260.1; found 261.1 (M+H$^+$).

Description For D155

Ethyl 3-{5-fluoro-6-[(Z)-(hydroxyamino)(imino) methyl]-1H-indol-3-yl}propanoate (D155)

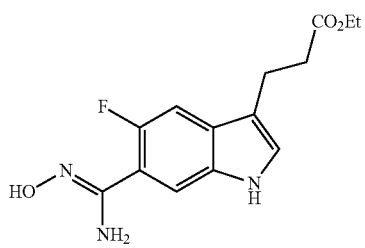

To a solution of ethyl 3-(6-cyano-5-fluoro-1H-indol-3-yl)propanoate (D154) (180 mg) in ethanol (50 mL) was added hydroxylamine hydrochloride (144 mg) and sodium bicarbonate (290 mg). The mixture was heated to reflux at 90° C. for 24 hours. The reaction mixture was then filtered and the filtrate was evaporated under vacuo to generate the designed product ethyl 3-{5-fluoro-6-[(Z)-(hydroxyamino)(imino) methyl]-1H-indol-3-yl}propanoate (D155) (190 mg), which was used without further purification. MS (ES): $C_{14}H_{16}FN_3O_3$ requires 293.1; found 294.1 (M+H$^+$).

Description For D156

Ethyl 3-[6-(5-{3-chloro-4-[(1-methylethyl)oxy]phenyl}-1,2,4-oxadiazol-3-yl)-5-fluoro-1H-indol-3-yl]propanoate (D156)

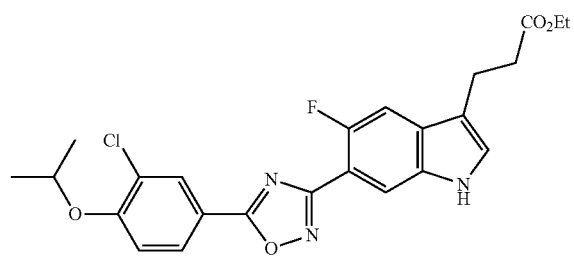

To a solution of 3-chloro-4-[(1-methylethyl)oxy]benzoic acid (132 mg) in tetrahydrofuran (THF) (12 mL) was added EDC (235 mg) and HOBt (188 mg) and the mixture was stirred at RT for half an hour. Ethyl 3-{5-fluoro-6-[(Z)-(hydroxyamino)(imino)methyl]-1H-indol-3-yl}propanoate (D155) (180 mg) was then added and the resulting mixture was stirred for another 1 hour. Finally, TBAF (642 mg) was added to the solution and the reaction vessel was sealed and heated in Biotage Initiator using initial high at 120° C. for 2 hours. After cooling the reaction, the solution was diluted with ethyl acetate (80 mL) and washed with water (2×60 mL). The organic layer was then concentrated under vacuo and the residue was chromatographed on silica gel eluting with EA

Description For D157

Ethyl 3-[6-(5-{3-cyano-4-[(1-methylethyl)oxy]phenyl}-1,2,4-oxadiazol-3-yl)-5-fluoro-1H-indol-3-yl]propanoate (D157)

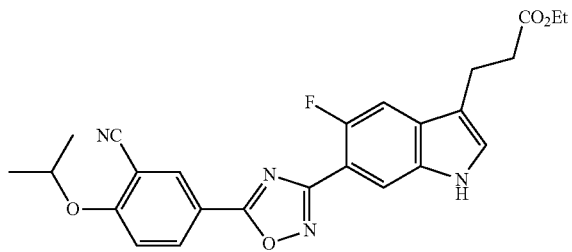

To a solution of 3-cyano-4-[(1-methylethyl)oxy]benzoic acid (200 mg) in tetrahydrofuran (THF) (10 mL) was added EDC (374 mg) and HOBt (299 mg). The mixture was stirred for half an hour. Ethyl 3-{5-fluoro-6-[(Z)-(hydroxyamino)(imino)methyl]-1H-indol-3-yl}propanoate (D155) (286 mg) was then added and the resulting mixture was stirred further for 1 hour. Finally, TBAF (1019 mg) was added to the solution and the reaction vessel was sealed and heated in macrowave at 120° C. for two hours. After cooling the reaction, the solution was diluted with ethyl acetate (80 mL) and washed with water (2×60 mL). The organic layer was then concentrated under vacuo and the residue was chromatographed on silica gel to give the designed product ethyl 3-[6-(5-{3-cyano-4-[(1-methylethyl)oxy]phenyl}-1,2,4-oxadiazol-3-yl)-5-fluoro-1H-indol-3-yl]propanoate (D157) (250 mg). MS (ES): $C_{25}H_{23}FN_4O_4$ requires 462.2; found 463.2 (M+H$^+$).

Description For D158

Ethyl 3-[6-(5-{5-chloro-6-[(1-methylethyl)oxy]-3-pyridinyl}-1,2,4-oxadiazol-3-yl)-5-fluoro-1H-indol-3-yl]propanoate (D158)

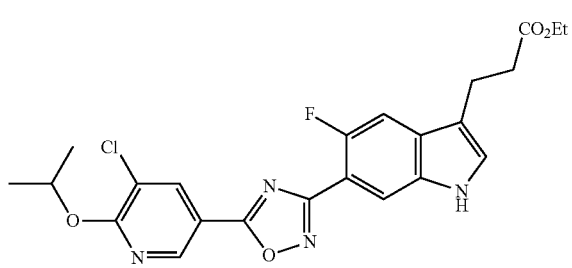

To a solution of 5-chloro-6-[(1-methylethyl)oxy]-3-pyridinecarboxylic acid (210 mg) in tetrahydrofuran (THF) (10 mL) was added EDC (373 mg) and HOBt (298 mg). The mixture was stirred for half an hour. Ethyl 3-{5-fluoro-6-[(Z)-(hydroxyamino)(imino)methyl]-1H-indol-3-yl}propanoate (D155) (286 mg) was then added and the resulting mixture was stirred further for 1 hour. Finally, TBAF (1019 mg) was added to the solution and the reaction vessel was sealed and heated in microwave at 120° C. for two hours. After cooling the reaction, the solution was diluted with ethyl acetate (80 mL) and washed with water (2×60 mL). The organic layer was then concentrated under vacuo and the residue was chromatographed on silica gel to give the designed product ethyl 3-[6-(5-{5-chloro-6-[(1-methylethyl)oxy]-3-pyridinyl}-1,2,4-oxadiazol-3-yl)-5-fluoro-1H-indol-3-yl]propanoate (D158) (280 mg). MS (ES): $C_{23}H_{22}ClFN_4O_4$ requires 472.1; found 473.2 (M+H$^+$).

Description For D159

(4-bromo-2-fluoro-6-iodophenyl)amine (D159)

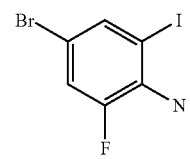

(4-bromo-2-fluorophenyl)amine (6 g) was dissolved in ethanol (200 mL), silver sulfate (10.8 g) was added and then iodine (8.8 g) was added in small portions. After the addition was complete, the reaction mixture was stirred at ambient temperature overnight. The reaction mixture was filtered and evaporated to leave a dark oil which was taken up in EtOAc, washed with saturated sodium thiosulphate (100 mL×2), sodium carbonate solution (100 mL×2) and water. The organic layer dried over anhydrous $Na_2SO_4$ and evaporated. The crude product was purified by column chromatography to give (4-bromo-2-fluoro-6-iodophenyl)amine (D159) (8.6 g) as a yellow solid. MS (ES): $C_6H_4BrFIN$ requires 315; found 315.9 (M+H$^+$).

Description For D160

3-(5-bromo-7-fluoro-1H-indol-2-yl)propanoic acid (D160)

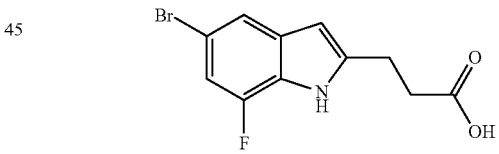

To a solution of (4-bromo-2-fluoro-6-iodophenyl)amine (D159) (2 g), 4-pentynoic acid (0.62 g) and copper(I) iodide (0.60 g) in DMF (4 mL) stirred under nitrogen at room temperature was added bis(triphenylphosphine)palladium(II) chloride (0.222 g), then triethylamine (2.2 mL) was added in a portion. The reaction mixture was stirred at 80° C. in microwave reactor for 2 hrs. The solid in the mixture was filtered, the filtrate was diluted with EtOAc (30 mL), washed with brine (80 mL) and water (50 mL×2). The organic layer was dried over anhydrous sodium sulfate. The dried solution was concentrated. The residue was purified by column chromatography to afford 3-(5-bromo-7-fluoro-1H-indol-2-yl)propanoic acid (D160) (700 mg) as a yellow solid. MS (ES): $C_{11}H_9BrFNO_2$ requires 285; found 286.0 (M+H$^+$). δH (CDCl$_3$, 400 MHz): 2.75 (2H, t), 3.07 (2H, t), 5.45 (1H, s), 7.05 (1H, d), 7.41 (1H, s).

Description For D161

Ethyl 3-(5-bromo-7-fluoro-1H-indol-2-yl)propanoate (D161)

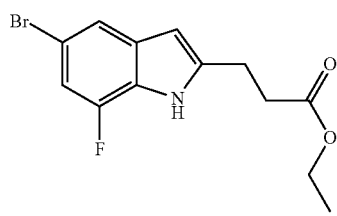

To a suspension of 3-(5-bromo-7-fluoro-1H-indol-2-yl)propanoic acid (D160) (1 g) in ethanol (15 mL) was added thionyl dichloride (0.083 g). The reaction mixture was stirred at room temperature overnight. The solvent was removed in vacuo. The residue was diluted with EtOAc (30 mL). The organic phase was washed with 2 M sodium carbonate solution (25 mL) and water (50 mL), dried over sodium sulphate and evaporated in vacuo to give the crude product ethyl 3-(5-bromo-7-fluoro-1H-indol-2-yl)propanoate (D161) (1.1 g) as a yellow solid. $\delta$H (CDCl$_3$, 400 MHz): 1.23 (3H, t), 2.73 (2H, t), 3.06 (2H, t), 4.16 (2H, m), 6.20 (1H, s), 7.05 (1H, d), 7.41 (1H, s), 8.85 (1H, s).

Description For D162

Ethyl 3-(5-cyano-7-fluoro-1H-indol-2-yl)propanoate (D162)

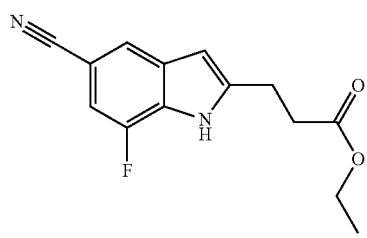

To a suspension of ethyl 3-(5-bromo-7-fluoro-1H-indol-2-yl)propanoate (D161) (650 mg), copper(I) iodide (394 mg) in DMF (5 mL) was added copper(I) cyanide (741 mg). The reaction vessel was sealed and heated in Biotage Initiator using initial very high to 200° C. for an hour. After cooling the reaction, the precipitate was filtered, and the filtrate was diluted with EtOAc (30 mL). The organic phase was washed with brine (25 mL), water (25 mL×2). The organic layer was dried over sodium sulphate and the crude product was purified by column chromatography to give ethyl 3-(5-cyano-7-fluoro-1H-indol-2-yl)propanoate (D162) (400 mg) as a yellow solid. MS (ES): $C_{14}H_{13}FN_2O_2$ requires 260; found 261.1 (M+H$^+$).

Description For D163

Ethyl 3-{7-fluoro-5-[(Z)-(hydroxyamino)(imino)methyl]-1H-indol-2-yl}propanoate (D163)

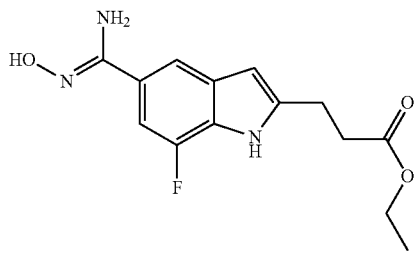

A mixture of ethyl 3-(5-cyano-7-fluoro-1H-indol-2-yl)propanoate (D162) (400 mg), sodium bicarbonate (387 mg) and hydroxylamine hydrochloride (214 mg) in ethanol (100 mL) was heated at reflux overnight. The inorganics were filtered off. The solid was washed well with ethanol. The filtrate was concentrated. The obtained solid was dried in vacuo to afford ethyl 3-{7-fluoro-5-[(Z)-(hydroxyamino)(imino)methyl]-1H-indol-2-yl}propanoate (D163) (428 mg) as a yellow solid. MS (ES): $C_{14}H_{16}FN_3O_3$ requires 293; found 294.2 (M+H$^+$).

Description For D164

Ethyl 3-[5-(5-{3-chloro-4-[(1-methylethyl)oxy]phenyl}-1,2,4-oxadiazol-3-yl)-7-fluoro-1H-indol-2-yl]propanoate (D164)

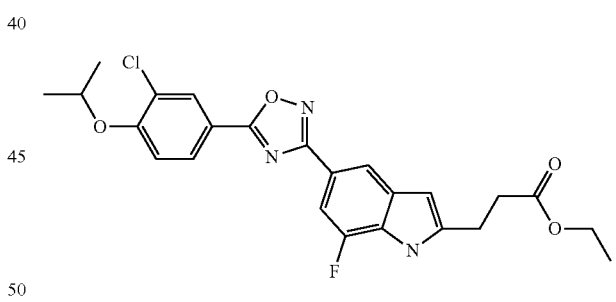

To a solution of 3-chloro-4-[(1-methylethyl)oxy]benzoic acid (307 mg) in tetrahydrofuran (30 mL) stirred at room temperature was added EDC (549 mg) and HOBT (439 mg). The reaction mixture was stirred at room temperature for 0.5 h. Then ethyl 3-{7-fluoro-5-[(Z)-(hydroxyamino)(imino)methyl]-1H-indol-2-yl}propanoate (D163) (420 mg) was added. The reaction mixture was stirred at room temperature for an hour, and then TBAF (3.7 g) was added. The reaction mixture was heated at reflux overnight. The organic solvent was evaporated off in vacuo and purified by column chromatography to give ethyl 3-[5-(5-{3-chloro-4-[(1-methylethyl)oxy]phenyl}-1,2,4-oxadiazol-3-yl)-7-fluoro-1H-indol-2-yl]propanoate (D164) (240 mg) as white solid. MS (ES): $C_{24}H_{23}ClFN_3O_4$ requires 471; found 472.2 (M+H$^+$).

Description For D165

Ethyl 3-[5-(5-{3-cyano-4-[(1-methylethyl)oxy]phenyl}-1,2,4-oxadiazol-3-yl)-7-fluoro-1H-indol-2-yl]propanoate (D165)

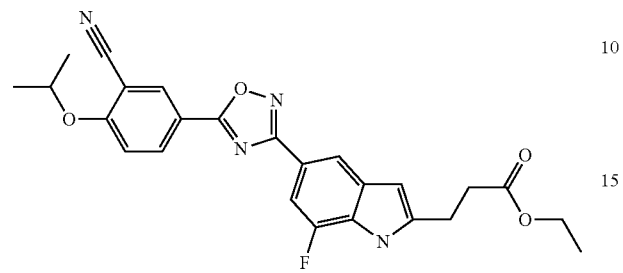

To a solution of 3-cyano-4-[(1-methylethyl)oxy]benzoic acid (150 mg) in tetrahydrofuran (30 mL) stirred at room temperature was added EDC (280 mg) and HOBT (223 mg). The reaction mixture was stirred at room temperature for 0.5 h. Then ethyl 3-{7-fluoro-5-[(Z)-(hydroxyamino)(imino)methyl]-1H-indol-2-yl}propanoate (D163) (214 mg) was added. The reaction mixture was stirred at room temperature for an hour, and then TBAF (763 mg) was added. The reaction mixture was sealed and heated in Biotage Initiator using initial high to 120° C. for 2 hrs. After cooling the reaction, the solvent was removed. The residue was diluted with EtOAc (30 mL). The organic phase was washed with water (25 mL×4) and dried over sodium sulphate and evaporated in vacuo. The crude product was purified by column chromatography to give ethyl 3-[5-(5-{3-cyano-4-[(1-methylethyl)oxy]phenyl}-1,2,4-oxadiazol-3-yl)-7-fluoro-1H-indol-2-yl]propanoate (D165) (180 mg) as a white solid. MS (ES): $C_{25}H_{23}FN_4O_4$ requires 462; found 463.2 (M+H$^+$).

Description For D166

Ethyl 3-[5-(5-{5-chloro-6-[(1-methylethyl)oxy]-3-pyridinyl}-1,2,4-oxadiazol-3-yl)-7-fluoro-1H-indol-2-yl]propanoate (D166)

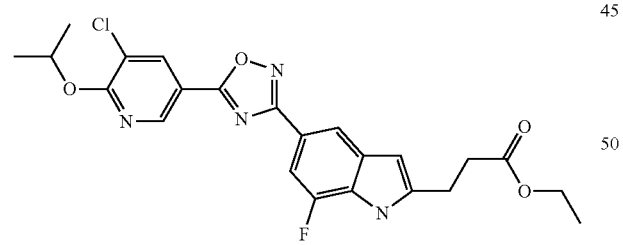

To a solution of 5-chloro-6-[(1-methylethyl)oxy]-3-pyridinecarboxylic acid (368 mg) in tetrahydrofuran (30 mL) stirred at room temperature was added EDC (654 mg) and HOBT (522 mg). The reaction mixture was stirred at room temperature for 0.5 h. Then ethyl 3-{7-fluoro-5-[(Z)-(hydroxyamino)(imino)methyl]-1H-indol-2-yl}propanoate (D163) (500 mg) was added. The reaction mixture was stirred at room temperature for an hour, and then TBAF (1.78 g) was added. The reaction mixture was sealed and heated in Biotage Initiator using initial high to 120° C. for 0.5 h. After cooling the reaction, the solvent was removed. The residue was diluted with EtOAc (30 mL), and the organic phase was washed with water (25 mL×4), dried over sodium sulphate and evaporated in vacuo. The crude product was purified by column chromatography to give ethyl 3-[5-(5-{5-chloro-6-[(1-methylethyl)oxy]-3-pyridinyl}-1,2,4-oxadiazol-3-yl)-7-fluoro-1H-indol-2-yl]propanoate (D166) (600 mg) as a yellow solid. MS (ES): $C_{23}H_{22}ClFN_4O_4$ requires 472; found 473.2 (M+H$^+$).

EXAMPLE 1

3-[7-(5-{3-Chloro-4-[(1-methylethyl)oxy]phenyl}-1,2,4-oxadiazol-3-yl)-1H-indol-3-yl]propanoic acid (E1)

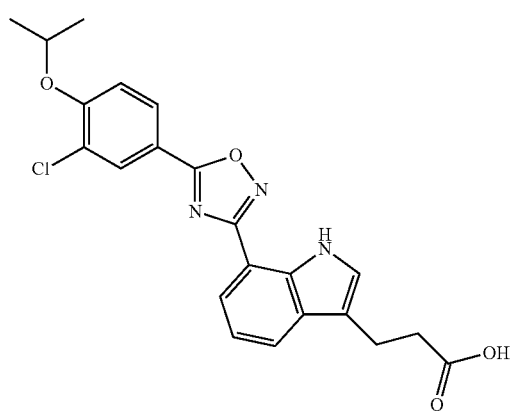

Trifluoroacetic acid (0.32 mL) was added to a solution of 1,1-dimethylethyl 3-[7-(5-{3-chloro-4-[(1-methylethyl)oxy]phenyl}-1,2,4-oxadiazol-3-yl)-1H-indol-3-yl]propanoate (D7) (40 mg) in dichloromethane (0.5 mL) at RT for 1 hour. The reaction mixture was concentrated. The residue was recrystallized from dichloromethane/ether to afford 3-[7-(5-{3-chloro-4-[(1-methylethyl)oxy]phenyl}-1,2,4-oxadiazol-3-yl)-1H-indol-3-yl]propanoic acid (E1) (30 mg) as a white solid. δH (DMSO-d$_6$, 400 MHz): 1.37 (6H, d), 2.65 (2H, q), 3.01 (2H, t), 4.91 (1H, m), 7.22 (1H, t), 7.28 (1H, d), 7.46 (1H, d), 7.83 (1H, d), 7.95 (1H, dd), 8.21 (1H, dd), 8.39 (1H, d), 10.86 (1H, s), 12.12 (1H, br s). MS (ES): $C_{22}H_{20}ClN_3O_4$ requires 425; found 425.9 (M+H$^+$).

EXAMPLE 2

3-[7-(5-{3-Chloro-4-[(1-methylethyl)oxy]phenyl}-1,2,4-oxadiazol-3-yl)-1-methyl-1H-indol-3-yl]propanoic acid (E2)

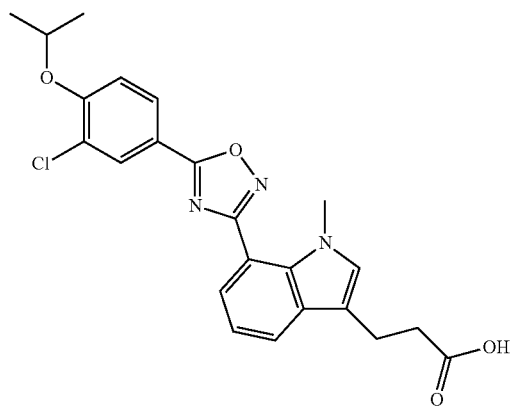

Trifluoroacetic acid (0.62 mL) was added to a solution of 1,1-dimethylethyl 3-[7-(5-{3-chloro-4-[(1-methylethyl)oxy]phenyl}-1,2,4-oxadiazol-3-yl)-1-methyl-1H-indol-3-yl]propanoate (D8) (80 mg) in dichloromethane (1 mL) at RT. The resulting solution was stirred for 1 hour. The reaction mixture was concentrated. The residue was recrystallized from ether/hexane to afford 3-[7-(5-{3-chloro-4-[(1-methylethyl)oxy]phenyl}-1,2,4-oxadiazol-3-yl)-1-methyl-1H-indol-3-yl]propanoic acid (E2) (45 mg) as a pale yellow solid. δH (DMSO-$d_6$, 400 MHz): 1.36 (6H, d), 2.65 (2H, q), 2.96 (2H, t), 3.63 (3H, s), 4.89 (1H, m), 7.18 (1H, t), 7.20 (1H, s), 7.45 (2H, m), 7.81 (1H, dd), 8.14 (1H, dd), 8.21 (1H, d), 12.14 (1H, br s). MS (ES): $C_{23}H_{22}ClN_3O_4$ requires 439; found 440.0 (M+H$^+$).

EXAMPLE 3

3-[7-(5-{3-Cyano-4-[(1-methylethyl)oxy]phenyl}-1,2,4-oxadiazol-3-yl)-1H-indol-3-yl]propanoic acid (E3)

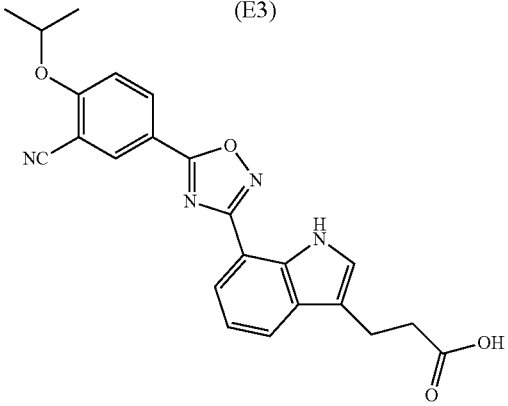

Trifluoroacetic acid (0.37 mL) was added to a solution of 1,1-dimethylethyl 3-[7-(5-{3-cyano-4-[(1-methylethyl)oxy]phenyl}-1,2,4-oxadiazol-3-yl)-1H-indol-3-yl]propanoate (D9) (45 mg) in dichloromethane (0.5 mL) at RT. The resulting solution was stirred for 2 hours. The reaction mixture was concentrated. The residue was recrystallized from dichloromethane to afford 3-[7-(5-{3-cyano-4-[(1-methylethyl)oxy]phenyl}-1,2,4-oxadiazol-3-yl)-1H-indol-3-yl]propanoic acid (E3) (27 mg) as a white solid. δH (DMSO-$d_6$, 400 MHz): 1.40 (6H, d), 2.67 (2H, t), 3.03 (2H, t), 5.01 (1H, m), 7.22 (1H, t), 7.28 (1H, d), 7.46 (1H, d), 7.83 (1H, d), 7.95 (1H, dd), 8.21 (1H, dd), 8.39 (1H, d), 10.86 (1H, s), 12.12 (1H, br s). MS (ES): $C_{23}H_{20}N_4O_4$ requires 416; found 417.1 (M+H$^+$).

EXAMPLE 4

3-[7-(5-{3-Cyano-4-[(1-methylethyl)oxy]phenyl}-1,2,4-oxadiazol-3-yl)-1-methyl-1H-indol-3-yl]propanoic acid (E4)

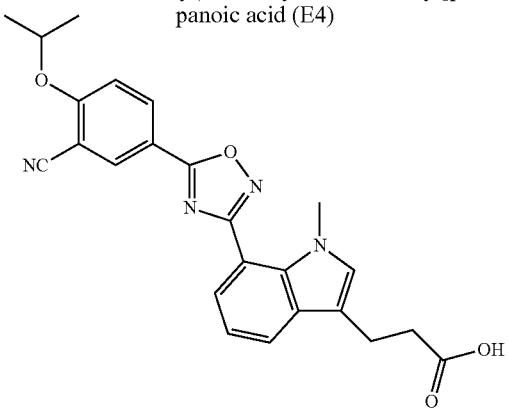

Trifluoroacetic acid (0.475 mL) was added to a solution of 1,1-dimethylethyl 3-[7-(5-{3-cyano-4-[(1-methylethyl)oxy]phenyl}-1,2,4-oxadiazol-3-yl)-1-methyl-1H-indol-3-yl]propanoate (D10) (60 mg) in dichloromethane (1 mL) at RT. The resulting solution was stirred for 45 min. The reaction mixture was concentrated. The residue was recrystallized from ether/hexane to afford 3-[7-(5-{3-cyano-4-[(1-methylethyl)oxy]phenyl}-1,2,4-oxadiazol-3-yl)-1-methyl-1H-indol-3-yl]propanoic acid (E4) (40 mg) as a pale yellow solid. δH (DMSO-$d_6$, 400 MHz): 1.39 (6H, d), 2.63 (2H, t), 2.97 (2H, t), 3.64 (3H, s), 4.99 (1H, m), 7.18 (1H, t), 7.21 (1H, s), 7.44 (1H, m), 7.57 (1H, d), 7.81 (1H, dd), 8.43 (1H, dd), 8.55 (1H, d), 12.12 (1H, br s). MS (ES): $C_{24}H_{22}N_4O_4$ requires 430; found 431.0 (M+H$^+$).

EXAMPLE 5

3-[6-(5-{3-Chloro-4-[(1-methylethyl)oxy]phenyl}-1,2,4-oxadiazol-3-yl)-1H-indol-3-yl]propanoic acid (E5)

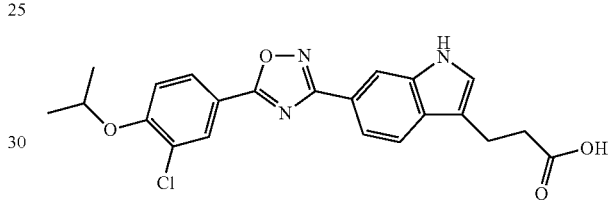

Trifluoroacetic acid (1.20 mL) was added to a solution of 1,1-dimethylethyl 3-[6-(5-{3-chloro-4-[(1-methylethyl)oxy]phenyl}-1,2,4-oxadiazol-3-yl)-1H-indol-3-yl]propanoate (D17) (150 mg) in dichloromethane (2 mL) at RT. The resulting solution was stirred for 1 hour. The reaction mixture was concentrated. The residue was recrystallized from dichloromethane/ether to afford 3-[6-(5-{3-chloro-4-[(1-methylethyl)oxy]phenyl}-1,2,4-oxadiazol-3-yl)-1H-indol-3-yl]propanoic acid (E5) (105 mg) as a pale pink solid. δH (DMSO-$d_6$, 400 MHz): 1.37 (6H, d), 2.64 (2H, t), 2.97 (2H, t), 4.89 (1H, m), 7.35 (1H, m), 7.45 (1H, d), 7.73 (2H, dd), 8.13 (2H, m), 8.34 (1H, s), 11.22 (1H, s), 12.13 (1H, br s). MS (ES): $C_{22}H_{20}ClN_3O_4$ requires 425; found 426.0 (M+H$^+$).

EXAMPLE 6

3-[6-(5-{3-Chloro-4-[(1-methylethyl)oxy]phenyl}-1,2,4-oxadiazol-3-yl)-1-methyl-1H-indol-3-yl]propanoic acid (E6)

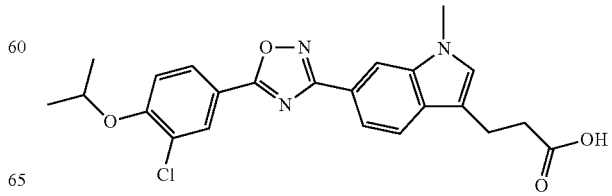

Trifluoroacetic acid (0.878 mL) was added to a solution of 1,1-dimethylethyl 3-[6-(5-{3-chloro-4-[(1-methylethyl)oxy]phenyl}-1,2,4-oxadiazol-3-yl)-1-methyl-1H-indol-3-yl]propanoate (D18) (113 mg) in dichloromethane (1.5 mL) at RT. The resulting solution was stirred for 30 min. The reaction mixture was concentrated. The residue was recrystallized from dichloromethane/ether to afford 3-[6-(5-{3-chloro-4-[(1-methylethyl)oxy]phenyl}-1,2,4-oxadiazol-3-yl)-1-methyl-1H-indol-3-yl]propanoic acid (E6) (55 mg) as a white solid. MS (ES) $C_{23}H_{22}ClN_3O_4$ requires 439; found 440.0 (M+H$^+$).

EXAMPLE 7

3-[6-(5-{3-Cyano-4-[(1-methylethyl)oxy]phenyl}-1,2,4-oxadiazol-3-yl)-1H-indol-3-yl]propanoic acid (E7)

Trifluoroacetic acid (0.856 mL) was added to a solution of 1,1-dimethylethyl 3-[6-(5-{3-cyano-4-[(1-methylethyl)oxy]phenyl}-1,2,4-oxadiazol-3-yl)-1H-indol-3-yl]propanoate (D19) (105 mg) in dichloromethane (1.5 mL) at RT. The resulting solution was stirred for 1.5 hours. The reaction mixture was concentrated. The residue was recrystallized from dichloromethane/ether to afford 3-[6-(5-{3-Cyano-4-[(1-methylethyl)oxy]phenyl}-1,2,4-oxadiazol-3-yl)-1H-indol-3-yl]propanoic acid (E7) (69 mg) as a white solid. δH (DMSO-d$_6$, 400 MHz): 1.39 (6H, d), 2.65 (2H, t), 2.97 (2H, t), 4.98 (1H, m), 7.36 (1H, d), 7.56 (1H, d), 7.72 (2H, t), 8.12 (1H, s), 8.42 (1H, dd), 8.51 (1H, d), 11.22 (1H, s), 12.12 (1H, br s). MS (ES): $C_{23}H_{20}N_4O_4$ requires 416. found 416.9 (M+H$^+$).

EXAMPLE 8

Sodium 5-(5-{3-chloro-4-[(1-methylethyl)oxy]phenyl}-1,2,4-oxadiazol-3-yl)-1H-indole-2-carboxylate (E8)

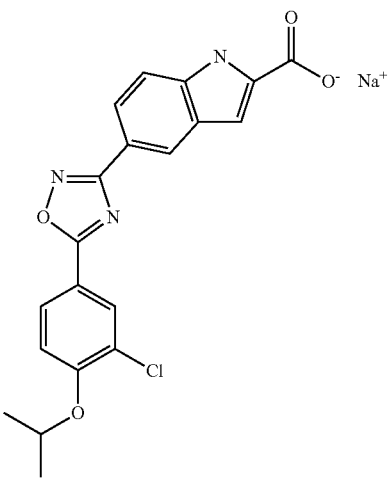

Aqueous NaOH solution (2 N, 2 mL) was added to a solution of 5-(5-{3-chloro-4-[(1-methylethyl)oxy]phenyl}-1,2,4-oxadiazol-3-yl)-1H-indole-2-carboxylate (D23) (65 mg) in ethanol (8 mL) at RT. The resulting solution was heated to 50° C. and stirred at that temperature for 30 min. The reaction mixture was cooled to RT and stirred for 30 min. Ethanol was evaporated. The solid was filtered and washed with water. The solid was collected and dried to afford sodium 5-(5-{3-chloro-4-[(1-methylethyl)oxy]phenyl}-1,2,4-oxadiazol-3-yl)-1H-indole-2-carboxylate (E8) (50 mg) as a white solid. δH (CD$_3$OD, 400 MHz): 1.44 (6H, d), 4.86 (1H, m), 7.08 (1H, d), 7.32 (1H, d), 7.56 (1H, d), 7.94 (1H, dd), 8.15 (1H, dd), 8.24 (1H, d), 8.43 (1H, t). MS (ES): $C_{20}H_{26}ClN_3O_4Na$ requires 419; found 398.1 (M—Na$^+$+2H$^+$).

EXAMPLE 9

Sodium 3-[5-(5-{3-chloro-4-[(1-methylethyl)oxy]phenyl}-1,2,4-oxadiazol-3-yl)-1H-indol-2-yl]propanoate (E9)

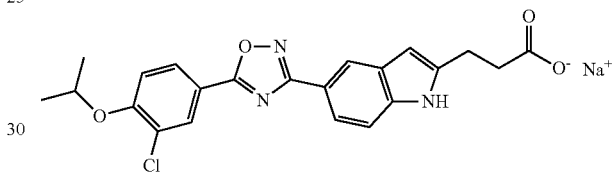

Aqueous NaOH solution (2 N, 2 mL) was added to a solution of ethyl 3-[5-(5-{3-chloro-4-[(1-methylethyl)oxy]phenyl}-1,2,4-oxadiazol-3-yl)-1H-indol-2-yl]propanoate (D33) (90 mg) in ethanol (20 mL) at RT. The resulting solution was stirred for 30 min. Ethanol was evaporated. Saturated aqueous sodium chloride solution (10 mL) was added. The mixture was extracted with EtOAc (2×50 mL). The organic fractions were combined. The combined solution was dried over anhydrous magnesium sulfate. The dried solution was concentrated. The residue was triturated with ether to afford sodium 3-[5-(5-{3-chloro-4-[(1-methylethyl)oxy]phenyl}-1,2,4-oxadiazol-3-yl)-1H-indol-2-yl]propanoate (E9) (80 mg) as a white solid. δH (CD$_3$OD, 400 MHz): 1.44 (6H, d), 2.62 (2H, t), 3.08 (2H, t), 4.87 (1H, m), 6.33 (1H, d), 7.33 (1H, d), 7.41 (1H, d), 7.80 (1H, dd), 8.14 (1H, dd), 8.24 (2H, dd). MS (ES): $C_{22}H_{19}ClN_3O_4Na$ requires 447; found 425.9 (M—Na$^+$+2H$^+$).

EXAMPLE 10

Sodium (2E)-3-[5-(5-{3-cyano-4-[(1-methylethyl)oxy]phenyl}-1,2,4-oxadiazol-3-yl)-1H-indol-2-yl]-2-propenoate (E10)

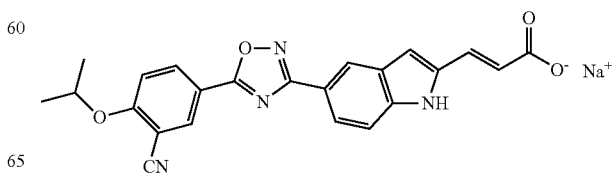

Aqueous NaOH solution (2 N, 2 mL) was added to a solution of ethyl (2E)-3-[5-(5-{3-cyano-4-[(1-methylethyl)oxy]phenyl}-1,2,4-oxadiazol-3-yl)-1H-indol-2-yl]-2-propenoate (D27) (20 mg) in ethanol (10 mL) and dioxane (5 mL) at RT. The resulting solution was stirred for 1 hour. Ethanol and dioxane were evaporated. The solid was filtered and washed with water. The solid was collected and dried to afford sodium (2E)-3-[5-(5-{3-cyano-4-[(1-methylethyl)oxy]phenyl}-1,2,4-oxadiazol-3-yl)-1H-indol-2-yl]-2-propenoate (E10) (8 mg) as a pale yellow solid. δH (DMSO-$d_6$, 400 MHz): 1.39 (6H, d), 4.99 (1H, m), 6.48 (1H, d), 6.66 (1H, s), 7.11 (1H, d), 7.46 (1H, d), 7.56 (1H, d), 7.77 (1H, d), 8.25 (1H, s), 8.42 (1H, dd) 8.51 (1H, d). MS (ES): $C_{25}H_{21}N_4O_4Na$ requires 436; found 415.0 (M—Na$^+$+2H$^+$).

EXAMPLE 11

[5-(5-{3-Chloro-4-[(1-methylethyl)oxy]phenyl}-1,2,4-oxadiazol-3-yl)-1H-indol-2-yl]methanol (E11)

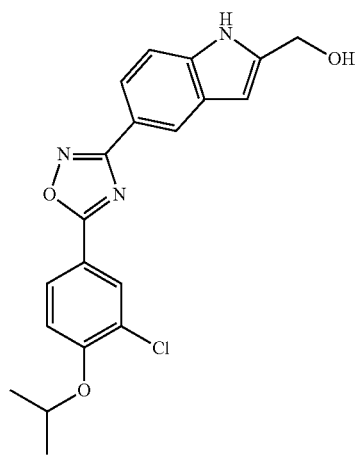

EDCI (144 mg) and HOBT (104 mg) were added to a solution of 3-chloro-4-[(1-methylethyl)oxy]benzoic acid (D32) (150 mg) in DMF (5 mL) at RT. The resulting solution was stirred for 10 min. N-Hydroxy-2-(hydroxymethyl)-1H-indole-5-carboximidamide (D25) (144 mg) was added and the reaction mixture was stirred at RT for 1 hour. The reaction mixture was heated to 80° C. and stirred at that temperature for 7 hours. EtOAc (50 mL) was added and the organic solution was washed with water (50 mL), saturated aqueous sodium bicarbonate solution (50 mL) and water (50 mL). The organic fraction was dried over anhydrous magnesium sulfate. The dried solution was concentrated. The residue was recrystallized from EtOAc/ether to afford [5-(5-{3-Chloro-4-[(1-methylethyl)oxy]phenyl}-1,2,4-oxadiazol-3-yl)-1H-indol-2-yl]methanol (E11) (95 mg) as a light brown solid. δH (DMSO-$d_6$, 400 MHz): 1.37 (6H, d), 4.65 (2H, d), 4.89 (1H, m), 5.36 (1H, t), 6.46 (1H, s), 7.47 (2H, m), 7.78 (1H, dd), 8.12 (1H, dd), 8.19 (1H, d), 8.27 (1H, s), 11.43 (1H, s). MS (ES): $C_{20}H_{18}ClN_3O_3$ requires 383; found 384.0 (M+H$^+$).

EXAMPLE 12

5-{3-[2-(Hydroxymethyl)-1H-indol-5-yl]-1,2,4-oxadiazol-5-yl}-2-[(1-methylethyl)oxy]benzonitrile (E12)

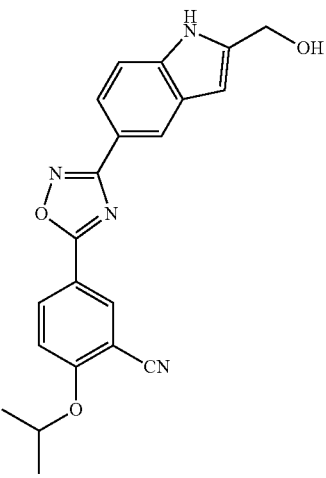

EDCI (144 mg) and HOBT (104 mg) were added to a solution of 3-cyano-4-[(1-methylethyl)oxy]benzoic acid (can be prepared as described on WO2005/58848, 144 mg) in DMF (5 mL) at RT. The resulting solution was stirred for 15 min. N-Hydroxy-2-(hydroxymethyl)-1H-indole-5-carboximidamide (D25) (144 mg) was added and the reaction mixture was stirred at RT for 1 hour. The reaction mixture was heated to 80° C. and stirred at that temperature for 4 hours. EtOAc (50 mL) was added and the organic solution was washed with water (50 mL), saturated aqueous sodium bicarbonate solution (50 mL) and water (50 mL). The organic fraction was dried over anhydrous magnesium sulfate. The dried solution was concentrated. The residue was recrystallized from EtOAc/ether to afford 5-{3-[2-(hydroxymethyl)-1H-indol-5-yl]-1,2,4-oxadiazol-5-yl}-2-[(1-methylethyl)oxy]benzonitrile (E12) (70 mg) as a light brown solid. δH (DMSO-$d_6$, 400 MHz): 1.39 (6H, d), 4.65 (2H, d), 4.99 (1H, m), 5.36 (1H, t), 6.46 (1H, s), 7.49 (1H, d), 7.56 (1H, d), 7.79 (1H, dd), 8.28 (1H, dd), 8.42 (1H, d), 8.52 (1H, d), 11.43 (1H, s). MS (ES): $C_{21}H_{18}N_4O_3$ requires 374; found 375.0 (M+H$^+$).

EXAMPLE 13

3-[7-(5-{5-Chloro-6-[(1-methylethyl)oxy]-3-pyridinyl}-1,2,4-oxadiazol-3-yl)-1H-indol-3-yl]propanoic acid (E13)

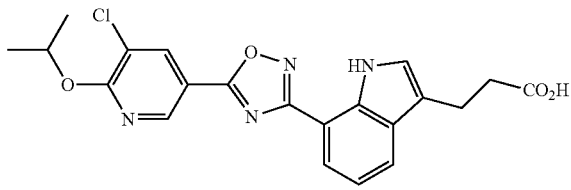

Sodium hydroxide (15 mg) was added to a solution of ethyl 3-[7-(5-{5-chloro-6-[(1-methylethyl)oxy]-3-pyridinyl}-1,2,4-oxadiazol-3-yl)-1H-indol-3-yl]propanoate (D36) (110 mg) in $^i$PrOH (4 mL) and water (4 mL). The resulting mixture was heated at 70° C. for 40 mins. Then 0.5 M HCl solution was added until pH was about 6. The solvent was concentrated, and the residue was dissolved in water. The precipitate was purified by Mass Directed Auto Prep to afford 3-[7-(5-{5-chloro-6-[(1-methylethyl)oxy]-3-pyridinyl}-1,2,4-oxadiazol-3-yl)-1H-indol-3-yl]propanoic acid (E13) (55 mg) as a white solid. δH (DMSO-$d_6$, 400 MHz): 1.40 (6H, d), 2.63 (2H, t), 3.00 (2H, t), 5.46 (1H, m), 7.21 (1H, t), 7.27 (1H, d), 7.82 (1H, d), 7.93 (1H, d), 8.75 (1H, d), 9.06 (1H, d), 10.87 (1H, s), 12.08 (1H, br s). MS (ES): $C_{21}H_{19}ClN_4O_4$ requires 426. found 427.1 (M+H$^+$).

EXAMPLE 14

3-[7-(5-{5-Chloro-6-[(1-methylethyl)oxy]-3-pyridinyl}-1,2,4-oxadiazol-3-yl)-1-methyl-1H-indol-3-yl]propanoic acid (E14)

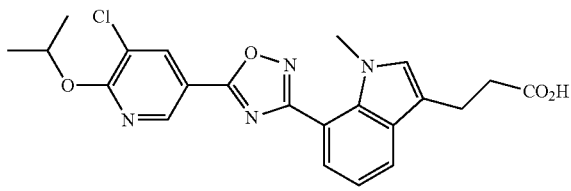

DABCO (111 mg) was added to a solution of 3-[7-(5-{5-chloro-6-[(1-methylethyl)oxy]-3-pyridinyl}-1,2,4-oxadiazol-3-yl)-1H-indol-3-yl]propanoic acid (E13) (100 mg) in dimethyl carbonate (3 mL) and DMF (2 mL). The resulting mixture was heated at reflux for 5 days. After cooling, the reaction was quenched with water, and extracted with EtOAc for 3 times. The combined organic solution was washed with brine, and dried over anhydrous sodium sulfate. The dried solution was concentrated. The residue was dissolved in THF (3 mL) and water (3 mL). Sodium hydroxide (40 mg) was added to the mixture. The resulting mixture was heated at 70° C. for 40 mins. Then 0.5 M HCl solution was added until pH was about 6. The solvent was concentrated, and the residue was dissolved in water. The precipitate was purified by Mass Directed Auto Prep to afford 3-[7-(5-{5-chloro-6-[(1-methylethyl)oxy]-3-pyridinyl}-1,2,4-oxadiazol-3-yl)-1-methyl-1H-indol-3-yl]propanoic acid (E14) (18 mg) as a white solid. δH (DMSO-$d_6$, 400 MHz): 1.38 (6H, d), 2.60 (2H, t), 2.96 (2H, t), 3.62 (3H, s), 5.44 (1H, m), 7.17 (1H, t), 7.19 (1H, s), 7.43 (1H, d), 7.80 (1H, d), 8.57 (1H, d), 8.95 (1H, d), 12.10 (1H, br s). MS (ES): $C_{22}H_{21}ClN_4O_4$ requires 440; found 441.1 (M+H$^+$).

EXAMPLE 15

3-(7-{5-[6-[(1-Methylethyl)oxy]-5-(trifluoromethyl)-3-pyridinyl]-1,2,4-oxadiazol-3-yl}-1H-indol-3-yl)propanoic acid (E15)

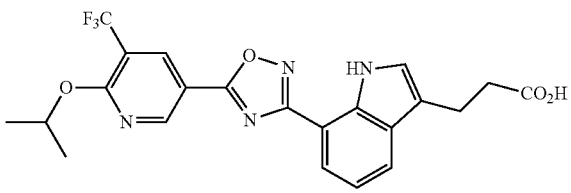

Sodium hydroxide (50 mg) was added to a solution of ethyl 3-(7-{5-[6-[(1-methylethyl)oxy]-5-(trifluoromethyl)-3-pyridinyl]-1,2,4-oxadiazol-3-yl}-1H-indol-3-yl)propanoate (D37) (83 mg) in isopropanol (5 mL), THF (3 mL), water (1.5 mL). The reaction mixture was stirred at room temperature overnight. The organic solvents were removed. 2 M HCl was used to adjust the pH value to around 6.0. The crude product was purified by Mass Directed Auto Prep to afford 3-(7-{5-[6-[(1-methylethyl)oxy]-5-(trifluoromethyl)-3-pyridinyl]-1,2,4-oxadiazol-3-yl}-1H-indol-3-yl)propanoic acid (E15) (40 mg). δH (DMSO-$d_6$, 400 MHz): 1.41 (6H, d), 2.64 (2H, t), 3.01 (2H, t), 5.56 (1H, m), 7.22 (1H, t), 7.29 (1H, d), 7.84 (1H, d), 7.96 (1H, dd), 8.79 (1H, d), 9.36 (1H, d), 10.86 (1H, s), 12.07 (1H, br s); MS (ES): $C_{22}H_{19}F_3N_4O_4$ requires 460; found 461.2 (M+H$^+$).

EXAMPLE 16

3-[7-(5-{5-Methyl-6-[(1-methylethyl)oxy]-3-pyridinyl}-1,2,4-oxadiazol-3-yl)-1H-indol-3-yl]propanoic acid (E16)

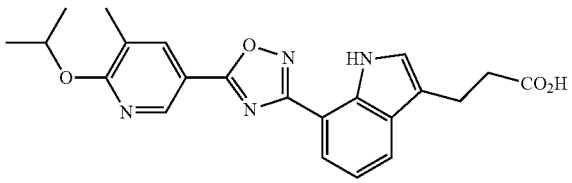

EDCI (432 mg) and HOBT (372 mg) were added to a solution of 5-methyl-6-[(1-methylethyl)oxy]-3-pyridinecarboxylic acid (220 mg) in THF (5 mL) at RT. The resulting solution was stirred for 30 mins. Ethyl 3-{7-[(Z)-(hydroxyamino)(imino)methyl]-1H-indol-3-yl}propanoate (D35) (465 mg) in THF (5 mL) was added and the reaction mixture was stirred at RT for 2 hours. TBAF (1.2 g) was then added. The reaction vessel was sealed and heated in Biotage Initiator using initial normal to 120° C. for 2 hours. More TBAF (1.2 g) was added. The reaction vessel was sealed again and heated in Biotage Initiator using initial normal to 120° C. for 2 hours. Part of ethyl 3-[7-(5-{5-methyl-6-[(1-methylethyl)oxy]-3-pyridinyl}-1,2,4-oxadiazol-3-yl)-1H-indol-3-yl]propanoate was hydrolyzed by TBAF to 3-[7-(5-{5-methyl-6-[(1-methylethyl)oxy]-3-pyridinyl}-1,2,4-oxadiazol-3-yl)-1H-indol-3-yl]propanoic acid (E16). After cooling, the reaction was quenched with water, and extracted with EtOAc for 3 times. The combined organic solution was washed with brine, dried over anhydrous sodium sulfate. The dried solution was concentrated. The residue was purified by column chromatography (50% EtOAc in hexane) to afford ethyl 3-[7-(5-{5-methyl-6-[(1-methylethyl)oxy]-3-pyridinyl}-1,2,4-oxadiazol-3-yl)-1H-indol-3-yl]propanoate (D119) (196 mg), MS (ES): $C_{24}H_{26}N_4O_4$ requires 434; found 435.2 (M+H$^+$) and 3-[7-(5-{5-methyl-6-[(1-methylethyl)oxy]-3-pyridinyl}-1,2,4-oxadiazol-3-yl)-1H-indol-3-yl]propanoic acid (E16) (100 mg) as a white solid. δH (DMSO-d$_6$, 400 MHz): 1.37 (6H, d), 2.24 (3H, s), 2.63 (2H, t), 2.99 (2H, t), 5.40 (1H, m), 7.21 (1H, t), 7.26 (1H, d), 7.81 (1H, d), 7.93 (1H, dd), 8.36 (1H, t), 8.95 (1H, d), 10.81 (1H, d), 12.12 (1H, br s). MS (ES): $C_{22}H_{22}N_4O_4$ requires 406; found 407.2 (M+H$^+$).

EXAMPLE 17

3-[1-Methyl-7-(5-{5-methyl-6-[(1-methylethyl)oxy]-3-pyridinyl}-1,2,4-oxadiazol-3-yl)-1H-indol-3-yl]propanoic acid (E17)

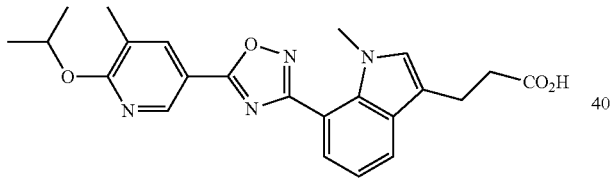

DABCO (20 mg) was added to a solution of ethyl 3-[7-(5-{5-methyl-6-[(1-methylethyl)oxy]-3-pyridinyl}-1,2,4-oxadiazol-3-yl)-1H-indol-3-yl]propanoate (D119) (188 mg) in dimethyl carbonate (2 mL) and DMF (0.2 mL). The resulting mixture was stirred at reflux for 1 day. After cooling, the reaction was quenched with water, and extracted with EtOAc for 3 times. The combined organic solution was washed with brine, dried over anhydrous sodium sulfate. The dried solution was concentrated. The residue was dissolved in $^i$PrOH (8 mL) and water (8 mL). Sodium hydroxide (40 mg) was added to the mixture. The resulting mixture was heated at 70° C. for 30 mins. Then 0.5 M HCl solution was added until pH was about 6. The solvent was concentrated, and the residue was dissolved in water. The precipitated solid was purified by Mass Directed Auto Prep to afford 3-[1-methyl-7-(5-{5-methyl-6-[(1-methylethyl)oxy]-3-pyridinyl}-1,2,4-oxadiazol-3-yl)-1H-indol-3-yl]propanoic acid (E17) (19 mg) as a white solid. δH (DMSO-d$_6$, 400 MHz): 1.35 (6H, d), 2.23 (3H, s), 2.60 (2H, t), 2.96 (2H, t), 3.62 (3H, s), 5.40 (1H, m), 7.16 (1H, d), 7.19 (1H, s), 7.43 (1H, d), 7.79 (1H, d), 8.29 (1H, s), 8.84 (1H, d), 12.12 (1H, br s). MS (ES): $C_{23}H_{24}N_4O_4$ requires 420; found 421.2 (M+H$^+$).

EXAMPLE 18

3-(7-{5-[6-[(1-Methylethyl)oxy]-5-(methyloxy)-3-pyridinyl]-1,2,4-oxadiazol-3-yl}-1H-indol-3-yl)propanoic acid (E18)

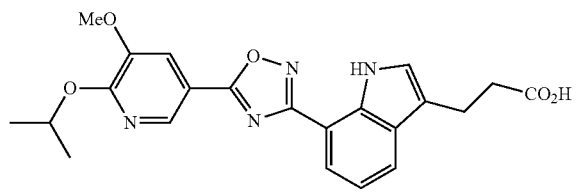

Sodium hydroxide (40 mg) was added to a solution of ethyl 3-(7-{5-[6-[(1-methylethyl)oxy]-5-(methyloxy)-3-pyridinyl]-1,2,4-oxadiazol-3-yl}-1H-indol-3-yl)propanoate (D38) (280 mg) in THF (3 mL) and water (3 mL). The resulting mixture was heated at 90° C. for 1 hour. Then 0.5 M HCl solution was added until pH was about 6. The solvent was concentrated, and the residue was dissolved in water. The precipitated solid was purified by Mass Directed Auto Prep to afford 3-(7-{5-[6-[(1-methylethyl)oxy]-5-(methyloxy)-3-pyridinyl]-1,2,4-oxadiazol-3-yl}-1H-indol-3-yl)propanoic acid (E18) (145 mg) as a white solid. δH (DMSO-d$_6$, 400 MHz): 1.36 (6H, d), 2.63 (2H, t), 3.00 (2H, t), 3.96 (3H, s), 5.43 (1H, m), 7.22 (1H, t), 7.27 (1H, d), 7.82 (1H, d), 7.92 (1H, d), 7.95 (1H, d), 8.68 (1H, d), 10.79 (1H, s), 12.10 (1H, br s). MS (ES): $C_{22}H_{22}N_4O_5$ requires 422; found 423.2 (M+H$^+$).

EXAMPLE 19

3-[7-(5-{3-Chloro-4-[(1-methylethyl)oxy]phenyl}-1,2,4-oxadiazol-3-yl)-4-fluoro-1H-indol-3-yl]propanoic acid (E19)

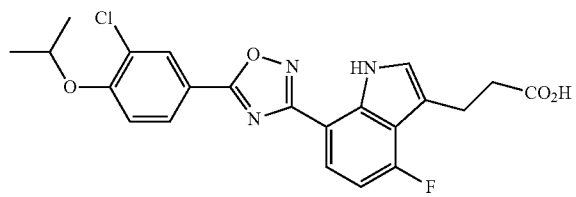

Sodium hydroxide (25 mg) was added to a solution of ethyl 3-[7-(5-{3-chloro-4-[(1-methylethyl)oxy]phenyl}-1,2,4-oxadiazol-3-yl)-4-fluoro-1H-indol-3-yl]propanoate (D46) (204 mg) in THF (3 mL) and water (3 mL). The reaction mixture was stirred at 90° C. for 1 hour. Then 0.5 M HCl was added until pH was about 6. The solvent was concentrated, and the residue was dissolved in water. The precipitated solid was purified by Mass Directed Auto Prep to afford 3-[7-(5-{3-chloro-4-[(1-methylethyl)oxy]phenyl}-1,2,4-oxadiazol-3-yl)-4-fluoro-1H-indol-3-yl]propanoic acid (E19) (127 mg) as a white needle crystal. δH (DMSO-d$_6$, 400 MHz): 1.36 (6H, d), 2.62 (2H, t), 3.06 (2H, t), 4.89 (1H, m), 6.98 (1H, dd), 7.25 (1H, d), 7.45 (1H, d), 7.91 (1H, dd), 8.19 (1H, dd), 8.35

(1H, d), 11.10 (1H, s), 12.14 (1H, br s). δF (DMSO-d$_6$, 376 MHz): −118.9. MS (ES): C$_{22}$H$_{19}$ClFN$_3$O$_4$ requires 443; found 444.1 (M+H$^+$).

EXAMPLE 20

3-[7-(5-{3-Chloro-4-[(1-methylethyl)oxy]phenyl}-1,2,4-oxadiazol-3-yl)-4-fluoro-1-methyl-1H-indol-3-yl]propanoic acid (E20)

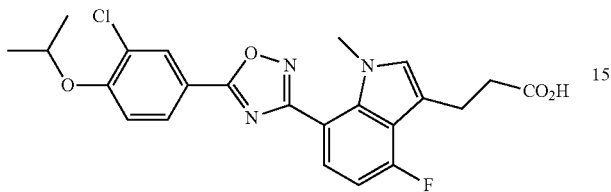

DABCO (121 mg) was added to a solution of ethyl 3-[7-(5-{3-chloro-4-[(1-methylethyl)oxy]phenyl}-1,2,4-oxadiazol-3-yl)-4-fluoro-1H-indol-3-yl]propanoate (D46) (340 mg) in DMF (2 mL) and dimethyl carbonate (2 mL). The reaction mixture was stirred at 94° C. for 3 days. Then the reaction was quenched with water, and extracted with EtOAc for 3 times. The combined organic solution was washed with brine, and dried over anhydrous sodium sulfate. The dried solution was concentrated to afford the crude product as a yellow solid. This solid was dissolved in THF (3 mL) and water (3 mL). Sodium hydroxide (40 mg) was then added to the mixture. The reaction mixture was stirred at 90° C. for 1 h. Then 0.5 M HCl was added until pH was about 6. The solvent was concentrated, and the residue was dissolved in water. The precipitated solid was purified by Mass Directed Auto Prep to afford 3-[7-(5-{3-chloro-4-[(1-methylethyl)oxy]phenyl}-1,2,4-oxadiazol-3-yl)-4-fluoro-1-methyl-1H-indol-3-yl]propanoic acid (E20) (83 mg) as a white solid. δH (DMSO-d$_6$, 400 MHz): 1.35 (6H, d), 2.59 (2H, t), 3.03 (2H, t), 3.62 (3H, s), 4.88 (1H, m), 6.95 (1H, dd), 7.22 (1H, s), 7.42 (2H, m), 8.12 (1H, dd), 8.19 (1H, d), 12.14 (1H, br s). δF (DMSO-d$_6$, 376 MHz): −120.6. MS (ES): C$_{23}$H$_{21}$ClFN$_3$O$_4$ requires 457; found 458.1 (M+H$^+$).

EXAMPLE 21

3-[7-(5-{3-Cyano-4-[(1-methylethyl)oxy]phenyl}-1,2,4-oxadiazol-3-yl)-4-fluoro-1H-indol-3-yl]propanoic acid (E21)

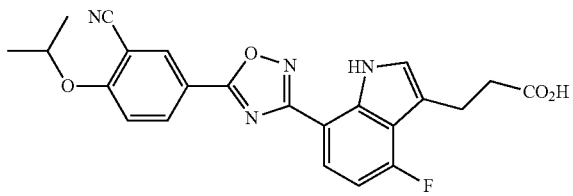

Sodium hydroxide (30 mg) was added to a solution of ethyl 3-[7-(5-{3-cyano-4-[(1-methylethyl)oxy]phenyl}-1,2,4-oxadiazol-3-yl)-4-fluoro-1H-indol-3-yl]propanoate (D47) (195 mg) in THF (3 mL) and water (3 mL). The reaction mixture was stirred at 90° C. for 1 hour. Then 0.5 M HCl was added until pH was about 6. The solvent was concentrated, and the residue was dissolved in water. The precipitated solid was purified by Mass Directed Auto Prep to afford 3-[7-(5-{3-cyano-4-[(1-methylethyl)oxy]phenyl}-1,2,4-oxadiazol-3-yl)-4-fluoro-1H-indol-3-yl]propanoic acid (E21) (78 mg) as a white solid. δH (DMSO-d$_6$, 400 MHz): 1.38 (6H, d), 2.62 (2H, t), 3.06 (2H, t), 4.99 (1H, m), 6.98 (1H, dd), 7.26 (1H, d), 7.55 (1H, d), 7.90 (1H, dd), 8.47 (1H, dd), 8.70 (1H, d), 11.12 (1H, s), 12.15 (1H, br s). δF (DMSO-d$_6$, 376 MHz): −118.0. MS (ES): C$_{23}$H$_{19}$FN$_4$O$_4$ requires 434; found 435.1 (M+H$^+$).

EXAMPLE 22

3-[7-(5-{5-Chloro-6-[(1-methylethyl)oxy]-3-pyridinyl}-1,2,4-oxadiazol-3-yl)-4-fluoro-1H-indol-3-yl]propanoic acid (E22)

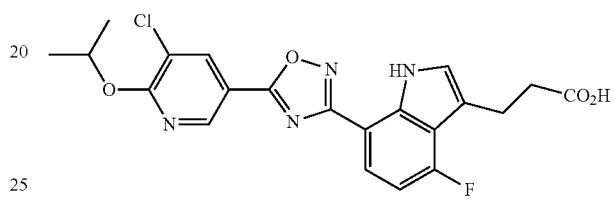

Sodium hydroxide (35 mg) was added to a solution of ethyl 3-[7-(5-{5-chloro-6-[(1-methylethyl)oxy]-3-pyridinyl}-1,2,4-oxadiazol-3-yl)-4-fluoro-1H-indol-3-yl]propanoate (D48) (222 mg) in THF (3 mL) and water (3 mL). The reaction mixture was stirred at 90° C. for 1 hour. Then 0.5 M HCl was added until pH was about 6. The solvent was concentrated, and the residue was dissolved in water. The precipitated solid was purified by Mass Directed Auto Prep to afford 3-[7-(5-{5-chloro-6-[(1-methylethyl)oxy]-3-pyridinyl}-1,2,4-oxadiazol-3-yl)-4-fluoro-1H-indol-3-yl]propanoic acid (E22) (137 mg) as a white solid. δH (DMSO-d$_6$, 400 MHz): 1.40 (6H, d), 2.62 (2H, t), 3.07 (2H, t), 5.46 (1H, m), 6.98 (1H, dd), 7.26 (1H, d), 7.91 (1H, dd), 8.72 (1H, d), 9.04 (1H, d), 11.09 (1H, s), 11.71 (1H, br s). δF (DMSO-d$_6$, 376 MHz): −118.7. MS (ES): C$_{21}$H$_{18}$ClFN$_4$O$_4$ requires 444; found 445.1 (M+H$^+$).

EXAMPLE 23

3-[7-(5-{5-Chloro-6-[(1-methylethyl)oxy]-3-pyridinyl}-1,2,4-oxadiazol-3-yl)-4-fluoro-1-methyl-1H-indol-3-yl]propanoic acid (E23)

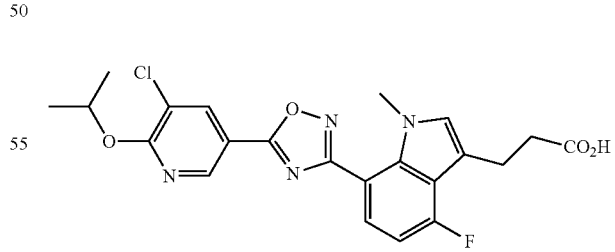

DABCO (45 mg) was added to a solution of 3-[7-(5-{5-chloro-6-[(1-methylethyl)oxy]-3-pyridinyl}-1,2,4-oxadiazol-3-yl)-4-fluoro-1H-indol-3-yl]propanoic acid (E22) (71 mg) in DMF (2 mL) and dimethyl carbonate (2 mL). The reaction mixture was stirred at 94° C. for 3 days. Then the reaction was quenched with water, and extracted with EtOAc for 3 times. The combined organic solution was washed with brine, and dried over anhydrous sodium sulfate. The dried solution was concentrated to afford the crude product as a brown solid. This solid was dissolved in THF (3 mL) and water (3 mL). Sodium hydroxide (40 mg) was then added to the mixture. The reaction mixture was stirred at 90° C. for 1 hour. Then 0.5 M HCl was added until pH was about 6. The solvent was concentrated, and the residue was dissolved in water. The precipitated solid was purified by Mass Directed Auto Prep to afford 3-[7-(5-{5-chloro-6-[(1-methylethyl) oxy]-3-pyridinyl}-1,2,4-oxadiazol-3-yl)-4-fluoro-1-methyl-1H-indol-3-yl]propanoic acid (E23) (27 mg) as a white solid. δH (DMSO-$d_6$, 400 MHz): 1.38 (6H, d), 2.60 (2H, t), 3.03 (2H, t), 3.63 (3H, s), 5.45 (1H, m), 6.96 (1H, dd), 7.22 (1H, s), 7.42 (1H, dd), 8.57 (1H, d), 8.94 (1H, d), 12.11 (1H, br s). δF (DMSO-$d_6$, 376 MHz): −120.4. MS (ES): $C_{22}H_{20}ClFN_4O_4$ requires 458; found 459.1 (M+H$^+$).

EXAMPLE 24

3-(4-Fluoro-7-{5-[6-[(1-methylethyl)oxy]-5-(trifluoromethyl)-3-pyridinyl]-1,2,4-oxadiazol-3-yl}-1H-indol-3-yl)propanoic acid (E24)

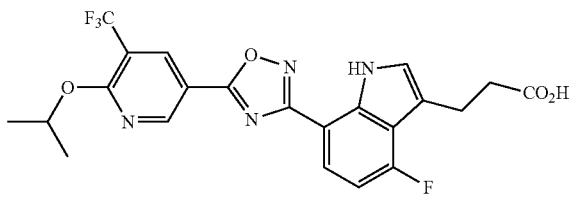

Sodium hydroxide (30 mg) was added to a solution of ethyl 3-(4-fluoro-7-{5-[6-[(1-methylethyl)oxy]-5-(trifluoromethyl)-3-pyridinyl]-1,2,4-oxadiazol-3-yl}-1H-indol-3-yl) propanoate (D49) (161 mg) in THF (3 mL) and water (3 mL). The reaction mixture was stirred at 90° C. for 1 hour. Then 0.5 M HCl was added until pH was about 6. The solvent was concentrated, and the residue was dissolved in water. The precipitated solid was purified by Mass Directed Auto Prep to afford 3-(4-fluoro-7-{5-[6-[(1-methylethyl)oxy]-5-(trifluoromethyl)-3-pyridinyl]-1,2,4-oxadiazol-3-yl}-1H-indol-3-yl)propanoic acid (E24) (93 mg) as a white solid. δH (DMSO-$d_6$, 400 MHz): 1.38 (6H, d), 2.62 (2H, t), 3.05 (2H, t), 5.54 (1H, m), 6.98 (1H, dd), 7.26 (1H, d), 7.92 (1H, dd), 8.74 (1H, d), 9.32 (1H, d), 11.12 (1H, s), 12.14 (1H, br s). δF (DMSO-$d_6$, 376 MHz): −118.6, −62.8. MS (ES): $C_{22}H_{18}F_4N_4O_4$ requires 478; found 479.1 (M+H$^+$).

EXAMPLE 25

3-(4-Fluoro-7-{5-[6-[(1-methylethyl)oxy]-5-(methyloxy)-3-pyridinyl]-1,2,4-oxadiazol-3-yl}-1H-indol-3-yl)propanoic acid (E25)

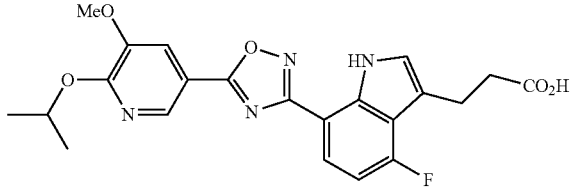

Sodium hydroxide (30 mg) was added to a solution of ethyl 3-(4-fluoro-7-{5-[6-[(1-methylethyl)oxy]-5-(methyloxy)-3-pyridinyl]-1,2,4-oxadiazol-3-yl}-1H-indol-3-yl)propanoate (D50) (157 mg) in THF (3 mL) and water (3 mL). The reaction mixture was stirred at 90° C. for 1 hour. Then 0.5 M HCl was added until pH was about 6. The solvent was concentrated, and the residue was dissolved in water. The precipitated solid was purified by Mass Directed Auto Prep to afford 3-(4-fluoro-7-{5-[6-[(1-methylethyl)oxy]-5-(methyloxy)-3-pyridinyl]-1,2,4-oxadiazol-3-yl}-1H-indol-3-yl)propanoic acid (E25) (110 mg) as a white solid. δH (DMSO-$d_6$, 400 MHz): 1.35 (6H, d), 2.62 (2H, t), 3.06 (2H, t), 3.95 (3H, s), 5.42 (1H, m), 6.99 (1H, dd), 7.26 (1H, d), 7.92 (2H, m), 8.67 (1H, d), 11.07 (1H, s), 12.14 (1H, br s). δF (DMSO-$d_6$, 376 MHz): −118.8. MS (ES): $C_{22}H_{21}FN_4O_5$ requires 440; found 441.2 (M+H$^+$).

EXAMPLE 26

3-[7-(5-{3-chloro-4-[(1-methylethyl)oxy]phenyl}-1,2,4-oxadiazol-3-yl)-1-ethyl-1H-indol-3-yl]propanoic acid (E26)

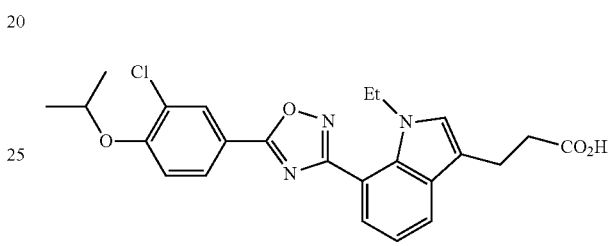

Sodium hydroxide (66 mg) was added to a solution of ethyl 3-[7-(5-{3-chloro-4-[(1-methylethyl)oxy]phenyl}-1,2,4-oxadiazol-3-yl)-1-ethyl-1H-indol-3-yl]propanoate (D120) (79 mg) in THF (5 mL), isopropanol (4 mL) and water (2 mL). The reaction mixture was stirred at room temperature overnight. The mixture was neutralized with 2 M HCl till pH ~6.0. The solvent was concentrated, and the residue was dissolved in water. The precipitated solid was purified by Mass Directed Auto Prep to afford 3-[7-(5-{3-chloro-4-[(1-methylethyl) oxy]phenyl}-1,2,4-oxadiazol-3-yl)-1-ethyl-1H-indol-3-yl] propanoic acid (E26) (42 mg). δH (DMSO-$d_6$, 400 MHz): 1.04 (3H, t), 1.37 (6H, d), 2.62 (2H, t), 2.98 (2H, t), 4.14 (2H, q), 4.89 (1H, m), 7.18 (1H, t), 7.27 (1H, s), 7.45 (2H, t), 7.81 (1H, dd), 8.13 (1H, dd), 8.20 (1H, d), 12.07 (1H, s); MS (ES): $C_{24}H_{24}ClN_3O_4$ requires 453; found 454.2 (M+H$^+$).

EXAMPLE 27

3-[7-(5-{3-chloro-4-[(1-methylethyl)oxy]phenyl}-1,2,4-oxadiazol-3-yl)-1-propyl-1H-indol-3-yl]propanoic acid (E27)

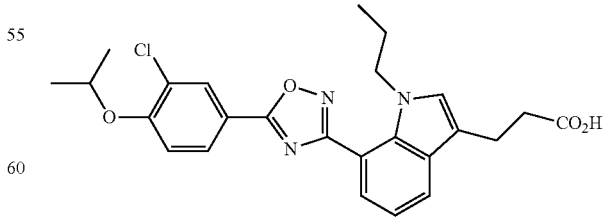

Sodium hydroxide (130 mg) was added to a solution of propyl 3-[7-(5-{3-chloro-4-[(1-methylethyl)oxy]phenyl}-1,2,4-oxadiazol-3-yl)-1-propyl-1H-indol-3-yl]propanoate (D121) (166 mg) in THF (5 mL), isopropanol (4 mL) and water (2 mL). The reaction mixture was stirred at room temperature overnight. The mixture was neutralized with 2 M HCl till pH ~6.0. The solvent was concentrated, and the residue was dissolved in water. The precipitated solid was purified by Mass Directed Auto Prep to afford 3-[7-(5-{3-chloro-4-[(1-methylethyl)oxy]phenyl}-1,2,4-oxadiazol-3-yl)-1-propyl-1H-indol-3-yl]propanoic acid (E27) (98 mg). δH (DMSO-d$_6$, 400 MHz): 0.54 (3H, t), 1.39 (8H, m), 2.62 (2H, t), 2.98 (2H, t), 4.08 (2H, t), 4.90 (1H, m), 7.17 (1H, t), 7.25 (1H, s), 7.44 (2H, m), 7.81 (1H, dd), 8.13 (1H, dd), 8.19 (1H, d), 12.07 (1H, br s); MS (ES): $C_{26}H_{26}ClN_3O_4$ requires 467; found 468.2 (M+H$^+$).

EXAMPLE 28

3-[7-(5-{3-chloro-4-[(1-methylethyl)oxy]phenyl}-1,2,4-oxadiazol-3-yl)-1-(1-methylethyl)-1H-indol-3-yl]propanoic acid (E28)

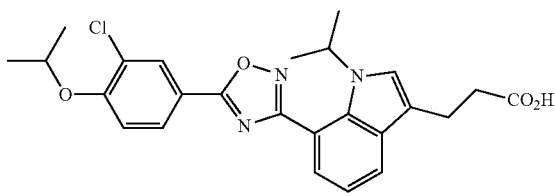

Sodium hydroxide (93 mg) was added to a solution of 1-methylethyl 3-[7-(5-{3-chloro-4-[(1-methylethyl)oxy]phenyl}-1,2,4-oxadiazol-3-yl)-1-(1-methylethyl)-1H-indol-3-yl]propanoate (D122) (60 mg) in THF (5 mL), isopropanol (4 mL) and water (2 mL). The reaction mixture was stirred at room temperature for 2 days. The mixture was neutralized with 2 M HCl till pH ~6.0. The solvent was concentrated, and the residue was dissolved in water. The precipitated solid was purified by Mass Directed Auto Prep to afford 3-[7-(5-{3-chloro-4-[(1-methylethyl)oxy]phenyl}-1,2,4-oxadiazol-3-yl)-1-(1-methylethyl)-1H-indol-3-yl]propanoic acid (E28) (28 mg). δH (DMSO-d$_6$, 400 MHz): 1.30 (6H, d), 1.37 (6H, d), 2.64 (2H, t), 3.00 (2H, t), 4.56 (1H, m), 4.89 (1H, m), 7.16 (1H, t), 7.37 (1H, dd), 7.46 (2H, m), 7.79 (1H, dd), 8.12 (1H, dd), 8.18 (1H, d), 12.07 (1H, br s); MS (ES): $C_{26}H_{26}ClN_3O_4$ requires 467; found 468.2 (M+H$^+$).

EXAMPLE 29

3-[1-butyl-7-(5-{3-chloro-4-[(1-methylethyl)oxy]phenyl}-1,2,4-oxadiazol-3-yl)-1H-indol-3-yl]propanoic acid (E29)

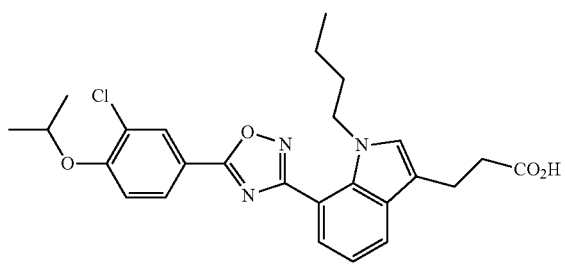

Sodium hydroxide (94 mg) was added to a solution of propyl 3-[1-butyl-7-(5-{3-chloro-4-[(1-methylethyl)oxy]phenyl}-1,2,4-oxadiazol-3-yl)-1H-indol-3-yl]propanoate (D123) (61 mg) in tetrahydrofuran (5 mL), isopropanol (4 mL) and water (2 mL). The reaction mixture was stirred at room temperature overnight. The mixture was neutralized with 2 M HCl till pH ~6.0. The solvent was concentrated, and the residue was dissolved in water. The precipitated solid was purified by Mass Directed Auto Prep to afford 3-[1-butyl-7-(5-{3-chloro-4-[(1-methylethyl)oxy]phenyl}-1,2,4-oxadiazol-3-yl)-1H-indol-3-yl]propanoic acid (E29) (30 mg). δH (DMSO-d$_6$, 400 MHz): 0.65 (3H, t), 0.96 (2H, m), 1.37 (8H, m), 2.62 (2H, t), 2.98 (2H, t), 4.10 (2H, t), 4.88 (1H, m), 7.17 (1H, t), 7.25 (1H, s), 7.44 (2H, m), 7.81 (1H, dd), 8.13 (1H, dd), 8.19 (1H, d), 12.05 (1H, br s); MS (ES): $C_{26}H_{28}ClN_3O_4$ requires 481; found 482.2 (M+H$^+$).

EXAMPLE 30

3-[7-(5-{3-chloro-4-[(1-methylethyl)oxy]phenyl}-1,2,4-oxadiazol-3-yl)-1-(2-methylpropyl)-1H-indol-3-yl]propanoic acid (E30)

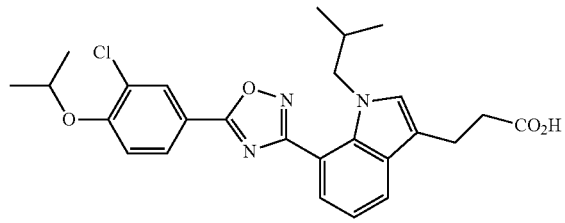

Sodium hydroxide (114 mg) was added to a solution of 2-methylpropyl 3-[7-(5-{3-chloro-4-[(1-methylethyl)oxy]phenyl}-1,2,4-oxadiazol-3-yl)-1-(2-methylpropyl)-1H-indol-3-yl]propanoate (D124) (77 mg) in THF (5 mL), isopropanol (4 mL) and water (2 mL). The reaction mixture was stirred at room temperature overnight. The mixture was neutralized with 2 M HCl till pH ~6.0. The solvent was concentrated, and the residue was dissolved in water. The precipitated solid was purified by Mass Directed Auto Prep to afford 3-[7-(5-{3-chloro-4-[(1-methylethyl)oxy]phenyl}-1,2,4-oxadiazol-3-yl)-1-(2-methylpropyl)-1H-indol-3-yl]propanoic acid (E30) (42 mg). δH (DMSO-d$_6$, 400 MHz): 0.52 (6H, d), 1.37 (6H, d), 1.51 (1H, m), 2.61 (2H, t), 2.99 (2H, t), 3.99 (2H, d), 4.89 (1H, m), 7.19 (1H, t), 7.22 (1H, s), 7.45 (2H, m), 7.82 (1H, dd), 8.14 (1H, dd), 8.21 (1H, d), 12.04 (1H, br s); MS (ES): $C_{26}H_{28}ClN_3O_4$ requires 481; found 482.2 (M+H$^+$).

EXAMPLE 31

[7-(5-{3-chloro-4-[(1-methylethyl)oxy]phenyl}-1,2,4-oxadiazol-3-yl)-1H-indol-3-yl]acetic acid (E3)

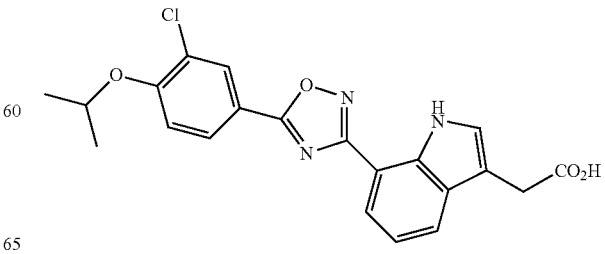

To methylmagnesium bromide solution (3 mol/L in diethyl ether, 0.4 mL) stirred under nitrogen at 0° C. was added a solution of 7-(5-{3-chloro-4-[(1-methylethyl)oxy]phenyl}-1,2,4-oxadiazol-3-yl)-1H-indole (D51) (354 mg) in diethyl ether (5 mL) dropwise. The reaction mixture was stirred at 0° C. for 30 mins. Ethyl bromoacetate (0.13 mL) in toluene (15 mL) was added dropwise. The resulting mixture was stirred at room temperature for 24 h. The reaction mixture was quenched with saturated ammonium chloride solution; the organic layer was separated and the solvent was evaporated off. The residue was dissolved in tetrahydrofuran (5 mL) and sodium hydroxide (40 mg) in water (5 mL) was added. The reaction mixture was stirred at room temperature for 6 hours. Evaporated off the organic solvent, extracted with ether (100 mL), the water layer was separated and acidified with HCl (1 M) to pH around 1. The solid was filtered and purified by Mass Directed Auto Prep to afford [7-(5-{3-chloro-4-[(1-methylethyl)oxy]phenyl}-1,2,4-oxadiazol-3-yl)-1H-indol-3-yl]acetic acid (E31) (86 mg) as a yellow solid. δH (DMSO-d$_6$, 400 MHz): 1.37 (6H, d), 3.74 (2H, s), 4.87-4.93 (1H, m), 7.22 (1H, t), 7.40 (1H, d), 7.45 (1H, d), 7.78 (1H, d), 7.95 (1H, d), 8.21 (1H, dd), 8.37 (1H, d), 10.91 (1H, s), 12.19 (1H, br s). MS (ES): $C_{21}H_{18}ClN_3O_4$ requires 411; found 412.1 (M+H$^+$).

EXAMPLE 32

4-[7-(5-{3-chloro-4-[(1-methylethyl)oxy]phenyl}-1,2,4-oxadiazol-3-yl)-1H-indol-3-yl]butanoic acid (E32)

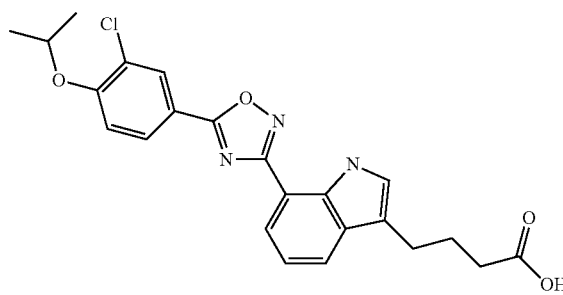

To a solution of ethyl 4-[7-(5-{3-chloro-4-[(1-methylethyl)oxy]phenyl}-1,2,4-oxadiazol-3-yl)-1H-indol-3-yl]butanoate (D53) (40 mg) in THF (5 mL) was added aqueous NaOH (2 M, 2 mL). The reaction mixture was stirred at 60° C. overnight. The mixture was acidified with HCl (2 M) to pH 4-5, and then partitioned between ethyl acetate (25 mL) and water (25 mL). The organic phase was washed with water (25 mL) and brine (25 mL), dried over anhydrous sodium sulphate and evaporated to give the crude product, which was purified by Mass Directed Auto Prep to afford 4-[7-(5-{3-chloro-4-[(1-methylethyl)oxy]phenyl}-1,2,4-oxadiazol-3-yl)-1H-indol-3-yl]butanoic acid (E32) (22 mg). δH (DMSO-d$_6$, 400 MHz): 1.36 (6H, d), 1.90 (2H, m), 2.28 (2H, t), 2.77 (2H, t), 4.89 (1H, m), 7.20 (1H, t), 7.26 (1H, d), 7.44 (1H, d), 7.80 (1H, d), 7.93 (1H, d), 8.20 (1H, dd), 8.37 (1H, d), 10.83 (1H, s), 12.05 (1H, br s). MS (ES): $C_{23}H_{22}ClN_3O_4$ requires 439; found 440.2 (M+H$^+$).

EXAMPLE 33

4-[7-(5-{3-chloro-4-[(1-methylethyl)oxy]phenyl}-1,2,4-oxadiazol-3-yl)-1H-indol-3-yl]-4-oxobutanoic acid (E33)

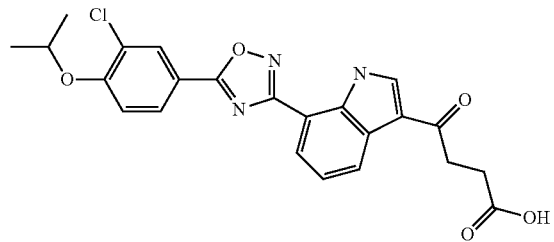

To a solution of ethyl 4-[7-(5-{3-chloro-4-[(1-methylethyl)oxy]phenyl}-1,2,4-oxadiazol-3-yl)-1H-indol-3-yl]-4-oxobutanoate (D52) (20 mg) in THF (2 mL) was added aqueous NaOH (2 M, 1 mL), the reaction was stirred at room temperature overnight. The mixture was acidified with aqueous HCl (2M) to pH 4-5, and then partitioned with ethyl acetate (10 mL) and water (10 mL). The organic phase was washed with water (10 mL) and brine (10 mL), dried over anhydrous sodium sulphate and evaporated to give the crude product, which was purified by Mass Directed Auto Prep to afford 4-[7-(5-{3-chloro-4-[(1-methylethyl)oxy]phenyl}-1,2,4-oxadiazol-3-yl)-1H-indol-3-yl]-4-oxobutanoic acid (E33) (12 mg). δH (DMSO-d$_6$, 400 MHz): 1.37 (6H, d), 2.59 (2H, t), 3.20 (2H, t), 4.91 (1H, m), 7.41 (1H, t), 7.47 (1H, d), 8.04 (1H, dd), 8.22 (1H, dd), 8.36 (1H, d), 8.41 (1H, d), 8.44 (1H, dd), 11.81 (1H, br s). MS (ES): $C_{23}H_{20}ClN_3O_5$ requires 453; found 454.2 (M+H$^+$).

EXAMPLE 34

5-[7-(5-{3-chloro-4-[(1-methylethyl)oxy]phenyl}-1,2,4-oxadiazol-3-yl)-1H-indol-3-yl]pentanoic acid (E34)

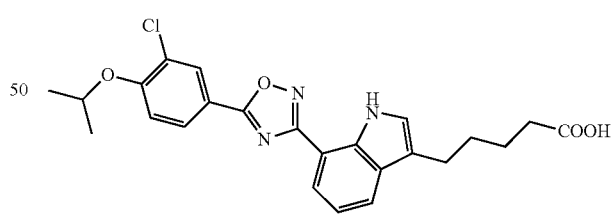

To a solution of ethyl 5-[7-(5-{3-chloro-4-[(1-methylethyl)oxy]phenyl}-1,2,4-oxadiazol-3-yl)-1H-indol-3-yl]pentanoate (D56) (120 mg) in tetrahydrofuran (5 mL) and methanol (5 mL) stirred at 20° C. was added a solution of sodium hydroxide (40 mg) in water (5 mL) in one charge. The reaction mixture was stirred at 20° C. for 8 hours. The reaction mixture was concentrated and then H$_2$SO$_4$ (0.1 M) solution was added dropwise to pH around 3. Extracted with EtOAc (100 mL), the organic layer was separated and the organic solvent was evaporated off. The residue was purified by Mass Directed Auto Prep to afford 5-[7-(5-{3-chloro-4-

[(1-methylethyl)oxy]phenyl}-1,2,4-oxadiazol-3-yl)-1H-indol-3-yl]pentanoic acid (E34) (70 mg). δH (DMSO-d6, 400 MHz): 1.37 (6H, d), 1.57-1.71 (4H, m), 2.27 (2H, t), 2.77 (2H, t), 4.88-4.92 (1H, m), 7.21 (1H, t), 7.26 (1H, d), 7.47 (1H, d), 7.80 (1H, d), 7.94 (1H, dd), 8.21 (1H, dd), 8.39 (1H, d), 10.82 (1H, s), 12.00 (1H, br s). MS (ES): $C_{24}H_{24}ClN_3O_4$ requires 453. found 454.2 (M+H$^+$).

EXAMPLE 35

4-[7-(5-{3-chloro-4-[(1-methylethyl)oxy]phenyl}-1,2,4-oxadiazol-3-yl)-1-methyl-1H-indol-3-yl]butanoic acid (E35)

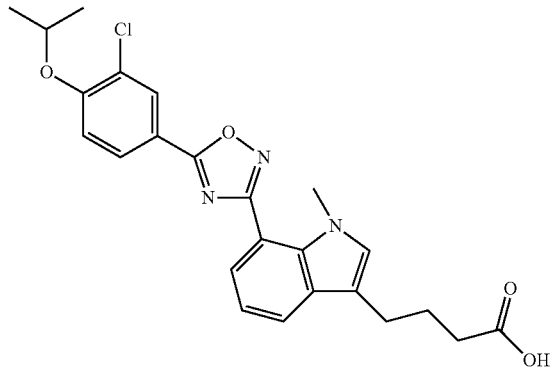

To a solution of ethyl 4-[7-(5-{3-chloro-4-[(1-methylethyl)oxy]phenyl}-1,2,4-oxadiazol-3-yl)-1-methyl-1H-indol-3-yl]butanoate (D57) (120 mg) in THF (5 mL) was added aqueous NaOH (2M, 2 mL). The reaction was stirred at 60° C. overnight. The mixture was acidified with aqueous HCl (2M) to pH 5-6, partitioned between ethyl acetate (20 mL) and water (20 mL). The organic phase was separated and dried over anhydrous sodium sulphate. After removing the solvent, the crude product was purified by TLC separation to afford 4-[7-(5-{3-chloro-4-[(1-methylethyl)oxy]phenyl}-1,2,4-oxadiazol-3-yl)-1-methyl-1H-indol-3-yl]butanoic acid (E35) (20 mg). δH (DMSO-d6, 400 MHz): 1.36 (6H, d), 1.89 (2H, m), 2.29 (2H, t), 2.74 (2H, t), 3.63 (3H, s), 4.88 (1H, m), 7.17 (2H, m), 7.44 (2H, m), 7.77 (1H, d), 8.12 (1H, dd), 8.19 (1H, d), 11.98 (1H, br s). MS (ES): $C_{24}H_{24}ClN_3O_4$ requires 453; found 454.2 (M+H$^+$).

EXAMPLE 36

(2R)-3-[7-(5-{3-chloro-4-[(1-methylethyl)oxy]phenyl}-1,2,4-oxadiazol-3-yl)-1-methyl-1H-indol-3-yl]-2-methylpropanoic acid (E36)

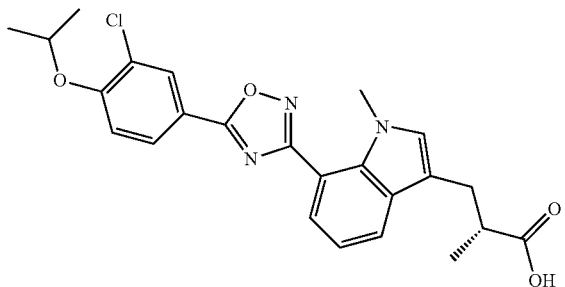

To a solution of methyl (2R)-3-[7-(5-{3-chloro-4-[(1-methylethyl)oxy]phenyl}-1,2,4-oxadiazol-3-yl)-1-methyl-1H-indol-3-yl]-2-methylpropanoate (D60) (80 mg) in THF (5 mL) was added aqueous NaOH (2 M, 1 mL). The reaction was stirred at 50° C. for 16 h. The mixture was acidified with aqueous HCl (2 M) to pH 4-5, partitioned between ethyl acetate (50 mL) and water (50 mL). The organic phase was washed with water (25 mL) and brine (25 mL), dried over anhydrous sodium sulphate and evaporated to give the crude product, which was purified by Mass Directed Auto Prep to afford (2R)-3-[7-(5-{3-chloro-4-[(1-methylethyl)oxy]phenyl}-1,2,4-oxadiazol-3-yl)-1-methyl-1H-indol-3-yl]-2-methylpropanoic acid (E36) (50 mg). δH (DMSO-d6, 400 MHz): 1.11 (3H, d), 1.35 (6H, d), 2.75 (2H, m), 3.04 (1H, m), 3.62 (3H, s), 4.88 (1H, m), 7.17 (2H, m), 7.43 (2H, m), 7.79 (1H, d), 8.13 (1H, dd), 8.20 (1H, d), 12.13 (1H, br s). MS (ES): $C_{24}H_{24}ClN_3O_4$ requires 453; found 454.2 (M+H$^+$).

EXAMPLE 37

(2E)-3-[7-(5-{3-chloro-4-[(1-methylethyl)oxy]phenyl}-1,2,4-oxadiazol-3-yl)-1-methyl-1H-indol-3-yl]-2-propenoic acid (E37)

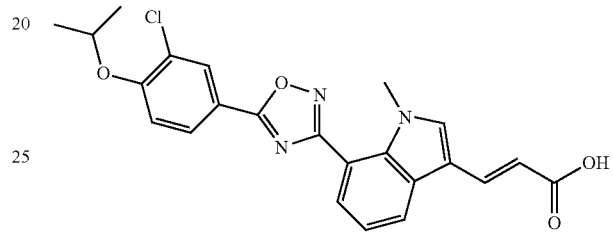

To a solution of ethyl (2E)-3-[7-(5-{3-chloro-4-[(1-methylethyl)oxy]phenyl}-1,2,4-oxadiazol-3-yl)-1-methyl-1H-indol-3-yl]-2-propenoate (D62) (40 mg) in THF (5 mL) was added aqueous NaOH (2 M, 1 mL). The reaction was stirred at 60° C. for 24 h. The mixture was cooled to room temperature and acidified with aqueous HCl (2 M) to pH 4-5, partitioned between ethyl acetate (25 mL) and water (25 mL). The organic phase was washed with water (25 mL) and brine (25 mL), dried over anhydrous sodium sulphate and evaporated to give the crude product, which was purified by Mass Directed Auto Prep to afford (2E)-3-[7-(5-{3-chloro-4-[(1-methylethyl)oxy]phenyl}-1,2,4-oxadiazol-3-yl)-1-methyl-1H-indol-3-yl]-2-propenoic acid (E37) (30 mg). δH (DMSO-d6, 400 MHz): 1.35 (6H, d), 3.70 (3H, s), 4.89 (1H, m), 6.38 (1H, d), 7.35 (1H, t), 7.45 (1H, d), 7.53 (1H, d), 7.81 (1H, d), 8.02 (1H, s), 8.14 (2H, m), 8.21 (1H, d), 12.04 (1H, br s). MS (ES): $C_{23}H_{20}ClN_3O_4$ requires 437. found 438.2 (M+H$^+$).

EXAMPLE 38

(2Z)-3-[7-(5-{3-chloro-4-[(1-methylethyl)oxy]phenyl}-1,2,4-oxadiazol-3-yl)-1-methyl-1H-indol-3-yl]-2-propenoic acid (E38)

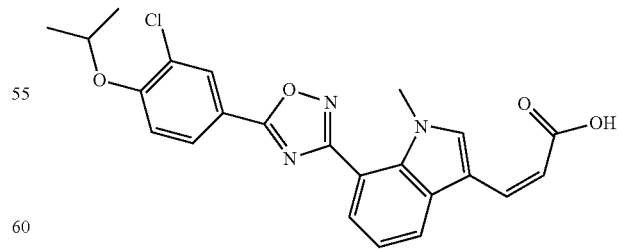

To a solution of methyl (2Z)-3-[7-(5-{3-chloro-4-[(1-methylethyl)oxy]phenyl}-1,2,4-oxadiazol-3-yl)-1-methyl-1H-indol-3-yl]-2-propenoate (D63) (30 mg) in THF (5 mL) was added aqueous NaOH (2 M, 1 mL). The reaction was stirred at 60° C. for 4 h. The mixture was cooled to room temperature and acidified with aqueous HCl (2 M) to pH 4-5, partitioned between ethyl acetate (25 mL) and water (25 mL). The organic phase was washed with water (25 mL), dried over anhydrous sodium sulphate and evaporated to give the crude product, which was purified by Mass Directed Auto Prep to afford (2Z)-3-[7-(5-{3-chloro-4-[(1-methylethyl)oxy]phenyl}-1,2,4-oxadiazol-3-yl)-1-methyl-1H-indol-3-yl]-2-propenoic acid (E38) (25 mg). δH (DMSO-d$_6$, 400 MHz): 1.36 (6H, d), 3.75 (3H, s), 4.89 (1H, m), 5.77 (1H, d), 7.34 (2H, m), 7.45 (1H, d), 7.52 (1H, dd), 8.07 (1H, dd), 8.14 (1H, dd), 8.21 (1H, d), 8.70 (1H, s), 12.02 (1H, br s). MS (ES): $C_{23}H_{20}ClN_3O_4$ requires 437; found 438.2 (M+H$^+$).

EXAMPLE 39 trans-2-[7-(5-{3-chloro-4-[(1-methylethyl)oxy]phenyl}-1,2,4-oxadiazol-3-yl)-1-methyl-1H-indol-3-yl]cyclopropanecarboxylic acid (E39)

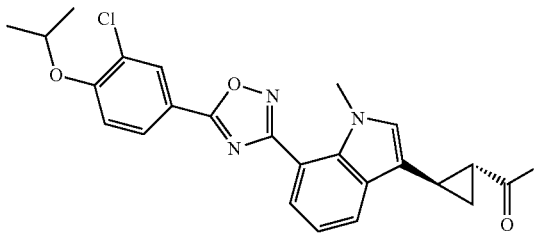

To a solution of trans-ethyl-2-[7-(5-{3-chloro-4-[(1-methylethyl)oxy]phenyl}-1,2,4-oxadiazol-3-yl)-1-methyl-1H-indol-3-yl]cyclopropanecarboxylate (D64) (20 mg) in THF (5 mL) was added aqueous NaOH (2 M, 1 mL). The reaction was stirred at 60° C. for 4 h. The mixture was cooled to room temperature and acidified with aqueous HCl (2 M) to pH 4-5, partitioned between ethyl acetate (25 mL) and water (25 mL). The organic phase was washed with water (25 mL) and brine (25 mL), dried over anhydrous sodium sulphate and evaporated to give the crude product, which was purified by Mass Directed Auto Prep to afford trans-2-[7-(5-{3-chloro-4-[(1-methylethyl)oxy]phenyl}-1,2,4-oxadiazol-3-yl)-1-methyl-1H-indol-3-yl]cyclopropanecarboxylic acid (E39) (4 mg). δH (DMSO-d$_6$, 400 MHz): 1.31 (1H, m), 1.35 (6H, d), 1.42 (1H, m), 1.72 (1H, m), 2.48 (1H, m), 3.60 (3H, s), 4.88 (1H, m), 7.21 (2H, m), 7.45 (2H, m), 7.82 (1H, dd), 8.12 (1H, dd), 8.19 (1H, d), 12.27 (1H, br s). MS (ES): $C_{24}H_{22}ClN_3O_4$ requires 451; found 452.2 (M+H$^+$).

EXAMPLE 40 cis-2-[7-(5-{3-chloro-4-[(1-methylethyl)oxy]phenyl}-1,2,4-oxadiazol-3-yl)-1-methyl-1H-indol-3-yl]cyclopropanecarboxylic acid (E40)

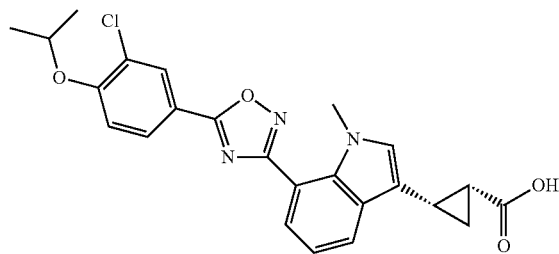

To a solution of cis-methyl-2-[7-(5-{3-chloro-4-[(1-methylethyl)oxy]phenyl}-1,2,4-oxadiazol-3-yl)-1-methyl-1H-indol-3-yl]cyclopropanecarboxylate (D65) (40 mg) in THF (5 mL) was added aqueous NaOH (2 M, 1 mL). The reaction was stirred at 60° C. for 4 h. The mixture was cooled to room temperature and acidified with aqueous HCl (2 M) to pH 4-5, partitioned between ethyl acetate (25 mL) and water (20 mL). The organic phase was washed with water (25 mL) and saturated brine (25 mL), dried over anhydrous sodium sulphate and evaporated to give the crude product, which was purified by Mass Directed Auto Prep to afford cis-2-[7-(5-{3-chloro-4-[(1-methylethyl)oxy]phenyl}-1,2,4-oxadiazol-3-yl)-1-methyl-1H-indol-3-yl]cyclopropanecarboxylic acid (E40) (20 mg). δH (DMSO-d$_6$, 400 MHz): 1.31 (1H, m), 1.36 (6H, d), 1.43 (1H, m), 1.72 (1H, m), 2.45 (1H, m), 3.61 (3H, s), 4.88 (1H, m), 7.21 (2H, m), 7.46 (2H, m), 7.82 (1H, dd), 8.12 (1H, dd), 8.19 (1H, d), 12.28 (1H, br s). MS (ES): $C_{24}H_{22}ClN_3O_4$ requires 451; found 452.2 (M+H$^+$).

EXAMPLE 41

3-(7-{5-[3,4-bis(ethyloxy)phenyl]-1,2,4-oxadiazol-3-yl}-1H-indol-3-yl)propanoic acid (E41)

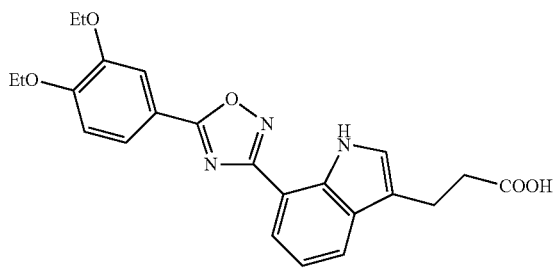

To a solution of ethyl 3-(7-{5-[3,4-bis(ethyloxy)phenyl]-1,2,4-oxadiazol-3-yl}-1H-indol-3-yl)propanoate (D66) (100 mg) in tetrahydrofuran (10 mL) and methanol (10 mL) stirred at room temperature was added a solution of sodium hydroxide (45 mg) in water (10 mL) in one charge. The reaction mixture was stirred at 20° C. overnight. The organic solvent was evaporated off and the mixture was acidified with HCl (1 M) solution to pH around 1. The solid was filtered and recrystallized from acetonitrile to afford 3-(7-{5-[3,4-bis(ethyloxy)phenyl]-1,2,4-oxadiazol-3-yl}-1H-indol-3-yl)propanoic acid (E41) (71 mg). δH (DMSO-d$_6$, 400 MHz): 1.37-1.41 (6H, m), 2.63 (2H, t), 3.00 (2H, t), 4.15-4.22 (4H, m), 7.21 (1H, t), 7.22 (1H, d), 7.27 (1H, d), 7.81 (1H, d), 7.87 (1H, dd), 7.95 (1H, dd), 10.73 (1H, s), 12.05 (1H, br s). MS (ES): $C_{23}H_{23}N_3O_5$ requires 421; found 422.2 (M+H$^+$).

EXAMPLE 42

3-(7-{5-[3,4-bis(ethyloxy)phenyl]-1,2,4-oxadiazol-3-yl}-1-methyl-1H-indol-3-yl)propanoic acid (E42)

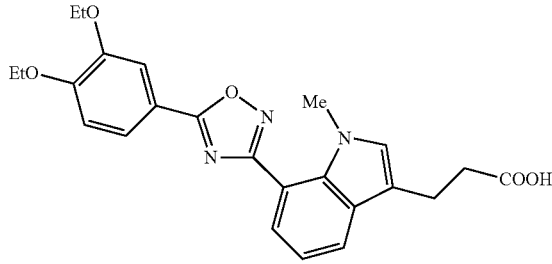

Ethyl 3-(7-{5-[3,4-bis(ethyloxy)phenyl]-1,2,4-oxadiazol-3-yl}-1H-indol-3-yl)propanoate (100 mg) (D66), DABCO (13 mg) and N,N-dimethylformamide (4 mL) was added to dimethyl carbonate (10 mL) successively. The reaction vessel was sealed and heated in Biotage Initiator using initial normal to 150° C. for 2 h. After cooling the reaction, the solvent was removed in vacuo. The residue was dissolved in tetrahydrofuran (5 mL) and methanol (5 mL), and then NaOH (27 mg) in water (5 mL) was added. The mixture was stir at 50° C. for 8 h. The organic solvent was evaporated off and the mixture was acidified with HCl (1 M) solution to pH around 1. Extracted with EtOAc (60 mL), the organic layer was separated and the organic solvent was evaporated off. The residue was purified by Mass Directed Auto Prep to afford 3-(7-{5-[3,4-bis(ethyloxy)phenyl]-1,2,4-oxadiazol-3-yl}-1-methyl-1H-indol-3-yl)propanoic acid (E42) (50 mg). δH (DMSO-d$_6$, 400 MHz): 1.35-1.39 (6H, m), 2.61 (2H, t), 2.97 (2H, t), 3.63 (3H, s), 4.12-4.19 (4H, m), 7.15-7.22 (3H, m), 7.43 (1H, dd), 7.65 (1H, d), 7.78 (1H, dd), 7.79 (1H, dd), 12.06 (1H, br s). MS (ES): $C_{24}H_{25}N_3O_5$ requires 435; found 436.2 (M+H$^+$).

EXAMPLE 43

3-(7-{5-[3,4-bis(methyloxy)phenyl]-1,2,4-oxadiazol-3-yl}-1H-indol-3-yl)propanoic acid (E43)

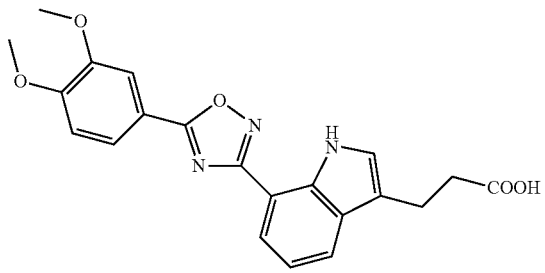

To a solution of ethyl 3-(7-{5-[3,4-bis(methyloxy)phenyl]-1,2,4-oxadiazol-3-yl}-1H-indol-3-yl)propanoate (D67) (100 mg) in tetrahydrofuran (10 mL) and methanol (10 mL) stirred at 20° C. was added a solution of sodium hydroxide (48 mg) in water (10 mL) in one charge. The reaction mixture was stirred at 20° C. for 4 h. The organic solvent was evaporated off and the mixture was acidified with HCl (1 M) solution to pH around 1. The solid was filtered and recrystallized from acetonitrile/EtOAc to afford 3-(7-{5-[3,4-bis(methyloxy)phenyl]-1,2,4-oxadiazol-3-yl}-1H-indol-3-yl)propanoic acid (E43) (72 mg). δH (DMSO-d$_6$, 400 MHz): 2.61 (2H, t), 2.99 (2H, t), 3.90 (3H, s), 3.93 (3H, s), 7.21 (1H, t), 7.23 (1H, d), 7.26 (1H, d), 7.75 (1H, d), 7.81 (1H, d), 7.90 (1H, dd), 7.95 (1H, dd), 10.74 (1H, s). MS (ES): $C_{21}H_{19}N_3O_6$ requires 393; found 394.1 (M+H$^+$).

EXAMPLE 44

3-(7-{5-[3,4-bis(methyloxy)phenyl]-1,2,4-oxadiazol-3-yl}-1-methyl-1H-indol-3-yl)propanoic acid (E44)

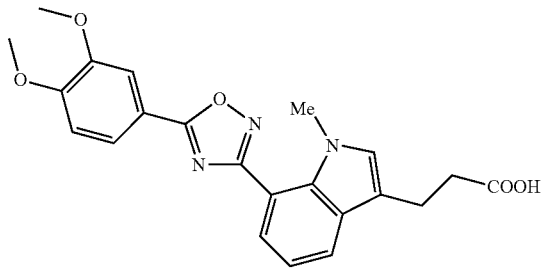

Ethyl 3-(7-{5-[3,4-bis(methyloxy)phenyl]-1,2,4-oxadiazol-3-yl}-1H-indol-3-yl)propanoate (100 mg) (D67), DABCO (27 mg) and N,N-dimethylformamide (3 mL) was added to dimethyl carbonate (10 mL) successively. The reaction vessel was sealed and heated in Biotage Initiator using initial normal to 150° C. for 2 h. After cooling the reaction, the solvent was removed in vacuo. The residue was dissolved in tetrahydrofuran (5 mL) and methanol (5 mL), and then NaOH (48 mg) in water (5 mL) was added. The mixture was stir at 50° C. for 8 h. The organic solvent was removed and the mixture was acidified with HCl (1 M) solution to pH around 1. Extracted with EtOAc (60 mL), the organic layer was separated and the organic solvent was evaporated off. The residue was purified by Mass Directed Auto Prep to afford 3-(7-{5-[3,4-bis(methyloxy)phenyl]-1,2,4-oxadiazol-3-yl}-1-methyl-1H-indol-3-yl)propanoic acid (E44) (56 mg). δH (DMSO-d$_6$, 400 MHz): 2.60 (2H, t), 2.96 (2H, t), 3.62 (3H, s), 3.88 (6H, s), 7.17 (1H, t), 7.19 (1H, s), 7.22 (1H, d), 7.43 (1H, dd), 7.66 (1H, d), 7.79 (1H, dd), 7.82 (1H, dd), 12.12 (1H, s). MS (ES): $C_{22}H_{21}N_3O_5$ requires 407; found 408.2 (M+H$^+$).

EXAMPLE 45

3-(7-{5-[3-chloro-4,5-bis(ethyloxy)phenyl]-1,2,4-oxadiazol-3-yl}-1H-indol-3-yl)propanoic acid (E45)

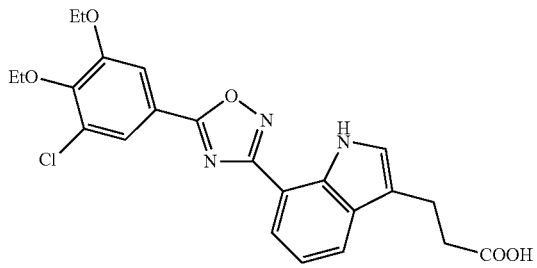

To a solution of methyl 3-(7-{5-[3-chloro-4,5-bis(ethyloxy)phenyl]-1,2,4-oxadiazol-3-yl}-1H-indol-3-yl)propanoate (D70) (20 mg) in tetrahydrofuran (5 mL) and methanol (5 mL) stirred at 20° C. was added a solution of sodium hydroxide (9 mg) in water (5 mL) in one charge. The reaction mixture was stirred at 20° C. for 4 h. The organic solvent was evaporated off and the mixture was acidified with HCl (1 M) solution to pH around 1. Extracted with EtOAc (60 mL), the organic layer was separated and the organic solvent was evaporated off. The residue was purified by Mass Directed Auto Prep to afford 3-(7-{5-[3-chloro-4,5-bis(ethyloxy)phenyl]-1,2,4-oxadiazol-3-yl}-1H-indol-3-yl)propanoic acid (E45) (4 mg) as a TFA salt. δH (DMSO-d$_6$, 400 MHz): 1.34 (3H, t), 1.43 (3H, t), 2.63 (2H, t), 3.00 (2H, t), 4.19 (2H, q), 4.27 (2H, q), 7.21 (1H, t), 7.27 (1H, d), 7.80-7.84 (2H, m), 7.95 (1H, d), 8.01 (1H, d), 10.81 (1H, s), 12.09 (1H, br s). MS (ES): $C_{23}H_{22}ClN_3O_5$ requires 455; found 456.2 (M+H$^+$).

EXAMPLE 46

N-{[7-(5-{3-chloro-4-[(1-methylethyl)oxy]phenyl}-1,2,4-oxadiazol-3-yl)-1H-indol-3-yl]methyl}-β-alanine (E46)

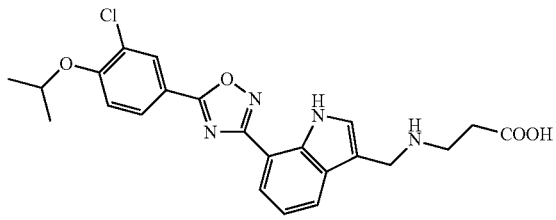

To a solution of ethyl N-{[7-(5-{3-chloro-4-[(1-methylethyl)oxy]phenyl}-1,2,4-oxadiazol-3-yl)-1H-indol-3-yl]methyl}-β-alaninate (D72) (176 mg) in tetrahydrofuran (10 mL) and methanol (5 mL) stirred at 20° C. was added a solution of sodium hydroxide (36 mg) in water (5 mL) in one charge. The reaction mixture was stirred at 20° C. for 6 hours. The reaction mixture was concentrated to about 5 mL and then $H_2SO_4$ (0.1 M) solution was added dropwise until no further white precipitate was formed. The solid was filtered and washed with EtOAc. The solid was collected and then was suspended in methanol (5 mL). The mixture was acidified with HCl (1 M) solution to pH around 1 to form a clear solution. After most of the solvent was evaporated off, the residue was freeze-dried to afford N-{[7-(5-{3-chloro-4-[(1-methylethyl)oxy]phenyl}-1,2,4-oxadiazol-3-yl)-1H-indol-3-yl]methyl}-β-alanine (E46) (109 mg) as a hydrochloride salt. δH (DMSO-$d_6$, 400 MHz): 1.38 (6H, d), 2.72 (2H, t), 3.16 (2H, t), 4.41 (2H, s), 4.90-4.93 (1H, m), 7.33 (1H, t), 7.48 (1H, d), 7.76 (1H, d), 8.02 (1H, d), 8.09 (1H, d), 8.23 (1H, dd), 8.40 (1H, d), 8.81 (1H, br), 11.36 (1H, s). MS (ES): $C_{23}H_{23}ClN_4O_4$ requires 454; found 366.1 (M—$NHC_2H_4COOH^+$).

EXAMPLE 47

N-{[7-(5-{3-chloro-4-[(1-methylethyl)oxy]phenyl}-1,2,4-oxadiazol-3-yl)-1H-indol-3-yl]methyl}glycine (E47)

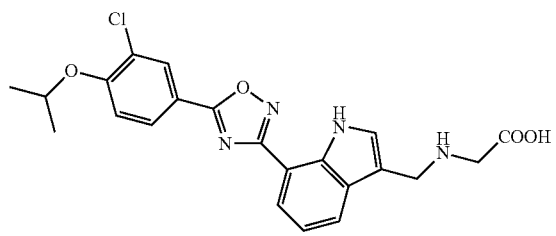

To a solution of ethyl N-{[7-(5-{3-chloro-4-[(1-methylethyl)oxy]phenyl}-1,2,4-oxadiazol-3-yl)-1H-indol-3-yl]methyl}glycinate (D73) (130 mg) in tetrahydrofuran (10 mL) and methanol (5 mL) stirred at 20° C. was added a solution of sodium hydroxide (28 mg) in water (5 mL) in one charge. The reaction mixture was stirred at 20° C. for 4 hours. The reaction mixture was concentrated to about 5 mL and then $H_2SO_4$ (0.1 M) solution was added dropwise until no further white precipitate was formed. The solid was filtered and washed with EtOAc. The solid was collected and then was suspended in methanol (5 mL). The mixture was acidified with HCl (1 M) solution to pH around 1 to form a clear solution. After most of the solvent was evaporated off, the residue was freeze-dried to afford N-{[7-(5-{3-chloro-4-[(1-methylethyl)oxy]phenyl}-1,2,4-oxadiazol-3-yl)-1H-indol-3-yl]methyl}glycine (E47) (48 mg) as a hydrochloride salt. δH (DMSO-$d_6$, 400 MHz): 1.38 (6H, d), 3.84 (2H, s), 4.43 (2H, s), 4.90-4.93 (1H, m), 7.34 (1H, t), 7.48 (1H, d), 7.72-7.73 (1H, m), 8.02 (1H, d), 8.05 (1H, d), 8.23 (1H, dd), 8.41 (1H, d), 9.34 (1H, br s), 11.38 (1H, s). MS (ES): $C_{22}H_{21}ClN_4O_4$ requires 440; found 366.1 (M—$NHCH_2COOH^+$).

EXAMPLE 48

1-{[7-(5-{3-chloro-4-[(1-methylethyl)oxy]phenyl}-1,2,4-oxadiazol-3-yl)-1H-indol-3-yl]methyl}-4-piperidinecarboxylic acid (E48)

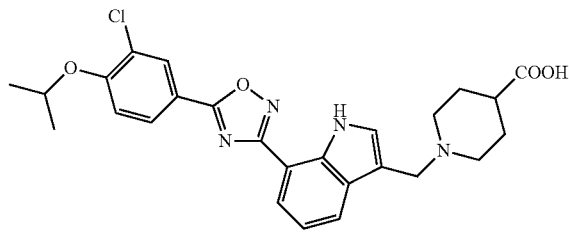

To a solution of ethyl 1-{[7-(5-{3-chloro-4-[(1-methylethyl)oxy]phenyl}-1,2,4-oxadiazol-3-yl)-1H-indol-3-yl]methyl}-4-piperidinecarboxylate (D74) (280 mg) in tetrahydrofuran (10 mL) and methanol (10 mL) stirred at 20° C. was added a solution of sodium hydroxide (54 mg) in water (10 mL) in one charge. The reaction mixture was stirred at 20° C. for 8 hours. The reaction mixture was concentrated and then $H_2SO_4$ (0.1 M) solution was added dropwise until no further white precipitate was formed. The solid was filtered and dried to afford 1-{[7-(5-{3-chloro-4-[(1-methylethyl)oxy]phenyl}-1,2,4-oxadiazol-3-yl)-1H-indol-3-yl]methyl}-4-piperidinecarboxylic acid (E48) (98 mg). δH (DMSO-$d_6$, 400 MHz): 1.38 (6H, d), 1.61-3.02 (9H, m), 3.95 (2H, s), 4.87-4.93 (1H, m), 7.26 (1H, t), 7.45-7.47 (2H, m), 7.96 (1H, s), 7.96 (1H, s), 8.21 (1H, dd), 8.37 (1H, d), 11.07 (1H, s). MS (ES): $C_{26}H_{27}ClN_4O_4$ requires 494; found 495.2 (M+H$^+$).

EXAMPLE 49

N-{[7-(5-{3-chloro-4-[(1-methylethyl)oxy]phenyl}-1,2,4-oxadiazol-3-yl)-1H-indol-3-yl]methyl}-D-alanine (E49)

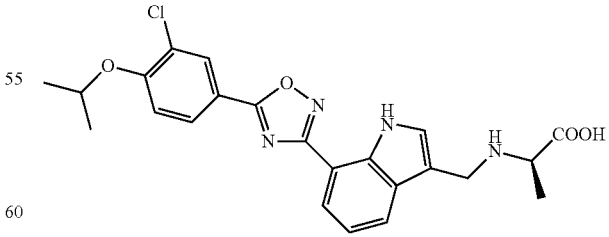

To a solution of methyl N-{[7-(5-{3-chloro-4-[(1-methylethyl)oxy]phenyl}-1,2,4-oxadiazol-3-yl)-1H-indol-3-yl]methyl}-D-alaninate (D75) (262 mg) in tetrahydrofuran (5 mL) and methanol (5 mL) stirred at 20° C. was added a solution of sodium hydroxide (60 mg) in water (5 mL) in one charge. The reaction mixture was stirred at 20° C. overnight. The reaction mixture was concentrated to about 5 mL and then HCl aquous solution was added dropwise until no further white precipitate was formed. The solid was filtered and washed with EtOAc. The solid was collected and then was suspended in methanol (5 mL) and water (5 mL). The mixture was acidified with HCl aquous solution to pH around 1 to form a clear solution. After most of the solvent was evaporated off, the residue was freeze-dried to afford N-{[7-(5-{3-chloro-4-[(1-methylethyl)oxy]phenyl}-1,2,4-oxadiazol-3-yl)-1H-indol-3-yl]methyl}-D-alanine (E49) (130 mg) as a hydrochloride salt. δH (MeOD-$d_4$, 400 MHz): 1.43 (6H, d), 1.64 (3H, d), 4.15 (1H, q), 4.54 (2H, q), 4.84-4.90 (1H, m), 7.31-7.37 (2H, m), 7.70 (1H, s), 8.03 (1H, d), 8.11 (1H, d), 8.18 (1H, dd), 8.30 (1H, d). MS (ES): $C_{23}H_{23}ClN_4O_4$ requires 454; found 366.1 (M—$NHC_2H_4COOH^+$).

EXAMPLE 50

N-{[7-(5-{3-chloro-4-[(1-methylethyl)oxy]phenyl}-1,2,4-oxadiazol-3-yl)-1H-indol-3-yl]methyl}-L-alanine (E50)

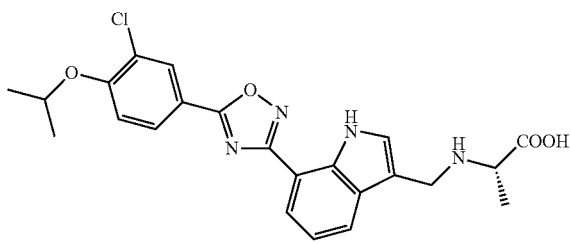

To a solution of methyl N-{[7-(5-{3-chloro-4-[(1-methylethyl)oxy]phenyl}-1,2,4-oxadiazol-3-yl)-1H-indol-3-yl]methyl}-L-alaninate (D76) (223 mg) in tetrahydrofuran (5 mL) and methanol (5 mL) stirred at 20° C. was added a solution of sodium hydroxide (60 mg) in water (5 mL) in one charge. The reaction mixture was stirred at 20° C. overnight. The reaction mixture was concentrated to about 5 mL and then HCl aquous solution was added dropwise until no further white precipitate was formed. The solid was filtered and washed with EtOAc. The solid was collected and then was suspended in methanol (5 mL) and water (5 mL). The mixture was acidified with HCl (1 M) solution to pH around 1 to form a clear solution. After most of the solvent was evaporated off, the residue was freeze-dried to afford N-{[7-(5-{3-chloro-4-[(1-methylethyl)oxy]phenyl}-1,2,4-oxadiazol-3-yl)-1H-indol-3-yl]methyl}-L-alanine (E50) (82 mg) as a hydrochloride salt. δH (DMSO-$d_6$, 400 MHz): 1.34 (3H, d), 1.38 (6H, d), 3.33 (1H, m), 4.28 (2H, q), 4.88-4.94 (1H, m), 7.31 (1H, t), 7.47 (1H, d), 7.64 (1H, d), 8.00 (1H, d), 8.05 (1H, d), 8.22 (1H, dd), 8.40 (1H, d), 11.26 (1H, br s). MS (ES): $C_{23}H_{23}ClN_4O_4$ requires 454; found 366.1 (M—$NHC_2H_3COOH^+$).

EXAMPLE 51

3-({[7-(5-{3-chloro-4-[(1-methylethyl)oxy]phenyl}-1,2,4-oxadiazol-3-yl)-1H-indol-3-yl]methyl}amino)butanoic acid (E51)

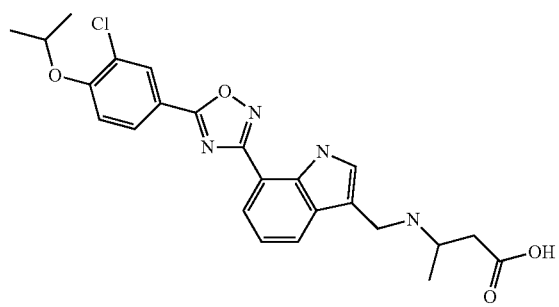

To a stirred solution of 7-(5-{3-chloro-4-[(1-methylethyl)oxy]phenyl}-1,2,4-oxadiazol-3-yl)-1-methyl-1H-indole-3-carbaldehyde (D61) (200 mg), 3-aminobutanoic acid (103 mg) and acetic acid (32 mg) in DCM (10 mL) was added NaBH(OAc)$_3$ (223 mg). The reaction was stirred at 40° C. for 24 h. After cooled to room temperature, the mixture was diluted with DCM (10 mL), washed with water (20 mL) and aqueous saturated sodium bicarbonate (20 mL). The organic phase was dried over anhydrous sodium sulphate, evaporated to give the crude product, which was purified by Mass Directed Auto Prep to afford 3-({[7-(5-{3-chloro-4-[(1-methylethyl)oxy]phenyl}-1,2,4-oxadiazol-3-yl)-1H-indol-3-yl]methyl}amino)butanoic acid (E51) (55 mg, as TFA salt). δH (DMSO-$d_6$, 400 MHz): 1.36 (9H, m), 2.57 (1H, m), 2.91 (1H, dd), 3.57 (1H, m), 4.46 (2H, s), 4.91 (1H, m), 7.33 (1H, t), 7.47 (1H, d), 7.72 (1H, d), 8.03 (1H, d), 8.05 (1H, d), 8.22 (1H, dd), 8.39 (1H, d), 11.37 (1H, s), 12.81 (1H, br s). MS (ES): $C_{24}H_{26}ClN_4O_4$ requires 468; found 366.1 (M—$C_4H_8NO_2^+$).

EXAMPLE 52

N-{[7-(5-{3-chloro-4-[(1-methylethyl)oxy]phenyl}-1,2,4-oxadiazol-3-yl)-1H-indol-3-yl]methyl}-N-methylglycine (E52)

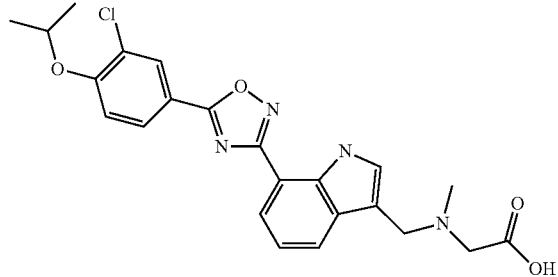

To a stirred solution of 7-(5-{3-chloro-4-[(1-methylethyl)oxy]phenyl}-1,2,4-oxadiazol-3-yl)-1-methyl-1H-indole-3- carbaldehyde (D61) (200 mg), N-methylglycine (93 mg) and acetic acid (32 mg) in DCM (10 mL) was added NaBH(OAc)$_3$ (223 mg). The reaction was stirred at 40° C. overnight. After cooled to room temperature, the reaction mixture was diluted with DCM (10 mL), washed with water (20 mL) and aqueous saturated sodium bicarbonate (20 mL). The organic phase was separated and dried over anhydrous sodium sulphate. After concentration, the residue was purified by Mass Directed Auto Prep to afford N-{[7-(5-{3-chloro-4-[(1-methylethyl)oxy]phenyl}-1,2,4-oxadiazol-3-yl)-1H-indol-3-yl]methyl}-N-methylglycine (E52) (210 mg, TFA salt). δH (DMSO-d$_6$, 400 MHz): 1.36 (6H, d), 2.80 (3H, s), 4.01 (2H, s), 4.57 (2H, s), 4.90 (1H, m), 7.35 (1H, t), 7.46 (1H, d), 7.75 (1H, d), 8.01 (1H, d), 8.07 (1H, d), 8.21 (1H, dd), 8.39 (1H, d), 11.48 (1H, br s). MS (ES): C$_{23}$H$_{23}$ClN$_4$O$_4$ requires 454; found 366.1 (M—C$_3$H$_6$NO$_2$$^+$).

EXAMPLE 53

N-{[7-(5-{3-chloro-4-[(1-methylethyl)oxy]phenyl}-1,2,4-oxadiazol-3-yl)-1H-indol-3-yl]methyl}-N-methyl-D-alanine (E53)

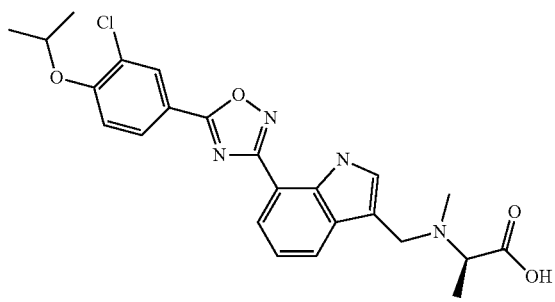

To a stirred solution of 7-(5-{3-chloro-4-[(1-methylethyl)oxy]phenyl}-1,2,4-oxadiazol-3-yl)-1H-indole-3-carbaldehyde (D61) (150 mg), methyl D-alaninate (81 mg) and acetic acid (24 mg) in DCM (10 mL) was added NaBH(OAc)$_3$ (167 mg). The mixture was stirred at 40° C. for 2 h, followed by addition of formaldehyde (120 mg). This mixture was stirred at 40° C. overnight. After concentration, the residue was dissolved in THF (5 mL), followed by addition of aqueous NaOH (2 M, 2 mL). The mixture was stirred at 50° C. for 2 h, and then acidified with HCl (2 M) to pH 4-5, partitioned between ethyl acetate (25 mL) and water (25 mL). The organic phase was washed with water (25 mL) and brine (25 mL), dried over anhydrous sodium sulphate, and evaporated to give the crude product, which was purified by Mass Directed Auto Prep to afford N-{[7-(5-{3-chloro-4-[(1-methylethyl)oxy]phenyl}-1,2,4-oxadiazol-3-yl)-1H-indol-3-yl]methyl}-N-methyl-D-alanine (E53) (35 mg). δH (DMSO-d$_6$, 400 MHz): 1.30 (3H, d), 1.36 (6H, d), 2.42 (3H, s), 3.40 (1H, q), 4.16 (2H, s), 4.90 (1H, m), 7.26 (1H, t), 7.45 (1H, d), 7.56 (1H, d), 7.97 (1H, d), 8.09 (1H, d), 8.21 (1H, dd), 8.38 (1H, d), 11.17 (1H, br s). MS (ES): C$_{24}$H$_{25}$ClN$_4$O$_4$ requires 468; found 366.1 (M—C$_4$H$_8$NO$_2$$^+$).

EXAMPLE 54

N-{[7-(5-{3-chloro-4-[(1-methylethyl)oxy]phenyl}-1,2,4-oxadiazol-3-yl)-1H-indol-3-yl]methyl}-N-methyl-L-alanine (E54)

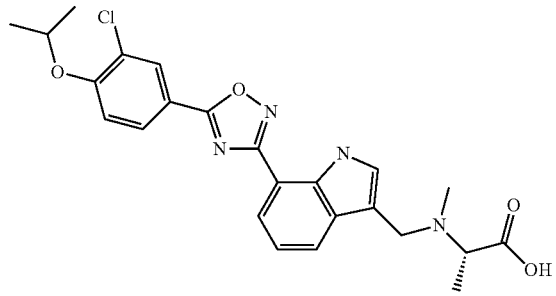

To a stirred solution of 7-(5-{3-chloro-4-[(1-methylethyl)oxy]phenyl}-1,2,4-oxadiazol-3-yl)-1H-indole-3-carbaldehyde (D71) (150 mg), methyl L-alaninate (81 mg) and acetic acid (24 mg) in DCM (10 mL) was added NaBH(OAc)$_3$ (167 mg). The mixture was stirred at 40° C. for 2 h, followed by addition of formaldehyde (120 mg). This mixture was stirred at 40° C. overnight. After concentration, the residue was dissolved in THF (5 mL), followed by addition of aqueous NaOH (2 M, 2 mL). The mixture was stirred at 60° C. overnight, and then acidified with aqueous HCl (2 M) to pH 4-5, partitioned between ethyl acetate (25 mL) and water (25 mL). The organic phase was washed with water (25 mL) and brine (25 mL), dried over anhydrous sodium sulphate, and evaporated to give the crude product, which was purified by Mass Directed Auto Prep to afford N-{[7-(5-{3-chloro-4-[(1-methylethyl)oxy]phenyl}-1,2,4-oxadiazol-3-yl)-1H-indol-3-yl]methyl}-N-methyl-L-alanine (E54) (13 mg). δH (DMSO-d$_6$, 400 MHz): 1.37 (6H, d), 1.56 (3H, d), 2.75 (3H, s), 4.17 (1H, q), 4.54 (2H, q), 4.90 (1H, m), 7.35 (1H, t), 7.46 (1H, d), 7.75 (1H, d), 8.03 (1H, d), 8.10 (1H, d), 8.21 (1H, dd), 8.39 (1H, d), 11.46 (1H, br s). MS (ES): C$_{24}$H$_{26}$ClN$_4$O$_4$ requires 468; found 366.1 (M—C$_4$H$_8$NO$_2$$^+$).

EXAMPLE 55

N-{[7-(5-{3-cyano-4-[(1-methylethyl)oxy]phenyl}-1,2,4-oxadiazol-3-yl)-1H-indol-3-yl]methyl}-N-methylglycine (E55)

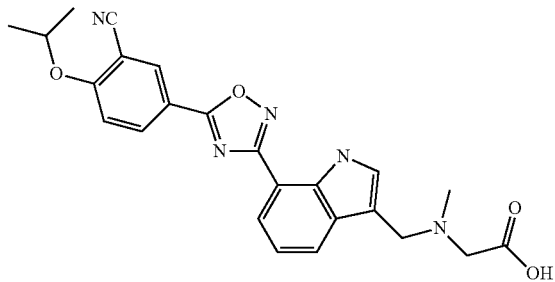

To a stirred solution of 5-[3-(3-formyl-1H-indol-7-yl)-1,2,4-oxadiazol-5-yl]-2-[(1-methylethyl)oxy]benzonitrile (200 mg), N-methylglycine (96 mg) and acetic acid (32 mg) in DCM (10 mL) was added NaBH(OAc)$_3$ (228 mg). The mixture was stirred at 40° C. overnight. After cooled to room temperature, the reaction mixture was diluted with DCM (10 mL), washed with water (20 mL) and aqueous saturated sodium bicarbonate (20 mL). The organic phase was separated and dried over anhydrous sodium sulphate. After concentration, the residue was purified by Mass Directed Auto Prep to afford N-{[7-(5-{3-cyano-4-[(1-methylethyl)oxy]phenyl}-1,2,4-oxadiazol-3-yl)-1H-indol-3-yl]methyl}-N-methylglycine (E55) (140 mg, TFA salt). δH (DMSO-d$_6$, 400 MHz): 1.38 (6H, d), 2.73 (3H, s), 3.80 (2H, s), 4.46 (2H, s), 4.98 (1H, m), 7.31 (1H, t), 7.55 (1H, d), 7.71 (1H, d), 7.98 (1H, d), 8.05 (1H, d), 8.48 (1H, dd), 8.71 (1H, d), 11.41 (1H, br s). MS (ES): C$_{24}$H$_{23}$N$_5$O$_4$ requires 445; found 357.2 (M—C$_3$H$_6$NO$_2{}^+$).

EXAMPLE 56

N-{[7-(5-{3-chloro-4-[(1-methylethyl)oxy]phenyl}-1,2,4-oxadiazol-3-yl)-1-methyl-1H-indol-3-yl]methyl}glycine (E56)

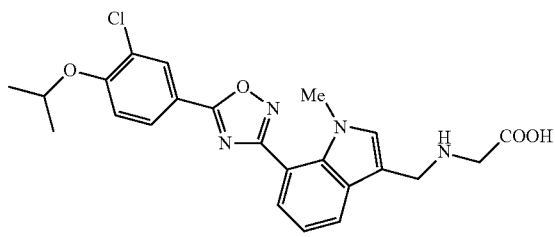

To a solution of ethyl N-{[7-(5-{3-chloro-4-[(1-methylethyl)oxy]phenyl}-1,2,4-oxadiazol-3-yl)-1-methyl-1H-indol-3-yl]methyl}glycinate (D77) (283 mg) in tetrahydrofuran (5 mL) and ethanol (5 mL) stirred at 20° C. was added a solution of sodium hydroxide (40 mg) in water (5 mL) in one charge. The reaction mixture was stirred at 20° C. overnight. The reaction mixture was concentrated to about 5 mL and then H$_2$SO$_4$ (0.1 M) solution was added dropwise until no further white precipitate was formed. The solid was filtered and washed with EtOAc. The solid was collected and then was suspended in methanol (5 mL). The mixture was acidified with HCl (1 M) solution to pH around 1 to form a clear solution. After most of the solvent was evaporated off, the residue was freeze-dried to afford N-{[7-(5-{3-chloro-4-[(1-methylethyl)oxy]phenyl}-1,2,4-oxadiazol-3-yl)-1-methyl-1H-indol-3-yl]methyl}glycine (E56) (150 mg) as a hydrochloride salt. δH (DMSO-d$_6$, 400 MHz): 1.37 (6H, d), 3.72 (3H, s), 3.85 (2H, s), 4.39 (2H, s), 4.87-4.93 (1H, m), 7.30 (1H, t), 7.47 (1H, d), 7.52 (1H, d), 7.62 (1H, s), 8.05 (1H, s), 8.14 (1H, dd), 8.21 (1H, d), 9.23 (1H, br s). MS (ES): C$_{23}$H$_{23}$ClN$_4$O$_4$ requires 454; found 380.1 (M—NHCH$_2$COOH$^+$).

EXAMPLE 57

1-{[7-(5-{3-chloro-4-[(1-methylethyl)oxy]phenyl}-1,2,4-oxadiazol-3-yl)-1-methyl-1H-indol-3-yl]methyl}-4-piperidinecarboxylic acid (E57)

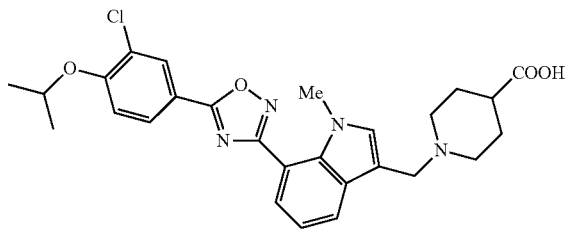

To a solution of ethyl 1-{[7-(5-{3-chloro-4-[(1-methylethyl)oxy]phenyl}-1,2,4-oxadiazol-3-yl)-1-methyl-1H-indol-3-yl]methyl}-4-piperidinecarboxylate (D79) (308 mg) in tetrahydrofuran (5 mL) and ethanol (5 mL) stirred at 20° C. was added a solution of sodium hydroxide (60 mg) in water (5 mL) in one charge. The reaction mixture was stirred at 20° C. overnight. The reaction mixture was concentrated and then H$_2$SO$_4$ (0.1 M) solution was added dropwise until no further white precipitate was formed. The solid was filtered and recrystallized from EtOAc to afford 1-{[7-(5-{3-chloro-4-[(1-methylethyl)oxy]phenyl}-1,2,4-oxadiazol-3-yl)-1-methyl-1H-indol-3-yl]methyl}-4-piperidinecarboxylic acid (E57) (140 mg). δH (DMSO-d$_6$, 400 MHz): 1.37 (6H, d), 1.49-2.21 (7H, m), 2.84-2.87 (2H, m), 3.65 (5H, s), 4.86-4.93 (1H, m), 7.18 (1H, t), 7.31 (1H, s), 7.44 (1H, dd), 7.46 (1H, d), 7.91 (1H, dd), 8.14 (1H, dd), 8.21 (1H, d), 12.06 (1H, br s). MS (ES): C$_{27}$H$_{29}$ClN$_4$O$_4$ requires 508; found 380.1 (M—NC$_5$H$_9$COOH$^+$).

EXAMPLE 58

N-{[7-(5-{3-chloro-4-[(1-methylethyl)oxy]phenyl}-1,2,4-oxadiazol-3-yl)-1-methyl-1H-indol-3-yl]methyl}-β-alanine (E58)

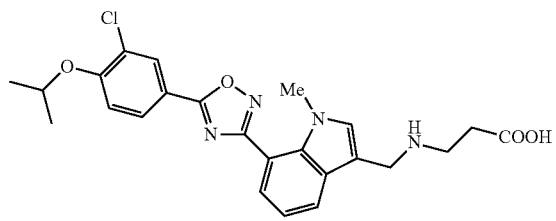

To a solution of ethyl N-{[7-(5-{3-chloro-4-[(1-methylethyl)oxy]phenyl}-1,2,4-oxadiazol-3-yl)-1-methyl-1H-indol-3-yl]methyl}-β-alaninate (D78) (287 mg) in tetrahydrofuran (5 mL) and ethanol (5 mL) stirred at 20° C. was added a solution of sodium hydroxide (60 mg) in water (5 mL) in one charge. The reaction mixture was stirred at 20° C. overnight. The reaction mixture was concentrated and then H$_2$SO$_4$ (0.1 M) solution was added dropwise until no further white precipitate was formed. The solid was filtered and recrystallized from EtOAc to afford N-{[7-(5-{3-chloro-4-[(1-methylethyl)oxy]phenyl}-1,2,4-oxadiazol-3-yl)-1-methyl-1H-indol-3-yl]methyl}-β-alanine (E58) (130 mg). δH (DMSO-d$_6$, 400 MHz): 1.36 (6H, d), 2.28 (2H, t), 2.91 (2H, t), 3.68 (3H, s), 4.11 (2H, s), 4.88-4.91 (1H, m), 7.23 (1H, t), 7.45-7.50 (3H, m), 7.96 (1H, dd), 8.14 (1H, dd), 8.21 (1H, d). MS (ES): C$_{24}$H$_{26}$ClN$_4$O$_4$ requires 468. found 380.1 (M—NHC$_2$H$_4$COOH$^+$).

EXAMPLE 59

N-{[7-(5-{3-chloro-4-[(1-methylethyl)oxy]phenyl}-1,2,4-oxadiazol-3-yl)-1-methyl-1H-indol-3-yl]methyl}-D-alanine (E59)

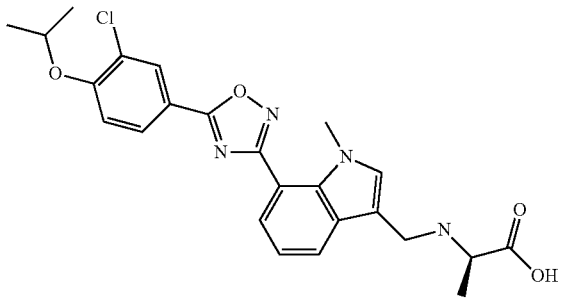

To a stirred solution of N-{[7-(5-{3-chloro-4-[(1-methylethyl)oxy]phenyl}-1,2,4-oxadiazol-3-yl)-1-methyl-1H-indol-3-yl]methyl}-D-alaninate (D80) (110 mg) in THF (2 mL) was added aqueous NaOH (2 M, 2 mL). The reaction was stirred at room temperature overnight. The reaction mixture was acidified with HCl (2 M) to pH 6-7. The resulting solid was separated and suspended in methanol (2 mL) with stirring, HCl (2M) was added until the solid dissolved completely. The solution was freeze dried to afford N-{[7-(5-{3-chloro-4-[(1-methylethyl)oxy]phenyl}-1,2,4-oxadiazol-3-yl)-1-methyl-1H-indol-3-yl]methyl}-D-alanine (E59) (60 mg, HCl salt). δH (DMSO-d$_6$, 400 MHz): 1.35 (6H, d), 1.48 (3H, d), 3.71 (3H, s), 3.86 (1H, q), 4.35 (2H, s), 4.89 (1H, m), 7.28 (1H, t), 7.45 (1H, d), 7.51 (1H, d), 7.60 (1H, s), 8.03 (1H, d), 8.13 (1H, d), 8.20 (1H, s). MS (ES): C$_{24}$H$_{26}$ClN$_4$O$_4$ requires 468; found 380.1 (M—C$_3$H$_6$NO$_2$$^+$).

EXAMPLE 60

N-{[7-(5-{3-chloro-4-[(1-methylethyl)oxy]phenyl}-1,2,4-oxadiazol-3-yl)-1-methyl-1H-indol-3-yl]methyl}-L-alanine (E60)

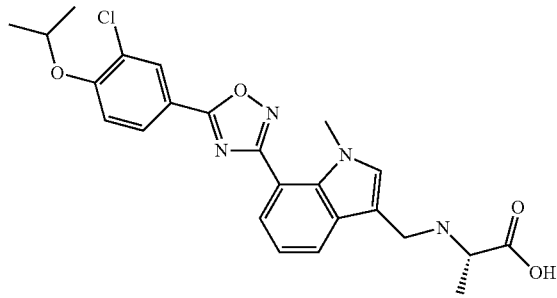

To a stirred solution of N-{[7-(5-{3-chloro-4-[(1-methylethyl)oxy]phenyl}-1,2,4-oxadiazol-3-yl)-1-methyl-1H-indol-3-yl]methyl}-L-alaninate (D81) (160 mg) in THF (2 mL) was added NaOH (2 M, 2 mL). The reaction was stirred at room temperature overnight. The reaction mixture was acidified with HCl (2 M) to pH 6-7. The resulting solid was separated and suspended in methanol (2 mL) with stirring, HCl (2 M) was added until the solid dissolved completely. The solution was freeze dried to afford N-{[7-(5-{3-chloro-4-[(1-methylethyl)oxy]phenyl}-1,2,4-oxadiazol-3-yl)-1-methyl-1H-indol-3-yl]methyl}-L-alanine (E60) (130 mg, HCl salt). δH (DMSO-d$_6$, 400 MHz): 1.35 (6H, d), 1.50 (3H, d), 3.70 (3H, s), 3.92 (1H, q), 4.36 (2H, s), 4.88 (1H, m), 7.28 (1H, t), 7.45 (1H, d), 7.51 (1H, d), 7.62 (1H, s), 8.04 (1H, d), 8.13 (1H, d), 8.20 (1H, d). MS (ES): C$_{24}$H$_{26}$ClN$_4$O$_4$ requires 468; found 380.2 (M—C$_3$H$_6$NO$_2$$^+$).

EXAMPLE 61

3-({[7-(5-{3-chloro-4-[(1-methylethyl)oxy]phenyl}-1,2,4-oxadiazol-3-yl)-1-methyl-1H-indol-3-yl]methyl}amino)butanoic acid (E61)

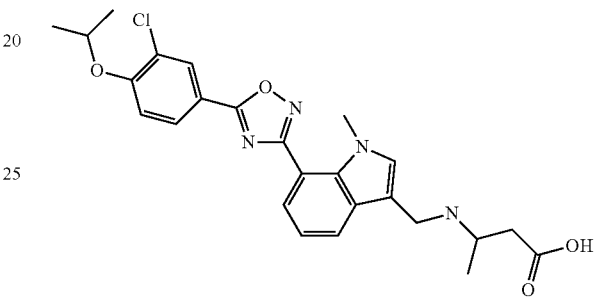

To a stirred solution of 7-(5-{3-chloro-4-[(1-methylethyl)oxy]phenyl}-1,2,4-oxadiazol-3-yl)-1-methyl-1H-indole-3-carbaldehyde (D61) (100 mg), 3-aminobutanoic acid (52 mg) and acetic acid (15 mg) in DCM (10 mL) was added NaBH(OAc)$_3$ (107 mg). The reaction was stirred at 40° C. for 24 h. After cooled to room temperature, the reaction mixture was diluted with DCM (10 mL), washed with water (20 mL) and aqueous saturated sodium bicarbonate (20 mL). The organic phase was separated and dried over anhydrous sodium sulphate. After concentration, the residue was purified by Mass Directed Auto Prep to afford 3-({[7-(5-{3-chloro-4-[(1-methylethyl)oxy]phenyl}-1,2,4-oxadiazol-3-yl)-1-methyl-1H-indol-3-yl]methyl}amino)butanoic acid (E61) as a white solid (23 mg, TFA salt). δH (DMSO-d$_6$, 400 MHz): 1.36 (9H, m), 2.57 (1H, m), 2.87 (1H, dd), 3.57 (1H, m), 3.72 (3H, s), 4.42 (2H, s), 4.89 (1H, m), 7.30 (1H, t), 7.45 (1H, d), 7.53 (1H, d), 7.61 (1H, s), 8.04 (1H, d), 8.13 (1H, t), 8.20 (1H, d), 8.67 (1H, br s). MS (ES): C$_{25}$H$_{27}$ClN$_4$O$_4$ requires 482; found 380.1 (M—C$_4$H$_8$NO$_2$$^+$).

EXAMPLE 62

N-{2-[7-(5-{3-chloro-4-[(1-methylethyl)oxy]phenyl}-1,2,4-oxadiazol-3-yl)-1H-indol-3-yl]ethyl}-β-alanine (E62)

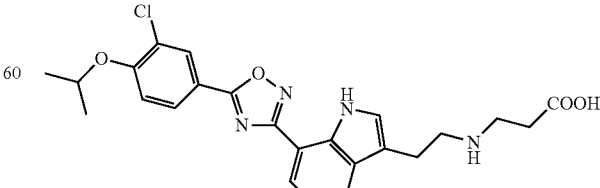

To a solution of ethyl N-{2-[7-(5-{3-chloro-4-[(1-methylethyl)oxy]phenyl}-1,2,4-oxadiazol-3-yl)-1H-indol-3-yl]ethyl}-β-alaninate (D85) (186 mg) in tetrahydrofuran (5 mL) and methanol (5 mL) stirred at 20° C. was added a solution of sodium hydroxide (40 mg) in water (5 mL) in one charge. The reaction mixture was stirred at 20° C. overnight. The reaction mixture was concentrated to about 5 mL and then HCl aquous solution was added dropwise until no further white precipitate was formed. The solid was filtered and washed with EtOAc. The solid was collected and then was suspended in methanol (5 mL) and water (5 mL). The mixture was acidified with HCl aquous solution to pH around 1 to form a clear solution. After most of the solvent was evaporated off, the residue was freeze-dried to afford N-{2-[7-(5-{3-chloro-4-[(1-methylethyl)oxy]phenyl}-1,2,4-oxadiazol-3-yl)-1H-indol-3-yl]ethyl}-β-alanine (E62) (130 mg) as a hydrochloride salt. δH (DMSO-$d_6$, 400 MHz): 1.38 (6H, d), 2.70 (2H, t), 3.12-3.29 (4H, m), 3.33 (2H, m), 4.88-4.94 (1H, m), 7.27 (1H, t), 7.41 (1H, d), 7.47 (1H, d), 7.90 (1H, d), 7.99 (1H, dd), 8.22 (1H, dd), 8.39 (1H, d), 8.71 (1H, br), 11.03 (1H, br s), 12.70 (1H, br s). MS (ES): $C_{24}H_{26}ClN_4O_4$ requires 468; found 469.2 (M+H$^+$).

EXAMPLE 63

N-{2-[7-(5-{3-chloro-4-[(1-methylethyl)oxy]phenyl}-1,2,4-oxadiazol-3-yl)-1H-indol-3-yl]ethyl}glycine (E63)

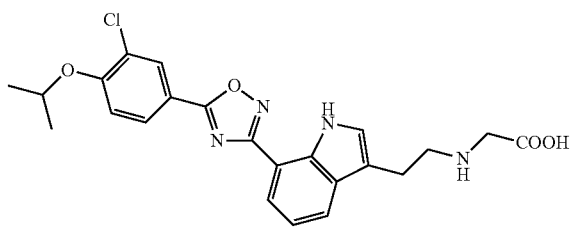

To a solution of ethyl N-{2-[7-(5-{3-chloro-4-[(1-methylethyl)oxy]phenyl}-1,2,4-oxadiazol-3-yl)-1H-indol-3-yl]ethyl}glycinate (D86) (132 mg) in tetrahydrofuran (5 mL) and methanol (5 mL) stirred at 20° C. was added a solution of sodium hydroxide (40 mg) in water (5 mL) in one charge. The reaction mixture was stirred at 20° C. overnight. The reaction mixture was concentrated to about 5 mL and then HCl aquous solution was added dropwise until no further white precipitate was formed. The solid was filtered and washed with EtOAc. The solid was collected and then was suspended in methanol (5 mL) and water (5 mL). The mixture was acidified with HCl (1 M) solution to pH around 1 to form a clear solution. After most of the solvent was evaporated off, the residue was freeze-dried to afford N-{2-[7-(5-{3-chloro-4-[(1-methylethyl)oxy]phenyl}-1,2,4-oxadiazol-3-yl)-1H-indol-3-yl]ethyl}glycine (E63) (80 mg) as a hydrochloride salt. δH (DMSO-$d_6$, 400 MHz): 1.37 (6H, d), 3.11-3.38 (4H, m), 3.61 (2H, s), 4.88-4.94 (1H, m), 7.26 (1H, t), 7.38 (1H, d), 7.47 (1H, d), 7.86 (1H, d), 7.97 (1H, d), 8.21 (1H, dd), 8.38 (1H, d), 11.00 (1H, br s). MS (ES): $C_{23}H_{23}ClN_4O_4$ requires 454; found 455.2 (M+H$^+$).

EXAMPLE 64

N-{2-[7-(5-{3-chloro-4-[(1-methylethyl)oxy]phenyl}-1,2,4-oxadiazol-3-yl)-1-methyl-1H-indol-3-yl]ethyl}glycine (E64)

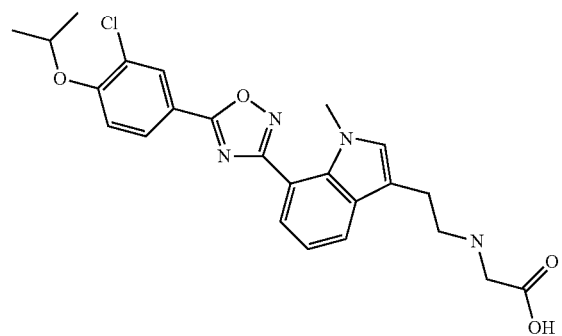

To a solution of ethyl N-{2-[7-(5-{3-chloro-4-[(1-methylethyl)oxy]phenyl}-1,2,4-oxadiazol-3-yl)-1-methyl-1H-indol-3-yl]ethyl}glycinate (D89) (20 mg) in THF (5 mL) was added aqueous NaOH (2 M, 1 mL). The reaction was stirred at 50° C. for 3 h. The mixture was cooled to room temperature and acidified with aqueous HCl (2 M) to pH 4-5. The mixture was partitioned between ethyl acetate (25 mL) and water (20 mL). The organic phase was evaporated to give the crude product, which was purified by Mass Directed Auto Prep to afford N-{2-[7-(5-{3-chloro-4-[(1-methylethyl)oxy]phenyl}-1,2,4-oxadiazol-3-yl)-1-methyl-1H-indol-3-yl]ethyl}glycine (E64) (13 mg, TFA salt). δH (DMSO-$d_6$, 400 MHz): 1.36 (6H, d), 3.10 (2H, t), 3.24 (2H, t), 3.65 (3H, s), 3.87 (2H, s), 4.88 (1H, m), 7.22 (1H, t), 7.30 (1H, s), 7.45 (1H, d), 7.47 (1H, dd), 7.83 (1H, dd), 8.12 (1H, dd), 8.18 (1H, d). MS (ES): $C_{24}H_{26}ClN_4O_4$ requires 468; found 469.2 (M+H$^+$).

EXAMPLE 65

N-{2-[7-(5-{3-chloro-4-[(1-methylethyl)oxy]phenyl}-1,2,4-oxadiazol-3-yl)-1-methyl-1H-indol-3-yl]ethyl}-β-alanine (E65)

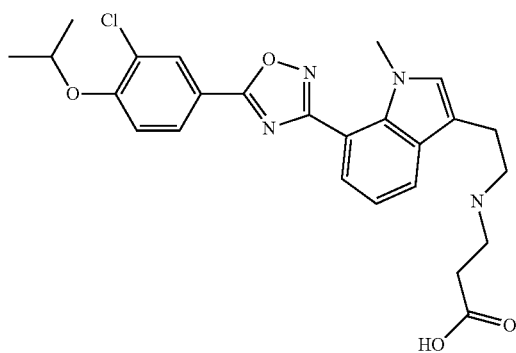

To a solution of ethyl N-{2-[7-(5-{3-chloro-4-[(1-methylethyl)oxy]phenyl}-1,2,4-oxadiazol-3-yl)-1-methyl-1H-indol-3-yl]ethyl}-β-alaninate (D90) (20 mg) in THF (5 mL) was added aqueous NaOH (2 M, 1 mL). The reaction was stirred at 50° C. for 3 h. The mixture was cooled to room temperature and acidified with aqueous HCl (2 M) to pH 4-5, and then partitioned between ethyl acetate (25 mL) and water (20 mL). The organic phase was evaporated to give the crude product, which was purified by Mass Directed Auto Prep to afford N-{2-[7-(5-{3-chloro-4-[(1-methylethyl)oxy]phenyl}-1,2,4-oxadiazol-3-yl)-1-methyl-1H-indol-3-yl]ethyl}-β-alanine (E65) (15 mg, TFA salt). δH (DMSO-d$_6$, 400 MHz): 1.36 (6H, d), 2.61 (2H, t), 3.06 (2H, t), 3.20 (4H, m), 3.65 (3H, s), 4.88 (1H, m), 7.22 (1H, t), 7.31 (1H, s), 7.45 (2H, m), 7.83 (1H, dd), 8.12 (1H, dd), 8.19 (1H, d). MS (ES): $C_{25}H_{27}ClN_4O_4$ requires 482; found 483.2 (M+H$^+$).

EXAMPLE 66

1-{2-[7-(5-{3-chloro-4-[(1-methylethyl)oxy]phenyl}-1,2,4-oxadiazol-3-yl)-1-methyl-1H-indol-3-yl]ethyl}-4-piperidinecarboxylic acid (E66)

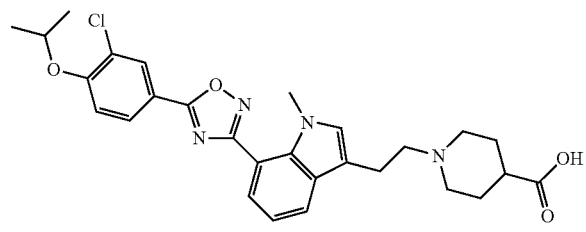

To a solution of ethyl 1-{2-[7-(5-{3-chloro-4-[(1-methylethyl)oxy]phenyl}-1,2,4-oxadiazol-3-yl)-1-methyl-1H-indol-3-yl]ethyl}-4-piperidinecarboxylate (D91) (30 mg) in THF (5 mL) was added aqueous NaOH (2 M, 1 mL). The reaction was stirred at 50° C. for 5 h. The mixture was cooled to room temperature and acidified with aqueous HCl (2 M) to pH 4-5, partitioned between ethyl acetate (50 mL) and water (50 mL). The organic phase was washed with water (50 mL) and brine (50 mL), dried over sodium sulphate and evaporated to give the crude product, which was purified by Mass Directed Auto Prep to afford 1-{2-[7-(5-{3-chloro-4-[(1-methylethyl)oxy]phenyl}-1,2,4-oxadiazol-3-yl)-1-methyl-1H-indol-3-yl]ethyl}-4-piperidinecarboxylic acid (E66) (1.8 mg, TFA salt). δH (DMSO-d$_6$, 400 MHz): 1.36 (6H, d), 1.75 (2H, m), 1.91 (1H, m), 2.11 (2H, m), 3.11 (4H, m), 3.48 (4H, m), 3.65 (3H, s), 4.89 (1H, m), 7.23 (1H, t), 7.33 (1H, s), 7.47 (2H, m), 7.87 (1H, dd), 8.12 (1H, dd), 8.19 (1H, d), 9.24 (1H, br s), 12.56 (1H, br s). MS (ES): $C_{28}H_{31}ClN_4O_4$ requires 522; found 523.2 (M+H$^+$).

EXAMPLE 67

1-{2-[7-(5-{3-chloro-4-[(1-methylethyl)oxy]phenyl}-1,2,4-oxadiazol-3-yl)-1-methyl-1H-indol-3-yl]ethyl}-3-azetidinecarboxylic acid (E67)

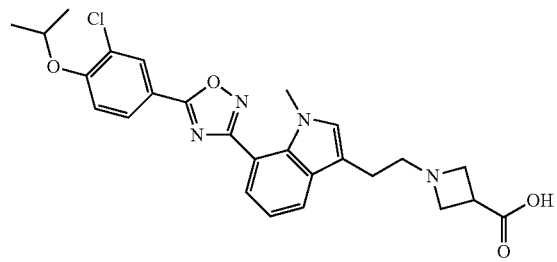

To a stirred solution of [7-(5-{3-chloro-4-[(1-methylethyl)oxy]phenyl}-1,2,4-oxadiazol-3-yl)-1-methyl-1H-indol-3-yl]acetaldehyde (D88) (50 mg), 3-azetidinecarboxylic acid (25 mg) and acetic acid (0.1 mL) in DCM (10 mL) was added sodium triacetoxyborohydride (78 mg). The reaction was stirred at 20° C. for 3 h. The mixture was concentrated and the residue was partitioned between ethyl acetate (25 mL) and aqueous HCl (2 M, 25 mL). The organic phase was washed with water (25 mL) and brine (25 mL), dried over sodium sulphate and evaporated to give the crude product, which was purified by Mass Directed Auto Prep to afford 1-{2-[7-(5-{3-chloro-4-[(1-methylethyl)oxy]phenyl}-1,2,4-oxadiazol-3-yl)-1-methyl-1H-indol-3-yl]ethyl}-3-azetidinecarboxylic acid (E67) (18 mg, TFA salt). δH (DMSO-d$_6$, 400 MHz): 1.36 (6H, d), 3.00 (2H, t), 3.47 (2H, t), 3.60 (1H, m), 3.65 (3H, s), 4.22 (4H, m), 4.88 (1H, m), 7.22 (1H, t), 7.31 (1H, s), 7.47 (2H, m), 7.87 (1H, dd), 8.12 (1H, dd), 8.19 (1H, d). MS (ES): $C_{26}H_{27}ClN_4O_4$ requires 494; found 495.2 (M+H$^+$).

EXAMPLE 68

1-({2-[7-(5-{3-chloro-4-[(1-methylethyl)oxy]phenyl}-1,2,4-oxadiazol-3-yl)-1-methyl-1H-indol-3-yl]ethyl}amino)cyclopropanecarboxylic acid (E68)

To a stirred solution of [7-(5-{3-chloro-4-[(1-methylethyl)oxy]phenyl}-1,2,4-oxadiazol-3-yl)-1-methyl-1H-indol-3-yl]acetaldehyde (D88) (50 mg), 1-aminocyclopropanecarboxylic acid (25 mg) and acetic acid (0.1 mL) in DCM (10 mL) was added sodium triacetoxyborohydride (52 mg). The reaction was stirred at 20° C. for 3 h. The mixture was concentrated and the residue was partitioned between ethyl acetate (25 mL) and aqueous HCl (2 M, 25 mL). The organic phase was washed with water (25 mL) and brine (25 mL), dried over anhydrous sodium sulphate and evaporated to give the crude product, which was purified by Mass Directed Auto Prep to afford 1-({2-[7-(5-{3-chloro-4-[(1-methylethyl)oxy]phenyl}-1,2,4-oxadiazol-3-yl)-1-methyl-1H-indol-3-yl]ethyl}amino)cyclopropanecarboxylic acid (E68) (8 mg, TFA salt). δH (DMSO-d$_6$, 400 MHz): 1.36 (6H, d), 1.41 (4H, m), 3.06 (2H, t), 3.31 (2H, t), 3.65 (3H, s), 4.88 (1H, m), 7.22 (1H, t), 7.33 (1H, s), 7.46 (2H, m), 7.81 (1H, dd), 8.12 (1H, dd), 8.19 (1H, d). MS (ES): $C_{26}H_{27}ClN_4O_4$ requires 494; found 495.2 (M+H$^+$).

EXAMPLE 69

1-{2-[7-(5-{3-chloro-4-[(1-methylethyl)oxy]phenyl}-1,2,4-oxadiazol-3-yl)-1-methyl-1H-indol-3-yl]ethyl}-L-proline (E69)

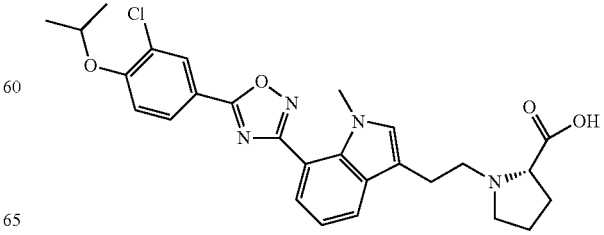

To a stirred solution of [7-(5-{3-chloro-4-[(1-methylethyl) oxy]phenyl}-1,2,4-oxadiazol-3-yl)-1-methyl-1H-indol-3-yl]acetaldehyde (D88) (50 mg), L-proline (28 mg) and acetic acid (0.1 mL) in DCM (10 mL) stirred at 20° C. was added sodium triacetoxyborohydride (52 mg). The reaction was stirred at 20° C. for 3 h. The mixture was concentrated and the residue was partitioned between ethyl acetate (25 mL) and aqueous HCl (2 M, 25 mL). The organic phase was washed with water (25 mL) and brine (25 mL), dried over anhydrous sodium sulphate and evaporated to give the crude product, which was purified by Mass Directed Auto Prep to afford 1-{2-[7-(5-{3-chloro-4-[(1-methylethyl)oxy]phenyl}-1,2,4-oxadiazol-3-yl)-1-methyl-1H-indol-3-yl]ethyl}-L-proline (E69) (12 mg, TFA salt). δH (DMSO-$d_6$, 400 MHz): 1.35 (6H, d), 1.71 (1H, m), 1.94 (2H, m), 2.16 (1H, m), 2.95 (1H, m), 3.05 (2H, m), 3.25 (2H, m), 3.60 (2H, m), 3.65 (3H, s), 4.88 (1H, m), 7.20 (1H, t), 7.31 (1H, s), 7.45 (2H, m), 7.86 (1H, dd), 8.13 (1H, dd), 8.20 (1H, d). MS (ES): $C_{27}H_{29}ClN_4O_4$ requires 508; found 509.2 (M+H$^+$).

EXAMPLE 70

N-{3-[7-(5-{3-chloro-4-[(1-methylethyl)oxy]phenyl}-1,2,4-oxadiazol-3-yl)-1H-indol-3-yl]propyl}glycine (E70)

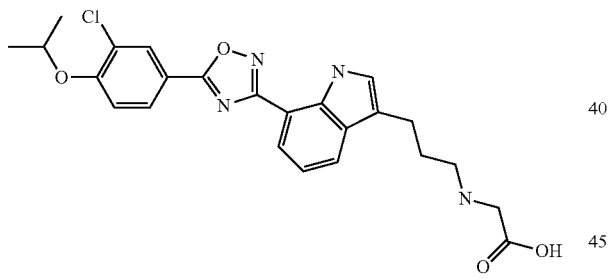

To a solution of ethyl N-{3-[7-(5-{3-chloro-4-[(1-methylethyl)oxy]phenyl}-1,2,4-oxadiazol-3-yl)-1H-indol-3-yl]propyl}glycinate (D93) (50 mg) in THF (5 mL) was added aqueous NaOH (2 M, 1 mL). The reaction was stirred at 20° C. overnight. The mixture was acidified with aqueous HCl (2 M) to pH 5-6, partitioned between ethyl acetate (25 mL) and water (10 mL). The organic phase was washed with water (20 mL) and brine (20 mL), dried over anhydrous sodium sulphate and evaporated to give the crude product, which was purified by Mass Directed Auto Prep to afford N-{3-[7-(5-{3-chloro-4-[(1-methylethyl)oxy]phenyl}-1,2,4-oxadiazol-3-yl)-1H-indol-3-yl]propyl}glycine (E70) (45 mg, TFA salts). δH (DMSO-$d_6$, 400 MHz): 1.37 (6H, d), 2.02 (2H, m), 2.82 (2H, t), 2.95 (2H, t), 3.69 (2H, s), 4.90 (1H, m), 7.23 (1H, t), 7.31 (1H, d), 7.45 (1H, d), 7.82 (1H, d), 7.95 (1H, d), 8.20 (1H, dd), 8.36 (1H, d), 10.85 (1H, s). MS (ES): $C_{24}H_{26}ClN_4O_4$ requires 468; found 469.2 (M+H$^+$).

EXAMPLE 71

N-{3-[7-(5-{3-chloro-4-[(1-methylethyl)oxy]phenyl}-1,2,4-oxadiazol-3-yl)-1H-indol-3-yl]propyl}-N-methylglycine (E71)

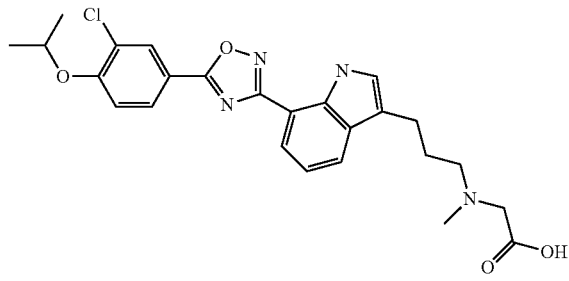

To a stirred solution of 3-[7-(5-{3-chloro-4-[(1-methylethyl)oxy]phenyl}-1,2,4-oxadiazol-3-yl)-1H-indol-3-yl]propanal (D92) (100 mg), N-methylglycine (43 mg) and acetic acid (0.1 mL) in DCM (15 mL) was added sodium triacetoxyborohydride (103 mg). The reaction was stirred at 40° C. for 3 h. The mixture was cooled to room temperature and partitioned between DCM (25 mL) and water (25 mL). The organic phase was washed with water (25 mL), dried over anhydrous sodium sulphate and evaporated to give the crude product, which was purified by Mass Directed Auto Prep to afford N-{3-[7-(5-{3-chloro-4-[(1-methylethyl)oxy]phenyl}-1,2,4-oxadiazol-3-yl)-1H-indol-3-yl]propyl}-N-methylglycine (E71) (80 mg, TFA salt). δH (DMSO-$d_6$, 400 MHz): 1.37 (6H, d), 2.08 (2H, m), 2.80 (2H, t), 2.82 (3H, s), 3.18 (2H, t), 4.07 (2H, s), 4.89 (1H, m), 7.23 (1H, t), 7.33 (1H, t), 7.45 (1H, d), 7.84 (1H, d), 7.96 (1H, d), 8.36 (1H, d), 10.87 (1H, s). MS (ES): $C_{26}H_{27}ClN_4O_4$ requires 482; found 483.2 (M+H$^+$).

EXAMPLE 72

N-{[7-(5-{3-chloro-4-[(1-methylethyl)oxy]phenyl}-1,2,4-oxadiazol-3-yl)-1H-indol-3-yl]carbonyl}glycine (E72)

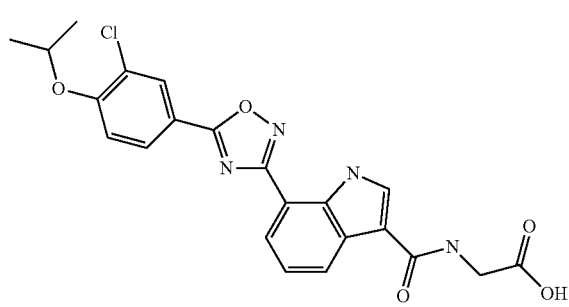

To a solution of ethyl N-{[7-(5-{3-chloro-4-[(1-methylethyl)oxy]phenyl}-1,2,4-oxadiazol-3-yl)-1H-indol-3-yl]carbonyl}glycinate (D96) (50 mg) in THF (5 mL) was added aqueous NaOH (2 M, 2 mL). The reaction was stirred at room temperature overnight. The mixture was acidified with aqueous HCl (2 M) to pH 4-5, partitioned between ethyl acetate (25 mL) and water (25 mL). The organic phase was washed with water (25 mL) and brine (25 mL), dried over anhydrous sodium sulphate and evaporated to give the crude product, which was purified by Mass Directed Auto Prep to afford N-{[7-(5-{3-chloro-4-[(1-methylethyl)oxy]phenyl}-1,2,4-oxadiazol-3-yl)-1H-indol-3-yl]carbonyl}glycine (E72) (28 mg). δH (DMSO-$d_6$, 400 MHz): 1.36 (6H, d), 3.93 (2H, d), 4.90 (1H, m), 7.34 (1H, t), 7.47 (1H, d), 8.00 (1H, dd), 8.23 (2H, m), 8.42 (2H, m), 8.54 (1H, t), 11.55 (1H, s), 12.54 (1H, br s). MS (ES): $C_{22}H_{19}ClN_4O_6$ requires 454; found 455.2 (M+H$^+$).

EXAMPLE 73

N-{[7-(5-{3-chloro-4-[(1-methylethyl)oxy]phenyl}-1,2,4-oxadiazol-3-yl)-1H-indol-3-yl]carbonyl}-β-alanine (E73)

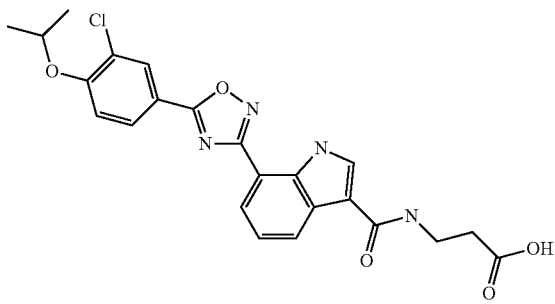

To a solution of ethyl N-{[7-(5-{3-chloro-4-[(1-methylethyl)oxy]phenyl}-1,2,4-oxadiazol-3-yl)-1H-indol-3-yl]carbonyl}-β-alaninate (D97) (60 mg) in THF (5 mL) was added aqueous NaOH (2 M, 2 mL). The reaction mixture was stirred at room temperature overnight. The mixture was acidified with aqueous HCl (2 M) to pH 4-5, partitioned between ethyl acetate (25 mL) and water (25 mL). The organic phase was washed with water (25 mL) and brine (25 mL), dried over anhydrous sodium sulphate and evaporated to give the crude product, which was purified by Mass Directed Auto Prep to afford N-{[7-(5-{3-chloro-4-[(1-methylethyl)oxy]phenyl}-1,2,4-oxadiazol-3-yl)-1H-indol-3-yl]carbonyl}-β-alanine (E73) (45 mg). δH (DMSO-$d_6$, 400 MHz): 1.36 (6H, d), 2.54 (2H, t), 3.47 (2H, t), 4.89 (1H, m), 7.32 (1H, t), 7.45 (1H, d), 7.99 (1H, dd), 8.17 (1H, d), 8.22 (2H, m), 8.38 (1H, d), 8.43 (1H, dd), 11.50 (1H, br s), 12.23 (1H, br s). MS (ES): $C_{23}H_{21}ClN_4O_6$ requires 468; found 469.2 (M+H$^+$).

EXAMPLE 74

4-({[7-(5-{3-chloro-4-[(1-methylethyl)oxy]phenyl}-1,2,4-oxadiazol-3-yl)-1H-indol-3-yl]carbonyl}amino)butanoic acid (E74)

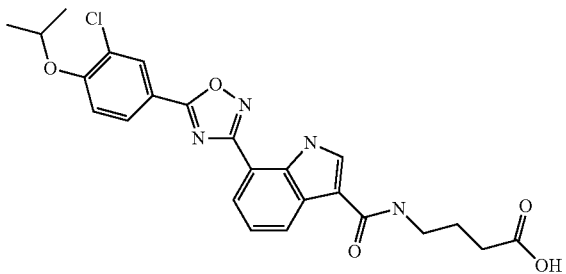

To a stirred solution of 7-(5-{3-chloro-4-[(1-methylethyl)oxy]phenyl}-1,2,4-oxadiazol-3-yl)-1H-indole-3-carboxylic acid (D94) (150 mg) and DMF (0.1 mL) in DCM (10 mL) was added a solution of oxalyl chloride (240 mg) in DCM (2 mL). After stirring for 1 h, the reaction mixture was concentrated and the residue was dissolved in THF (10 mL), followed by addition of ethyl 4-aminobutanoate (99 mg) and Et$_3$N (190 mg). The reaction was stirred at room temperature for 0.5 h. The solvent was evaporated, the residue was dissolved in THF (5 mL) and NaOH (2 M, 2 mL) was added. The reaction was stirred at room temperature overnight. The mixture was acidified with aqueous HCl (2 M) to pH 4-5, partitioned between ethyl acetate (25 mL) and water (25 mL). The organic phase was washed with water (20 mL) and brine (20 mL), dried over sodium sulphate and evaporated to give the crude product, which was purified by Mass Directed Auto Prep to afford 4-({[7-(5-{3-chloro-4-[(1-methylethyl)oxy]phenyl}-1,2,4-oxadiazol-3-yl)-1H-indol-3-yl]carbonyl}amino)butanoic acid (E74) (65 mg). δH (DMSO-$d_6$, 400 MHz): 1.36 (6H, d), 1.77 (2H, m), 2.30 (2H, t), 3.29 (2H, t), 4.89 (1H, m), 7.32 (1H, t), 7.44 (1H, d), 7.99 (1H, dd), 8.19 (3H, m), 8.37 (1H, d), 8.44 (1H, d), 11.50 (1H, s), 12.08 (1H, s). MS (ES): $C_{24}H_{23}ClN_4O_5$ requires 482; found 483.2 (M+H$^+$).

EXAMPLE 75

N-{[7-(5-{3-chloro-4-[(1-methylethyl)oxy]phenyl}-1,2,4-oxadiazol-3-yl)-1H-indol-3-yl]carbonyl}-N-methyl-β-alanine (E75)

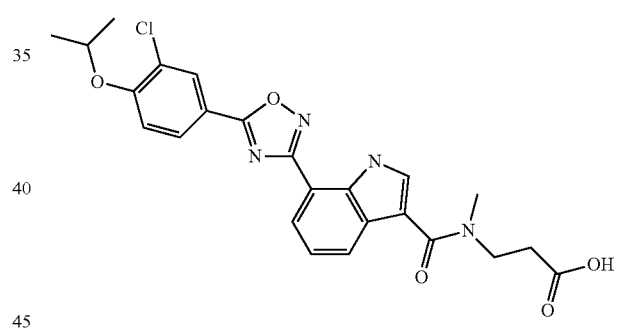

To a stirred solution of 7-(5-{3-chloro-4-[(1-methylethyl)oxy]phenyl}-1,2,4-oxadiazol-3-yl)-1H-indole-3-carboxylic acid (D94) (150 mg) and DMF (0.1 mL) in DCM (10 mL) was added a solution of oxalyl chloride (240 mg) in DCM (2 mL). After stirring for 1 h, the reaction mixture was concentrated and the residue was dissolved in THF (10 mL), followed by addition of ethyl N-methyl-8-alaninate (99 mg) and Et$_3$N (190 mg). The reaction was stirred at room temperature for 0.5 h and then concentrated. The residue was dissolved in THF (5 mL) and aqueous NaOH (2 M, 2 mL) was added. The reaction mixture was stirred at 50° C. overnight. The mixture was acidified with aqueous HCl (2 M) to pH 4-5, partitioned between ethyl acetate (25 mL) and water (25 mL). The organic phase was washed with water (20 mL) and brine (20 mL), dried over sodium sulphate and evaporated to give the crude product, which was purified by Mass Directed Auto Prep to afford N-{[7-(5-{3-chloro-4-[(1-methylethyl)oxy]phenyl}-1,2,4-oxadiazol-3-yl)-1H-indol-3-yl]carbonyl}-N-methyl-β-alanine (E75) (35 mg). δH (DMSO-$d_6$, 400 MHz): 1.37 (6H, d), 2.61 (2H, t), 3.12 (3H, s), 3.72 (2H, t), 4.90 (1H, m), 7.31 (1H, t), 7.46 (1H, d), 7.75 (1H, d), 8.00 (2H, m), 8.21

(1H, dd), 8.41 (1H, d), 11.49 (1H, s), 12.33 (1H, s). MS (ES): $C_{24}H_{23}ClN_4O_6$ requires 482; found 483.2 (M+H$^+$).

EXAMPLE 76

N-{[7-(5-{3-chloro-4-[(1-methylethyl)oxy]phenyl}-1,2,4-oxadiazol-3-yl)-1-methyl-1H-indol-3-yl]carbonyl}-β-alanine (E76)

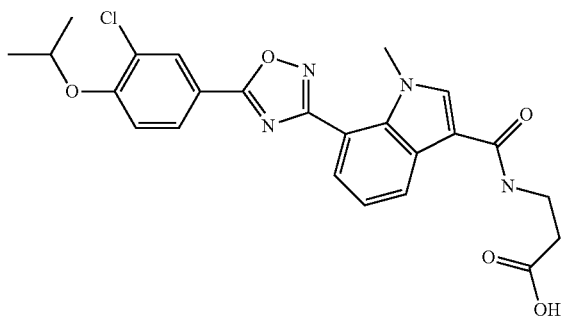

To a solution of ethyl N-{[7-(5-{3-chloro-4-[(1-methylethyl)oxy]phenyl}-1,2,4-oxadiazol-3-yl)-1-methyl-1H-indol-3-yl]carbonyl}-β-alaninate (D95) (200 mg) in THF (5 mL) was added aqueous NaOH (2 M, 1 mL). The reaction was stirred at 20° C. for 4 h. The mixture was acidified with aqueous HCl (2 M), partitioned between ethyl acetate (25 mL) and water (20 mL). The organic phase was washed with water (20 mL) and brine (20 mL), dried over sodium sulphate and evaporated to give the crude product, which was purified by Mass Directed Auto Prep to afford N-{[7-(5-{3-chloro-4-[(1-methylethyl)oxy]phenyl}-1,2,4-oxadiazol-3-yl)-1-methyl-1H-indol-3-yl]carbonyl}-6-alanine (E76) (150 mg). δH (DMSO-d$_6$, 400 MHz): 1.36 (6H, d), 2.45 (2H, t), 3.46 (2H, t), 3.70 (3H, s), 4.88 (1H, m), 7.29 (1H, t), 7.44 (1H, d), 7.49 (1H, d), 8.02 (1H, s), 8.08 (1H, br s), 8.13 (1H, dd), 8.20 (1H, d), 8.44 (1H, dd). MS (ES): $C_{24}H_{23}ClN_4O_6$ requires 482; found 483.1 (M+H$^+$).

EXAMPLE 77

N-{3-[7-(5-{3-chloro-4-[(1-methylethyl)oxy]phenyl}-1,2,4-oxadiazol-3-yl)-1H-indol-3-yl]propanoyl}glycine (E77)

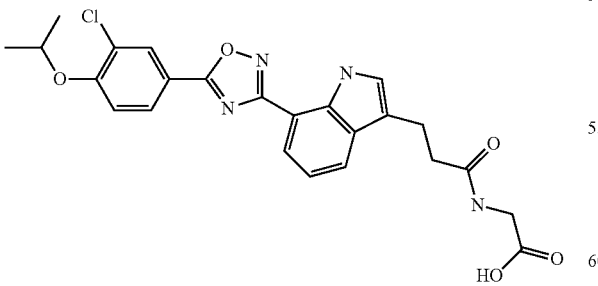

To a solution of ethyl N-{3-[7-(5-{3-chloro-4-[(1-methylethyl)oxy]phenyl}-1,2,4-oxadiazol-3-yl)-1H-indol-3-yl]propanoyl}glycinate (D125) (150 mg) in THF (15 mL) was added aqueous NaOH (2 M, 2 mL). The reaction was stirred at 20° C. for 3 h. The mixture was acidified with aqueous HCl (2 M) to pH 5-6, partitioned between ethyl acetate (50 mL) and water (25 mL). The organic phase was dried over sodium sulphate and evaporated to give the crude product, which was purified by Mass Directed Auto Prep to afford N-{3-[7-(5-{3-chloro-4-[(1-methylethyl)oxy]phenyl}-1,2,4-oxadiazol-3-yl)-1H-indol-3-yl]propanoyl}glycine (E77) (120 mg). δH (DMSO-d$_6$, 400 MHz): 1.36 (6H, d), 2.56 (2H, t), 2.99 (2H, t), 3.76 (2H, d), 4.89 (1H, m), 7.21 (1H, t), 7.27 (1H, s), 7.44 (1H, d), 7.82 (1H, d), 7.93 (1H, d), 8.20 (2H, m), 8.37 (1H, d), 10.78 (1H, s), 12.46 (1H, s). MS (ES): $C_{24}H_{23}ClN_4O_6$ requires 482; found 483.2 (M+H$^+$).

EXAMPLE 78

1-{[6-(5-{5-chloro-6-[(1-methylethyl)oxy]-3-pyridinyl}-1,2,4-oxadiazol-3-yl)-1H-indol-3-yl]methyl}-4-piperidinecarboxylic acid (E78)

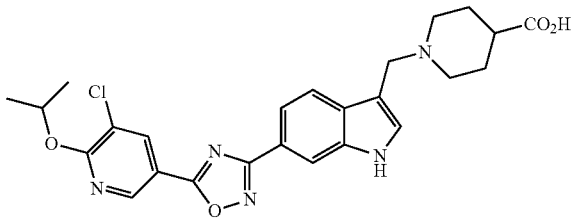

Sodium hydroxide (19 mg) was added to a solution of ethyl 1-{[6-(5-{5-chloro-6-[(1-methylethyl)oxy]-3-pyridinyl}-1,2,4-oxadiazol-3-yl)-1H-indol-3-yl]methyl}-4-piperidinecarboxylate (D103) (134 mg) in $^i$PrOH (4 mL) and water (4 mL). The resulting mixture was heated at 70° C. for 40 mins. Then 0.5 M HCl solution was added until pH was about 6. The solvent was concentrated, and the residue was dissolved in water. The precipitated solid was purified by Mass Directed Auto Prep to afford 1-{[6-(5-{5-chloro-6-[(1-methylethyl)oxy]-3-pyridinyl}-1,2,4-oxadiazol-3-yl)-1H-indol-3-yl]methyl}-4-piperidinecarboxylic acid (E78) (118 mg) as a pale red-white solid. δH (DMSO-d$_6$, 400 MHz): 1.37 (6H, d), 1.55 (2H, m), 1.77 (2H, m), 2.01 (2H, m), 2.18 (1H, m), 2.85 (2H, m), 3.67 (2H, m), 5.46 (1H, m), 7.46 (1H, s), 7.73 (1H, dd), 7.81 (1H, d), 8.14 (1H, s), 8.56 (1H, d), 8.94 (1H, d), 11.37 (1H, s), 12.02 (1H, br s). MS (ES): $C_{26}H_{26}ClN_6O_4$ requires 495; found 496.2 (M+H$^+$).

EXAMPLE 79

({2-[7-(5-{3-chloro-4-[(1-methylethyl)oxy]phenyl}-1,2,4-oxadiazol-3-yl)-1-methyl-1H-indol-3-yl]ethyl}oxy)acetic acid (E79)

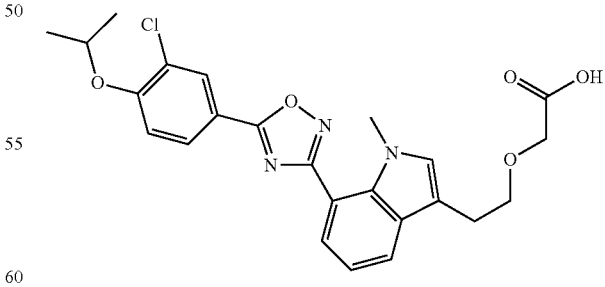

To a solution of ethyl ({2-[7-(5-{3-chloro-4-[(1-methylethyl)oxy]phenyl}-1,2,4-oxadiazol-3-yl)-1-methyl-1H-indol-3-yl]ethyl}oxy)acetate (D104) (20 mg) in THF (5 mL) was added aqueous NaOH (2 M, 1 mL). The reaction was stirred at 20° C. for 4 h. The mixture was acidified with aqueous HCl (2 M) to pH 4-5. After concentration, the residue was partitioned between ethyl acetate (25 mL) and water (25 mL). The organic phase was washed with brine (25 mL), dried over anhydrous sodium sulphate and evaporated to give the crude product, which was purified by Mass Directed Auto Prep to afford ({2-[7-(5-{3-chloro-4-[(1-methylethyl)oxy]phenyl}-1,2,4-oxadiazol-3-yl)-1-methyl-1H-indol-3-yl]ethyl}oxy)acetic acid (E79) (11 mg). δH (DMSO-$d_6$, 400 MHz): 1.36 (6H, d), 2.98 (2H, t), 3.63 (3H, s), 3.74 (2H, t), 4.05 (2H, s), 4.89 (1H, m), 7.17 (1H, t), 7.26 (1H, s), 7.44 (2H, m), 7.81 (1H, dd), 8.13 (1H, dd), 8.19 (1H, d), 12.57 (1H, br s). MS (ES): $C_{24}H_{24}ClN_3O_6$ requires 469; found 470.2 (M+H$^+$).

EXAMPLE 80

({3-[7-(5-{3-chloro-4-[(1-methylethyl)oxy]phenyl}-1,2,4-oxadiazol-3-yl)-1-methyl-1H-indol-3-yl]propyl}oxy)acetic acid (E80)

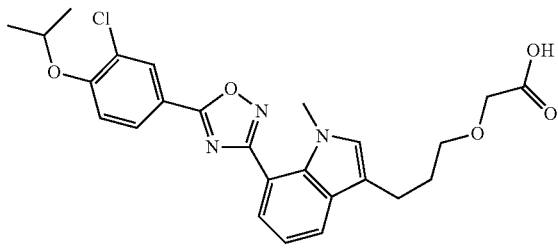

To a solution of ethyl ({3-[7-(5-{3-chloro-4-[(1-methylethyl)oxy]phenyl}-1,2,4-oxadiazol-3-yl)-1-methyl-1H-indol-3-yl]propyl}oxy)acetate (D105) (80 mg) in THF (10 mL) was added NaOH (2 M, 2 mL). The reaction was stirred at 20° C. for 3 h. The mixture was acidified with aqueous HCl (2 M) to pH 4-5, partitioned between ethyl acetate (25 mL) and water (25 mL). The organic phase was washed with water (25 mL) and brine (25 mL), dried over anhydrous sodium sulphate and evaporated to give the crude product, which was purified by Mass Directed Auto Prep to afford ({3-[7-(5-{3-chloro-4-[(1-methylethyl)oxy]phenyl}-1,2,4-oxadiazol-3-yl)-1-methyl-1H-indol-3-yl]propyl}oxy)acetic acid (E80) (50 mg). δH (DMSO-$d_6$, 400 MHz): 1.35 (6H, d), 1.89 (2H, m), 2.49 (2H, t), 3.52 (2H, t), 3.63 (3H, s), 4.01 (2H, s), 4.87 (1H, m), 7.17 (2H, m), 7.42 (2H, m), 7.77 (1H, dd), 8.12 (1H, dd), 8.19 (1H, d), 12.56 (1H, br s). MS (ES): $C_{25}H_{26}ClN_3O_5$ requires 483; found 484.2 (M+H$^+$).

EXAMPLE 81

3-[6-(5-{5-Chloro-6-[(1-methylethyl)oxy]-3-pyridinyl}-1,2,4-oxadiazol-3-yl)-1H-indol-3-yl]propanoic acid (E81)

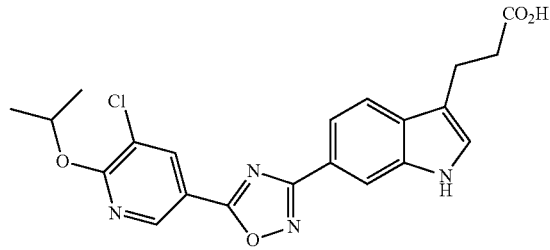

Sodium hydroxide (40 mg) was added to a solution of ethyl 3-[6-(5-{5-chloro-6-[(1-methylethyl)oxy]-3-pyridinyl}-1,2,4-oxadiazol-3-yl)-1H-indol-3-yl]propanoate (D108) (300 mg) in $^i$PrOH (10 mL) and water (10 mL). The resulting mixture was heated at 70° C. for 40 mins. Then 0.5 M HCl solution was added until pH was about 6. The solvent was concentrated, and the residue was dissolved in water. The precipitated solid was purified by Mass Directed Auto Prep to afford 3-[6-(5-{5-chloro-6-[(1-methylethyl)oxy]-3-pyridinyl}-1,2,4-oxadiazol-3-yl)-1H-indol-3-yl]propanoic acid (E81) (150 mg) as a white solid. δH (DMSO-$d_6$, 400 MHz): 1.39 (6H, d), 2.61 (2H, t), 2.97 (2H, t), 5.46 (1H, m), 7.34 (1H, d), 7.71 (2H, m), 8.12 (1H, s), 8.54 (1H, s), 8.92 (1H, s), 11.18 (1H, s), 12.05 (1H, br s). MS (ES): $C_{21}H_{19}ClN_4O_4$ requires 426; found 427.2 (M+H$^+$).

EXAMPLE 82

3-[6-(5-{5-Chloro-6-[(1-methylethyl)oxy]-3-pyridinyl}-1,2,4-oxadiazol-3-yl)-1-methyl-1H-indol-3-yl]propanoic acid (E82)

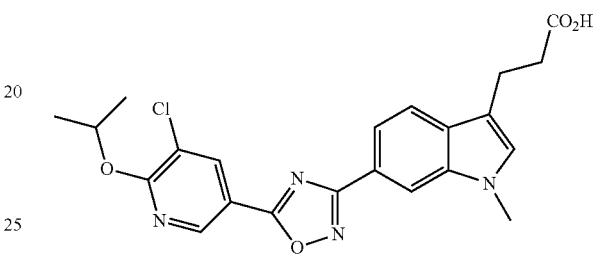

DABCO (64 mg) was added to a solution of 3-[6-(5-{5-chloro-6-[(1-methylethyl)oxy]-3-pyridinyl}-1,2,4-oxadiazol-3-yl)-1H-indol-3-yl]propanoic acid (E81) (60 mg) in dimethyl carbonate (3 mL) and DMF (2 mL). The resulting mixture was heated at reflux for 5 days. After cooling, the reaction was quenched with water, and extracted with EtOAc for 3 times. The combined organic solution was washed with brine, and dried over anhydrous sodium sulfate. The dried solution was concentrated. The residue was dissolved in $^i$PrOH (3 mL) and water (3 mL). Sodium hydroxide (20 mg) was added to the mixture. The resulting mixture was heated at 90° C. for 1 hour. Then 0.5 M HCl solution was added until pH was about 6. The solvent was concentrated, and the residue was dissolved in water. The precipitated solid was purified by Mass Directed Auto Prep to afford 3-[6-(5-{5-chloro-6-[(1-methylethyl)oxy]-3-pyridinyl}-1,2,4-oxadiazol-3-yl)-1-methyl-1H-indol-3-yl]propanoic acid (E82) (18 mg) as an off-white solid. δH (DMSO-$d_6$, 400 MHz): 1.38 (6H, d), 2.60 (2H, t), 2.96 (2H, t), 3.84 (3H, s), 5.46 (1H, m), 7.32 (1H, s), 7.75 (2H, m), 8.12 (1H, s), 8.57 (1H, d), 8.94 (1H, d), 12.08 (1H, br s). MS (ES): $C_{22}H_{21}ClN_4O_4$ requires 440. found 441.1.

EXAMPLE 83

3-(6-{5-[6-[(1-Methylethyl)oxy]-5-(trifluoromethyl)-3-pyridinyl]-1,2,4-oxadiazol-3-yl}-1H-indol-3-yl)propanoic acid (E83)

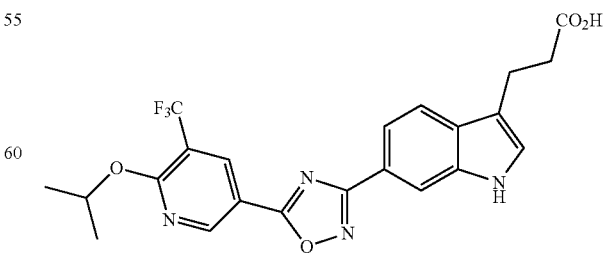

Sodium hydroxide (37 mg) was added to a solution of ethyl 3-(6-{5-[6-[(1-methylethyl)oxy]-5-(trifluoromethyl)-3-pyridinyl]-1,2,4-oxadiazol-3-yl}-1H-indol-3-yl)propanoate (D109) (300 mg) in $^i$PrOH (10 mL) and water (10 mL). The resulting mixture was heated at 70° C. for 40 mins. Then 0.5 M HCl solution was added until pH was about 6. The solvent was concentrated, and the residue was dissolved in water. The precipitated solid was purified by Mass Directed Auto Prep to afford 3-(6-{5-[6-[(1-methylethyl)oxy]-5-(trifluoromethyl)-3-pyridinyl]-1,2,4-oxadiazol-3-yl}-1H-indol-3-yl)propanoic acid (E83) (111 mg) as a white solid. δH (DMSO-$d_6$, 400 MHz): 1.38 (6H, d), 2.61 (2H, t), 2.97 (2H, t), 5.55 (1H, m), 7.34 (1H, d), 7.72 (2H, m), 8.13 (1H, t), 8.63 (1H, d), 9.20 (1H, d), 11.16 (1H, d), 12.05 (1H, br s). MS (ES): $C_{22}H_{19}F_3N_4O_4$ requires 460; found 461.2 (M+H$^+$).

EXAMPLE 84

3-[6-(5-{5-Fluoro-6-[(1-methylethyl)oxy]-3-pyridinyl}-1,2,4-oxadiazol-3-yl)-1H-indol-3-yl]propanoic acid (E84)

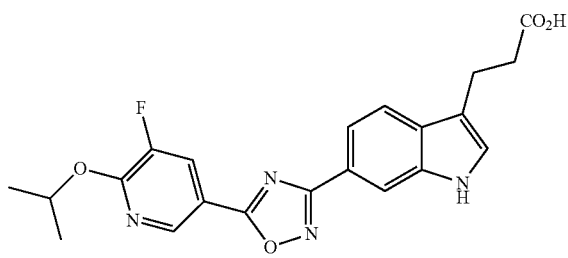

Sodium hydroxide (8 mg) was added to a solution of ethyl 3-[6-(5-{5-fluoro-6-[(1-methylethyl)oxy]-3-pyridinyl}-1,2,4-oxadiazol-3-yl)-1H-indol-3-yl]propanoate (D110) (60 mg) in $^i$PrOH (5 mL) and water (5 mL). The resulting mixture was heated at 70° C. for 40 mins. Then 0.5 M HCl solution was added until pH was about 6. The solvent was concentrated, and the residue was dissolved in water. The precipitated solid was purified by Mass Directed Auto Prep to afford 3-[6-(5-{5-fluoro-6-[(1-methylethyl)oxy]-3-pyridinyl}-1,2,4-oxadiazol-3-yl)-1H-indol-3-yl]propanoic acid (E84) (12 mg) as a white solid. δH (DMSO-$d_6$, 400 MHz): 1.39 (6H, d), 2.61 (2H, t), 2.96 (2H, t), 5.47 (1H, m), 7.35 (1H, d), 7.72 (2H, d), 8.11 (1H, t), 8.37 (1H, dd), 8.81 (1H, d), 11.23 (1H, d), 12.11 (1H, br s). MS (ES): $C_{21}H_{19}FN_4O_4$ requires 410; found 411.2 (M+H$^+$).

EXAMPLE 85

3-[6-(5-{5-Methyl-6-[(1-methylethyl)oxy]-3-pyridinyl}-1,2,4-oxadiazol-3-yl)-1H-indol-3-yl]propanoic acid (E85)

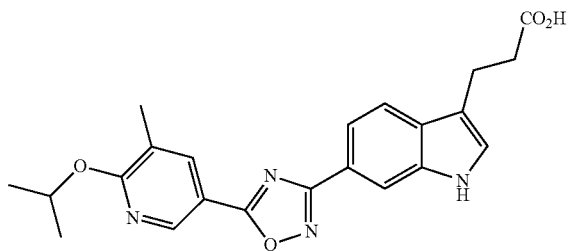

Sodium hydroxide (43 mg) was added to a solution of ethyl 3-[6-(5-{5-methyl-6-[(1-methylethyl)oxy]-3-pyridinyl}-1,2,4-oxadiazol-3-yl)-1H-indol-3-yl]propanoate (D111) (310 mg) in $^i$PrOH (10 mL) and water (10 mL). The resulting mixture was heated at 70° C. for 40 mins. Then 0.5 M HCl solution was added until pH was about 6. The solvent was concentrated, and the residue was dissolved in water. The precipitated solid was purified by Mass Directed Auto Prep to afford 3-[6-(5-{5-methyl-6-[(1-methylethyl)oxy]-3-pyridinyl}-1,2,4-oxadiazol-3-yl)-1H-indol-3-yl]propanoic acid (E85) (150 mg) as a white solid. δH (DMSO-$d_6$, 400 MHz): 1.35 (6H, d), 2.24 (3H, s), 2.61 (2H, t), 2.96 (2H, t), 5.40 (1H, m), 7.34 (1H, d), 7.70 (2H, d), 8.11 (1H, t), 8.28 (1H, dd), 8.82 (1H, dd), 11.20 (1H, s), 12.11 (1H, br s). MS (ES): $C_{22}H_{22}N_4O_4$ requires 406; found 407.2 (M+H$^+$).

EXAMPLE 86

3-[1-Methyl-6-(5-{5-methyl-6-[(1-methylethyl)oxy]-3-pyridinyl}-1,2,4-oxadiazol-3-yl)-1H-indol-3-yl]propanoic acid (E86)

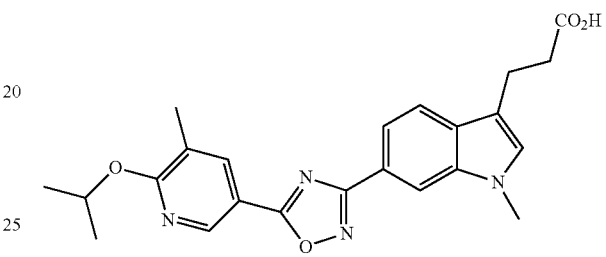

DABCO (110 mg) was added to a solution of 3-[6-(5-{5-methyl-6-[(1-methylethyl)oxy]-3-pyridinyl}-1,2,4-oxadiazol-3-yl)-1H-indol-3-yl]propanoic acid (E85) (100 mg) in dimethyl carbonate (3 mL) and DMF (2 mL). The resulting mixture was heated at reflux for 5 days. After cooling, the reaction was quenched with water, and extracted with EtOAc for 3 times. The combined organic solution was washed with brine, and dried over anhydrous sodium sulfate. The dried solution was concentrated. The residue was dissolved in $^i$PrOH (3 mL) and water (3 mL). Sodium hydroxide (30 mg) was added to the mixture. The resulting mixture was heated at 90° C. for 1 hour. Then 0.5 M HCl solution was added until pH was about 6. The solvent was concentrated, and the residue was dissolved in water. The precipitated solid was purified by Mass Directed Auto Prep to afford 3-[1-methyl-6-(5-{5-methyl-6-[(1-methylethyl)oxy]-3-pyridinyl}-1,2,4-oxadiazol-3-yl)-1H-indol-3-yl]propanoic acid (E86) (55 mg) as an off-white solid. δH (DMSO-$d_6$, 400 MHz): 1.36 (6H, d), 2.24 (3H, s), 2.60 (2H, t), 2.95 (2H, t), 3.83 (3H, s), 5.41 (1H, m), 7.31 (1H, s), 7.74 (2H, m), 8.10 (1H, s), 8.29 (1H, d), 8.82 (1H, d), 12.10 (1H, br s). MS (ES): $C_{23}H_{24}N_4O_4$ requires 420; found 421.2 (M+H$^+$).

EXAMPLE 87

3-(6-{5-[6-[(1-Methylethyl)oxy]-5-(methyloxy)-3-pyridinyl]-1,2,4-oxadiazol-3-yl}-1H-indol-3-yl)propanoic acid (E87)

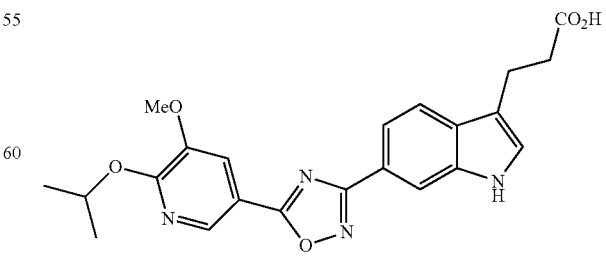

Sodium hydroxide (50 mg) was added to a solution of 3-(6-{5-[6-[(1-methylethyl)oxy]-5-(methyloxy)-3-pyridinyl]-1,2,4-oxadiazol-3-yl}-1H-indol-3-yl)propanoate (D112) (258 mg) in THF (3 mL) and water (3 mL). The resulting mixture was heated at 90° C. for 1 hour. Then 0.5 M HCl solution was added until pH was about 6. The solvent was concentrated, and the residue was dissolved in water. The precipitated solid was purified by Mass Directed Auto Prep to afford 3-(6-{5-[6-[(1-methylethyl)oxy]-5-(methyloxy)-3-pyridinyl]-1,2,4-oxadiazol-3-yl}-1H-indol-3-yl)propanoic acid (E87) (158 mg) as a white solid. δH (DMSO-$d_6$, 400 MHz): 1.35 (6H, d), 2.61 (2H, t), 2.97 (2H, t), 3.94 (3H, s), 5.42 (1H, m), 7.34 (1H, d), 7.72 (2H, m), 7.82 (1H, d), 8.13 (1H, s), 8.54 (1H, d), 11.18 (1H, s), 12.08 (1H, br s). MS (ES): $C_{22}H_{22}N_4O_5$ requires 422; found 423.2.

EXAMPLE 88

3-[5-(5-{3-chloro-4-[(1-methylethyl)oxy]phenyl}-1,2,4-oxadiazol-3-yl)-1-methyl-1H-indol-2-yl]propanoic acid (E88)

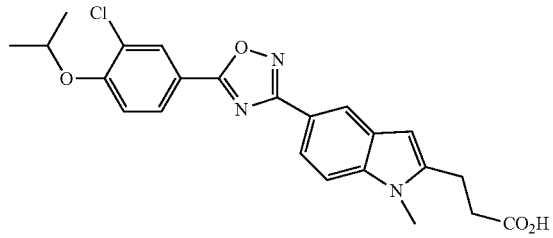

Sodium hydroxide (57 mg) was added to a solution of ethyl 3-[5-(5-{3-chloro-4-[(1-methylethyl)oxy]phenyl}-1,2,4-oxadiazol-3-yl)-1-methyl-1H-indol-2-yl]propanoate (E113) (67 mg) in THF (5 mL), isopropanol (5 mL) and water (2.5 mL). The reaction mixture was stirred at room temperature overnight. The mixture was neutralized with 2 M HCl till pH ~6.0. The solvent was concentrated, and the residue was dissolved in water. The precipitated solid was purified by Mass Directed Auto Prep to afford 3-[5-(5-{3-chloro-4-[(1-methylethyl)oxy]phenyl}-1,2,4-oxadiazol-3-yl)-1-methyl-1H-indol-2-yl]propanoic acid (E88) (1 mg). δH (DMSO-$d_6$, 400 MHz): 1.36 (6H, d), 2.71 (2H, t), 3.02 (2H, t), 3.75 (3H, s), 4.88 (1H, m), 6.40 (1H, s), 7.44 (1H, d), 7.59 (1H, d), 7.81 (1H, dd), 8.11 (1H, dd), 8.18 (1H, d), 8.24 (1H, d), 12.33 (1H, br); MS (ES): $C_{23}H_{22}ClN_3O_4$ requires 439; found 440.2 (M+H$^+$).

EXAMPLE 89

3-[5-(5-{3-cyano-4-[(1-methylethyl)oxy]phenyl}-1,2,4-oxadiazol-3-yl)-1H-indol-2-yl]propanoic acid (E89)

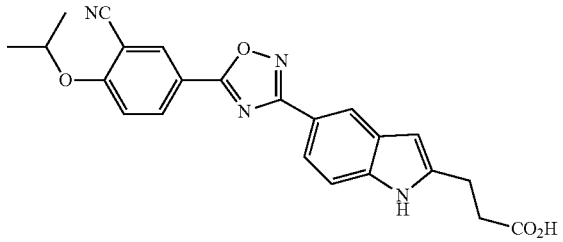

Sodium hydroxide (61 mg) was added to a solution of ethyl 3-[5-(5-{3-cyano-4-[(1-methylethyl)oxy]phenyl}-1,2,4-oxadiazol-3-yl)-1H-indol-2-yl]propanoate (D114) (68 mg) in THF (5 mL), isopropanol (5 mL) and water (2.5 mL). The reaction mixture was stirred at room temperature overnight. The mixture was neutralized with 2M HCl till pH ~6.0. The solvent was concentrated, and the residue was dissolved in water. The precipitated solid was purified by Mass Directed Auto Prep to afford 3-[5-(5-{3-cyano-4-[(1-methylethyl)oxy]phenyl}-1,2,4-oxadiazol-3-yl)-1H-indol-2-yl]propanoic acid (E89) (6 mg). δH (DMSO-$d_6$, 400 MHz): 1.38 (6H, d), 2.69 (2H, t), 2.98 (2H, t), 4.97 (1H, m), 6.33 (1H, s), 7.44 (1H, d), 7.55 (1H, d), 7.75 (1H, dd), 8.21 (1H, s), 8.40 (1H, dd), 8.49 (1H, d), 11.34 (1H, s), 12.25 (1H, s); MS (ES): $C_{23}H_{20}N_4O_4$ requires 416; found 417.2 (M+H$^+$).

EXAMPLE 90

3-[5-(5-{5-chloro-6-[(1-methylethyl)oxy]-3-pyridinyl}-1,2,4-oxadiazol-3-yl)-1H-indol-2-yl]propanoic acid (E90)

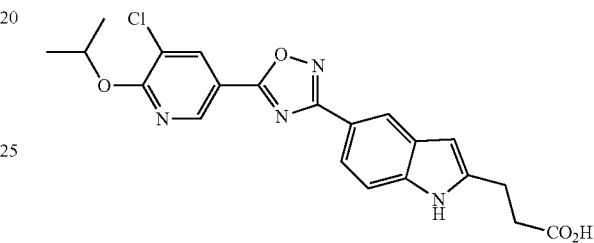

Sodium hydroxide (24 mg) was added to a solution of ethyl 3-[5-(5-{5-chloro-6-[(1-methylethyl)oxy]-3-pyridinyl}-1,2,4-oxadiazol-3-yl)-1H-indol-2-yl]propanoate (D115) (54 mg) in THF (1 mL), isopropanol (1 mL) and water (0.5 mL). The reaction mixture was stirred at room temperature until LCMS showed no starting material. The mixture was neutralized with 2 M HCl till pH ~6.0. The crude product was purified by Mass Directed Auto Prep to afford 3-[5-(5-{5-chloro-6-[(1-methylethyl)oxy]-3-pyridinyl}-1,2,4-oxadiazol-3-yl)-1H-indol-2-yl]propanoic acid (E90) (19 mg). δH (DMSO-$d_6$, 400 MHz): 1.39 (6H, d), 2.70 (2H, t), 2.99 (2H, t), 5.46 (1H, m), 6.34 (1H, s), 7.45 (1H, d), 7.76 (1H, dd), 8.22 (1H, s), 8.55 (1H, d), 8.93 (1H, d), 11.35 (1H, s), 12.26 (1H, s); MS (ES): $C_{21}H_{19}ClN_4O_4$ requires 426; found 427.1 (M+H$^+$).

EXAMPLE 91

3-[5-(5-{5-chloro-6-[(1-methylethyl)oxy]-3-pyridinyl}-1,2,4-oxadiazol-3-yl)-1-methyl-1H-indol-2-yl]propanoic acid (E91)

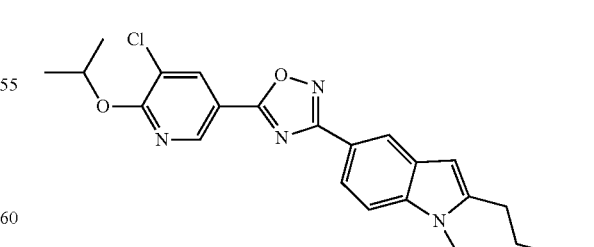

Sodium hydroxide (63 mg) was added to a solution of methyl 3-[5-(5-{5-chloro-6-[(1-methylethyl)oxy]-3-pyridinyl}-1,2,4-oxadiazol-3-yl)-1-methyl-1H-indol-2-yl]propanoate (D116) (72 mg) in THF (5 mL), isopropanol (5 mL)

and water (2.5 mL). The reaction mixture was stirred at room temperature overnight. The mixture was neutralized with 2 M HCl till pH ~6.0. The solvent was concentrated, and the residue was dissolved in water. The precipitated solid was purified by Mass Directed Auto Prep to afford 3-[5-(5-{5-chloro-6-[(1-methylethyl)oxy]-3-pyridinyl}-1,2,4-oxadiazol-3-yl)-1-methyl-1H-indol-2-yl]propanoic acid (E91) (12 mg). δH (DMSO-$d_6$, 400 MHz): 1.39 (6H, d), 2.71 (2H, t), 3.03 (2H, t), 3.75 (3H, s), 5.46 (1H, m), 6.40 (1H, s), 7.60 (1H, d), 7.82 (1H, dd), 8.24 (1H, d), 8.56 (1H, d), 8.93 (1H, d), 12.33 (1H, s); MS (ES): $C_{22}H_{21}ClN_4O_4$ requires 440; found 441.1 (M+H$^+$).

EXAMPLE 92

3-(5-{5-[6-[(1-methylethyl)oxy]-5-(trifluoromethyl)-3-pyridinyl]-1,2,4-oxadiazol-3-yl}-1H-indol-2-yl)propanoic acid (E92)

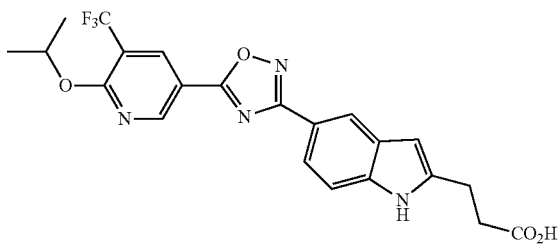

Sodium hydroxide (36 mg) was added to a solution of ethyl 3-(5-{5-[6-[(1-methylethyl)oxy]-5-(trifluoromethyl)-3-pyridinyl]-1,2,4-oxadiazol-3-yl}-1H-indol-2-yl)propanoate (D117) (89 mg) in THF (1 mL), isopropanol (1 mL) and water (0.5 mL). The mixture was stirred at room temperature until LCMS showed no starting material. The mixture was neutralized with 2 M HCl till pH ~6.0. The crude product was purified by Mass Directed Auto Prep to afford of 3-(5-{5-[6-[(1-methylethyl)oxy]-5-(trifluoromethyl)-3-pyridinyl]-1,2,4-oxadiazol-3-yl}-1H-indol-2-yl)propanoic acid (E92) (40 mg). δH (DMSO-$d_6$, 400 MHz): 1.39 (6H, d), 2.70 (2H, t), 2.99 (2H, t), 5.55 (1H, m), 6.35 (1H, s), 7.46 (1H, d), 7.77 (1H, dd), 8.23 (1H, s), 8.64 (1H, d), 9.22 (1H, d), 11.36 (1H, s), 12.25 (1H, s); MS (ES): $C_{22}H_{19}F_3N_4O_4$ requires 460; found 461.2 (M+H$^+$).

EXAMPLE 93

3-(5-{5-[6-[(1-methylethyl)oxy]-5-(methyloxy)-3-pyridinyl]-1,2,4-oxadiazol-3-yl}-1H-indol-2-yl)propanoic acid (E93)

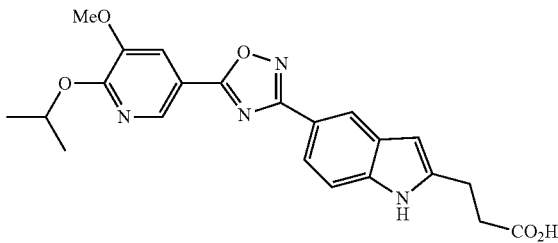

Sodium hydroxide (3 mg) was added to a solution of ethyl 3-(5-{5-[6-[(1-methylethyl)oxy]-5-(methyloxy)-3-pyridinyl]-1,2,4-oxadiazol-3-yl}-1H-indol-2-yl)propanoate (D118) (35 mg) in THF (5 mL), isopropanol (5 mL) and water (2.5 mL). The reaction mixture was stirred at room temperature overnight. The mixture was neutralized with 2 M HCl till pH ~6.0. The crude product was purified by Mass Directed Auto Prep to afford 3-(5-{5-[6-[(1-methylethyl)oxy]-5-(methyloxy)-3-pyridinyl]-1,2,4-oxadiazol-3-yl}-1H-indol-2-yl)propanoic acid (E93) (5 mg). δH (DMSO-$d_6$, 400 MHz): 1.35 (6H, d), 2.70 (2H, t), 2.99 (2H, t), 3.94 (3H, s), 5.42 (1H, m), 6.34 (1H, s), 7.45 (1H, d), 7.76 (1H, dd), 7.83 (1H, d), 8.23 (1H, s), 8.54 (1H, d), 11.34 (1H, s), 12.26 (1H, s); MS (ES): $C_{22}H_{22}N_4O_5$ requires 422; found 423.2 (M+H$^+$).

EXAMPLE 94/D94

7-(5-{3-chloro-4-[(1-methylethyl)oxy]phenyl}-1,2,4-oxadiazol-3-yl)-1H-indole-3-carboxylic acid (E94/D94)

See Description for D94

EXAMPLE 95/D95

7-(5-{3-chloro-4-[(1-methylethyl)oxy]phenyl}-1,2,4-oxadiazol-3-yl)-1-methyl-1H-indole-3-carboxylic acid (E95/D95)

See Description for D95

EXAMPLE 96

3-[7-(5-{3-cyano-4-[(1-methylethyl)oxy]phenyl}-1,2,4-oxadiazol-3-yl)-4-fluoro-1-methyl-1H-indol-3-yl]propanoic acid (E96)

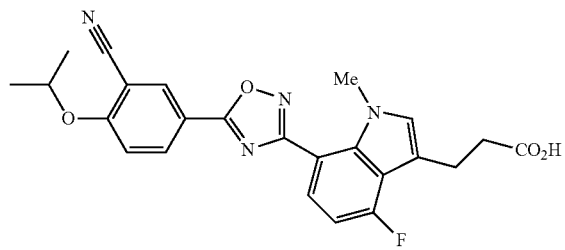

To a solution of ethyl 3-[7-(5-{3-cyano-4-[(1-methylethyl)oxy]phenyl}-1,2,4-oxadiazol-3-yl)-4-fluoro-1-methyl-1H-indol-3-yl]propanoate (D130) (349 mg) in tetrahydrofuran (THF) (10 mL), Isopropanol (5 mL) and water (2 mL), was added sodium hydroxide (293 mg). The reaction mixture was stirred at room temperature overnight. LCMS showed the reaction was complete. The reaction mixture was neutralized with 2 M HCl till pH ~6.0. After removing part of organic solvent, the residue was purified by MDAP to give 3-[7-(5-{3-cyano-4-[(1-methylethyl)oxy]phenyl}-1,2,4-oxadiazol-3-yl)-4-fluoro-1-methyl-1H-indol-3-yl]propanoic acid (E96) (204 mg). δH (DMSO-$d_6$, 400 MHz): 1.38 (6H, d), 2.61 (2H, t), 3.04 (2H, t), 3.63 (3H, s), 4.95-5.01 (1H, m), 6.96 (1H, dd), 7.23 (1H, s), 7.43 (1H, dd), 7.55 (1H, d), 8.42 (1H, dd), 8.53

(1H, d), 12.15 (1H, s); δF (DMSO-d$_6$, 376 MHz): −120.5; MS (ES): C$_{24}$H$_{21}$FN$_4$O$_4$ requires 448; found 449.2 (M+H$^+$).

EXAMPLE 97

3-[7-(5-{3-Chloro-4-[(1-methylethyl)oxy]phenyl}-1,2,4-oxadiazol-3-yl)-5-fluoro-1H-indol-3-yl]propanoic acid (E97)

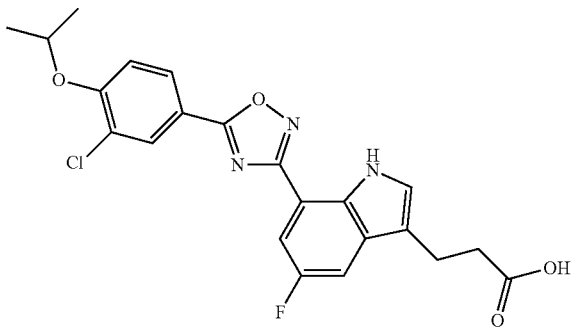

Sodium hydroxide (40 mg) was added to a solution of ethyl 3-[7-(5-{3-chloro-4-[(1-methylethyl)oxy]phenyl}-1,2,4-oxadiazol-3-yl)-5-fluoro-1H-indol-3-yl]propanoate (D137) (287 mg) in THF (3 mL) and water (3 mL). The reaction mixture was stirred at 90° C. for 1 hour. Then 0.5 M HCl was added until pH was about 6. The solvent was concentrated, and the residue was dissolved in water. The precipitated solid was purified by MDAP to afford 3-[7-(5-{3-chloro-4-[(1-methylethyl)oxy]phenyl}-1,2,4-oxadiazol-3-yl)-5-fluoro-1H-indol-3-yl]propanoic acid (E97) (147 mg) as a white solid. δH (DMSO-d$_6$, 400 MHz): 1.36 (6H, d), 2.61 (2H, t), 2.96 (2H, t), 4.87-4.93 (1H, m), 7.35 (1H, s), 7.46 (1H, d), 7.65-7.70 (2H, m), 8.21 (1H, d), 8.39 (1H, d), 10.96 (1H, s), 12.12 (1H, br s); δF (DMSO-d$_6$, 376 MHz): −124.9; MS (ES): C$_{22}$H$_{19}$ClFN$_3$O$_4$ requires 443; found 444.1 (M+H$^+$).

EXAMPLE 98

3-[7-(5-{3-Chloro-4-[(1-methylethyl)oxy]phenyl}-1,2,4-oxadiazol-3-yl)-5-fluoro-1-methyl-1H-indol-3-yl]propanoic acid (E98)

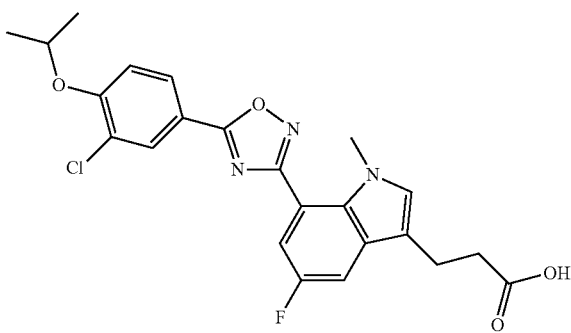

Potassium hydroxide (100 mg) was added to a solution of ethyl 3-[7-(5-{3-chloro-4-[(1-methylethyl)oxy]phenyl}-1,2,4-oxadiazol-3-yl)-5-fluoro-1H-indol-3-yl]propanoate (D137) (210 mg) and iodomethane (0.28 mL) in DMSO (3 mL) at RT. The reaction mixture was stirred at RT overnight. Then the reaction was quenched with saturated ammonium chloride, and the residue was extracted with EA for 3 times. The combined organic solution was washed with brine, and dried over anhydrous sodium sulfate. The dried solution was concentrated to afford the crude product as a yellow oil.

This oil was dissolved in THF (3 mL) and water (3 mL). Sodium hydroxide (40 mg) was then added to the mixture. The reaction mixture was stirred at 90° C. for 1 hour. Then 0.5 M HCl was added until pH was about 6. The solvent was removed, and the residue was dissolved in water. The precipitate was purified by MDAP to afford 3-[7-(5-{3-chloro-4-[(1-methylethyl)oxy]phenyl}-1,2,4-oxadiazol-3-yl)-5-fluoro-1-methyl-1H-indol-3-yl]propanoic acid (E98) (51 mg) as an off-white solid. δH (DMSO-d$_6$, 400 MHz): 1.35 (6H, d), 2.59 (2H, t), 2.93 (2H, t), 3.62 (3H, s), 4.86-4.92 (1H, m), 7.28 (1H, s), 7.30 (1H, dd), 7.45 (1H, d), 7.63 (1H, dd), 8.13 (1H, dd), 8.20 (1H, d), 12.12 (1H, br s); δF (DMSO-d$_6$, 376 MHz): −125.6; MS (ES): C$_{23}$H$_{21}$ClFN$_3$O$_4$ requires 457. found 458.1 (M+H$^+$).

EXAMPLE 99

3-[7-(5-{3-Cyano-4-[(1-methylethyl)oxy]phenyl}-1,2,4-oxadiazol-3-yl)-5-fluoro-1H-indol-3-yl]propanoic acid (E99)

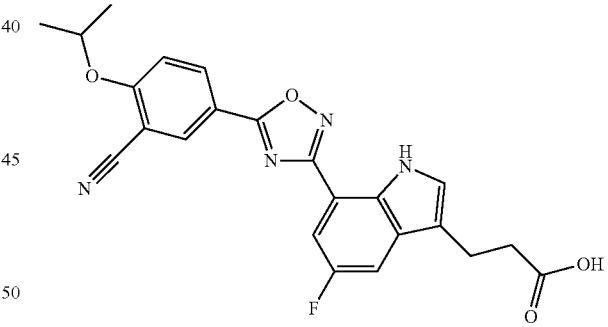

Sodium hydroxide (100 mg) was added to a solution of ethyl 3-[7-(5-{3-cyano-4-[(1-methylethyl)oxy]phenyl}-1,2,4-oxadiazol-3-yl)-5-fluoro-1H-indol-3-yl]propanoate (D138) (230 mg) in THF (4 mL) and water (4 mL). The reaction mixture was stirred at 90° C. for 3 hours. Then 0.5 M HCl was added until pH was about 6. The solvent was concentrated, and the residue was dissolved in water. The precipitate was purified by MDAP and recrystallized in MeCN to afford 3-[7-(5-{3-cyano-4-[(1-methylethyl)oxy]phenyl}-1,2,4-oxadiazol-3-yl)-5-fluoro-1H-indol-3-yl]propanoic acid (E99) (135 mg) as an off-white solid. δH (DMSO-d$_6$, 400 MHz): 1.39 (6H, d), 2.63 (2H, t), 2.97 (2H, t), 4.96-5.02 (1H, m), 7.36 (1H, d), 7.55 (1H, d), 7.64-7.69 (2H, m), 8.49 (1H, dd), 8.72 (1H, d), 10.97 (1H, s), 12.13 (1H, br s). δF (DMSO-$d_6$, 376 MHz): −124.9. MS (ES): $C_{23}H_{19}FN_4O_4$ requires 434; found 435.2 ($M+H^+$).

EXAMPLE 100

3-[7-(5-{3-Cyano-4-[(1-methylethyl)oxy]phenyl}-1,2,4-oxadiazol-3-yl)-5-fluoro-1-methyl-1H-indol-3-yl]propanoic acid (E100)

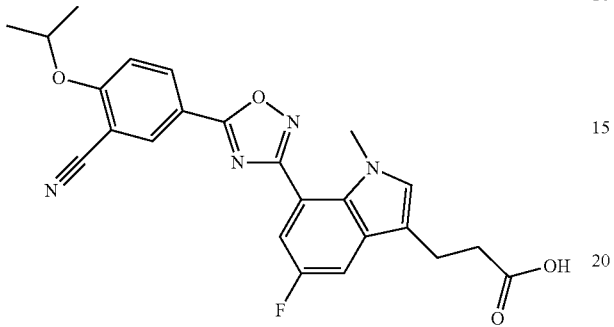

Potassium hydroxide (291 mg) was added to a solution of ethyl 3-[7-(5-{3-cyano-4-[(1-methylethyl)oxy]phenyl}-1,2,4-oxadiazol-3-yl)-5-fluoro-1H-indol-3-yl]propanoate (D138) (600 mg) and iodomethane (1.22 mL) in DMSO (3 mL) at RT. The reaction mixture was stirred at RT overnight. Then the reaction was quenched with saturated ammonium chloride, and the residue was extracted with EA for 3 times. The combined organic solution was washed with brine, and dried over anhydrous sodium sulfate. The dried solution was concentrated to afford the crude product as a yellow oil. This oil was dissolved in THF (4 mL) and water (4 mL). Sodium hydroxide (100 mg) was then added to the mixture. The reaction mixture was stirred at 90° C. for 1 hour, and at RT for another 24 hours. Then 0.5 M HCl was added until pH was about 6. The solvent was removed, and the residue was dissolved in water. The precipitate was purified by MDAP to afford 3-[7-(5-{3-cyano-4-[(1-methylethyl)oxy]phenyl}-1,2,4-oxadiazol-3-yl)-5-fluoro-1-methyl-1H-indol-3-yl]propanoic acid (E100) (304 mg) as an off-white solid. δH (DMSO-$d_6$, 400 MHz): 1.37 (6H, d), 2.59 (2H, t), 2.93 (2H, t), 3.62 (3H, s), 4.95-5.01 (1H, m), 7.29 (1H, s), 7.31 (1H, d), 7.56 (1H, d), 7.64 (1H, dd), 8.42 (1H, dd), 8.55 (1H, d), 12.12 (1H, br s). δF (DMSO-$d_6$, 376 MHz): −125.6. MS (ES): $C_{24}H_{21}FN_4O_4$ requires 448; found 449.2 ($M+H^+$).

EXAMPLE 101

3-[7-(5-{5-Chloro-6-[(1-methylethyl)oxy]-3-pyridinyl}-1,2,4-oxadiazol-3-yl)-5-fluoro-1H-indol-3-yl]propanoic acid (E101)

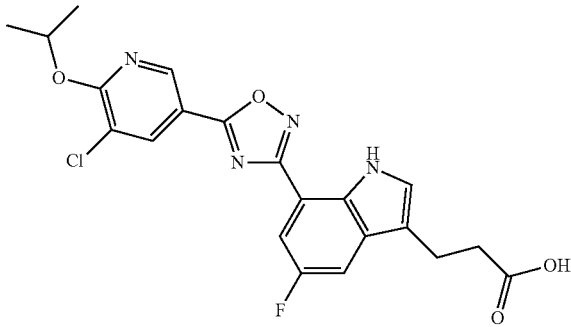

Sodium hydroxide (40 mg) was added to a solution of ethyl 3-[7-(5-{5-chloro-6-[(1-methylethyl)oxy]-3-pyridinyl}-1,2,4-oxadiazol-3-yl)-5-fluoro-1H-indol-3-yl]propanoate (D139) (330 mg) in THF (3 mL) and water (3 mL). The reaction mixture was stirred at 90° C. for 1 hour. Then 0.5 M HCl was added until pH was about 6. The solvent was concentrated, and the residue was dissolved in water. The precipitated solid was purified by MDAP to afford 3-[7-(5-{5-chloro-6-[(1-methylethyl)oxy]-3-pyridinyl}-1,2,4-oxadiazol-3-yl)-5-fluoro-1H-indol-3-yl]propanoic acid (E101) (150 mg) as a white solid. δH (DMSO-$d_6$, 400 MHz): 1.39 (6H, d), 2.62 (2H, t), 2.96 (2H, t), 5.43-5.49 (1H, m), 7.35 (1H, d), 7.65-7.69 (2H, m), 8.77 (1H, s), 9.07 (1H, s), 10.99 (1H, s), 12.13 (1H, br s). δF (DMSO-$d_6$, 376 MHz): −124.9. MS (ES): $C_{21}H_{18}ClFN_4O_4$ requires 444. found 445.1 ($M+H^+$).

EXAMPLE 102

3-[7-(5-{5-Chloro-6-[(1-methylethyl)oxy]-3-pyridinyl}-1,2,4-oxadiazol-3-yl)-5-fluoro-1-methyl-1H-indol-3-yl]propanoic acid (E102)

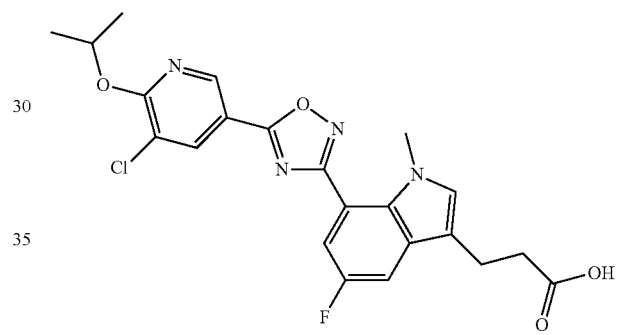

Potassium hydroxide (90 mg) was added to a solution of ethyl 3-[7-(5-{5-chloro-6-[(1-methylethyl)oxy]-3-pyridinyl}-1,2,4-oxadiazol-3-yl)-5-fluoro-1H-indol-3-yl]propanoate (D139) (189 mg) and iodomethane (0.25 mL) in DMSO (3 mL) at RT. The reaction mixture was stirred at RT for 5 hours. Then the reaction was quenched with saturated ammonium chloride, and extracted with EA for 3 times. The combined organic solution was washed with brine and dried over anhydrous sodium sulfate. The dried solution was concentrated to afford the crude product as a yellow oil. This oil was dissolved in THF (3 mL) and water (3 mL). Sodium hydroxide (40 mg) was then added to the mixture. The reaction mixture was stirred at 90° C. for 1 hour, and at RT for another 24 hours. Then 0.5 M HCl was added until pH was about 6. The solvent was concentrated, and the residue was dissolved in water. The precipitated solid was purified by MDAP to afford 3-[7-(5-{5-chloro-6-[(1-methylethyl)oxy]-3-pyridinyl}-1,2,4-oxadiazol-3-yl)-5-fluoro-1-methyl-1H-indol-3-yl]propanoic acid (E102) (112 mg) as an off-white solid. δH (DMSO-$d_6$, 400 MHz): 1.38 (6H, d), 2.58 (2H, t), 2.93 (2H, t), 3.62 (3H, s), 5.42-5.48 (1H, m), 7.29 (1H, s), 7.30 (1H, dd), 7.65 (1H, dd), 8.59 (1H, d), 8.96 (1H, d), 12.13 (1H, br s). δF (DMSO-$d_6$, 376 MHz): −125.6. MS (ES): $C_{22}H_{20}ClFN_4O_4$ requires 458; found 459.1 ($M+H^+$).

EXAMPLE 103

3-[7-(5-{3-Chloro-4-[(1-methylethyl)oxy]phenyl}-1,
2,4-oxadiazol-3-yl)-6-fluoro-1H-indol-3-yl]propanoic acid (E103)

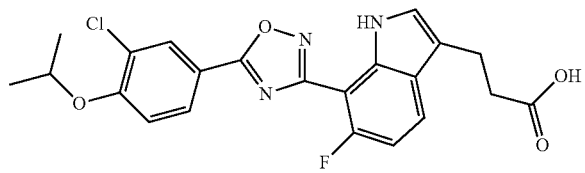

To a solution of ethyl 3-[7-(5-{3-chloro-4-[(1-methylethyl)oxy]phenyl}-1,2,4-oxadiazol-3-yl)-6-fluoro-1H-indol-3-yl]propanoate (D146) (320 mg) in isopropanol (7 mL) and water (7.00 mL) was added NaOH (6.78 mL, 0.5 M aqueous solution) at room temperature. The reaction suspension was stirred at 90° C. for 2 hours, and the solution turned clear. Isopropanol was removed in vacuo and water (8 mL) was added to the residue. The aqueous solution was acidified to pH=1 and extracted with ethyl acetate (3×10 mL). The combined organic phases were dried over sodium sulphate. The organic solution was concentrated and the residue was purified by MDAP to afford 3-[7-(5-{3-chloro-4-[(1-methylethyl)oxy]phenyl}-1,2,4-oxadiazol-3-yl)-6-fluoro-1H-indol-3-yl]propanoic acid (E103) (140 mg) as a white solid. δH (DMSO-$d_6$, 400 MHz): 1.31 (6H, d), 2.56 (2H, t), 2.92 (2H, t), 4.85 (1H, m), 7.03 (1H, m), 7.22 (1H, s), 7.39 (1H, d), 7.74 (1H, m), 8.21 (1H, dd), 8.47 (1H, d), 11.01 (1H, s), 12.07 (1H, s). MS (ES): $C_{22}H_{19}ClFN_3O_4$ requires 443; found 444.2 (M+H$^+$).

EXAMPLE 104

3-[7-(5-{3-Chloro-4-[(1-methylethyl)oxy]phenyl}-1,
2,4-oxadiazol-3-yl)-6-fluoro-1-methyl-1H-indol-3-yl]propanoic acid (E104)

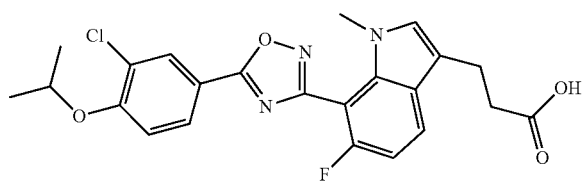

To a solution of ethyl 3-[7-(5-{3-chloro-4-[(1-methylethyl)oxy]phenyl}-1,2,4-oxadiazol-3-yl)-6-fluoro-1-methyl-1H-indol-3-yl]propanoate (D147) (330 mg) in isopropanol (7 mL) and water (7 mL) was added NaOH (6.79 mL, 0.5 M aqueous solution) at room temperature. The reaction suspension was stirred at 90° C. for 2 hours, and the solution turned clear. Isopropanol was removed in vacuo and water (8 mL) was added to the residue. The aqueous solution was acidified to pH=1 and extracted with ethyl acetate (3×10 mL). The combined organic phase was dried over sodium sulphate. The organic solution was concentrated and the residue was purified by MDAP to afford 3-[7-(5-{3-chloro-4-[(1-methylethyl)oxy]phenyl}-1,2,4-oxadiazol-3-yl)-6-fluoro-1-methyl-1H-indol-3-yl]propanoic acid (E104) (136 mg) as a white solid. δH (DMSO-$d_6$, 400 MHz): 1.29 (6H, s), 2.53 (2H, t), 2.87 (2H, t), 3.29 (3H, s), 4.83 (1H, m), 7.02 (1H, m), 7.10 (1H, s), 7.39 (1H, d), 7.75 (1H, m), 8.07 (1H, dd), 8.14 (1H, d), 12.07 (1H, s). MS (ES): $C_{23}H_{21}ClFN_3O_4$ requires 457; found 458.2 (M+H$^+$).

EXAMPLE 105

3-[7-(5-{3-Cyano-4-[(1-methylethyl)oxy]phenyl}-1,
2,4-oxadiazol-3-yl)-6-fluoro-1H-indol-3-yl]propanoic acid (E105)

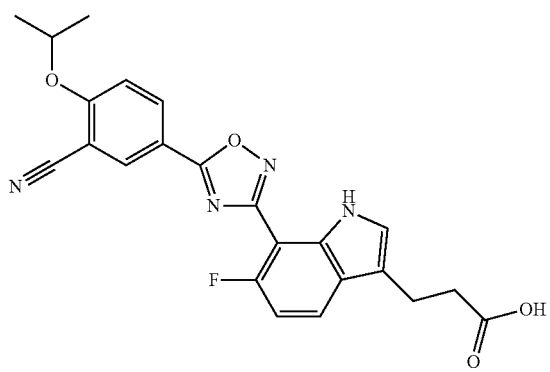

Sodium hydroxide (25 mg) was added to a solution of ethyl 3-[7-(5-{3-cyano-4-[(1-methylethyl)oxy]phenyl}-1,2,4-oxadiazol-3-yl)-6-fluoro-1H-indol-3-yl]propanoate (D148) (875 mg) in THF (4 mL) and water (4 mL). The reaction mixture was stirred at 90° C. for 1 hour, and then at RT for another 24 hours. Then 0.5 M HCl was added until pH was about 6. The solvent was removed, and the residue was dissolved in water. The precipitated solid was purified by MDAP to afford 3-[7-(5-{3-cyano-4-[(1-methylethyl)oxy]phenyl}-1,2,4-oxadiazol-3-yl)-6-fluoro-1H-indol-3-yl]propanoic acid (E105) (101.6 mg) as an off-white solid. δH (DMSO-$d_6$, 400 MHz): 1.39 (6H, d), 2.63 (2H, t), 2.99 (2H, t), 4.98-5.04 (1H, m), 7.10 (1H, dd), 7.30 (1H, s), 7.56 (1H, d), 7.81 (1H, dd), 8.56 (1H, dd), 8.90 (1H, d), 11.11 (1H, s), 12.14 (1H, br s); δF (DMSO-$d_6$, 376 MHz): −115.5; MS (ES): $C_{23}H_{19}FN_4O_4$ requires 434; found 435.2 (M+H$^+$).

EXAMPLE 106

3-[7-(5-{3-Cyano-4-[(1-methylethyl)oxy]phenyl}-1,
2,4-oxadiazol-3-yl)-6-fluoro-1-methyl-1H-indol-3-yl]propanoic acid (E106)

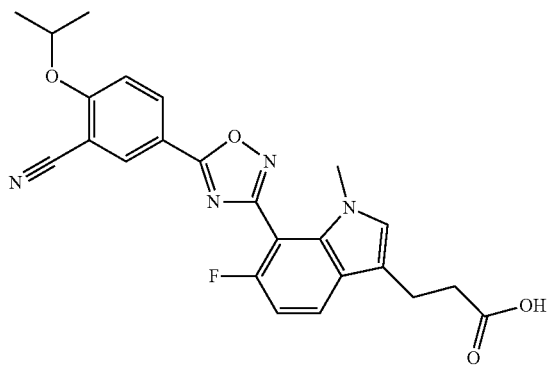

Potassium hydroxide (237 mg) was added to a solution of ethyl 3-[7-(5-{3-cyano-4-[(1-methylethyl)oxy]phenyl}-1,2,4-oxadiazol-3-yl)-6-fluoro-1H-indol-3-yl]propanoate (D148) (450 mg) and iodomethane (0.76 mL) in DMSO (5 mL) at RT. The reaction mixture was stirred at RT for 4 hours.

Then the reaction was quenched with saturated ammonium chloride, and extracted with EtOAc for 3 times. The combined organic solution was washed with brine, and dried over anhydrous sodium sulfate. The dried solution was concentrated to afford the crude product as a brown oil. This oil was dissolved in THF (4 mL) and water (4 mL). Sodium hydroxide (100 mg) was then added to the mixture. The reaction mixture was stirred at 90° C. for 1 hour, and then at RT for another 24 hours. Then 0.5 M HCl was added until pH was about 6. The solvent was concentrated, and the residue was dissolved in water. The precipitated solid was purified by MDAP to afford 3-[7-(5-{3-cyano-4-[(1-methylethyl)oxy]phenyl}-1,2,4-oxadiazol-3-yl)-6-fluoro-1-methyl-1H-indol-3-yl]propanoic acid (E106) (249 mg) as an off-white solid. δH (DMSO-d$_6$, 400 MHz): 1.31 (6H, d), 2.53 (2H, t), 2.88 (2H, t), 3.33 (3H, s), 4.89-4.95 (1H, m), 7.02 (1H, t), 7.11 (1H, s), 7.50 (1H, d), 7.75 (1H, dd), 8.36 (1H, dd), 8.49 (1H, d), 12.06 (1H, br s); δF (DMSO-d$_6$, 376 MHz): −123.0; MS (ES): C$_{24}$H$_{21}$FN$_4$O$_4$ requires 448; found 449.1 (M+H$^+$).

EXAMPLE 107

3-[7-(5-{5-Chloro-6-[(1-methylethyl)oxy]-3-pyridinyl}-1,2,4-oxadiazol-3-yl)-6-fluoro-1H-indol-3-yl]propanoic acid (E107)

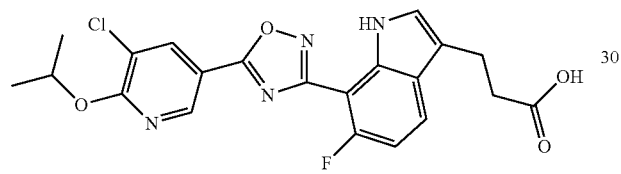

To a solution of ethyl 3-[7-(5-{5-chloro-6-[(1-methylethyl)oxy]-3-pyridinyl}-1,2,4-oxadiazol-3-yl)-6-fluoro-1H-indol-3-yl]propanoate (D149) (260 mg) in isopropanol (7 mL) and water (7 mL) was added NaOH (5.5 mL, 0.5 M aq) at room temperature. The reaction suspension was stirred at 90° C. for 2 hours, and the solution turned clear. Isopropanol was removed in vacuo and water (8 mL) was added to the residue. The aqueous solution was acidified to pH=1 and extracted with ethyl acetate (3×10 mL). The combined organic phase was dried over sodium sulphate. The organic solution was concentrated and purified by MDAP to afford 3-[7-(5-{5-chloro-6-[(1-methylethyl)oxy]-3-pyridinyl}-1,2,4-oxadiazol-3-yl)-6-fluoro-1H-indol-3-yl]propanoic acid (E107) (174 mg) as a white solid. δH (DMSO-d$_6$, 400 MHz): 1.34 (6H, d), 2.57 (2H, t), 2.92 (2H, t), 5.40 (1H, m), 7.03 (1H, m), 7.22 (1H, d), 7.74 (1H, m), 8.82 (1H, d), 9.08 (1H, d), 11.04 (1H, s), 12.08 (1H, s). MS (ES): C$_{21}$H$_{18}$ClFN$_4$O$_4$ requires 444; found 445.2 (M+H$^+$).

EXAMPLE 108

3-[7-(5-{5-Chloro-6-[(1-methylethyl)oxy]-3-pyridinyl}-1,2,4-oxadiazol-3-yl)-6-fluoro-1-methyl-1H-indol-3-yl]propanoic acid (E108)

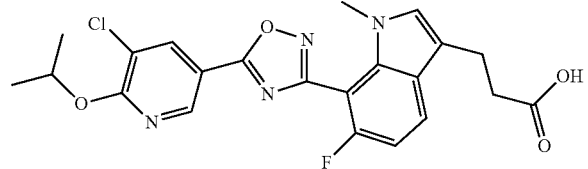

To a solution of ethyl 3-[7-(5-{5-chloro-6-[(1-methylethyl)oxy]-3-pyridinyl}-1,2,4-oxadiazol-3-yl)-6-fluoro-1-methyl-1H-indol-3-yl]propanoate (D150) (270 mg) in isopropanol (7 mL) and water (7 mL) was added NaOH (5.6 mL, 0.5 M aq) at room temperature. The reaction suspension was stirred at 90° C. for 2 hours until the solution turned clear. Isopropanol was removed in vacuo and water (8 mL) was added to the residue. The aqueous solution was acidified to pH=1 and extracted with ethyl acetate (3×10 mL). The combined organic phase was dried over sodium sulphate. The organic solution was concentrated and the residue was purified by MDAP to afford 3-[7-(5-{5-chloro-6-[(1-methylethyl)oxy]-3-pyridinyl}-1,2,4-oxadiazol-3-yl)-6-fluoro-1-methyl-1H-indol-3-yl]propanoic acid (E108) (72 mg) as a white solid. δH (DMSO-d$_6$, 400 MHz): 1.32 (6H, d), 2.53 (2H, t), 2.88 (2H, t), 3.28 (3H, s), 5.39 (1H, m), 7.02 (1H, m), 7.11 (1H, s), 7.75 (1H, m), 8.53 (1H, d), 8.90 (1H, d), 12.07 (1H, s). MS (ES): C$_{22}$H$_{20}$ClFN$_4$O$_4$ requires 458; found 459.2 (M+H$^+$).

EXAMPLE 109

3-[6-(5-{3-Chloro-4-[(1-methylethyl)oxy]phenyl}-1,2,4-oxadiazol-3-yl)-5-fluoro-1H-indol-3-yl]propanoic acid (E109)

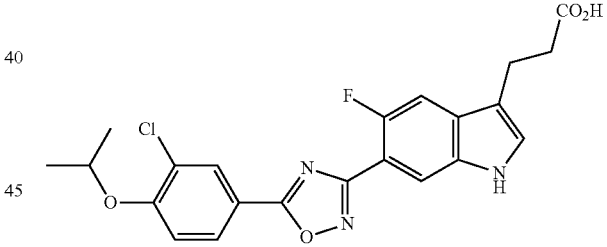

To a solution of ethyl 3-[6-(5-{3-chloro-4-[(1-methylethyl)oxy]phenyl}-1,2,4-oxadiazol-3-yl)-5-fluoro-1H-indol-3-yl]propanoate (D156) (120 mg) in isopropanol (25 mL) and water (5 mL) was added 0.5 mL of 20% aqueous NaOH solution. The reaction mixture was stirred at 20° C. overnight. Afterwards, the mixture was adjusted to pH 3 by addion of 6 M HCl and evaporated. The residue was treated with 6 mL DMF and filtered. The filtrate was purified by MDAP to give the designed product 3-[6-(5-{3-chloro-4-[(1-methylethyl)oxy]phenyl}-1,2,4-oxadiazol-3-yl)-5-fluoro-1H-indol-3-yl]propanoic acid (E109) (45 mg). δH (DMSO-d$_6$, 400 MHz): 1.30 (6H, d), 2.59 (2H, t), 2.88 (2H, t), 4.82 (1H, m), 7.37 (1H, s), 7.38 (1H, d), 7.48 (1H, d), 8.04 (1H, dd), 8.06 (1H, d), 8.12 (1H, d), 11.20 (1H, s); δF (DMSO-d$_6$, 376 MHz): −121.5; MS (ES): C$_{22}$H$_{19}$ClFN$_3$O$_4$ requires 443.1; found 444.2 (M+H$^+$).

EXAMPLE 110

3-[6-(5-{3-Cyano-4-[(1-methylethyl)oxy]phenyl}-1,2,4-oxadiazol-3-yl)-5-fluoro-1H-indol-3-yl]propanoic acid (E110)

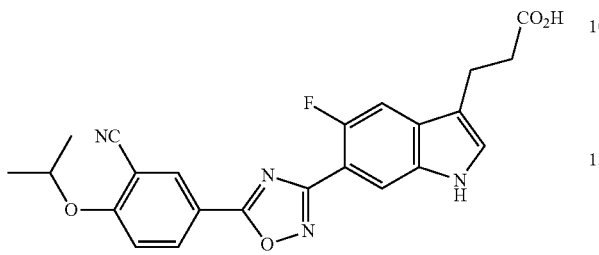

To a solution of ethyl 3-[6-(5-{3-cyano-4-[(1-methylethyl)oxy]phenyl}-1,2,4-oxadiazol-3-yl)-5-fluoro-1H-indol-3-yl]propanoate (D157) (180 mg) in isopropanol (25 mL) and water (5 mL) was added 0.8 mL 20% aqueous NaOH solution. The reaction mixture was stirred at 20° C. overnight. Afterwards, the mixture was adjusted to pH 3 by addion of 6 M HCl and evaporated. The residue was treated with 6 mL DMF and filtered. The filtrate was purified by MDAP to give the designed product 3-[6-(5-{3-cyano-4-[(1-methylethyl)oxy]phenyl}-1,2,4-oxadiazol-3-yl)-5-fluoro-1H-indol-3-yl]propanoic acid (E110) (115 mg). δH (DMSO-d$_6$, 400 MHz): 1.32 (6H, d), 2.55 (2H, t), 2.88 (2H, t), 4.92 (1H, m), 7.37 (1H, s), 7.47 (1H, d), 7.50 (1H, d), 8.05 (1H, d), 8.35 (1H, dd), 8.44 (1H, d), 11.23 (1H, s), 12.05 (1H, s); δF (DMSO-d$_6$, 376 MHz): −121.7; MS (ES): C$_{23}$H$_{19}$FN$_4$O$_4$ requires 434; found 435.2 (M+H$^+$).

EXAMPLE 111

3-[6-(5-{5-Chloro-6-[(1-methylethyl)oxy]-3-pyridinyl}-1,2,4-oxadiazol-3-yl)-5-fluoro-1H-indol-3-yl]propanoic acid (E111)

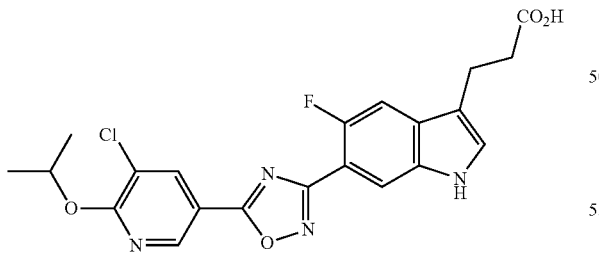

To a solution of ethyl 3-[6-(5-{5-chloro-6-[(1-methylethyl)oxy]-3-pyridinyl}-1,2,4-oxadiazol-3-yl)-5-fluoro-1H-indol-3-yl]propanoate (D158) (250 mg) in isopropanol (20 mL) and water (4 mL) was added 0.8 mL of 20% NaOH aqueous solution. The mixture was then stirred overnight. Afterwards, the solution was adjusted to pH 3 by addition of concentrated HCl and evaporated in vacuo. The residue was treated with 8 mL DMF. The insolubles were filtered and the filtrate was purified by MDAP. The solvent was freeze dried to give 3-[6-(5-{5-chloro-6-[(1-methylethyl)oxy]-3-pyridinyl}-1,2,4-oxadiazol-3-yl)-5-fluoro-1H-indol-3-yl]propanoic acid (E111) (80 mg). δH (DMSO-d$_6$, 400 MHz): 1.32 (6H, d), 2.54 (2H, t), 2.88 (2H, t), 5.40 (1H, m), 7.37 (1H, s), 7.48 (1H, d), 8.05 (1H, d), 8.50 (1H, d), 8.87 (1H, d), 11.24 (1H, s), 12.05 (1H, s); δF (DMSO-d$_6$, 376 MHz): −121.6; MS (ES): C$_{21}$H$_{18}$ClFN$_4$O$_4$ requires 444; found 445.2 (M+H$^+$).

EXAMPLE 112

3-[5-(5-{3-Chloro-4-[(1-methylethyl)oxy]phenyl}-1,2,4-oxadiazol-3-yl)-7-fluoro-1H-indol-2-yl]propanoic acid (E112)

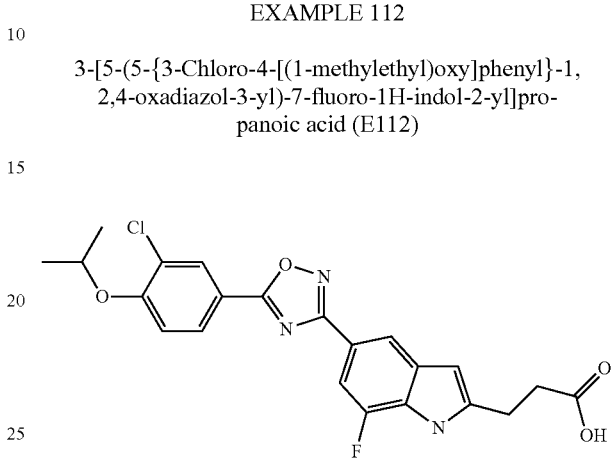

To a suspension of ethyl 3-[5-(5-{3-chloro-4-[(1-methylethyl)oxy]phenyl}-1,2,4-oxadiazol-3-yl)-7-fluoro-1H-indol-2-yl]propanoate (D164) (240 mg) in isopropanol (15 mL) was added 20% sodium hydroxide (509 mg) solution, then the reaction mixture was stirred at room temperature overnight. The mixture was acidified with HCl (2 M) to pH 4. The solvent of the reaction was removed by evaporation. The residue was dissolved in DMF (5 mL), the precipitation was filtered then the filtrate was purified by Mass Directed Auto Prep to afford 3-[5-(5-{3-chloro-4-[(1-methylethyl)oxy]phenyl}-1,2,4-oxadiazol-3-yl)-7-fluoro-1H-indol-2-yl]propanoic acid (E112) (75.3 mg) as a white solid. δH (DMSO-d$_6$, 400 MHz): 1.30 (6H, d), 2.65 (2H, t), 2.93 (2H, t), 4.8 (1H, m), 6.38 (1H, s), 7.36 (1H, d), 7.44 (1H, d), 8.01 (1H, s), 8.05 (1H, d), 8.11 (1H, s), 11.76 (1H, s), 12.20 (1H, s); δF (DMSO-d$_6$, 376 MHz): −132.6; MS (ES): C$_{22}$H$_{19}$ClFN$_3$O$_4$ requires 443; found 444.2 (M+H$^+$).

EXAMPLE 113

3-[5-(5-{3-Cyano-4-[(1-methylethyl)oxy]phenyl}-1,2,4-oxadiazol-3-yl)-7-fluoro-1H-indol-2-yl]propanoic acid (E113)

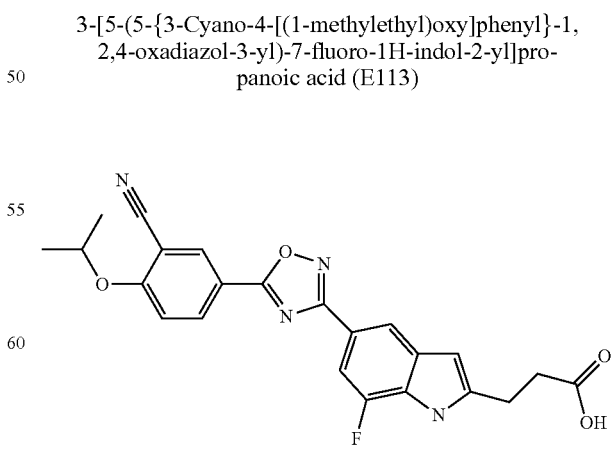

To a suspension of ethyl 3-[5-(5-{3-cyano-4-[(1-methylethyl)oxy]phenyl}-1,2,4-oxadiazol-3-yl)-7-fluoro-1H-indol-2-yl]propanoate (D165) (310 mg) in isopropanol (20 mL) was added 20% sodium hydroxide (670 mg) solution. Then the reaction mixture was stirred at room temperature overnight. The mixture was acidified with HCl (2 M) to pH 4. The solvent of the reaction was removed by evaporation. The residue was dissolved in DMF (5 mL), the precipitation was filtered then the filtrate was purified by Mass Directed Auto Prep to afford 3-[5-(5-{3-cyano-4-[(1-methylethyl)oxy]phenyl}-1,2,4-oxadiazol-3-yl)-7-fluoro-1H-indol-2-yl]propanoic acid (E113) (54.6 mg) as a white solid. δH (DMSO-$d_6$, 400 MHz): 1.38 (6H, d), 2.70 (2H, t), 2.99 (2H, t), 4.97 (1H, m), 6.44 (1H, s), 7.49 (1H, d), 7.54 (1H, d), 8.07 (1H, s), 8.39 (1H, dd), 8.50 (1H, d), 11.82 (1H, s). δF (DMSO-$d_6$, 376 MHz): −132.6; MS (ES): $C_{23}H_{19}FN_4O_4$ requires 434; found 435.2 (M+H$^+$).

EXAMPLE 114

3-[5-(5-{5-Chloro-6-[(1-methylethyl)oxy]-3-pyridinyl}-1,2,4-oxadiazol-3-yl)-7-fluoro-1H-indol-2-yl] propanoic acid (E114)

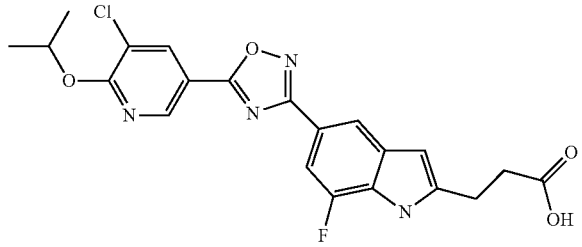

To a suspension of ethyl 3-[5-(5-{5-chloro-6-[(1-methylethyl)oxy]-3-pyridinyl}-1,2,4-oxadiazol-3-yl)-7-fluoro-1H-indol-2-yl]propanoate (D166) (720 mg) in isopropanol (20 mL) was added 20% sodium hydroxide (1.52 g) solution, then the reaction mixture was stirred at room temperature overnight. The mixture was acidified with HCl (2 M) to pH 4. The solvent of the reaction was removed by evaporation. The residue was dissolved in DMF (5 mL). The precipitation was filtered and the filtrate was purified by Mass Directed Auto Prep to afford 3-[5-(5-{5-chloro-6-[(1-methylethyl)oxy]-3-pyridinyl}-1,2,4-oxadiazol-3-yl)-7-fluoro-1H-indol-2-yl] propanoic acid (E114) (41 mg) as a white solid. δH (DMSO-$d_6$, 400 MHz): 1.32 (6H, s), 2.65 (2H, t), 2.94 (2H, t), 5.38 (1H, m), 6.38 (1H, s), 7.43 (1H, d), 8.01 (1H, s), 8.48 (1H, d), 8.85 (1H, d), 11.78 (1H, s); δF (DMSO-$d_6$, 376 MHz): −132.6; MS (ES): $C_{21}H_{18}ClFN_4O_4$ requires 444. found 445.2 (M+H$^+$).

Membrane Preparation

For membrane preparations all steps were performed at 4° C. Rat hepatoma cells stably expressing the human S1P1 receptor or Rat Basophilic Leukaemia cells (RBL) stably expressing human S1P3 receptor were grown to 80% confluency before being harvested into 10 ml Phospho-Buffered Saline (PBS) and centrifuged at 1200 rpm for 5 minutes. After removal of the supernatant, the pellet was re-suspended and cells were homogenised within a glass Warning blender for 2 bursts of 15 secs in 200 mls of buffer (50 mM HEPES, 1 mM leupeptin, 25 μg/ml bacitracin, 1 mM EDTA, 1 mM PMSF, 2 μM pepstatin A). The blender was plunged into ice for 5 mins after the first burst and 10-40 mins after the final burst to allow foam to dissipate. The material was then spun at 500 g for 20 mins and the supernatant spun for 36 mins at 48,000 g. The pellet was resuspended in the same buffer as above but without PMSF and pepstatin A. The material was then forced through a 0.6 mm needle, made up to the required volume, (usually ×4 the volume of the original cell pellet), aliquoted and stored frozen at −80° C.

S1P1 GTPγS Assay

Human S1P1 rat hepatoma membranes (1.5 μg/well) were adhered to a wheatgerm agglutinin (WGA)-coated scintillation proximity assay (SPA) beads (0.125 mg/well) in assay buffer (HEPES 20 mM, MgCl$_2$ 10 mM, NaCl 100 mM and pH adjusted to 7.4 using KOH 5M, GDP 10 μM FAC (final assay concentration) and saponin 90 μg/ml FAC was also added).

After 30 minutes pre-coupling on ice the bead and membrane suspension was dispensed into a white Greiner polypropylene LV384-well plate (5 μl/well), containing 0.1 μl of the compound. 5 μl/well [$^{35}$S]-GTPγS (0.5 nM final radioligand conc) made up in assay buffer was then added to agonist plates. The final assay cocktail (10.1 μl) was then centrifuged at 1000 rpm for 5 minutes then read immediately on a Viewlux reader.

All test compounds were dissolved in DMSO at a concentration of 10 mM and were prepared in 100% DMSO using a 1 in 4 dilution step to provide 11 point dose response curves. The dilutions were transferred to the assay plates ensuring that the DMSO concentration was constant across the plate for all assays. All data was normalized to the mean of 16 high and 16 low control wells on each plate. A four parameter curve fit was then applied.

Exemplified compounds of the invention that were tested in this assay had a pEC50>5.

S1P1 Tango Assay

Recombinant EDG1-bla/U2OS cells (contain the human Endothelial Differentiation Gene 1 (EDG1) linked to a TEV protease site and a Gal4-VP16 transcription factor stably integrated into the Tango GPCR-bla U2OS parental cell line) were suspended in assay medium (Invitrogen Freestyle Expression Medium) at a density of 312, 500 cells/ml. Add 100 μl/well of the assay medium to the cell-free control wells (column 12) and 100 μl/well of the cell suspension to the test compound wells (row 2-8, column 1-10), the unstimulated control wells (DMSO) (column 11), and stimulated control wells (S1P) (row 1, column 1-10) in a Corning black-well, clear bottom 96-well plate. Cells were incubated at 37° C., 5% CO$_2$ for 44-48 h.

Add 25 μl of 5× stock solution of test compounds in assay medium with 0.5% DMSO to the test compound wells, 25 μl of 5× stock solution of agonist (S1P) in assay medium with 0.5% DMSO to the stimulated compound wells, and 25 μl of 5× stock solution of 0.5% DMSO in assay medium to the unstimulated control and cell-free control wells.

After incubation at 37° C., 5% CO$_2$ for 5 h, 25 μl of 6× substrate mixture (6 μl Solution A (1 mg LiveBLAzer™-FRET B/G substrate (CCF4-AM) in 912 μl DMSO) plus 60 μl Solution B plus 934 μl Solution C) was added to each well and incubate at room temperature for 2 h in dark. The plate was finally read on EnVision for two emission channels (460 nm and 530 nm).

All test compounds were dissolved in DMSO at a concentration of 10 mM and were prepared in 100% DMSO using a 1 in 5 dilution step to provide 10 point dose response curves. The dilutions were transferred to the assay plates ensuring that the DMSO concentration was constant across the plate for all assays.

Calculate the blue/green emission ratio (460 nm/530 nm) for each well, by dividing the background-subtracted Blue emission values by the background-subtracted Green emission values. The dose response curve is based on sigmoidal dose-response model. All ratio data was normalized based upon the maximum emission ratio of positive control (S1P) and minimum emission ratio of negative control (DMSO) on each plate. The intrinsic activity (IA) of each compound would be the normalized percentage of its maximum response after curve fitting.

Exemplified compounds of the invention tested in at least one of the above assays had a pEC50>5 and all except for Examples 8, 29, 30, 44 and 78 had a pEC50>6. Examples 1, 2, 19, 20, 21, 36, 46, 48, 50-64, 67, 68, 75, 79, 80, 89, 101, 104, 106, 111 had a pEC50>8 in at least one of the above assays. Examples 3, 7, 47, 49, 58, 73, 74, 76, 97-100, 102, 103, 105, 109 and 110 had a pEC50>9 in at least one of the above assays.

S1P3

S1P3 membranes from rat basophilic leukaemia cells (RBL-2H3) (1.5 µg/well) were adhered to WGA-coated SPA beads (0.125 mg/well) in assay buffer (HEPES 20 mM, MgCl$_2$ 3 mM, NaCl 100 mM and pH adjusted to 7.4 using KOH 5M), GDP 10 µM FAC and saponin 90 µg/ml FAC was also added).

After 30 minutes pre-coupling on ice the bead and membrane suspension was dispensed into a white Greiner polypropylene LV384-well plate (5 µl/well), containing 0.1 µl of the compound. 5 µl/well [$^{35}$S]-GTPγS (0.5 nM final radioligand conc) made up in assay buffer was then added to agonist plates. The final assay cocktail (10.1 µl) was centrifuged at 1000 rpm for 5 minutes then read immediately on a Viewlux reader.

All test compounds were dissolved in DMSO at a concentration of 10 mM and were prepared in 100% DMSO using a 1 in 4 dilution step to provide 11 point dose response curves. The dilutions were transferred to the assay plates ensuring that the DMSO concentration was constant across the plate for all assays.

All data was normalized to the mean of 16 high and 16 low control wells on each plate. A four parameter curve fit was then applied.

All exemplified compounds tested in this assay had a pEC50<6 many had a pEC50 of 5.

S1P3 GeneBlazer Assay

GeneBLAzer EDG3-Ga15-NFAT-bla HEK 293T cells (contain the human Endothelial Differentiation G-protein Coupled Receptor 3 (EDG3) and a beta-lactamase reporter gene under control of a NFAT response element and a promiscuous G Protein, Ga15, stably integrated into the GeneBLAzer Ga15-NFAT-bla HEK 293T cell line) were suspended in assay medium (99% DMEM, 1% Dialyzed FBS, 0.1 mM NEAA, 25 mM HEPES (pH 7.3), 100 U/ml penicillin, 100 µg/ml streptomycin) at a density of 312, 500 cells/ml. Add 100 µl/well of the assay medium to the cell-free control wells (column 12) and 100 µl/well of the cell suspension to the test compound wells (row 2-8, column 1-10), the unstimulated control wells (DMSO) (column 11), and stimulated control wells (SIP) (row 1, column 1-10) in a Corning black-well, clear bottom 96-well plate. Cells were incubated at 37° C., 5% CO2 for 24 h.

Add 25 µl of 5× stock solution of test compounds in assay medium with 0.5% DMSO to the test compound wells, 25 µl of 5× stock solution of agonist (S1P) in assay medium with 0.5% DMSO to the stimulated compound wells, and 25 µl of 5× stock solution of 0.5% DMSO in assay medium to the unstimulated control and cell-free Control wells.

After incubation at 37° C., 5% CO2 for 5 h, 25 µl of 6× substrate mixture (6 µl Solution A (1 mg LiveBLAzer™-FRET B/G Substrate (CCF4-AM) in 912 µl DMSO) plus 60 µl Solution B plus 934 µl Solution C) was added to each well and incubate at room temperature for 2 h in dark. The plate was finally read on EnVision for two emission channels (460 nm and 530 nm).

All test compounds were dissolved in DMSO at a concentration of 10 mM and were prepared in 100% DMSO using a 1 in 5 dilution step to provide 10 point dose response curves. The dilutions were transferred to the assay plates ensuring that the DMSO concentration was constant across the plate for all assays.

Calculate the blue/green emission ratio (460 nm/530 nm) for each well, by dividing the background-subtracted Blue emission values by the background-subtracted green emission values. The dose response curve is based on sigmoidal dose-response model. All ratio data was normalized based upon the maximum emission ratio of positive control (S1P) and minimum emission ratio of negative control (DMSO) on each plate. The intrinsic activity (IA) of each compound would be the normalized percentage of its maximum response after curve fitting.

Exemplified compounds of the invention tested in at least one of the above assays had a pEC50<6 (except for Example 40 with an EC50 of 6.5), many had a pEC50 of 5.

The invention claimed is:
1. A compound of formula (I) or a pharmaceutically acceptable salt thereof:

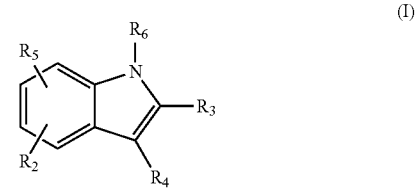

(I)

wherein
R$_5$ is (a) and attached at any one of positions 4, 5, 6 or 7 of the indole group;

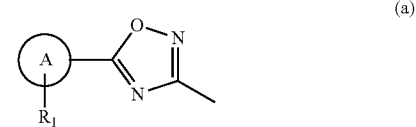

(a)

A is a phenyl or a 5 or 6-membered heteroaryl ring;
R$_1$ is hydrogen or up to three substituents independently selected from halogen, C$_{(1-6)}$alkyl, C$_{(3-6)}$cycloalkyl, C$_{(1-6)}$alkoxy, C$_{(3-6)}$cycloalkyloxy, trifluoromethoxy, difluoromethoxy, trifluoromethyl, cyano, nitro, optionally substituted piperidine, optionally substituted pyrrolidine, optionally substituted phenyl and optionally substituted 5 or 6 membered heteroaryl rings;
when R$_1$ is phenyl, piperidine, pyrrolidine or a 5 or 6 membered heteroaryl ring it may be substituted by up to three substituents selected from halogen, C$_{(1-6)}$alkyl, C$_{(1-6)}$alkoxy, trifluoromethoxy, difluoromethoxy, C$_{3-6}$cycloalkyl, trifluoromethyl and cyano;
R$_2$ is hydrogen or up to three substituents independently selected from halogen, C$_{(1-4)}$alkyl, C$_{(1-4)}$alkoxy, trifluoromethoxy, difluoromethoxy, trifluoromethyl and cyano;
one of R$_3$ and R$_4$ is hydrogen or C$_{(1-6)}$alkyl and the other is Z—COOH or C$_{(1-6)}$alkylOH;

Z is absent, $C_{(1-6)}$alkyl or $C_{(2-6)}$alkenyl;
when Z is $C_{(1-6)}$alkyl it is optionally interrupted by cyclopropyl, piperidinyl, azetidinyl, pyrrolidinyl, N or O and optionally substituted by O, cyclopropyl halogen or methyl, when Z is $C_{(2-6)}$alkenyl it is optionally substituted by methyl.
$R_6$ is hydrogen or $C_{(1-6)}$alkyl.

2. A compound of formula (I) of claim 1, or a pharmaceutically acceptable salt thereof, wherein:
$R_5$ is (a) and attached at positions 6 or 7 of the indole group;
A is phenyl or pyridyl;
$R_1$ is $C_{(1-6)}$alkoxy and one other substituent independently selected from halogen, $C_{(1-6)}$alkoxy, trifluoromethyl, $C_{(1-6)}$alkyl and cyano;
$R_2$ is halogen or hydrogen;
one of $R_3$ and $R_4$ is hydrogen and the other is Z—COOH or $CH_2OH$;
Z is $C_{(1-6)}$alkyl optionally interrupted by cyclopropyl, piperidinyl, azetidinyl, pyrrolidinyl, N or O and optionally substituted by O, cyclopropyl, halogen or methyl, or Z is $C_{(2-6)}$alkenyl optionally substituted by methyl; and
$R_6$ is hydrogen, methyl, ethyl, propyl or butyl.

3. A compound selected from:
3-[7-(5-{3-Chloro-4-[(1-methylethyl)oxy]phenyl}-1,2,4-oxadiazol-3-yl)-1H-indol-3-yl]propanoic acid;
3-[7-(5-{3-Chloro-4-[(1-methylethyl)oxy]phenyl}-1,2,4-oxadiazol-3-yl)-1-methyl-1H-indol-3-yl]propanoic acid;
3-[7-(5-{3-Cyano-4-[(1-methylethyl)oxy]phenyl}-1,2,4-oxadiazol-3-yl)-1H-indol-3-yl]propanoic acid;
3-[7-(5-{3-Cyano-4-[(1-methylethyl)oxy]phenyl}-1,2,4-oxadiazol-3-yl)-1-methyl-1H-indol-3-yl]propanoic acid;
3-[6-(5-{3-Chloro-4-[(1-methylethyl)oxy]phenyl}-1,2,4-oxadiazol-3-yl)-1H-indol-3-yl]propanoic acid;
3-[6-(5-{3-chloro-4-[(1-methylethyl)oxy]phenyl}-1,2,4-oxadiazol-3-yl)-1-methyl-1H-indol-3-yl]propanoic acid;
3-[6-(5-{3-Cyano-4-[(1-methylethyl)oxy]phenyl}-1,2,4-oxadiazol-3-yl)-1H-indol-3-yl]propanoic acid;
5-(5-{3-chloro-4-[(1-methylethyl)oxy]phenyl}-1,2,4-oxadiazol-3-yl)-1H-indole-2-carboxylic acid;
3-[5-(5-{3-chloro-4-[(1-methylethyl)oxy]phenyl}-1,2,4-oxadiazol-3-yl)-1H-indol-2-yl]propanoic acid;
(2E)-3-[5-(5-{3-cyano-4-[(1-methylethyl)oxy]phenyl}-1,2,4-oxadiazol-3-yl)-1H-indol-2-yl]-2-propenoic acid;
[5-(5-{3-Chloro-4-[(1-methylethyl)oxy]phenyl}-1,2,4-oxadiazol-3-yl)-1H-indol-2-yl]methanol;
5-{3-[2-(Hydroxymethyl)-1H-indol-5-yl]-1,2,4-oxadiazol-5-yl]-2-[(1-methylethyl)oxy]benzonitrile;
3-[7-(5-{5-Chloro-6-[(1-methylethyl)oxy]-3-pyridinyl}-1,2,4-oxadiazol-3-yl)-1H-indol-3-yl]propanoic acid;
3-[7-(5-{5-Chloro-6-[(1-methylethyl)oxy]-3-pyridinyl}-1,2,4-oxadiazol-3-yl)-1-methyl-1H-indol-3-yl]propanoic acid;
3-(7-{5-[6-[(1-Methylethyl)oxy]-5-(trifluoromethyl)-3-pyridinyl]-1,2,4-oxadiazol-3-yl}-1H-indol-3-yl)propanoic acid;
3-[7-(5-{5-Methyl-6-[(1-methylethyl)oxy]-3-pyridinyl}-1,2,4-oxadiazol-3-yl)-1H-indol-3-yl]propanoic acid;
3-[1-Methyl-7-(5-{5-methyl-6-[(1-methylethyl)oxy]-3-pyridinyl}-1,2,4-oxadiazol-3-yl)-1H-indol-3-yl]propanoic acid;
3-(7-{5-[6-[(1-Methylethyl)oxy]-5-(methyloxy)-3-pyridinyl]-1,2,4-oxadiazol-3-yl}-1H-indol-3-yl)propanoic acid;
3-[7-(5-{3-Chloro-4-[(1-methylethyl)oxy]phenyl}-1,2,4-oxadiazol-3-yl)-4-fluoro-1H-indol-3-yl]propanoic acid;
3-[7-(5-{3-Chloro-4-[(1-methylethyl)oxy]phenyl}-1,2,4-oxadiazol-3-yl)-4-fluoro-1-methyl-1H-indol-3-yl]propanoic acid;
3-[7-(5-{3-Cyano-4-[(1-methylethyl)oxy]phenyl}-1,2,4-oxadiazol-3-yl)-4-fluoro-1H-indol-3-yl]propanoic acid;
3-[7-(5-{5-Chloro-6-[(1-methylethyl)oxy]-3-pyridinyl}-1,2,4-oxadiazol-3-yl)-4-fluoro-1H-indol-3-yl]propanoic acid;
3-[7-(5-{5-Chloro-6-[(1-methylethyl)oxy]-3-pyridinyl}-1,2,4-oxadiazol-3-yl)-4-fluoro-1-methyl-1H-indol-3-yl]propanoic acid;
3-(4-Fluoro-7-{5-[6-[(1-methylethyl)oxy]-5-(trifluoromethyl)-3-pyridinyl]-1,2,4-oxadiazol-3-yl}-1H-indol-3-yl)propanoic acid;
3-(4-Fluoro-7-{5-[6-[(1-methylethyl)oxy]-5-(methyloxy)-3-pyridinyl]-1,2,4-oxadiazol-3-yl}-1H-indol-3-yl)propanoic acid;
3-[7-(5-{3-chloro-4-[(1-methylethyl)oxy]phenyl}-1,2,4-oxadiazol-3-yl)-1-ethyl-1H-indol-3-yl]propanoic acid;
3-[7-(5-{3-chloro-4-[(1-methylethyl)oxy]phenyl}-1,2,4-oxadiazol-3-yl)-1-propyl-1H-indol-3-yl]propanoic acid;
3-[7-(5-{3-chloro-4-[(1-methylethyl)oxy]phenyl}-1,2,4-oxadiazol-3-yl)-1-(1-methylethyl)-1H-indol-3-yl]propanoic acid;
3-[1-butyl-7-(5-{3-chloro-4-[(1-methylethyl)oxy]phenyl}-1,2,4-oxadiazol-3-yl)-1H-indol-3-yl]propanoic acid;
3-[7-(5-{3-chloro-4-[(1-methylethyl)oxy]phenyl}-1,2,4-oxadiazol-3-yl)-1-(2-methylpropyl)-1H-indol-3-yl]propanoic acid;
[7-(5-{3-chloro-4-[(1-methylethyl)oxy]phenyl}-1,2,4-oxadiazol-3-O-1H-indol-3-yl]acetic acid;
4-[7-(5-{3-chloro-4-[(1-methylethyl)oxy]phenyl}-1,2,4-oxadiazol-3-yl)-1H-indol-3-yl]butanoic acid;
4-[7-(5-{3-chloro-4-[(1-methylethyl)oxy]phenyl}-1,2,4-oxadiazol-3-yl)-1H-indol-3-yl]-4-oxobutanoic acid;
5-[7-(5-{3-chloro-4-[(1-methylethyl)oxy]phenyl}-1,2,4-oxadiazol-3-yl)-1H-indol-3-yl]pentanoic acid;
4-[7-(5-{3-chloro-4-[(1-methylethyl)oxy]phenyl}-1,2,4-oxadiazol-3-yl)-1-methyl-1H-indol-3-yl]butanoic acid;
(2R)-3-[7-(5-{3-chloro-4-[(1-methylethyl)oxy]phenyl}-1,2,4-oxadiazol-3-yl)-1-methyl-1H-indol-3-yl]-2-methylpropanoic acid;
(2E)-3-[7-(5-{3-chloro-4-[(1-methylethyl)oxy]phenyl}-1,2,4-oxadiazol-3-yl)-1-methyl-1H-indol-3-yl]-2-propenoic acid;
(2Z)-3-[7-(5-{3-chloro-4-[(1-methylethyl)oxy]phenyl}-1,2,4-oxadiazol-3-yl)-1-methyl-1H-indol-3-yl]-2-propenoic acid;
trans-2-[7-(5-{3-chloro-4-[(1-methylethyl)oxy]phenyl}-1,2,4-oxadiazol-3-yl)-1-methyl-1H-indol-3-yl]cyclopropanecarboxylic acid;
cis-2-[7-(5-{3-chloro-4-[(1-methylethyl)oxy]phenyl}-1,2,4-oxadiazol-3-yl)-1-methyl-1H-indol-3-yl]cyclopropanecarboxylic acid;
3-(7-{5-[3,4-bis(ethyloxy)phenyl]-1,2,4-oxadiazol-3-yl}-1H-indol-3-yl)propanoic acid;
3-(7-{5-[3,4-bis(ethyloxy)phenyl]-1,2,4-oxadiazol-3-yl}-1-methyl-1H-indol-3-yl)propanoic acid;
3-(7-{5-[3,4-bis(methyloxy)phenyl]-1,2,4-oxadiazol-3-yl}-1H-indol-3-yl)propanoic acid;

3-(7-{5-[3,4-bis(methyloxy)phenyl]-1,2,4-oxadiazol-3-yl}-1-methyl-1H-indol-3-yl)propanoic acid;

3-(7-{5-[3-chloro-4,5-bis(ethyloxy)phenyl]-1,2,4-oxadiazol-3-yl}-1H-indol-3-yl)propanoic acid;

N-{[7-(5-{3-chloro-4-[(1-methylethyl)oxy]phenyl}-1,2,4-oxadiazol-3-yl)-1H-indol-3-yl]methyl}-β-alanine;

N-{[7-(5-{3-chloro-4-[(1-methylethyl)oxy]phenyl}-1,2,4-oxadiazol-3-yl)-1H-indol-3-yl]methyl}glycine;

1-{[7-(5-{3-chloro-4-[(1-methylethyl)oxy]phenyl}-1,2,4-oxadiazol-3-yl)-1H-indol-3-yl]methyl}-4-piperidinecarboxylic acid;

N-{[7-(5-{3-chloro-4-[(1-methylethyl)oxy]phenyl}-1,2,4-oxadiazol-3-yl)-1H-indol-3-yl]methyl}-D-alanine;

N-{[7-(5-{3-chloro-4-[(1-methylethyl)oxy]phenyl}-1,2,4-oxadiazol-3-yl)-1H-indol-3-yl]methyl}-L-alanine;

3-({[7-(5-{3-chloro-4-[(1-methylethyl)oxy]phenyl}-1,2,4-oxadiazol-3-yl)-1H-indol-3-yl]methyl}amino)butanoic acid;

N-{[7-(5-{3-chloro-4-[(1-methylethyl)oxy]phenyl}-1,2,4-oxadiazol-3-yl)-1H-indol-3-yl]methyl}-N-methylglycine;

N-{[7-(5-{3-chloro-4-[(1-methylethyl)oxy]phenyl}-1,2,4-oxadiazol-3-yl)-1H-indol-3-yl]methyl}-N-methyl-D-alanine;

N-{[7-(5-{3-chloro-4-[(1-methylethyl)oxy]phenyl}-1,2,4-oxadiazol-3-yl)-1H-indol-3-yl]methyl}-N-methyl-L-alanine;

N-{[7-(5-{3-cyano-4-[(1-methylethyl)oxy]phenyl}-1,2,4-oxadiazol-3-yl)-1H-indol-3-yl]methyl}-N-methylglycine;

N-{[7-(5-{3-chloro-4-[(1-methylethyl)oxy]phenyl}-1,2,4-oxadiazol-3-yl)-1-methyl-1H-indol-3-yl]methyl}glycine;

1-{[7-(5-{3-chloro-4-[(1-methylethyl)oxy]phenyl}-1,2,4-oxadiazol-3-yl)-1-methyl-1H-indol-3-yl]methyl}-4-piperidinecarboxylic acid;

N-{[7-(5-{3-chloro-4-[(1-methylethyl)oxy]phenyl}-1,2,4-oxadiazol-3-yl)-1-methyl-1H-indol-3-yl]methyl}-β-alanine;

N-{[7-(5-{3-chloro-4-[(1-methylethyl)oxy]phenyl}-1,2,4-oxadiazol-3-yl)-1-methyl-1H-indol-3-yl]methyl}-D-alanine;

N-{[7-(5-{3-chloro-4-[(1-methylethyl)oxy]phenyl}-1,2,4-oxadiazol-3-yl)-1-methyl-1H-indol-3-yl]methyl}-L-alanine;

3-({[7-(5-{3-chloro-4-[(1-methylethyl)oxy]phenyl}-1,2,4-oxadiazol-3-yl)-1-methyl-1H-indol-3-yl]methyl}amino)butanoic acid;

N-{2-[7-(5-{3-chloro-4-[(1-methylethyl)oxy]phenyl}-1,2,4-oxadiazol-3-yl)-1H-indol-3-yl]ethyl}-β-alanine;

N-{2-[7-(5-{3-chloro-4-[(1-methylethyl)oxy]phenyl}-1,2,4-oxadiazol-3-yl)-1H-indol-3-yl]ethyl}glycine;

N-{2-[7-(5-{3-chloro-4-[(1-methylethyl)oxy]phenyl}-1,2,4-oxadiazol-3-yl)-1-methyl-1H-indol-3-yl]ethyl}glycine;

N-{2-[7-(5-{3-chloro-4-[(1-methylethyl)oxy]phenyl}-1,2,4-oxadiazol-3-yl)-1-methyl-1H-indol-3-yl]ethyl}-alanine;

1-{2-[7-(5-{3-chloro-4-[(1-methylethyl)oxy]phenyl}-1,2,4-oxadiazol-3-yl)-1-methyl-1H-indol-3-yl]ethyl}-4-piperidinecarboxylic acid;

1-{2-[7-(5-{3-chloro-4-[(1-methylethyl)oxy]phenyl}-1,2,4-oxadiazol-3-yl)-1-methyl-1H-indol-3-yl]ethyl}-3-azetidinecarboxylic acid;

1-({2-[7-(5-{3-chloro-4-[(1-methylethyl)oxy]phenyl}-1,2,4-oxadiazol-3-yl)-1-methyl-1H-indol-3-yl]ethyl}amino)cyclopropanecarboxylic acid;

1-{2-[7-(5-{3-chloro-4-[(1-methylethyl)oxy]phenyl}-1,2,4-oxadiazol-3-yl)-1-methyl-1H-indol-3-yl]ethyl}-L-proline;

N-{3-[7-(5-{3-chloro-4-[(1-methylethyl)oxy]phenyl}-1,2,4-oxadiazol-3-yl)-1H-indol-3-yl]propyl}glycine;

N-{3-[7-(5-{3-chloro-4-[(1-methylethyl)oxy]phenyl}-1,2,4-oxadiazol-3-yl)-1H-indol-3-yl]propyl}-N-methylglycine;

N-{[7-(5-{3-chloro-4-[(1-methylethyl)oxy]phenyl}-1,2,4-oxadiazol-3-yl)-1H-indol-3-yl]carbonyl}glycine;

N-{[7-(5-{3-chloro-4-[(1-methylethyl)oxy]phenyl}-1,2,4-oxadiazol-3-yl)-1H-indol-3-yl]carbonyl}-alanine;

4-({[7-(5-{3-chloro-4-[(1-methylethyl)oxy]phenyl}-1,2,4-oxadiazol-3-yl)-1H-indol-3-yl]carbonyl}amino)butanoic acid;

N-{[7-(5-{3-chloro-4-[(1-methylethyl)oxy]phenyl}-1,2,4-oxadiazol-3-yl)-1H-indol-3-yl]carbonyl}-N-methylalanine;

N-{[7-(5-{3-chloro-4-[(1-methylethyl)oxy]phenyl}-1,2,4-oxadiazol-3-yl)-1-methyl-1H-indol-3-yl]carbonyl}-alanine;

N-{3-[7-(5-{3-chloro-4-[(1-methylethyl)oxy]phenyl}-1,2,4-oxadiazol-3-yl)-1H-indol-3-yl]propanoyl}glycine;

1-{[6-(5-{5-chloro-6-[(1-methylethyl)oxy]-3-pyridinyl}-1,2,4-oxadiazol-3-yl)-1H-indol-3-yl]methyl}-4-piperidinecarboxylic acid;

({2-[7-(5-{3-chloro-4-[(1-methylethyl)oxy]phenyl}-1,2,4-oxadiazol-3-yl)-1-methyl-1H-indol-3-yl]ethyl}oxy)acetic acid;

({3-[7-(5-{3-chloro-4-[(1-methylethyl)oxy]phenyl}-1,2,4-oxadiazol-3-yl)-1-methyl-1H-indol-3-yl]propyl}oxy)acetic acid;

3-[6-(5-{5-Chloro-6-[(1-methylethyl)oxy]-3-pyridinyl}-1,2,4-oxadiazol-3-yl)-1H-indol-3-yl]propanoic acid;

3-[6-(5-{5-Chloro-6-[(1-methylethyl)oxy]-3-pyridinyl}-1,2,4-oxadiazol-3-yl)-1-methyl-1H-indol-3-yl]propanoic acid;

3-(6-{5-[6-[(1-Methylethyl)oxy]-5-(trifluoromethyl)-3-pyridinyl]-1,2,4-oxadiazol-3-yl}-1H-indol-3-yl)propanoic acid;

3-[6-(5-{5-Fluoro-6-[(1-methylethyl)oxy]-3-pyridinyl}-1,2,4-oxadiazol-3-yl)-1H-indol-3-yl]propanoic acid;

3-[6-(5-{5-Methyl-6-[(1-methylethyl)oxy]-3-pyridinyl}-1,2,4-oxadiazol-3-yl)-1H-indol-3-yl]propanoic acid;

3-[1-Methyl-6-(5-{5-methyl-6-[(1-methylethyl)oxy]-3-pyridinyl}-1,2,4-oxadiazol-3-yl)-1H-indol-3-yl]propanoic acid;

3-(6-{5-[6-[(1-Methylethyl)oxy]-5-(methyloxy)-3-pyridinyl]-1,2,4-oxadiazol-3-yl}-1H-indol-3-yl)propanoic acid;

3-[5-(5-{3-chloro-4-[(1-methylethyl)oxy]phenyl}-1,2,4-oxadiazol-3-yl)-1-methyl-1H-indol-2-yl]propanoic acid;

3-[5-(5-{3-cyano-4-[(1-methylethyl)oxy]phenyl}-1,2,4-oxadiazol-3-yl)-1H-indol-2-yl]propanoic acids;

3-[5-(5-{5-chloro-6-[(1-methylethyl)oxy]-3-pyridinyl}-1,2,4-oxadiazol-3-yl)-1H-indol-2-yl]propanoic acid;

3-[5-(5-{5-chloro-6-[(1-methylethyl)oxy]-3-pyridinyl}-1,2,4-oxadiazol-3-yl)-1-methyl-1H-indol-2-yl]propanoic acid;

3-(5-{5-[6-[(1-methylethyl)oxy]-5-(trifluoromethyl)-3-pyridinyl]-1,2,4-oxadiazol-3-yl}-1H-indol-2-yl)propanoic 3-(5-{5-[6-[(1-methylethyl)oxy]-5-(methyloxy)-3-pyridinyl]-1,2,4-oxadiazol-3-yl}-1H-indol-2-yl)propanoic acid 7-(5-{3-chloro-4-[(1-methylethyl)oxy]phenyl}-1,2,4-oxadiazol-3-yl)-1H-indole-3-carboxylic acid;

7-(5-{3-chloro-4-[(1-methylethyl)oxy]phenyl}-1,2,4-oxadiazol-3-yl)-1-methyl-1H-indole-3-carboxylic acid;

3-[7-(5-{3-cyano-4-[(1-methylethyl)oxy]phenyl}-1,2,4-oxadiazol-3-yl)-4-fluoro-1-methyl-1H-indol-3-yl]propanoic acid;

3-[7-(5-{3-Chloro-4-[(1-methylethyl)oxy]phenyl}-1,2,4-oxadiazol-3-yl)-5-fluoro-1H-indol-3-yl]propanoic acid;

3-[7-(5-{3-Chloro-4-[(1-methylethyl)oxy]phenyl}-1,2,4-oxadiazol-3-yl)-5-fluoro-1-methyl-1H-indol-3-yl]propanoic acid;

3-[7-(5-{3-Cyano-4-[(1-methylethyl)oxy]phenyl}-1,2,4-oxadiazol-3-yl)-5-fluoro-1H-indol-3-yl]propanoic acid;

3-[7-(5-{3-Cyano-4-[(1-methylethyl)oxy]phenyl}-1,2,4-oxadiazol-3-yl)-5-fluoro-1-methyl-1H-indol-3-yl]propanoic acid;

3-[7-(5-{5-Chloro-6-[(1-methylethyl)oxy]-3-pyridinyl}-1,2,4-oxadiazol-3-yl)-5-fluoro-1H-indol-3-yl]propanoic acid;

3-[7-(5-{5-Chloro-6-[(1-methylethyl)oxy]-3-pyridinyl}-1,2,4-oxadiazol-3-yl)-5-fluoro-1H-indol-3-yl]propanoic acid;

3-[7-(5-{5-Chloro-6-[(1-methylethyl)oxy]-3-pyridinyl}-1,2,4-oxadiazol-3-yl)-5-fluoro-1-methyl-1H-indol-3-yl]propanoic acid;

3-[7-(5-{3-Chloro-4-[(1-methylethyl)oxy]phenyl}-1,2,4-oxadiazol-3-yl)-6-fluoro-1H-indol-3-yl]propanoic acid;

3-[7-(5-{3-Chloro-4-[(1-methylethyl)oxy]phenyl}-1,2,4-oxadiazol-3-yl)-6-fluoro-1-methyl-1H-indol-3-yl]propanoic acid;

3-[7-(5-{3-Cyano-4-[(1-methylethyl)oxy]phenyl}-1,2,4-oxadiazol-3-yl)-6-fluoro-1H-indol-3-yl]propanoic acid;

3-[7-(5-{3-Cyano-4-[(1-methylethyl)oxy]phenyl}-1,2,4-oxadiazol-3-yl)-6-fluoro-1-methyl-1H-indol-3-yl]propanoic acid;

3-[7-(5-{5-Chloro-6-[(1-methylethyl)oxy]-3-pyridinyl}-1,2,4-oxadiazol-3-yl)-6-fluoro-1H-indol-3-yl]propanoic acid;

3-[7-(5-{5-Chloro-6-[(1-methylethyl)oxy]-3-pyridinyl}-1,2,4-oxadiazol-3-yl)-6-fluoro-1-methyl-1H-indol-3-yl]propanoic acid;

3-[6-(5-{3-Chloro-4-[(1-methyl ethyl)oxy]phenyl}-1,2,4-oxadiazol-3-yl)-5-fluoro-1H-indol-3-yl]propanoic acid;

3-[6-(5-{3-Cyano-4-[(1-methylethyl)oxy]phenyl}-1,2,4-oxadiazol-3-yl)-5-fluoro-1H-indol-3-yl]propanoic acid;

3-[6-(5-{5-Chloro-6-[(1-methylethyl)oxy]-3-pyridinyl}-1,2,4-oxadiazol-3-yl)-5-fluoro-1H-indol-3-yl]propanoic acid;

3-[5-(5-{3-Chloro-4-[(1-methyl ethyl)oxy]phenyl}-1,2,4-oxadiazol-3-yl)-7-fluoro-1H-indol-2-yl]propanoic acid;

3-[5-(5-{3-Cyano-4-[(1-methylethyl)oxy]phenyl}-1,2,4-oxadiazol-3-yl)-7-fluoro-1H-indol-2-yl]propanoic acid; and 3-[5-(5-{5-Chloro-6-[(1-methylethyl)oxy]-3-pyridinyl}-1,2,4-oxadiazol-3-yl)-7-fluoro-1H-indol-2-yl]propanoic acid;

and pharmaceutically acceptable salts thereof.

4. A pharmaceutical composition comprising a compound of formula (I) or a pharmaceutically acceptable salt thereof according to claim 1.

\* \* \* \* \*